United States Patent
Chong et al.

(10) Patent No.: US 11,866,746 B2
(45) Date of Patent: Jan. 9, 2024

(54) COMPOSITIONS COMPRISING A VARIANT CAS12I4 POLYPEPTIDE AND USES THEREOF

(71) Applicant: ARBOR BIOTECHNOLOGIES, INC., Cambridge, MA (US)

(72) Inventors: Shaorong Chong, Arlington, MA (US); Wei-Cheng Lu, Cambridge, MA (US); Brendan Jay Hilbert, Natick, MA (US); Quinton Norman Wessells, Cambridge, MA (US); Tia Marie Ditommaso, Waltham, MA (US); Anthony James Garrity, Hingham, MA (US)

(73) Assignee: ARBOR BIOTECHNOLOGIES, INC., Cambridge, MA (US)

( * ) Notice: Subject to any disclaimer, the term of this patent is extended or adjusted under 35 U.S.C. 154(b) by 10 days.

(21) Appl. No.: 18/148,818

(22) Filed: Dec. 30, 2022

(65) Prior Publication Data
US 2023/0295589 A1    Sep. 21, 2023

Related U.S. Application Data

(63) Continuation of application No. PCT/US2022/016214, filed on Feb. 11, 2022.

(60) Provisional application No. 63/154,437, filed on Feb. 26, 2021, provisional application No. 63/148,421, filed on Feb. 11, 2021.

(51) Int. Cl.
| | |
|---|---|
| *C12N 9/22* | (2006.01) |
| *C12N 15/11* | (2006.01) |
| *C12N 15/10* | (2006.01) |
| *C12N 5/071* | (2010.01) |
| *C12N 15/90* | (2006.01) |

(52) U.S. Cl.
CPC ............. *C12N 9/22* (2013.01); *C12N 5/0686* (2013.01); *C12N 15/102* (2013.01); *C12N 15/11* (2013.01); *C12N 15/907* (2013.01); *C12N 2310/20* (2017.05); *C12N 2800/80* (2013.01)

(58) Field of Classification Search
CPC ....................................................... C12N 9/22
See application file for complete search history.

(56) References Cited

FOREIGN PATENT DOCUMENTS

WO     2019/178427 A1    9/2019

OTHER PUBLICATIONS

Huang et al., "Structural basis for two metal-ion catalysis of DNA cleavage by Cas12i2", Nature Communications, 2020, 11:5241. 14 pages.*
Yan et al., "Suppl. Material for Functionally Diverse Tye V CRISPR-Cas Systems" Science (2018) pp. 1-68.
International Search Report and Written Opinion for International Application No. PCT/US2022/016214 dated Sep. 13, 2022.

* cited by examiner

*Primary Examiner* — Suzanne M Noakes
(74) *Attorney, Agent, or Firm* — K&L Gates LLP

(57) ABSTRACT

The present invention relates to variant Cas12i4 polypeptides, methods of producing the variant Cas12i4 polypeptides, processes for characterizing the variant Cas12i4 polypeptides, cells comprising the variant Cas12i4 polypeptides, and methods of using the variant Cas12i4 polypeptides. The invention further relates to complexes comprising a variant Cas12i4 polypeptide and an RNA guide, methods of producing the complexes, processes for characterizing the complexes, cells comprising the complexes, and methods of using the complexes.

20 Claims, 12 Drawing Sheets
Specification includes a Sequence Listing.

SEQUENCE LISTING

```
Sequence total quantity: 228
SEQ ID NO: 1              moltype = DNA  length = 3222
FEATURE                   Location/Qualifiers
misc_feature              1..3222
                          note = Synthetic Construct
source                    1..3222
                          mol_type = other DNA
                          organism = synthetic construct
SEQUENCE: 1
atggcttcca tctctaggcc atacggcacc aagctgcgac cggacgcacg gaagaaggag    60
atgctcgata agttctttaa tacactgact aagggtcagc gcgtgttcgc agacctggcc   120
ctgtgcatct atggctccct gaccctggag atggccaagt ctctggagcc agaaagtgat   180
tcagaactgg tgtgcgctat tgggtggttt cggctggtgg acaagaccat ctggtccaag   240
gatggcatca agcaggagaa tctggtgaaa cagtacgaag cctattccgg aaaggaggct   300
tctgaagtgg tcaaaacata cctgaacagc cccagctccg acaagtacgt gtggatcgat   360
tgcaggcaga aattcctgag gtttcagcgc gagctcggca ctcgcaacct gtccgaggac   420
ttcgaatgta tgctctttga acagtacatt agactgacca agggcgagat cgaagggtat   480
gccgctattt caaatatgtt cggaaacggc gagaaggaag accggagcaa gaaaagaatg   540
tacgctacac ggatgaaaga ttggctggag gcaaacgaaa atatcacttg ggagcagtat   600
agagaggccc tgaagaacca gctgaatgct aaaaacctgg agcaggttgt ggccaattac   660
aagggggaacg ctggcgggggc agacccccttc tttaagtata gcttctccaa agagggaatg   720
gtgagcaaga aagaacatgc acagcagctc gacaagttca aaaccgtcct gaagaacaaa   780
gcccgggacc tgaattttcc aaacaaggag aagctgaagc agtacctgga ggccgaaatc   840
ggcattccgg tcgacgctaa cgtgtactcc cagatgttct ctaacggggt gagtgaggtc   900
cagcctaaga ccacacggaa tatgtcttt agtaacgaga aactggatct gctcactgaa   960
ctgaaggacc tgaacaaggg cgatgggttc gagtacgcca gagaagtgct gaacgggttc  1020
tttgactccg agctccacac taccgaggat aagtttaata tcacctctag gtacctggga  1080
ggcgacaaat caaaccgcct gagcaaactc tataagatct ggaagaaaga gggtgtggac  1140
tgcgaggaag gcattcagca gttctgtgaa gccgtcaaag ataagatggg ccagatcccc  1200
attcgaaatg tgctgaagta cctgtggcag ttccgggaga cagtcagtgc cgaggatttt  1260
```

```
gaagcagccg ctaaggctaa ccatctggag gaaaagatca gccgggtgaa agcccaccca 1320
atcgtgatta gcaataggta ctgggctttt gggacttccg cactggtggg aaacattatg 1380
cccgcagaca agaggcatca gggagagtat gccggtcaga atttcaaaat gtggctggag 1440
gctgaactgc actacgatgg caagaaagca aagcaccatc tgccttttta taacgcccgc 1500
ttctttgagg aagtgtactg ctatcacccc tctgtcgcg agatcactcc tttcaaaacc 1560
aagcagtttg gctgtgaaat cgggaaggac attccagatt acgtgagcgt cgctctgaag 1620
gacaatccgt ataagaaagc aaccaaacga atcctgcgtg caatctacaa tcccgtcgcc 1680
aacacaactg gcgttgataa gaccacaaac tgcagcttca tgatcaaacg cgagaatgac 1740
gaatataagc tggtcatcaa ccgaaaaatt tccgtggatc ggctaaggaa aatcgaagtg 1800
ggcaggacaa ttatggggta cgaccgcaat cagacagcta gcgatactta ttggattggg 1860
cggctggtgc cacctggaac ccggggcgca taccgcatcg gagagtggag cgtccagtat 1920
attaagtccg ggcctgtcct gtctagtact cagggagtta acaattccac taccgaccag 1980
ctggtgtaca acggcatgcc atcaagctcc gagcggttca aggcctggaa gaaagccaga 2040
atggcttta tccgaaaact cattcgtcag ctgaatgacg agggactgga atctaaggt 2100
caggattata tccccgagaa cccttctagt ttcgatgtgc ggggcgaaac cctgtacgtc 2160
tttaacagta attatctgaa ggccctggtg agcaaacaca gaaaggccaa gaaacctgtt 2220
gaggggatcc tggacgagat tgaagcctgg acatctaaag acaaggattc atgcagcctg 2280
atgcggtcga gcagcctgag cgatgcttcc atgcagggaa tcgccagcct gaagagtcta 2340
attaacagct acttcaacaa gaatggctgt aaaaccatcg aggacaaaga aaagtttaat 2400
cccgtgctgt atgccaagct ggttgaggtg aacagcgga gaacaaacaa gcggtctgag 2460
aaagtgggaa gaatcgcagg tagtctggag cagctggccc tgctgaacgg ggttgaggtg 2520
gtcatcggcg aagctgacct gggggaggtc gaaaaaggaa agagtaagaa acagaattca 2580
cggaacatgg attggtgcgc aaagcaggtg gcacagcggc tggagtacaa actggccttc 2640
catggaatcg gttactttgg agtgaacccc atgtatacca gccaccagga ccctttcgaa 2700
cataggcgcg tggctgatca catcgtcatg cgagcacgtt ttgaggaagt caacgtggag 2760
aacattgccg aatggcacgt gcgaaatttc tcaaactgcg tgctgcaga cagcggcact 2820
gggctgtact ataagcaggc caccatggac ttcctgaaac attacggtct ggaggaacac 2880
gctgagggcc tggaaaataa gaaaatcaag ttctatgact tagaaagat cctggaggat 2940
aaaaacctga caagcgtgat cattccaaag aggggcgggc gcatctacat ggccaccaac 3000
ccagtgacat ccgactctac cccgattaca tacgccggca agacttataa taggtgtaac 3060
gctgatgagg tggcagccgc taatatcgtt atttctgtgc tggctccccg cagtaagaaa 3120
aacgaggaac aggacgatat ccctctgatt accaagaaag ccgagagtaa gtcaccaccg 3180
aaagaccgga gagatcaaa aacaagccag ctgcctcaga aa 3222
```

```
SEQ ID NO: 2         moltype = AA   length = 1074
FEATURE              Location/Qualifiers
REGION               1..1074
                     note = Synthetic Construct
source               1..1074
                     mol_type = protein
                     organism = synthetic construct
SEQUENCE: 2
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLE   480
AELHYDGKKA KHHLPFYNAR FFEEVYCYHP SVAEITPFKT KQFGCEIGKD IPDYVSVALK   540
DNPYKKATKR ILRAIYNPVA NTTGVDKTTN CSFMIKREND EYKLVINRKI SVDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NEEQDDIPLI TKKAESKSPP KDRKRSKTSQ LPQK        1074
```

```
SEQ ID NO: 3         moltype = AA   length = 1074
FEATURE              Location/Qualifiers
REGION               1..1074
                     note = Synthetic Construct
source               1..1074
                     mol_type = protein
                     organism = synthetic construct
SEQUENCE: 3
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLE   480
AELHYDGKKA KHHLPFYNAR FFEEVYCYHP SVAEITPFKT KQFGCEIGKD IPDYVSVALK   540
DNPYKKATKR ILRAIYNPVA NTTGVDKTTN CSFMIKREND EYKLVINRKI SRDRPKRIEV   600
```

```
GRTIMGYDRN QTASDTYWIG RLVPPGTRGA YRIGEWSVQY IKSGPVLSST QGVNNSTTDQ    660
LVYNGMPSSS ERFKAWKKAR MAFIRKLIRQ LNDEGLESKG QDYIPENPSS FDVRGETLYV    720
FNSNYLKALV SKHRKAKKPV EGILDEIEAW TSKDKDSCSL MRLSSLSDAS MQGIASLKSL    780
INSYFNKNGC KTIEDKEKFN PVLYAKLVEV EQRRTNKRSE KVGRIAGSLE QLALLNGVEV    840
VIGEADLGEV EKGKSKKQNS RNMDWCAKQV AQRLEYKLAF HGIGYFGVNP MYTSHQDPFE    900
HRRVADHIVM RARFEEVNVE NIAEWHVRNF SNYLRADSGT GLYYKQATMD FLKHYGLEEH    960
AEGLENKKIK FYDFRKILED KNLTSVIIPK RGGRIYMATN PVTSDSTPIT YAGKTYNRCN   1020
ADEVAAANIV ISVLAPRSKK NREQDDIPLI TKKAESKSPP KDRKRSKTSQ LPQK         1074

SEQ ID NO: 4           moltype = AA   length = 1074
FEATURE                Location/Qualifiers
REGION                 1..1074
                       note = Synthetic Construct
source                 1..1074
                       mol_type = protein
                       organism = synthetic construct
SEQUENCE: 4
MASISRPYGT KLRPDARKKE MLDKFFNTLT KGQRVFADLA LCIYGSLTLE MAKSLEPESD     60
SELVCAIGWF RLVDKTIWSK DGIKQENLVK QYEAYSGKEA SEVVKTYLNS PSSDKYVWID    120
CRQKFLRFQR ELGTRNLSED FECMLFEQYI RLTKGEIEGY AAISNMFGNG EKEDRSKKRM    180
YATRMKDWLE ANENITWEQY REALKNQLNA KNLEQVVANY KGNAGGADPF FKYSFSKEGM    240
VSKKEHAQQL DKFKTVLKNK ARDLNFPNKE KLKQYLEAEI GIPVDANVYS QMFSNGVSEV    300
QPKTTRNMSF SNEKLDLLTE LKDLNKGDGF EYAREVLNGF FDSELHTTED KFNITSRYLG    360
GDKSNRLSKL YKIWKKEGVD CEEGIQQFCE AVKDKMGQIP IRNVLKYLWQ FRETVSAEDF    420
EAAAKANHLE EKISRVKAHP IVISNRYWAF GTSALVGNIM PADKRHQGEY AGQNFKMWLR    480
AELHYDGKKA KHHLPFYNAR FFEEVYCYHP SVAEITPFKT KQFGCEIGKD IPDYVSALK    540
DNPYKKATKR ILRAIYNPVA NTTRVDKTTN CSFMIKREND EYKLVINRKI SRDRPKRIEV    600
GRTIMGYDRN QTASDTYWIG RLVPPGTRGA YRIGEWSVQY IKSGPVLSST QGVNNSTTDQ    660
LVYNGMPSSS ERFKAWKKAR MAFIRKLIRQ LNDEGLESKG QDYIPENPSS FDVRGETLYV    720
FNSNYLKALV SKHRKAKKPV EGILDEIEAW TSKDKDSCSL MRLSSLSDAS MQGIASLKSL    780
INSYFNKNGC KTIEDKEKFN PVLYAKLVEV EQRRTNKRSE KVGRIAGSLE QLALLNGVEV    840
VIGEADLGEV EKGKSKKQNS RNMDWCAKQV AQRLEYKLAF HGIGYFGVNP MYTSHQDPFE    900
HRRVADHIVM RARFEEVNVE NIAEWHVRNF SNYLRADSGT GLYYKQATMD FLKHYGLEEH    960
AEGLENKKIK FYDFRKILED KNLTSVIIPK RGGRIYMATN PVTSDSTPIT YAGKTYNRCN   1020
ADEVAAANIV ISVLAPRSKK NREQDDIPLI TKKAESKSPP KDRKRSKTSQ LPQK         1074

SEQ ID NO: 5           moltype = AA   length = 1074
FEATURE                Location/Qualifiers
REGION                 1..1074
                       note = Synthetic Construct
source                 1..1074
                       mol_type = protein
                       organism = synthetic construct
SEQUENCE: 5
MASISRPYGT KLRPDARKKE MLDKFFNTLT KGQRVFADLA LCIYGSLTLE MAKSLEPESD     60
SELVCAIGWF RLVDKTIWSK DGIKQENLVK QYEAYSGKEA SEVVKTYLNS PSSDKYVWID    120
CRQKFLRFQR ELGTRNLSED FECMLFEQYI RLTKGEIEGY AAISNMFGNG EKEDRSKKRM    180
YATRMKDWLE ANENITWEQY REALKNQLNA KNLEQVVANY KGNAGGADPF FKYSFSKEGM    240
VSKKEHAQQL DKFKTVLKNK ARDLNFPNKE KLKQYLEAEI GIPVDANVYS QMFSNGVSEV    300
QPKTTRNMSF SNEKLDLLTE LKDLNKGDGF EYAREVLNGF FDSELHTTED KFNITSRYLG    360
GDKSNRLSKL YKIWKKEGVD CEEGIQQFCE AVKDKMGQIP IRNVLKYLWQ FRETVSAEDF    420
EAAAKANHLE EKISRVKAHP IVISNRYWAF GTSALVGNIM PADKRHQGEY AGQNFKMWLR    480
AELHYDGKKA KHHLPFYNAR FFEEVYCYHP SVAEITPFKT KQFGCEIGKD IPDYVSALK    540
DNPYKKATKR ILRAIYNPVA NTTRVDKTTN CSFMIKREND EYKLVINRKI SVDRPKRIEV    600
GRTIMGYDRN QTASDTYWIG RLVPPGTRGA YRIGEWSVQY IKSGPVLSST QGVNNSTTDQ    660
LVYNGMPSSS ERFKAWKKAR MAFIRKLIRQ LNDEGLESKG QDYIPENPSS FDVRGETLYV    720
FNSNYLKALV SKHRKAKKPV EGILDEIEAW TSKDKDSCSL MRLSSLSDAS MQGIASLKSL    780
INSYFNKNGC KTIEDKEKFN PVLYAKLVEV EQRRTNKRSE KVGRIAGSLE QLALLNGVEV    840
VIGEADLGEV EKGKSKKQNS RNMDWCAKQV AQRLEYKLAF HGIGYFGVNP MYTSHQDPFE    900
HRRVADHIVM RARFEEVNVE NIAEWHVRNF SNYLRADSGT GLYYKQATMD FLKHYGLEEH    960
AEGLENKKIK FYDFRKILED KNLTSVIIPK RGGRIYMATN PVTSDSTPIT YAGKTYNRCN   1020
ADEVAAANIV ISVLAPRSKK NEEQDDIPLI TKKAESKSPP KDRKRSKTSQ LPQK         1074

SEQ ID NO: 6           moltype = AA   length = 1074
FEATURE                Location/Qualifiers
REGION                 1..1074
                       note = Synthetic Construct
source                 1..1074
                       mol_type = protein
                       organism = synthetic construct
SEQUENCE: 6
MASISRPYGT KLRPDARKKE MLDKFFNTLT KGQRVFADLA LCIYGSLTLE MAKSLEPESD     60
SELVCAIGWF RLVDKTIWSK DGIKQENLVK QYEAYSGKEA SEVVKTYLNS PSSDKYVWID    120
CRQKFLRFQR ELGTRNLSED FECMLFEQYI RLTKGEIEGY AAISNMFGNG EKEDRSKKRM    180
YATRMKDWLE ANENITWEQY REALKNQLNA KNLEQVVANY KGNAGGADPF FKYSFSKEGM    240
VSKKEHAQQL DKFKTVLKNK ARDLNFPNKE KLKQYLEAEI GIPVDANVYS QMFSNGVSEV    300
QPKTTRNMSF SNEKLDLLTE LKDLNKGDGF EYAREVLNGF FDSELHTTED KFNITSRYLG    360
GDKSNRLSKL YKIWKKEGVD CEEGIQQFCE AVKDKMGQIP IRNVLKYLWQ FRETVSAEDF    420
EAAAKANHLE EKISRVKAHP IVISNRYWAF GTSALVGNIM PADKRHQGEY AGQNFKMWLR    480
```

```
AELHYDGKKA KHHLPFYNAR FFEEVYCYHP SVAEITPFKT KQFGCEIGKD IPDYVSVALK   540
DNPYKKATKR ILRAIYNPVA NTTGVDKTTN CSFMIKREND EYKLVINRKI SRDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NEEQDDIPLI TKKAESKSPP KDRKRSKTSQ LPQK        1074

SEQ ID NO: 7            moltype = AA  length = 1074
FEATURE                 Location/Qualifiers
REGION                  1..1074
                        note = Synthetic Construct
source                  1..1074
                        mol_type = protein
                        organism = synthetic construct
SEQUENCE: 7
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPDVANYS QMFSNGVSEV    300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLR   480
AELHYDGKKA KHHLPFYNAR FFEEVYCYHP SVAEITPFKT KQFGCEIGKD IPDYVSVALK   540
DNPYKKATKR ILRAIYNPVA NTTGVDKTTN CSFMIKREND EYKLVINRKI SVDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NREQDDIPLI TKKAESKSPP KDRKRSKTSQ LPQK        1074

SEQ ID NO: 8            moltype = AA  length = 1074
FEATURE                 Location/Qualifiers
REGION                  1..1074
                        note = Synthetic Construct
source                  1..1074
                        mol_type = protein
                        organism = synthetic construct
SEQUENCE: 8
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPDVANYS QMFSNGVSEV    300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLR   480
AGLHYDGKKA KHHLPFYNAR FFEEVYCYHP SVAEITPFKT KQFGCEIGKD IPDYVSVALK   540
DNPYKKATKR ILRAIYNPVA NTTGVDKTTN CSFMIKREND EYKLVINRKI SVDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NEEQDDIPLI TKKAESKSPP KDRKRSKTSQ LPQK        1074

SEQ ID NO: 9            moltype = AA  length = 1074
FEATURE                 Location/Qualifiers
REGION                  1..1074
                        note = Synthetic Construct
source                  1..1074
                        mol_type = protein
                        organism = synthetic construct
SEQUENCE: 9
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPDVANYS QMFSNGVSEV    300
QPKTTRNMSF SNEKLDLLTE LKDLNKGDGF EYAREVLNGF FDSELHTTED KFNITSRYLG   360
```

```
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLE   480
AELHYDGKKA KHHLPFYNAR FFEEVYCYHP SVAEITPFKT KQFGCEIGKD IPDYVSVALK   540
DNPYKKATKR ILRAIYNPVA NTTRVDKTTN CSFMIKREND EYKLVINRKI SRDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NEEQDDIPLI TKKAESKSPP KDRKRSKTSQ LPQK        1074

SEQ ID NO: 10           moltype = AA   length = 1074
FEATURE                 Location/Qualifiers
REGION                  1..1074
                        note = Synthetic Construct
source                  1..1074
                        mol_type = protein
                        organism = synthetic construct
SEQUENCE: 10
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLE   480
AELHYDGKKA KHHLPFYNAR FFEEVYCYHP SVAEITPFKT KQFGCEIGKD IPDYVSVALK   540
DNPYKKATKR ILRAIYNPVA NTTRVDKTTN CSFMIKREND EYKLVINRKI SVDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NREQDDIPLI TKKAESKSPP KDRKRSKTSQ LPQK        1074

SEQ ID NO: 11           moltype = AA   length = 1074
FEATURE                 Location/Qualifiers
REGION                  1..1074
                        note = Synthetic Construct
source                  1..1074
                        mol_type = protein
                        organism = synthetic construct
SEQUENCE: 11
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLE   480
AGLHYDGKKA KHHLPFYNAR FFEEVYCYHP SVAEITPFKT KQFGCEIGKD IPDYVSVALK   540
DNPYKKATKR ILRAIYNPVA NTTRVDKTTN CSFMIKREND EYKLVINRKI SVDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NEEQDDIPLI TKKAESKSPP KDRKRSKTSQ LPQK        1074

SEQ ID NO: 12           moltype = AA   length = 1074
FEATURE                 Location/Qualifiers
REGION                  1..1074
                        note = Synthetic Construct
source                  1..1074
                        mol_type = protein
                        organism = synthetic construct
SEQUENCE: 12
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
```

```
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLE   480
AGLHYDGKKA KHHLPFYNAR FFEEVYCYHP SVAEITPFKT KQFGCEIGKD IPDYVSVALK   540
DNPYKKATKR ILRAIYNPVA NTTGVDKTTN CSFMIKREND EYKLVINRKI SRDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NEEQDDIPLI TKKAESKSPP KDRKRSKTSQ LPQK        1074

SEQ ID NO: 13           moltype = AA   length = 1074
FEATURE                 Location/Qualifiers
REGION                  1..1074
                        note = Synthetic Construct
source                  1..1074
                        mol_type = protein
                        organism = synthetic construct
SEQUENCE: 13
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLE   480
AGLHYDGKKA KHHLPFYNAR FFEEVYCYHP SVAEITPFKT KQFGCEIGKD IPDYVSVALK   540
DNPYKKATKR ILRAIYNPVA NTTGVDKTTN CSFMIKREND EYKLVINRKI SVDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NREQDDIPLI TKKAESKSPP KDRKRSKTSQ LPQK        1074

SEQ ID NO: 14           moltype = AA   length = 1074
FEATURE                 Location/Qualifiers
REGION                  1..1074
                        note = Synthetic Construct
source                  1..1074
                        mol_type = protein
                        organism = synthetic construct
SEQUENCE: 14
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLR   480
AELHYDGKKA KHHLPFYNAR FFEEVYCYHP SVAEITPFKT KQFGCEIGKD IPDYVSVALK   540
DNPYKKATKR ILRAIYNPVA NTTRVDKTTN CSFMIKREND EYKLVINRKI SRDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NEEQDDIPLI TKKAESKSPP KDRKRSKTSQ LPQK        1074

SEQ ID NO: 15           moltype = AA   length = 1074
FEATURE                 Location/Qualifiers
REGION                  1..1074
                        note = Synthetic Construct
source                  1..1074
                        mol_type = protein
                        organism = synthetic construct
SEQUENCE: 15
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
```

```
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLR   480
AELHYDGKKA KHHLPFYNAR FFEEVYCYHP SVAEITPFKT KQFGCEIGKD IPDYVSVALK   540
DNPYKKATKR ILRAIYNPVA NTTRVDKTTN CSFMIKREND EYKLVINRKI SVDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NREQDDIPLI TKKAESKSPP KDRKRSKTSQ LPQK        1074

SEQ ID NO: 16          moltype = AA  length = 1074
FEATURE                Location/Qualifiers
REGION                 1..1074
                       note = Synthetic Construct
source                 1..1074
                       mol_type = protein
                       organism = synthetic construct
SEQUENCE: 16
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLR   480
AGLHYDGKKA KHHLPFYNAR FFEEVYCYHP SVAEITPFKT KQFGCEIGKD IPDYVSVALK   540
DNPYKKATKR ILRAIYNPVA NTTRVDKTTN CSFMIKREND EYKLVINRKI SVDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NEEQDDIPLI TKKAESKSPP KDRKRSKTSQ LPQK        1074

SEQ ID NO: 17          moltype = AA  length = 1074
FEATURE                Location/Qualifiers
REGION                 1..1074
                       note = Synthetic Construct
source                 1..1074
                       mol_type = protein
                       organism = synthetic construct
SEQUENCE: 17
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLR   480
AELHYDGKKA KHHLPFYNAR FFEEVYCYHP SVAEITPFKT KQFGCEIGKD IPDYVSVALK   540
DNPYKKATKR ILRAIYNPVA NTTGVDKTTN CSFMIKREND EYKLVINRKI SRDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NREQDDIPLI TKKAESKSPP KDRKRSKTSQ LPQK        1074

SEQ ID NO: 18          moltype = AA  length = 1074
FEATURE                Location/Qualifiers
REGION                 1..1074
                       note = Synthetic Construct
source                 1..1074
                       mol_type = protein
                       organism = synthetic construct
SEQUENCE: 18
```

```
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLR   480
AGLHYDGKKA KHHLPFYNAR FFEEVYCYHP SVAEITPFKT KQFGCEIGKD IPDYVSVALK   540
DNPYKKATKR ILRAIYNPVA NTTGVDKTTN CSFMIKREND EYKLVINRKI SRDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NEEQDDIPLI TKKAESKSPP KDRKRSKTSQ LPQK        1074

SEQ ID NO: 19           moltype = AA   length = 1074
FEATURE                 Location/Qualifiers
REGION                  1..1074
                        note = Synthetic Construct
source                  1..1074
                        mol_type = protein
                        organism = synthetic construct
SEQUENCE: 19
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLR   480
AGLHYDGKKA KHHLPFYNAR FFEEVYCYHP SVAEITPFKT KQFGCEIGKD IPDYVSVALK   540
DNPYKKATKR ILRAIYNPVA NTTGVDKTTN CSFMIKREND EYKLVINRKI SVDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NREQDDIPLI TKKAESKSPP KDRKRSKTSQ LPQK        1074

SEQ ID NO: 20           moltype = AA   length = 1074
FEATURE                 Location/Qualifiers
REGION                  1..1074
                        note = Synthetic Construct
source                  1..1074
                        mol_type = protein
                        organism = synthetic construct
SEQUENCE: 20
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLE   480
AELHYDGKKA KHHLPFYNAR FFEEVYCYHP SVAEITPFKT KQFGCEIGKD IPDYVSVALK   540
DNPYKKATKR ILRAIYNPVA NTTRVDKTTN CSFMIKREND EYKLVINRKI SRDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NREQDDIPLI TKKAESKSPP KDRKRSKTSQ LPQK        1074

SEQ ID NO: 21           moltype = AA   length = 1074
FEATURE                 Location/Qualifiers
REGION                  1..1074
                        note = Synthetic Construct
source                  1..1074
                        mol_type = protein
```

```
                        organism = synthetic construct
SEQUENCE: 21
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLE   480
AGLHYDGKKA KHHLPFYNAR FFEEVYCYHP SVAEITPFKT KQFGCEIGKD IPDYVSVALK   540
DNPYKKATKR ILRAIYNPVA NTTRVDKTTN CSFMIKREND EYKLVINRKI SRDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NEEQDDIPLI TKKAESKSPP KDRKRSKTSQ LPQK        1074

SEQ ID NO: 22           moltype = AA   length = 1074
FEATURE                 Location/Qualifiers
REGION                  1..1074
                        note = Synthetic Construct
source                  1..1074
                        mol_type = protein
                        organism = synthetic construct
SEQUENCE: 22
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLE   480
AGLHYDGKKA KHHLPFYNAR FFEEVYCYHP SVAEITPFKT KQFGCEIGKD IPDYVSVALK   540
DNPYKKATKR ILRAIYNPVA NTTRVDKTTN CSFMIKREND EYKLVINRKI SVDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NREQDDIPLI TKKAESKSPP KDRKRSKTSQ LPQK        1074

SEQ ID NO: 23           moltype = AA   length = 1074
FEATURE                 Location/Qualifiers
REGION                  1..1074
                        note = Synthetic Construct
source                  1..1074
                        mol_type = protein
                        organism = synthetic construct
SEQUENCE: 23
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLE   480
AGLHYDGKKA KHHLPFYNAR FFEEVYCYHP SVAEITPFKT KQFGCEIGKD IPDYVSVALK   540
DNPYKKATKR ILRAIYNPVA NTTGVDKTTN CSFMIKREND EYKLVINRKI SRDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NREQDDIPLI TKKAESKSPP KDRKRSKTSQ LPQK        1074

SEQ ID NO: 24           moltype = AA   length = 1074
FEATURE                 Location/Qualifiers
REGION                  1..1074
                        note = Synthetic Construct
```

```
                              source          1..1074
                                              mol_type = protein
                                              organism = synthetic construct
SEQUENCE: 24
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLR   480
AGLHYDGKKA KHHLPFYNAR FFEEVYCYHP SVAEITPFKT KQFGCEIGKD IPDYVSVALK   540
DNPYKKATKR ILRAIYNPVA NTTRVDKTTN CSFMIKREND EYKLVINRKI SRDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NEEQDDIPLI TKKAESKSPP KDRKRSKTSQ LPQK        1074

SEQ ID NO: 25              moltype = AA   length = 1074
FEATURE                    Location/Qualifiers
REGION                     1..1074
                           note = Synthetic Construct
source                     1..1074
                           mol_type = protein
                           organism = synthetic construct
SEQUENCE: 25
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLR   480
AGLHYDGKKA KHHLPFYNAR FFEEVYCYHP SVAEITPFKT KQFGCEIGKD IPDYVSVALK   540
DNPYKKATKR ILRAIYNPVA NTTRVDKTTN CSFMIKREND EYKLVINRKI SVDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NREQDDIPLI TKKAESKSPP KDRKRSKTSQ LPQK        1074

SEQ ID NO: 26              moltype = AA   length = 1074
FEATURE                    Location/Qualifiers
REGION                     1..1074
                           note = Synthetic Construct
source                     1..1074
                           mol_type = protein
                           organism = synthetic construct
SEQUENCE: 26
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLR   480
AGLHYDGKKA KHHLPFYNAR FFEEVYCYHP SVAEITPFKT KQFGCEIGKD IPDYVSVALK   540
DNPYKKATKR ILRAIYNPVA NTTGVDKTTN CSFMIKREND EYKLVINRKI SRDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NREQDDIPLI TKKAESKSPP KDRKRSKTSQ LPQK        1074

SEQ ID NO: 27              moltype = AA   length = 1074
FEATURE                    Location/Qualifiers
```

```
REGION                  1..1074
                        note = Synthetic Construct
source                  1..1074
                        mol_type = protein
                        organism = synthetic construct
SEQUENCE: 27
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLE   480
AGLHYDGKKA KHHLPFYNAR FFEEVYCYHP SVAEITPFKT KQFGCEIGKD IPDYVSVALK   540
DNPYKKATKR ILRAIYNPVA NTTRVDKTTN CSFMIKREND EYKLVINRKI SRDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NREQDDIPLI TKKAESKSPP KDRKRSKTSQ LPQK        1074

SEQ ID NO: 28           moltype = AA  length = 1074
FEATURE                 Location/Qualifiers
REGION                  1..1074
                        note = Synthetic Construct
source                  1..1074
                        mol_type = protein
                        organism = synthetic construct
SEQUENCE: 28
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLR   480
AGLHYDGKKA KHHLPFYNAR FFEEVYCYHP SVAEITPFKT KQFGCEIGKD IPDYVSVALK   540
DNPYKKATKR ILRAIYNPVA NTTRVDKTTN CSFMIKREND EYKLVINRKI SRDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NREQDDIPLI TKKAESKSPP KDRKRSKTSQ LPQK        1074

SEQ ID NO: 29           moltype = AA  length = 1074
FEATURE                 Location/Qualifiers
REGION                  1..1074
                        note = Synthetic Construct
source                  1..1074
                        mol_type = protein
                        organism = synthetic construct
SEQUENCE: 29
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLR   480
AELHYDGKKA KHHLPFYNAR FFEEVYCYHP SVAEITPFKT KQFGCEIGKD IPDYVSVALK   540
DNPYKKATKR ILRAIYNPVA NTTRVDKRTN CSFMIKREND EYKLVINRKI SRDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NREQDDIPLI TKKAESKSPP KDRKRSKTSQ LPQK        1074
```

```
SEQ ID NO: 30              moltype = AA   length = 1074
FEATURE                    Location/Qualifiers
REGION                     1..1074
                           note = Synthetic Construct
source                     1..1074
                           mol_type = protein
                           organism = synthetic construct
SEQUENCE: 30
MASISRPYGT KLRPDARKKE MLDKFFNTLT KGQRVFADLA LCIYGSLTLE MAKSLEPESD   60
SELVCAIGWF RLVDKTIWSK DGIKQENLVK QYEAYSGKEA SEVVKTYLNS PSSDKYVWID  120
CRQKFLRFQR ELGTRNLSED FECMLFEQYI RLTKGEIEGY AAISNMFGNG EKEDRSKKRM  180
YATRMKDWLE ANENITWEQY REALKNQLNA KNLEQVVANY KGNAGGADPF FKYSFSKEGM  240
VSKKEHAQQL DKFKTVLKNK ARDLNFPNKE KLKQYLEAEI GIPVDANVYS QMFSNGVSEV  300
QPKTTRNMSF SNEKLDLLTE LKDLNKGDGF EYAREVLNGF FDSELHTTED KFNITSRYLG  360
GDKSNRLSKL YKIWKKEGVD CEEGIQQFCE AVKDKMGQIP IRNVLKYLWQ FRETVSAEDF  420
EAAAKANHLE EKISRVKAHP IVISNRYWAF GTSALVGNIM PADKRHQGEY AGQNFKMWLR  480
AELHYDGKKA KHHLPFYNAR FFEEVYCYHP SVAEITPFKT KQFGCEIGKD IPDYVSVALK  540
DNPYKKATKR ILRAIYNPVA NTTRVDKTTN CSFMIKREND EYKLVINRKI RRDRPKRIEV  600
GRTIMGYDRN QTASDTYWIG RLVPPGTRGA YRIGEWSVQY IKSGPVLSST QGVNNSTTDQ  660
LVYNGMPSSS ERFKAWKKAR MAFIRKLIRQ LNDEGLESKG QDYIPENPSS FDVRGETLYV  720
FNSNYLKALV SKHRKAKKPV EGILDEIEAW TSKDKDSCSL MRLSSLSDAS MQGIASLKSL  780
INSYFNKNGC KTIEDKEKFN PVLYAKLVEV EQRRTNKRSE KVGRIAGSLE QLALLNGVEV  840
VIGEADLGEV EKGKSKKQNS RNMDWCAKQV AQRLEYKLAF HGIGYFGVNP MYTSHQDPFE  900
HRRVADHIVM RARFEEVNVE NIAEWHVRNF SNYLRADSGT GLYYKQATMD FLKHYGLEEH  960
AEGLENKKIK FYDFRKILED KNLTSVIIPK RGGRIYMATN PVTSDSTPIT YAGKTYNRCN 1020
ADEVAAANIV ISVLAPRSKK NREQDDIPLI TKKAESKSPP KDRKRSKTSQ LPQK       1074

SEQ ID NO: 31              moltype = AA   length = 1074
FEATURE                    Location/Qualifiers
REGION                     1..1074
                           note = Synthetic Construct
source                     1..1074
                           mol_type = protein
                           organism = synthetic construct
SEQUENCE: 31
MASISRPYGT KLRPDARKKE MLDKFFNTLT KGQRVFADLA LCIYGSLTLE MAKSLEPESD   60
SELVCAIGWF RLVDKTIWSK DGIKQENLVK QYEAYSGKEA SEVVKTYLNS PSSDKYVWID  120
CRQKFLRFQR ELGTRNLSED FECMLFEQYI RLTKGEIEGY AAISNMFGNG EKEDRSKKRM  180
YATRMKDWLE ANENITWEQY REALKNQLNA KNLEQVVANY KGNAGGADPF FKYSFSKEGM  240
VSKKEHAQQL DKFKTVLKNK ARDLNFPNKE KLKQYLEAEI GIPVDANVYS QMFSNGVSEV  300
QPKTTRNMSF SNEKLDLLTE LKDLNKGDGF EYAREVLNGF FDSELHTTED KFNITSRYLG  360
GDKSNRLSKL YKIWKKEGVD CEEGIQQFCE AVKDKMGQIP IRNVLKYLWQ FRETVSAEDF  420
EAAAKANHLE EKISRVKAHP IVISNRYWAF GTSALVGNIM PADKRHQGEY AGQNFKMWLR  480
AELHYDGKKA KHHLPFYNAR FFEEVYCYHP SVAEITPFKT KQFGCEIGKD IPDYVSVALK  540
DNPYKKATKR ILRAIYNPVA NTTRVDKTTN CSFMIKREND EYKLVINRKI SRDRPKRIEV  600
GRTIMGYDRN QTASDTYWIG RLVPPGTRGA YRIGEWSVQY IKSGPVLSST QGVNNSTTDQ  660
LVYNGMPSSS ERFKAWKKAR MAFIRKLIRQ LNDEGLESKG QDYIPENPSS FDVRGETLYV  720
FNSNYLKALV SKHRKAKKPV EGILDEIEAW TSKDKDSCSL MRLSSLSDAS MQGIASLKSL  780
INSYFNKNGC KTIEDKEKFN PVLYAKLVEV EQRRTNKRSE KVGRIAGSLE QLALLNGVEV  840
VIGEAGLGEV EKGKSKKQNS RNMDWCAKQV AQRLEYKLAF HGIGYFGVNP MYTSHQDPFE  900
HRRVADHIVM RARFEEVNVE NIAEWHVRNF SNYLRADSGT GLYYKQATMD FLKHYGLEEH  960
AEGLENKKIK FYDFRKILED KNLTSVIIPK RGGRIYMATN PVTSDSTPIT YAGKTYNRCN 1020
ADEVAAANIV ISVLAPRSKK NREQDDIPLI TKKAESKSPP KDRKRSKTSQ LPQK       1074

SEQ ID NO: 32              moltype = AA   length = 1074
FEATURE                    Location/Qualifiers
REGION                     1..1074
                           note = Synthetic Construct
source                     1..1074
                           mol_type = protein
                           organism = synthetic construct
SEQUENCE: 32
MASISRPYGT KLRPDARKKE MLDKFFNTLT KGQRVFADLA LCIYGSLTLE MAKSLEPESD   60
SELVCAIGWF RLVDKTIWSK DGIKQENLVK QYEAYSGKEA SEVVKTYLNS PSSDKYVWID  120
CRQKFLRFQR ELGTRNLSED FECMLFEQYI RLTKGEIEGY AAISNMFGNG EKEDRSKKRM  180
YATRMKDWLE ANENITWEQY REALKNQLNA KNLEQVVANY KGNAGGADPF FKYSFSKEGM  240
VSKKEHAQQL DKFKTVLKNK ARDLNFPNKE KLKQYLEAEI GIPVDANVYS QMFSNGVSEV  300
QPKTTRNMSF SNEKLDLLTE LKDLNKGDGF EYAREVLNGF FDSELHTTED KFNITSRYLG  360
GDKSNRLSKL YKIWKKEGVD CEEGIQQFCE AVKDKMGQIP IRNVLKYLWQ FRETVSAEDF  420
EAAAKANHLE EKISRVKAHP IVISNRYWAF GTSALVGNIM PADKRHQGEY AGQNFKMWLR  480
AELHYDGKKA KHHLPFYNAR FFEEVYCYHP SVAEITPFKT KQFGCEIGKD IPDYVSVALK  540
DNPYKKATKR ILRAIYNPVA NTTRVDKTTN CSFMIKREND EYKLVINRKI SRDRPKRIEV  600
GRTIMGYDRN QTASDTYWIG RLVPPGTRGA YRIGEWSVQY IKSGPVLSST QGVNNSTTDQ  660
LVYNGMPSSS ERFKAWKKAR MAFIRKLIRQ LNDEGLESKG QDYIPENPSS FDVRGETLYV  720
FNSNYLKALV SKHRKAKKPV EGILDEIEAW TSKDKDSCSL MRLSSLSDAS MQGIASLKSL  780
INSYFNKNGC KTIEDKEKFN PVLYAKLVEV EQRRTNKRSE KVGRIAGSLE QLALLNGVEV  840
VIGEADLGEV EKGKSKKQNS RNMDWCAKQV AQRLEYKLAF HGIGYRGVNP MYTSHQDPFE  900
HRRVADHIVM RARFEEVNVE NIAEWHVRNF SNYLRADSGT GLYYKQATMD FLKHYGLEEH  960
AEGLENKKIK FYDFRKILED KNLTSVIIPK RGGRIYMATN PVTSDSTPIT YAGKTYNRCN 1020
```

```
ADEVAAANIV ISVLAPRSKK NREQDDIPLI TKKAESKSPP KDRKRSKTSQ LPQK         1074

SEQ ID NO: 33             moltype = AA   length = 1074
FEATURE                   Location/Qualifiers
REGION                    1..1074
                          note = Synthetic Construct
source                    1..1074
                          mol_type = protein
                          organism = synthetic construct
SEQUENCE: 33
MASISRPYGT KLRPDARKKE MLDKFFNTLT KGQRVFADLA LCIYGSLTLE MAKSLEPESD   60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLR   480
AELHYDGKKA KHHLPFYNAR FFEEVYCYHP SVAEITPFKT KQFGCEIGKD IPDYVSVALK   540
DNPYKKATKR ILRAIYNPVA NTTRVDKRTN CSFMIKREND EYKLVINRKI RRDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN   1020
ADEVAAANIV ISVLAPRSKK NREQDDIPLI TKKAESKSPP KDRKRSKTSQ LPQK         1074

SEQ ID NO: 34             moltype = AA   length = 1074
FEATURE                   Location/Qualifiers
REGION                    1..1074
                          note = Synthetic Construct
source                    1..1074
                          mol_type = protein
                          organism = synthetic construct
SEQUENCE: 34
MASISRPYGT KLRPDARKKE MLDKFFNTLT KGQRVFADLA LCIYGSLTLE MAKSLEPESD   60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLR   480
AELHYDGKKA KHHLPFYNAR FFEEVYCYHP SVAEITPFKT KQFGCEIGKD IPDYVSVALK   540
DNPYKKATKR ILRAIYNPVA NTTRVDKRTN CSFMIKREND EYKLVINRKI SRDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEAGLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN   1020
ADEVAAANIV ISVLAPRSKK NREQDDIPLI TKKAESKSPP KDRKRSKTSQ LPQK         1074

SEQ ID NO: 35             moltype = AA   length = 1074
FEATURE                   Location/Qualifiers
REGION                    1..1074
                          note = Synthetic Construct
source                    1..1074
                          mol_type = protein
                          organism = synthetic construct
SEQUENCE: 35
MASISRPYGT KLRPDARKKE MLDKFFNTLT KGQRVFADLA LCIYGSLTLE MAKSLEPESD   60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLR   480
AELHYDGKKA KHHLPFYNAR FFEEVYCYHP SVAEITPFKT KQFGCEIGKD IPDYVSVALK   540
DNPYKKATKR ILRAIYNPVA NTTRVDKRTN CSFMIKREND EYKLVINRKI SRDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYRGVNP MYTSHQDPFE   900
```

```
HRRVADHIVM RARFEEVNVE NIAEWHVRNF SNYLRADSGT GLYYKQATMD FLKHYGLEEH    960
AEGLENKKIK FYDFRKILED KNLTSVIIPK RGGRIYMATN PVTSDSTPIT YAGKTYNRCN   1020
ADEVAAANIV ISVLAPRSKK NREQDDIPLI TKKAESKSPP KDRKRSKTSQ LPQK         1074

SEQ ID NO: 36              moltype = AA   length = 1074
FEATURE                    Location/Qualifiers
REGION                     1..1074
                           note = Synthetic Construct
source                     1..1074
                           mol_type = protein
                           organism = synthetic construct
SEQUENCE: 36
MASISRPYGT KLRPDARKKE MLDKFFNTLT KGQRVFADLA LCIYGSLTLE MAKSLEPESD     60
SELVCAIGWF RLVDKTIWSK DGIKQENLVK QYEAYSGKEA SEVVKTYLNS PSSDKYVWID    120
CRQKFLRFQR ELGTRNLSED FECMLFEQYI RLTKGEIEGY AAISNMFGNG EKEDRSKKRM    180
YATRMKDWLE ANENITWEQY REALKNQLNA KNLEQVVANY KGNAGGADPF FKYSFSKEGM    240
VSKKEHAQQL DKFKTVLKNK ARDLNFPNKE KLKQYLEAEI GIPVDANVYS QMFSNGVSEV    300
QPKTTRNMSF SNEKLDLLTE LKDLNKGDGF EYAREVLNGF FDSELHTTED KFNITSRYLG    360
GDKSNRLSKL YKIWKKEGVD CEEGIQQFCE AVKDKMGQIP IRNVLKYLWQ FRETVSAEDF    420
EAAAKANHLE EKISRVKAHP IVISNRYWAF GTSALVGNIM PADKRHQGEY AGQNFKMWLR    480
AELHYDGKKA KHHLPFYNAR FFEEVYCYHP SVAEITPFKT KQFGCEIGKD IPDYVSVALK    540
DNPYKKATKR ILRAIYNPVA NTTRVDKTTN CSFMIKREND EYKLVINRKI RRDRPKRIEV    600
GRTIMGYDRN QTASDTYWIG RLVPPGTRGA YRIGEWSVQY IKSGPVLSST QGVNNSTTDQ    660
LVYNGMPSSS ERFKAWKKAR MAFIRKLIRQ LNDEGLESKG QDYIPENPSS FDVRGETLYV    720
FNSNYLKALV SKHRKAKKPV EGILDEIEAW TSKDKDSCSL MRLSSLSDAS MQGIASLKSL    780
INSYFNKNGC KTIEDKEKFN PVLYAKLVEV EQRRTNKRSE KVGRIAGSLE QLALLNGVEV    840
VIGEAGLGEV EKGKSKKQNS RNMDWCAKQV AQRLEYKLAF HGIGYFGVNP MYTSHQDPFE    900
HRRVADHIVM RARFEEVNVE NIAEWHVRNF SNYLRADSGT GLYYKQATMD FLKHYGLEEH    960
AEGLENKKIK FYDFRKILED KNLTSVIIPK RGGRIYMATN PVTSDSTPIT YAGKTYNRCN   1020
ADEVAAANIV ISVLAPRSKK NREQDDIPLI TKKAESKSPP KDRKRSKTSQ LPQK         1074

SEQ ID NO: 37              moltype = AA   length = 1074
FEATURE                    Location/Qualifiers
REGION                     1..1074
                           note = Synthetic Construct
source                     1..1074
                           mol_type = protein
                           organism = synthetic construct
SEQUENCE: 37
MASISRPYGT KLRPDARKKE MLDKFFNTLT KGQRVFADLA LCIYGSLTLE MAKSLEPESD     60
SELVCAIGWF RLVDKTIWSK DGIKQENLVK QYEAYSGKEA SEVVKTYLNS PSSDKYVWID    120
CRQKFLRFQR ELGTRNLSED FECMLFEQYI RLTKGEIEGY AAISNMFGNG EKEDRSKKRM    180
YATRMKDWLE ANENITWEQY REALKNQLNA KNLEQVVANY KGNAGGADPF FKYSFSKEGM    240
VSKKEHAQQL DKFKTVLKNK ARDLNFPNKE KLKQYLEAEI GIPVDANVYS QMFSNGVSEV    300
QPKTTRNMSF SNEKLDLLTE LKDLNKGDGF EYAREVLNGF FDSELHTTED KFNITSRYLG    360
GDKSNRLSKL YKIWKKEGVD CEEGIQQFCE AVKDKMGQIP IRNVLKYLWQ FRETVSAEDF    420
EAAAKANHLE EKISRVKAHP IVISNRYWAF GTSALVGNIM PADKRHQGEY AGQNFKMWLR    480
AELHYDGKKA KHHLPFYNAR FFEEVYCYHP SVAEITPFKT KQFGCEIGKD IPDYVSVALK    540
DNPYKKATKR ILRAIYNPVA NTTRVDKTTN CSFMIKREND EYKLVINRKI RRDRPKRIEV    600
GRTIMGYDRN QTASDTYWIG RLVPPGTRGA YRIGEWSVQY IKSGPVLSST QGVNNSTTDQ    660
LVYNGMPSSS ERFKAWKKAR MAFIRKLIRQ LNDEGLESKG QDYIPENPSS FDVRGETLYV    720
FNSNYLKALV SKHRKAKKPV EGILDEIEAW TSKDKDSCSL MRLSSLSDAS MQGIASLKSL    780
INSYFNKNGC KTIEDKEKFN PVLYAKLVEV EQRRTNKRSE KVGRIAGSLE QLALLNGVEV    840
VIGEADLGEV EKGKSKKQNS RNMDWCAKQV AQRLEYKLAF HGIGYRGVNP MYTSHQDPFE    900
HRRVADHIVM RARFEEVNVE NIAEWHVRNF SNYLRADSGT GLYYKQATMD FLKHYGLEEH    960
AEGLENKKIK FYDFRKILED KNLTSVIIPK RGGRIYMATN PVTSDSTPIT YAGKTYNRCN   1020
ADEVAAANIV ISVLAPRSKK NREQDDIPLI TKKAESKSPP KDRKRSKTSQ LPQK         1074

SEQ ID NO: 38              moltype = AA   length = 1074
FEATURE                    Location/Qualifiers
REGION                     1..1074
                           note = Synthetic Construct
source                     1..1074
                           mol_type = protein
                           organism = synthetic construct
SEQUENCE: 38
MASISRPYGT KLRPDARKKE MLDKFFNTLT KGQRVFADLA LCIYGSLTLE MAKSLEPESD     60
SELVCAIGWF RLVDKTIWSK DGIKQENLVK QYEAYSGKEA SEVVKTYLNS PSSDKYVWID    120
CRQKFLRFQR ELGTRNLSED FECMLFEQYI RLTKGEIEGY AAISNMFGNG EKEDRSKKRM    180
YATRMKDWLE ANENITWEQY REALKNQLNA KNLEQVVANY KGNAGGADPF FKYSFSKEGM    240
VSKKEHAQQL DKFKTVLKNK ARDLNFPNKE KLKQYLEAEI GIPVDANVYS QMFSNGVSEV    300
QPKTTRNMSF SNEKLDLLTE LKDLNKGDGF EYAREVLNGF FDSELHTTED KFNITSRYLG    360
GDKSNRLSKL YKIWKKEGVD CEEGIQQFCE AVKDKMGQIP IRNVLKYLWQ FRETVSAEDF    420
EAAAKANHLE EKISRVKAHP IVISNRYWAF GTSALVGNIM PADKRHQGEY AGQNFKMWLR    480
AELHYDGKKA KHHLPFYNAR FFEEVYCYHP SVAEITPFKT KQFGCEIGKD IPDYVSVALK    540
DNPYKKATKR ILRAIYNPVA NTTRVDKTTN CSFMIKREND EYKLVINRKI SRDRPKRIEV    600
GRTIMGYDRN QTASDTYWIG RLVPPGTRGA YRIGEWSVQY IKSGPVLSST QGVNNSTTDQ    660
LVYNGMPSSS ERFKAWKKAR MAFIRKLIRQ LNDEGLESKG QDYIPENPSS FDVRGETLYV    720
FNSNYLKALV SKHRKAKKPV EGILDEIEAW TSKDKDSCSL MRLSSLSDAS MQGIASLKSL    780
```

```
INSYFNKNGC KTIEDKEKFN PVLYAKLVEV EQRRTNKRSE KVGRIAGSLE QLALLNGVEV    840
VIGEAGLGEV EKGKSKKQNS RNMDWCAKQV AQRLEYKLAF HGIGYRGVNP MYTSHQDPFE    900
HRRVADHIVM RARFEEVNVE NIAEWHVRNF SNYLRADSGT GLYYKQATMD FLKHYGLEEH    960
AEGLENKKIK FYDFRKILED KNLTSVIIPK RGGRIYMATN PVTSDSTPIT YAGKTYNRCN   1020
ADEVAAANIV ISVLAPRSKK NREQDDIPLI TKKAESKSPP KDRKRSKTSQ LPQK         1074

SEQ ID NO: 39           moltype = AA   length = 1074
FEATURE                 Location/Qualifiers
REGION                  1..1074
                        note = Synthetic Construct
source                  1..1074
                        mol_type = protein
                        organism = synthetic construct
SEQUENCE: 39
MASISRPYGT KLRPDARKKE MLDKFFNTLT KGQRVFADLA LCIYGSLTLE MAKSLEPESD     60
SELVCAIGWF RLVDKTIWSK DGIKQENLVK QYEAYSGKEA SEVVKTYLNS PSSDKYVWID    120
CRQKFLRFQR ELGTRNLSED FECMLFEQYI RLTKGEIEGY AAISNMFGNG EKEDRSKKRM    180
YATRMKDWLE ANENITWEQY REALKNQLNA KNLEQVVANY KGNAGGADPF FKYSFSKEGM    240
VSKKEHAQQL DKFKTVLKNK ARDLNFPNKE KLKQYLEAEI GIPVDANVYS QMFSNGVSEV    300
QPKTTRNMSF SNEKLDLLTE LKDLNKGDGF EYAREVLNGF FDSELHTTED KFNITSRYLG    360
GDKSNRLSKL YKIWKKEGVD CEEGIQQFCE AVKDKMGQIP IRNVLKYLWQ FRETVSAEDF    420
EAAAKANHLE EKISRVKAHP IVISNRYWAF GTSALVGNIM PADKRHQGEY AGQNFKMWLR    480
AELHYDGKKA KHHLPFYNAR FFEEVYCYHP SVAEITPFKT KQFGCEIGKD IPDYVSVALK    540
DNPYKKATKR ILRAIYNPVA NTTRVDKRTN CSFMIKREND EYKLVINRKI RRDRPKRIEV    600
GRTIMGYDRN QTASDTYWIG RLVPPGTRGA YRIGEWSVQY IKSGPVLSST QGVNNSTTDQ    660
LVYNGMPSSS ERFKAWKKAR MAFIRKLIRQ LNDEGLESKG QDYIPENPSS FDVRGETLYV    720
FNSNYLKALV SKHRKAKKPV EGILDEIEAW TSKDKDSCSL MRLSSLSDAS MQGIASLKSL    780
INSYFNKNGC KTIEDKEKFN PVLYAKLVEV EQRRTNKRSE KVGRIAGSLE QLALLNGVEV    840
VIGEAGLGEV EKGKSKKQNS RNMDWCAKQV AQRLEYKLAF HGIGYFGVNP MYTSHQDPFE    900
HRRVADHIVM RARFEEVNVE NIAEWHVRNF SNYLRADSGT GLYYKQATMD FLKHYGLEEH    960
AEGLENKKIK FYDFRKILED KNLTSVIIPK RGGRIYMATN PVTSDSTPIT YAGKTYNRCN   1020
ADEVAAANIV ISVLAPRSKK NREQDDIPLI TKKAESKSPP KDRKRSKTSQ LPQK         1074

SEQ ID NO: 40           moltype = AA   length = 1074
FEATURE                 Location/Qualifiers
REGION                  1..1074
                        note = Synthetic Construct
source                  1..1074
                        mol_type = protein
                        organism = synthetic construct
SEQUENCE: 40
MASISRPYGT KLRPDARKKE MLDKFFNTLT KGQRVFADLA LCIYGSLTLE MAKSLEPESD     60
SELVCAIGWF RLVDKTIWSK DGIKQENLVK QYEAYSGKEA SEVVKTYLNS PSSDKYVWID    120
CRQKFLRFQR ELGTRNLSED FECMLFEQYI RLTKGEIEGY AAISNMFGNG EKEDRSKKRM    180
YATRMKDWLE ANENITWEQY REALKNQLNA KNLEQVVANY KGNAGGADPF FKYSFSKEGM    240
VSKKEHAQQL DKFKTVLKNK ARDLNFPNKE KLKQYLEAEI GIPVDANVYS QMFSNGVSEV    300
QPKTTRNMSF SNEKLDLLTE LKDLNKGDGF EYAREVLNGF FDSELHTTED KFNITSRYLG    360
GDKSNRLSKL YKIWKKEGVD CEEGIQQFCE AVKDKMGQIP IRNVLKYLWQ FRETVSAEDF    420
EAAAKANHLE EKISRVKAHP IVISNRYWAF GTSALVGNIM PADKRHQGEY AGQNFKMWLR    480
AELHYDGKKA KHHLPFYNAR FFEEVYCYHP SVAEITPFKT KQFGCEIGKD IPDYVSVALK    540
DNPYKKATKR ILRAIYNPVA NTTRVDKRTN CSFMIKREND EYKLVINRKI RRDRPKRIEV    600
GRTIMGYDRN QTASDTYWIG RLVPPGTRGA YRIGEWSVQY IKSGPVLSST QGVNNSTTDQ    660
LVYNGMPSSS ERFKAWKKAR MAFIRKLIRQ LNDEGLESKG QDYIPENPSS FDVRGETLYV    720
FNSNYLKALV SKHRKAKKPV EGILDEIEAW TSKDKDSCSL MRLSSLSDAS MQGIASLKSL    780
INSYFNKNGC KTIEDKEKFN PVLYAKLVEV EQRRTNKRSE KVGRIAGSLE QLALLNGVEV    840
VIGEADLGEV EKGKSKKQNS RNMDWCAKQV AQRLEYKLAF HGIGYRGVNP MYTSHQDPFE    900
HRRVADHIVM RARFEEVNVE NIAEWHVRNF SNYLRADSGT GLYYKQATMD FLKHYGLEEH    960
AEGLENKKIK FYDFRKILED KNLTSVIIPK RGGRIYMATN PVTSDSTPIT YAGKTYNRCN   1020
ADEVAAANIV ISVLAPRSKK NREQDDIPLI TKKAESKSPP KDRKRSKTSQ LPQK         1074

SEQ ID NO: 41           moltype = AA   length = 1074
FEATURE                 Location/Qualifiers
REGION                  1..1074
                        note = Synthetic Construct
source                  1..1074
                        mol_type = protein
                        organism = synthetic construct
SEQUENCE: 41
MASISRPYGT KLRPDARKKE MLDKFFNTLT KGQRVFADLA LCIYGSLTLE MAKSLEPESD     60
SELVCAIGWF RLVDKTIWSK DGIKQENLVK QYEAYSGKEA SEVVKTYLNS PSSDKYVWID    120
CRQKFLRFQR ELGTRNLSED FECMLFEQYI RLTKGEIEGY AAISNMFGNG EKEDRSKKRM    180
YATRMKDWLE ANENITWEQY REALKNQLNA KNLEQVVANY KGNAGGADPF FKYSFSKEGM    240
VSKKEHAQQL DKFKTVLKNK ARDLNFPNKE KLKQYLEAEI GIPVDANVYS QMFSNGVSEV    300
QPKTTRNMSF SNEKLDLLTE LKDLNKGDGF EYAREVLNGF FDSELHTTED KFNITSRYLG    360
GDKSNRLSKL YKIWKKEGVD CEEGIQQFCE AVKDKMGQIP IRNVLKYLWQ FRETVSAEDF    420
EAAAKANHLE EKISRVKAHP IVISNRYWAF GTSALVGNIM PADKRHQGEY AGQNFKMWLR    480
AELHYDGKKA KHHLPFYNAR FFEEVYCYHP SVAEITPFKT KQFGCEIGKD IPDYVSVALK    540
DNPYKKATKR ILRAIYNPVA NTTRVDKRTN CSFMIKREND EYKLVINRKI SRDRPKRIEV    600
GRTIMGYDRN QTASDTYWIG RLVPPGTRGA YRIGEWSVQY IKSGPVLSST QGVNNSTTDQ    660
```

```
LVYNGMPSSS ERFKAWKKAR MAFIRKLIRQ LNDEGLESKG QDYIPENPSS FDVRGETLYV    720
FNSNYLKALV SKHRKAKKPV EGILDEIEAW TSKDKDSCSL MRLSSLSDAS MQGIASLKSL    780
INSYFNKNGC KTIEDKEKFN PVLYAKLVEV EQRRTNKRSE KVGRIAGSLE QLALLNGVEV    840
VIGEAGLGEV EKGKSKKQNS RNMDWCAKQV AQRLEYKLAF HGIGYRGVNP MYTSHQDPFE    900
HRRVADHIVM RARFEEVNVE NIAEWHVRNF SNYLRADSGT GLYYKQATMD FLKHYGLEEH    960
AEGLENKKIK FYDFRKILED KNLTSVIIPK RGGRIYMATN PVTSDSPIT YAGKTYNRCN    1020
ADEVAAANIV ISVLAPRSKK NREQDDIPLI TKKAESKSPP KDRKRSKTSQ LPQK         1074

SEQ ID NO: 42            moltype = AA  length = 1074
FEATURE                  Location/Qualifiers
REGION                   1..1074
                         note = Synthetic Construct
source                   1..1074
                         mol_type = protein
                         organism = synthetic construct
SEQUENCE: 42
MASISRPYGT KLRPDARKKE MLDKFFNTLT KGQRVFADLA LCIYGSLTLE MAKSLEPESD     60
SELVCAIGWF RLVDKTIWSK DGIKQENLVK QYEAYSGKEA SEVVKTYLNS PSSDKYVWID    120
CRQKFLRFQR ELGTRNLSED FECMLFEQYI RLTKGEIEGY AAISNMFGNG EKEDRSKKRM    180
YATRMKDWLE ANENITWEQY REALKNQLNA KNLEQVVANY KGNAGGADPF FKYSFSKEGM    240
VSKKEHAQQL DKFKTVLKNK ARDLNFPNKE KLKQYLEAEI GIPVDANVYS QMFSNGVSEV    300
QPKTTRNMSF SNEKLDLLTE LKDLNKGDGF EYAREVLNGF FDSELHTTED KFNITSRYLG    360
GDKSNRLSKL YKIWKKEGVD CEEGIQQFCE AVKDKMGQIP IRNVLKYLWQ FRETVSAEDF    420
EAAAKANHLE EKISRVKAHP IVISNRYWAF GTSALVGNIM PADKRHQGEY AGQNFKMWLR    480
AELHYDGKKA KHHLPFYNAR FFEEVYCYHP SVAEITPFKT KQFGCEIGKD IPDYVSVALK    540
DNPYKKATKR ILRAIYNPVA NTTRVDKTTN CSFMIKREND EYKLVINRKI RRDRPKRIEV    600
GRTIMGYDRN QTASDTYWIG RLVPPGTRGA YRIGEWSVQY IKSGPVLSST QGVNNSTTDQ    660
LVYNGMPSSS ERFKAWKKAR MAFIRKLIRQ LNDEGLESKG QDYIPENPSS FDVRGETLYV    720
FNSNYLKALV SKHRKAKKPV EGILDEIEAW TSKDKDSCSL MRLSSLSDAS MQGIASLKSL    780
INSYFNKNGC KTIEDKEKFN PVLYAKLVEV EQRRTNKRSE KVGRIAGSLE QLALLNGVEV    840
VIGEAGLGEV EKGKSKKQNS RNMDWCAKQV AQRLEYKLAF HGIGYRGVNP MYTSHQDPFE    900
HRRVADHIVM RARFEEVNVE NIAEWHVRNF SNYLRADSGT GLYYKQATMD FLKHYGLEEH    960
AEGLENKKIK FYDFRKILED KNLTSVIIPK RGGRIYMATN PVTSDSPIT YAGKTYNRCN    1020
ADEVAAANIV ISVLAPRSKK NREQDDIPLI TKKAESKSPP KDRKRSKTSQ LPQK         1074

SEQ ID NO: 43            moltype = AA  length = 1074
FEATURE                  Location/Qualifiers
REGION                   1..1074
                         note = Synthetic Construct
source                   1..1074
                         mol_type = protein
                         organism = synthetic construct
SEQUENCE: 43
MASISRPYGT KLRPDARKKE MLDKFFNTLT KGQRVFADLA LCIYGSLTLE MAKSLEPESD     60
SELVCAIGWF RLVDKTIWSK DGIKQENLVK QYEAYSGKEA SEVVKTYLNS PSSDKYVWID    120
CRQKFLRFQR ELGTRNLSED FECMLFEQYI RLTKGEIEGY AAISNMFGNG EKEDRSKKRM    180
YATRMKDWLE ANENITWEQY REALKNQLNA KNLEQVVANY KGNAGGADPF FKYSFSKEGM    240
VSKKEHAQQL DKFKTVLKNK ARDLNFPNKE KLKQYLEAEI GIPVDANVYS QMFSNGVSEV    300
QPKTTRNMSF SNEKLDLLTE LKDLNKGDGF EYAREVLNGF FDSELHTTED KFNITSRYLG    360
GDKSNRLSKL YKIWKKEGVD CEEGIQQFCE AVKDKMGQIP IRNVLKYLWQ FRETVSAEDF    420
EAAAKANHLE EKISRVKAHP IVISNRYWAF GTSALVGNIM PADKRHQGEY AGQNFKMWLR    480
AELHYDGKKA KHHLPFYNAR FFEEVYCYHP SVAEITPFKT KQFGCEIGKD IPDYVSVALK    540
DNPYKKATKR ILRAIYNPVA NTTRVDKRTN CSFMIKREND EYKLVINRKI RRDRPKRIEV    600
GRTIMGYDRN QTASDTYWIG RLVPPGTRGA YRIGEWSVQY IKSGPVLSST QGVNNSTTDQ    660
LVYNGMPSSS ERFKAWKKAR MAFIRKLIRQ LNDEGLESKG QDYIPENPSS FDVRGETLYV    720
FNSNYLKALV SKHRKAKKPV EGILDEIEAW TSKDKDSCSL MRLSSLSDAS MQGIASLKSL    780
INSYFNKNGC KTIEDKEKFN PVLYAKLVEV EQRRTNKRSE KVGRIAGSLE QLALLNGVEV    840
VIGEAGLGEV EKGKSKKQNS RNMDWCAKQV AQRLEYKLAF HGIGYRGVNP MYTSHQDPFE    900
HRRVADHIVM RARFEEVNVE NIAEWHVRNF SNYLRADSGT GLYYKQATMD FLKHYGLEEH    960
AEGLENKKIK FYDFRKILED KNLTSVIIPK RGGRIYMATN PVTSDSPIT YAGKTYNRCN    1020
ADEVAAANIV ISVLAPRSKK NREQDDIPLI TKKAESKSPP KDRKRSKTSQ LPQK         1074

SEQ ID NO: 44            moltype = AA  length = 1074
FEATURE                  Location/Qualifiers
REGION                   1..1074
                         note = Synthetic Construct
source                   1..1074
                         mol_type = protein
                         organism = synthetic construct
SEQUENCE: 44
MASISRPYGT KLRPDARKKE MLDKFFNTLT KGQRVFADLA LCIYGSLTLE MAKSLEPESD     60
SELVCAIGWF RLVDKTIWSK DGIKQENLVK QYEAYSGKEA SEVVKTYLNS PSSDKYVWID    120
CRQKFLRFQR ELGTRNLSED FECMLFEQYI RLTKGEIEGY AAISNMFGNG EKEDRSKKRM    180
YATRMKDWLE ANENITWEQY REALKNQLNA KNLEQVVANY KGNAGGADPF FKYSFSKEGM    240
VSKKEHAQQL DKFKTVLKNK ARDLNFPNKE KLKQYLEAEI GIPVDANVYS QMFSNGVSEV    300
QPKTTRNMSF SNEKLDLLTE LKDLNKGDGF EYAREVLNGF FDSELHTTED KFNITSRYLG    360
GDKSNRLSKL YKIWKKEGVD CEEGIQQFCE AVKDKMGQIP IRNVLKYLWQ FRETVSAEDF    420
EAAAKANHLE EKISRVKAHP IVISNRYWAF GTSALVGNIM PADKRHQGEY AGQNFKMWLR    480
AELHYDGKKA KHHLPFYNAR FFEEVYCYHP SVAEITPFKT KQFGCEIGKD IPDYVSVALK    540
```

```
DNPYKKATKR ILRAIYNPVA NTTGVDKRTN CSFMIKREND EYKLVINRKI SRDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NEEQDDIPLI TKKAESKSPP KDRKRSKTSQ LPQK        1074

SEQ ID NO: 45           moltype = AA   length = 1074
FEATURE                 Location/Qualifiers
REGION                  1..1074
                        note = Synthetic Construct
source                  1..1074
                        mol_type = protein
                        organism = synthetic construct
SEQUENCE: 45
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF PKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLR   480
AELHYDGKKA KHHLPFYNAR FFEEVYCYHP SVAEITPFKT KQFGCEIGKD IPDYVSVALK   540
DNPYKKATKR ILRAIYNPVA NTTGVDKRTN CSFMIKREND EYKLVINRKI SVDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEAGLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NEEQDDIPLI TKKAESKSPP KDRKRSKTSQ LPQK        1074

SEQ ID NO: 46           moltype = AA   length = 1074
FEATURE                 Location/Qualifiers
REGION                  1..1074
                        note = Synthetic Construct
source                  1..1074
                        mol_type = protein
                        organism = synthetic construct
SEQUENCE: 46
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF PKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLR   480
AELHYDGKKA KHHLPFYNAR FFEEVYCYHP SVAEITPFKT KQFGCEIGKD IPDYVSVALK   540
DNPYKKATKR ILRAIYNPVA NTTGVDKRTN CSFMIKREND EYKLVINRKI SVDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYRGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NEEQDDIPLI TKKAESKSPP KDRKRSKTSQ LPQK        1074

SEQ ID NO: 47           moltype = AA   length = 1074
FEATURE                 Location/Qualifiers
REGION                  1..1074
                        note = Synthetic Construct
source                  1..1074
                        mol_type = protein
                        organism = synthetic construct
SEQUENCE: 47
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF PKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
```

-continued

```
EAAAKANHLE EKISRVKAHP IVISNRYWAF GTSALVGNIM PADKRHQGEY AGQNFKMWLR   480
AELHYDGKKA KHHLPFYNAR FFEEVYCYHP SVAEITPFKT KQFGCEIGKD IPDYVSVALK   540
DNPYKKATKR ILRAIYNPVA NTTGVDKTTN CSFMIKREND EYKLVINRKI SRDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEAGLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NEEQDDIPLI TKKAESKSPP KDRKRSKTSQ LPQK        1074

SEQ ID NO: 48          moltype = AA  length = 1074
FEATURE                Location/Qualifiers
REGION                 1..1074
                       note = Synthetic Construct
source                 1..1074
                       mol_type = protein
                       organism = synthetic construct
SEQUENCE: 48
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLR   480
AELHYDGKKA KHHLPFYNAR FFEEVYCYHP SVAEITPFKT KQFGCEIGKD IPDYVSVALK   540
DNPYKKATKR ILRAIYNPVA NTTGVDKTTN CSFMIKREND EYKLVINRKI SRDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYRGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NEEQDDIPLI TKKAESKSPP KDRKRSKTSQ LPQK        1074

SEQ ID NO: 49          moltype = AA  length = 1074
FEATURE                Location/Qualifiers
REGION                 1..1074
                       note = Synthetic Construct
source                 1..1074
                       mol_type = protein
                       organism = synthetic construct
SEQUENCE: 49
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLR   480
AELHYDGKKA KHHLPFYNAR FFEEVYCYHP SVAEITPFKT KQFGCEIGKD IPDYVSVALK   540
DNPYKKATKR ILRAIYNPVA NTTGVDKTTN CSFMIKREND EYKLVINRKI SVDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEAGLGEV EKGKSKKQNS RNMDWCAKQV AQRLEYKLAF HGIGYRGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NEEQDDIPLI TKKAESKSPP KDRKRSKTSQ LPQK        1074

SEQ ID NO: 50          moltype = AA  length = 1074
FEATURE                Location/Qualifiers
REGION                 1..1074
                       note = Synthetic Construct
source                 1..1074
                       mol_type = protein
                       organism = synthetic construct
SEQUENCE: 50
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
```

```
QPKTTRNMSF SNEKLDLLTE LKDLNKGDGF EYAREVLNGF FDSELHTTED KFNITSRYLG  360
GDKSNRLSKL YKIWKKEGVD CEEGIQQFCE AVKDKMGQIP IRNVLKYLWQ FRETVSAEDF  420
EAAAKANHLE EKISRVKAHP IVISNRYWAF GTSALVGNIM PADKRHQGEY AGQNFKMWLE  480
AELHYDGKKA KHHLPFYNAR FFEEVYCYHP SVAEITPFKT KQFGCEIGKD IPDYVSVALK  540
DNPYKKATKR ILRAIYNPVA NTTGVDKRTN CSFMIKREND EYKLVINRKI SRDRPKRIEV  600
GRTIMGYDRN QTASDTYWIG RLVPPGTRGA YRIGEWSVQY IKSGPVLSST QGVNNSTTDQ  660
LVYNGMPSSS ERFKAWKKAR MAFIRKLIRQ LNDEGLESKG QDYIPENPSS FDVRGETLYV  720
FNSNYLKALV SKHRKAKKPV EGILDEIEAW TSKDKDSCSL MRLSSLSDAS MQGIASLKSL  780
INSYFNKNGC KTIEDKEKFN PVLYAKLVEV EQRRTNKRSE KVGRIAGSLE QLALLNGVEV  840
VIGEAGLGEV EKGKSKKQNS RNMDWCAKQV AQRLEYKLAF HGIGYFGVNP MYTSHQDPFE  900
HRRVADHIVM RARFEEVNVE NIAEWHVRNF SNYLRADSGT GLYYKQATMD FLKHYGLEEH  960
AEGLENKKIK FYDFRKILED KNLTSVIIPK RGGRIYMATN PVTSDSTPIT YAGKTYNRCN 1020
ADEVAAANIV ISVLAPRSKK NEEQDDIPLI TKKAESKSPP KDRKRSKTSQ LPQK       1074

SEQ ID NO: 51          moltype = AA   length = 1074
FEATURE                Location/Qualifiers
REGION                 1..1074
                       note = Synthetic Construct
source                 1..1074
                       mol_type = protein
                       organism = synthetic construct
SEQUENCE: 51
MASISRPYGT KLRPDARKKE MLDKFFNTLT KGQRVFADLA LCIYGSLTLE MAKSLEPESD   60
SELVCAIGWF RLVDKTIWSK DGIKQENLVK QYEAYSGKEA SEVVKTYLNS PSSDKYVWID  120
CRQKFLRFQR ELGTRNLSED FECMLFEQYI RLTKGEIEGY AAISNMFGNG EKEDRSKKRM  180
YATRMKDWLE ANENITWEQY REALKNQLNA KNLEQVVANY KGNAGGADPF PKYSFSKEGM  240
VSKKEHAQQL DKFKTVLKNK ARDLNFPNKE KLKQYLEAEI GIPVDANVYS QMFSNGVSEV  300
QPKTTRNMSF SNEKLDLLTE LKDLNKGDGF EYAREVLNGF FDSELHTTED KFNITSRYLG  360
GDKSNRLSKL YKIWKKEGVD CEEGIQQFCE AVKDKMGQIP IRNVLKYLWQ FRETVSAEDF  420
EAAAKANHLE EKISRVKAHP IVISNRYWAF GTSALVGNIM PADKRHQGEY AGQNFKMWLE  480
AELHYDGKKA KHHLPFYNAR FFEEVYCYHP SVAEITPFKT KQFGCEIGKD IPDYVSVALK  540
DNPYKKATKR ILRAIYNPVA NTTGVDKRTN CSFMIKREND EYKLVINRKI SRDRPKRIEV  600
GRTIMGYDRN QTASDTYWIG RLVPPGTRGA YRIGEWSVQY IKSGPVLSST QGVNNSTTDQ  660
LVYNGMPSSS ERFKAWKKAR MAFIRKLIRQ LNDEGLESKG QDYIPENPSS FDVRGETLYV  720
FNSNYLKALV SKHRKAKKPV EGILDEIEAW TSKDKDSCSL MRLSSLSDAS MQGIASLKSL  780
INSYFNKNGC KTIEDKEKFN PVLYAKLVEV EQRRTNKRSE KVGRIAGSLE QLALLNGVEV  840
VIGEADLGEV EKGKSKKQNS RNMDWCAKQV AQRLEYKLAF HGIGYRGVNP MYTSHQDPFE  900
HRRVADHIVM RARFEEVNVE NIAEWHVRNF SNYLRADSGT GLYYKQATMD FLKHYGLEEH  960
AEGLENKKIK FYDFRKILED KNLTSVIIPK RGGRIYMATN PVTSDSTPIT YAGKTYNRCN 1020
ADEVAAANIV ISVLAPRSKK NEEQDDIPLI TKKAESKSPP KDRKRSKTSQ LPQK       1074

SEQ ID NO: 52          moltype = AA   length = 1074
FEATURE                Location/Qualifiers
REGION                 1..1074
                       note = Synthetic Construct
source                 1..1074
                       mol_type = protein
                       organism = synthetic construct
SEQUENCE: 52
MASISRPYGT KLRPDARKKE MLDKFFNTLT KGQRVFADLA LCIYGSLTLE MAKSLEPESD   60
SELVCAIGWF RLVDKTIWSK DGIKQENLVK QYEAYSGKEA SEVVKTYLNS PSSDKYVWID  120
CRQKFLRFQR ELGTRNLSED FECMLFEQYI RLTKGEIEGY AAISNMFGNG EKEDRSKKRM  180
YATRMKDWLE ANENITWEQY REALKNQLNA KNLEQVVANY KGNAGGADPF FKYSFSKEGM  240
VSKKEHAQQL DKFKTVLKNK ARDLNFPNKE KLKQYLEAEI GIPVDANVYS QMFSNGVSEV  300
QPKTTRNMSF SNEKLDLLTE LKDLNKGDGF EYAREVLNGF FDSELHTTED KFNITSRYLG  360
GDKSNRLSKL YKIWKKEGVD CEEGIQQFCE AVKDKMGQIP IRNVLKYLWQ FRETVSAEDF  420
EAAAKANHLE EKISRVKAHP IVISNRYWAF GTSALVGNIM PADKRHQGEY AGQNFKMWLE  480
AELHYDGKKA KHHLPFYNAR FFEEVYCYHP SVAEITPFKT KQFGCEIGKD IPDYVSVALK  540
DNPYKKATKR ILRAIYNPVA NTTGVDKRTN CSFMIKREND EYKLVINRKI SRDRPKRIEV  600
GRTIMGYDRN QTASDTYWIG RLVPPGTRGA YRIGEWSVQY IKSGPVLSST QGVNNSTTDQ  660
LVYNGMPSSS ERFKAWKKAR MAFIRKLIRQ LNDEGLESKG QDYIPENPSS FDVRGETLYV  720
FNSNYLKALV SKHRKAKKPV EGILDEIEAW TSKDKDSCSL MRLSSLSDAS MQGIASLKSL  780
INSYFNKNGC KTIEDKEKFN PVLYAKLVEV EQRRTNKRSE KVGRIAGSLE QLALLNGVEV  840
VIGEAGLGEV EKGKSKKQNS RNMDWCAKQV AQRLEYKLAF HGIGYRGVNP MYTSHQDPFE  900
HRRVADHIVM RARFEEVNVE NIAEWHVRNF SNYLRADSGT GLYYKQATMD FLKHYGLEEH  960
AEGLENKKIK FYDFRKILED KNLTSVIIPK RGGRIYMATN PVTSDSTPIT YAGKTYNRCN 1020
ADEVAAANIV ISVLAPRSKK NEEQDDIPLI TKKAESKSPP KDRKRSKTSQ LPQK       1074

SEQ ID NO: 53          moltype = AA   length = 1074
FEATURE                Location/Qualifiers
REGION                 1..1074
                       note = Synthetic Construct
source                 1..1074
                       mol_type = protein
                       organism = synthetic construct
SEQUENCE: 53
MASISRPYGT KLRPDARKKE MLDKFFNTLT KGQRVFADLA LCIYGSLTLE MAKSLEPESD   60
SELVCAIGWF RLVDKTIWSK DGIKQENLVK QYEAYSGKEA SEVVKTYLNS PSSDKYVWID  120
CRQKFLRFQR ELGTRNLSED FECMLFEQYI RLTKGEIEGY AAISNMFGNG EKEDRSKKRM  180
```

```
YATRMKDWLE ANENITWEQY REALKNQLNA KNLEQVVANY KGNAGGADPF PKYSFSKEGM    240
VSKKEHAQQL DKFKTVLKNK ARDLNFPNKE KLKQYLEAEI GIPVDANVYS QMFSNGVSEV    300
QPKTTRNMSF SNEKLDLLTE LKDLNKGDGF EYAREVLNGF FDSELHTTED KFNITSRYLG    360
GDKSNRLSKL YKIWKKEGVD CEEGIQQFCE AVKDKMGQIP IRNVLKYLWQ FRETVSAEDF    420
EAAAKANHLE EKISRVKAHP IVISNRYWAF GTSALVGNIM PADKRHQGEY AGQNFKMWLE    480
AELHYDGKKA KHHLPFYNAR FFEEVYCYHP SVAEITPFKT KQFGCEIGKD IPDYVSVALK    540
DNPYKKATKR ILRAIYNPVA NTTGVDKTTN CSFMIKREND EYKLVINRKI SRDRPKRIEV    600
GRTIMGYDRN QTASDTYWIG RLVPPGTRGA YRIGEWSVQY IKSGPVLSST QGVNNSTTDQ    660
LVYNGMPSSS ERFKAWKKAR MAFIRKLIRQ LNDEGLESKG QDYIPENPSS FDVRGETLYV    720
FNSNYLKALV SKHRKAKKPV EGILDEIEAW TSKDKDSCSL MRLSSLSDAS MQGIASLKSL    780
INSYFNKNGC KTIEDKEKFN PVLYAKLVEV EQRRTNKRSE KVGRIAGSLE QLALLNGVEV    840
VIGEAGLGEV EKGKSKKQNS RNMDWCAKQV AQRLEYKLAF HGIGYRGVNP MYTSHQDPFE    900
HRRVADHIVM RARFEEVNVE NIAEWHVRNF SNYLRADSGT GLYYKQATMD FLKHYGLEEH    960
AEGLENKKIK FYDFRKILED KNLTSVIIPK RGGRIYMATN PVTSDSTPIT YAGKTYNRCN    1020
ADEVAAANIV ISVLAPRSKK NEEQDDIPLI TKKAESKSPP KDRKRSKTSQ LPQK           1074

SEQ ID NO: 54            moltype = AA   length = 1074
FEATURE                  Location/Qualifiers
REGION                   1..1074
                         note = Synthetic Construct
source                   1..1074
                         mol_type = protein
                         organism = synthetic construct
SEQUENCE: 54
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID    120
CRQKFLRFQR ELGTRNLSED FECMLFEQYI RLTKGEIEGY AAISNMFGNG EKEDRSKKRM    180
YATRMKDWLE ANENITWEQY REALKNQLNA KNLEQVVANY KGNAGGADPF PKYSFSKEGM    240
VSKKEHAQQL DKFKTVLKNK ARDLNFPNKE KLKQYLEAEI GIPVDANVYS QMFSNGVSEV    300
QPKTTRNMSF SNEKLDLLTE LKDLNKGDGF EYAREVLNGF FDSELHTTED KFNITSRYLG    360
GDKSNRLSKL YKIWKKEGVD CEEGIQQFCE AVKDKMGQIP IRNVLKYLWQ FRETVSAEDF    420
EAAAKANHLE EKISRVKAHP IVISNRYWAF GTSALVGNIM PADKRHQGEY AGQNFKMWLR    480
AELHYDGKKA KHHLPFYNAR FFEEVYCYHP SVAEITPFKT KQFGCEIGKD IPDYVSVALK    540
DNPYKKATKR ILRAIYNPVA NTTGVDKRTN CSFMIKREND EYKLVINRKI SRDRPKRIEV    600
GRTIMGYDRN QTASDTYWIG RLVPPGTRGA YRIGEWSVQY IKSGPVLSST QGVNNSTTDQ    660
LVYNGMPSSS ERFKAWKKAR MAFIRKLIRQ LNDEGLESKG QDYIPENPSS FDVRGETLYV    720
FNSNYLKALV SKHRKAKKPV EGILDEIEAW TSKDKDSCSL MRLSSLSDAS MQGIASLKSL    780
INSYFNKNGC KTIEDKEKFN PVLYAKLVEV EQRRTNKRSE KVGRIAGSLE QLALLNGVEV    840
VIGEAGLGEV EKGKSKKQNS RNMDWCAKQV AQRLEYKLAF HGIGYFGVNP MYTSHQDPFE    900
HRRVADHIVM RARFEEVNVE NIAEWHVRNF SNYLRADSGT GLYYKQATMD FLKHYGLEEH    960
AEGLENKKIK FYDFRKILED KNLTSVIIPK RGGRIYMATN PVTSDSTPIT YAGKTYNRCN    1020
ADEVAAANIV ISVLAPRSKK NEEQDDIPLI TKKAESKSPP KDRKRSKTSQ LPQK           1074

SEQ ID NO: 55            moltype = AA   length = 1074
FEATURE                  Location/Qualifiers
REGION                   1..1074
                         note = Synthetic Construct
source                   1..1074
                         mol_type = protein
                         organism = synthetic construct
SEQUENCE: 55
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID    120
CRQKFLRFQR ELGTRNLSED FECMLFEQYI RLTKGEIEGY AAISNMFGNG EKEDRSKKRM    180
YATRMKDWLE ANENITWEQY REALKNQLNA KNLEQVVANY KGNAGGADPF PKYSFSKEGM    240
VSKKEHAQQL DKFKTVLKNK ARDLNFPNKE KLKQYLEAEI GIPVDANVYS QMFSNGVSEV    300
QPKTTRNMSF SNEKLDLLTE LKDLNKGDGF EYAREVLNGF FDSELHTTED KFNITSRYLG    360
GDKSNRLSKL YKIWKKEGVD CEEGIQQFCE AVKDKMGQIP IRNVLKYLWQ FRETVSAEDF    420
EAAAKANHLE EKISRVKAHP IVISNRYWAF GTSALVGNIM PADKRHQGEY AGQNFKMWLR    480
AELHYDGKKA KHHLPFYNAR FFEEVYCYHP SVAEITPFKT KQFGCEIGKD IPDYVSVALK    540
DNPYKKATKR ILRAIYNPVA NTTGVDKRTN CSFMIKREND EYKLVINRKI SRDRPKRIEV    600
GRTIMGYDRN QTASDTYWIG RLVPPGTRGA YRIGEWSVQY IKSGPVLSST QGVNNSTTDQ    660
LVYNGMPSSS ERFKAWKKAR MAFIRKLIRQ LNDEGLESKG QDYIPENPSS FDVRGETLYV    720
FNSNYLKALV SKHRKAKKPV EGILDEIEAW TSKDKDSCSL MRLSSLSDAS MQGIASLKSL    780
INSYFNKNGC KTIEDKEKFN PVLYAKLVEV EQRRTNKRSE KVGRIAGSLE QLALLNGVEV    840
VIGEADLGEV EKGKSKKQNS RNMDWCAKQV AQRLEYKLAF HGIGYRGVNP MYTSHQDPFE    900
HRRVADHIVM RARFEEVNVE NIAEWHVRNF SNYLRADSGT GLYYKQATMD FLKHYGLEEH    960
AEGLENKKIK FYDFRKILED KNLTSVIIPK RGGRIYMATN PVTSDSTPIT YAGKTYNRCN    1020
ADEVAAANIV ISVLAPRSKK NEEQDDIPLI TKKAESKSPP KDRKRSKTSQ LPQK           1074

SEQ ID NO: 56            moltype = AA   length = 1074
FEATURE                  Location/Qualifiers
REGION                   1..1074
                         note = Synthetic Construct
source                   1..1074
                         mol_type = protein
                         organism = synthetic construct
SEQUENCE: 56
MASISRPYGT KLRPDARKKE MLDKFFNTLT KGQRVFADLA LCIYGSLTLE MAKSLEPESD    60
```

```
SELVCAIGWF RLVDKTIWSK DGIKQENLVK QYEAYSGKEA SEVVKTYLNS PSSDKYVWID    120
CRQKFLRFQR ELGTRNLSED FECMLFEQYI RLTKGEIEGY AAISNMFGNG EKEDRSKKRM    180
YATRMKDWLE ANENITWEQY REALKNQLNA KNLEQVVANY KGNAGGADPF FKYSFSKEGM    240
VSKKEHAQQL DKFKTVLKNK ARDLNFPNKE KLKQYLEAEI GIPVDANVYS QMFSNGVSEV    300
QPKTTRNMSF SNEKLDLLTE LKDLNKGDGF EYAREVLNGF FDSELHTTED KFNITSRYLG    360
GDKSNRLSKL YKIWKKEGVD CEEGIQQFCE AVKDKMGQIP IRNVLKYLWQ FRETVSAEDF    420
EAAAKANHLE EKISRVKAHP IVISNRYWAF GTSALVGNIM PADKRHQGEY AGQNFKMWLR    480
AELHYDGKKA KHHLPFYNAR FFEEVYCYHP SVAEITPFKT KQFGCEIGKD IPDYVSVALK    540
DNPYKKATKR ILRAIYNPVA NTTGVDKRTN CSFMIKREND EYKLVINRKI SVDRPKRIEV    600
GRTIMGYDRN QTASDTYWIG RLVPPGTRGA YRIGEWSVQY IKSGPVLSST QGVNNSTTDQ    660
LVYNGMPSSS ERFKAWKKAR MAFIRKLIRQ LNDEGLESKG QDYIPENPSS FDVRGETLYV    720
FNSNYLKALV SKHRKAKKPV EGILDEIEAW TSKDKDSCSL MRLSSLSDAS MQGIASLKSL    780
INSYFNKNGC KTIEDKEKFN PVLYAKLVEV EQRRTNKRSE KVGRIAGSLE QLALLNGVEV    840
VIGEAGLGEV EKGKSKKQNS RNMDWCAKQV AQRLEYKLAF HGIGYRGVNP MYTSHQDPFE    900
HRRVADHIVM RARFEEVNVE NIAEWHVRNF SNYLRADSGT GLYYKQATMD FLKHYGLEEH    960
AEGLENKKIK FYDFRKILED KNLTSVIIPK RGGRIYMATN PVTSDSTPIT YAGKTYNRCN   1020
ADEVAAANIV ISVLAPRSKK NEEQDDIPLI TKKAESKSPP KDRKRSKTSQ LPQK          1074

SEQ ID NO: 57            moltype = AA  length = 1074
FEATURE                  Location/Qualifiers
REGION                   1..1074
                         note = Synthetic Construct
source                   1..1074
                         mol_type = protein
                         organism = synthetic construct
SEQUENCE: 57
MASISRPYGT KLRPDARKKE MLDKFFNTLT KGQRVFADLA LCIYGSLTLE MAKSLEPESD     60
SELVCAIGWF RLVDKTIWSK DGIKQENLVK QYEAYSGKEA SEVVKTYLNS PSSDKYVWID    120
CRQKFLRFQR ELGTRNLSED FECMLFEQYI RLTKGEIEGY AAISNMFGNG EKEDRSKKRM    180
YATRMKDWLE ANENITWEQY REALKNQLNA KNLEQVVANY KGNAGGADPF FKYSFSKEGM    240
VSKKEHAQQL DKFKTVLKNK ARDLNFPNKE KLKQYLEAEI GIPVDANVYS QMFSNGVSEV    300
QPKTTRNMSF SNEKLDLLTE LKDLNKGDGF EYAREVLNGF FDSELHTTED KFNITSRYLG    360
GDKSNRLSKL YKIWKKEGVD CEEGIQQFCE AVKDKMGQIP IRNVLKYLWQ FRETVSAEDF    420
EAAAKANHLE EKISRVKAHP IVISNRYWAF GTSALVGNIM PADKRHQGEY AGQNFKMWLR    480
AELHYDGKKA KHHLPFYNAR FFEEVYCYHP SVAEITPFKT KQFGCEIGKD IPDYVSVALK    540
DNPYKKATKR ILRAIYNPVA NTTGVDKTTN CSFMIKREND EYKLVINRKI SRDRPKRIEV    600
GRTIMGYDRN QTASDTYWIG RLVPPGTRGA YRIGEWSVQY IKSGPVLSST QGVNNSTTDQ    660
LVYNGMPSSS ERFKAWKKAR MAFIRKLIRQ LNDEGLESKG QDYIPENPSS FDVRGETLYV    720
FNSNYLKALV SKHRKAKKPV EGILDEIEAW TSKDKDSCSL MRLSSLSDAS MQGIASLKSL    780
INSYFNKNGC KTIEDKEKFN PVLYAKLVEV EQRRTNKRSE KVGRIAGSLE QLALLNGVEV    840
VIGEAGLGEV EKGKSKKQNS RNMDWCAKQV AQRLEYKLAF HGIGYRGVNP MYTSHQDPFE    900
HRRVADHIVM RARFEEVNVE NIAEWHVRNF SNYLRADSGT GLYYKQATMD FLKHYGLEEH    960
AEGLENKKIK FYDFRKILED KNLTSVIIPK RGGRIYMATN PVTSDSTPIT YAGKTYNRCN   1020
ADEVAAANIV ISVLAPRSKK NEEQDDIPLI TKKAESKSPP KDRKRSKTSQ LPQK          1074

SEQ ID NO: 58            moltype = AA  length = 1074
FEATURE                  Location/Qualifiers
REGION                   1..1074
                         note = Synthetic Construct
source                   1..1074
                         mol_type = protein
                         organism = synthetic construct
SEQUENCE: 58
MASISRPYGT KLRPDARKKE MLDKFFNTLT KGQRVFADLA LCIYGSLTLE MAKSLEPESD     60
SELVCAIGWF RLVDKTIWSK DGIKQENLVK QYEAYSGKEA SEVVKTYLNS PSSDKYVWID    120
CRQKFLRFQR ELGTRNLSED FECMLFEQYI RLTKGEIEGY AAISNMFGNG EKEDRSKKRM    180
YATRMKDWLE ANENITWEQY REALKNQLNA KNLEQVVANY KGNAGGADPF FKYSFSKEGM    240
VSKKEHAQQL DKFKTVLKNK ARDLNFPNKE KLKQYLEAEI GIPVDANVYS QMFSNGVSEV    300
QPKTTRNMSF SNEKLDLLTE LKDLNKGDGF EYAREVLNGF FDSELHTTED KFNITSRYLG    360
GDKSNRLSKL YKIWKKEGVD CEEGIQQFCE AVKDKMGQIP IRNVLKYLWQ FRETVSAEDF    420
EAAAKANHLE EKISRVKAHP IVISNRYWAF GTSALVGNIM PADKRHQGEY AGQNFKMWLE    480
AELHYDGKKA KHHLPFYNAR FFEEVYCYHP SVAEITPFKT KQFGCEIGKD IPDYVSVALK    540
DNPYKKATKR ILRAIYNPVA NTTGVDKRTN CSFMIKREND EYKLVINRKI SRDRPKRIEV    600
GRTIMGYDRN QTASDTYWIG RLVPPGTRGA YRIGEWSVQY IKSGPVLSST QGVNNSTTDQ    660
LVYNGMPSSS ERFKAWKKAR MAFIRKLIRQ LNDEGLESKG QDYIPENPSS FDVRGETLYV    720
FNSNYLKALV SKHRKAKKPV EGILDEIEAW TSKDKDSCSL MRLSSLSDAS MQGIASLKSL    780
INSYFNKNGC KTIEDKEKFN PVLYAKLVEV EQRRTNKRSE KVGRIAGSLE QLALLNGVEV    840
VIGEAGLGEV EKGKSKKQNS RNMDWCAKQV AQRLEYKLAF HGIGYRGVNP MYTSHQDPFE    900
HRRVADHIVM RARFEEVNVE NIAEWHVRNF SNYLRADSGT GLYYKQATMD FLKHYGLEEH    960
AEGLENKKIK FYDFRKILED KNLTSVIIPK RGGRIYMATN PVTSDSTPIT YAGKTYNRCN   1020
ADEVAAANIV ISVLAPRSKK NEEQDDIPLI TKKAESKSPP KDRKRSKTSQ LPQK          1074

SEQ ID NO: 59            moltype = AA  length = 1074
FEATURE                  Location/Qualifiers
REGION                   1..1074
                         note = Synthetic Construct
source                   1..1074
                         mol_type = protein
                         organism = synthetic construct
```

```
SEQUENCE: 59
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF FKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KFNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLR   480
AELHYDGKKA KHHLPFYNAR FFEEVYCYHP SVAEITPFKT KQFGCEIGKD IPDYVSVALK   540
DNPYKKATKR ILRAIYNPVA NTTGVDKRTN CSFMIKREND EYKLVINRKI SRDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEAGLGEV EKGKSKKQNS RNMDWCAKQV AQRLEYKLAF HGIGYRGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NEEQDDIPLI TKKAESKSPP KDRKRSKTSQ LPQK        1074

SEQ ID NO: 60           moltype = RNA   length = 36
FEATURE                 Location/Qualifiers
misc_feature            1..36
                        note = Synthetic Construct
source                  1..36
                        mol_type = other RNA
                        organism = synthetic construct
SEQUENCE: 60
tctcaacgat agtcagacat gtgtcctcag tgacac                              36

SEQ ID NO: 61           moltype = RNA   length = 22
FEATURE                 Location/Qualifiers
misc_feature            1..22
                        note = Synthetic Construct
source                  1..22
                        mol_type = other RNA
                        organism = synthetic construct
SEQUENCE: 61
agacatgtgt cctcagtgac ac                                             22

SEQ ID NO: 62           moltype = RNA   length = 40
FEATURE                 Location/Qualifiers
misc_feature            1..40
                        note = Synthetic Construct
source                  1..40
                        mol_type = other RNA
                        organism = synthetic construct
SEQUENCE: 62
agacatgtgt cctcagtgac acgtagcctc tcccgctctg                          40

SEQ ID NO: 63           moltype = RNA   length = 40
FEATURE                 Location/Qualifiers
misc_feature            1..40
                        note = Synthetic Construct
source                  1..40
                        mol_type = other RNA
                        organism = synthetic construct
SEQUENCE: 63
agacatgtgt cctcagtgac acgggaagtg gttggtcagc                          40

SEQ ID NO: 64           moltype = RNA   length = 40
FEATURE                 Location/Qualifiers
misc_feature            1..40
                        note = Synthetic Construct
source                  1..40
                        mol_type = other RNA
                        organism = synthetic construct
SEQUENCE: 64
agacatgtgt cctcagtgac acggggaggc ctggagtcat                          40

SEQ ID NO: 65           moltype = DNA   length = 592
FEATURE                 Location/Qualifiers
misc_feature            1..592
                        note = Synthetic Construct
source                  1..592
                        mol_type = other DNA
                        organism = synthetic construct
SEQUENCE: 65
cgcaaagtgt tgggattaca ggcgtgagcc cggccattct gagactgtgt tgcaggcatt    60
```

```
gtacatcttc gcctgatgca cagcaggtat ctcctgccac aaggaaaacc tcctgcagaa    120
ccacagtagg gatgcaacac gctacccct gtgttgacct tgatgctaca ctctcaccca    180
ccgcaccaac cttgatgcta cactctcacc caccgcacca accttgatgc tacactctca   240
cccaccgcac caaccttgat gctacactct cacccaccgc accaaccttg atgctacact   300
ctcacccacc gcaccaacct tgatgctaca ctctcaccca ctgcaccaac cttgatgcta   360
cactgttgcc tgcgtttctc cttgacattc tttgtagcct ctcccgctct ggttcagggc   420
ccagctaggg atccagatct gggtgattta ggctccctct gtctggatca gtcctccttt   480
tcccttggac cccagggagg ccgggaatgg cctccagggg gtctgtgaac tttctgacgt   540
tgtatttcc tgcagaaatt gctcataact tgcatcagct tctcagaggg gg             592

SEQ ID NO: 66             moltype = DNA  length = 614
FEATURE                   Location/Qualifiers
misc_feature              1..614
                          note = Synthetic Construct
source                    1..614
                          mol_type = other DNA
                          organism = synthetic construct
SEQUENCE: 66
cctgagccca tcactgttgc aaaggtgaca ggaaggcctg gtgatgtgcg caccctggag    60
ccaggctatg ggcccggtca cattgaaacc atatggggca agtgtgggt gaggaaagtc    120
aagatgaggt cacaggggaa gggagaatgg attttcgtag gcccaagcag cagctgtgct   180
gcagggacac gcagcagcac catgtcctgt gcagaaggga ccctccctgg ccactttgca   240
caggggcatg gaactggcag gaagaagaca tgatgtgttt ttgaaacatt tgaagccagc   300
tcacttggaa ttccagcatc caagtcagct ggaagagggg gagttaccct tggaggcagg   360
cggaatcgac cattggatag ctccaagtgc tgacaagggc ggacacggga gctgatttct   420
gcctggtggg aaaggtgatg attccagcta ctttgggaag tggttggtca gcatgatta   480
tagccgaagg cccagctttt gccttgttct agcagttcca ctcctgggca gcccgagaga   540
ggccttccca accatgggca gatgttcatc atagtattgt ttgcagtagt aagaggtcgg   600
agcccacacc aaag                                                     614

SEQ ID NO: 67             moltype = DNA  length = 490
FEATURE                   Location/Qualifiers
misc_feature              1..490
                          note = Synthetic Construct
source                    1..490
                          mol_type = other DNA
                          organism = synthetic construct
SEQUENCE: 67
aggacaaagt acaaacggca gaagctggag gaggaagggc ctgagtccga gcagaagaag    60
aagggctccc atcacatcaa ccggtggcgc attgccacga agcaggccaa tggggaggac   120
atcgatgtca cctccaatga ctagggtggg caaccacaaa cccacgaggg cagagtgctg   180
cttgctgctg gccaggcccc tgcgtgggcc caagctggac tctggccact ccctggccag   240
gctttgggga ggcctggagt catggcccca caggggcgg cgccattgac                300
agagggacaa gcaatgggct ggctgaggcc tgggaccact tggccttctc ctcggagagc   360
ctgcctgcct gggcgggccc gcccgccacc gcagcctccc agctgctctc cgtgtctcca   420
atctcccttt tgttttgatg catttctgtt ttaatttatt ttccaggcac cactgtagtt   480
tagtgatccc                                                           490

SEQ ID NO: 68             moltype = DNA  length = 25
FEATURE                   Location/Qualifiers
misc_feature              1..25
                          note = Synthetic Construct
source                    1..25
                          mol_type = other DNA
                          organism = synthetic construct
SEQUENCE: 68
cgcaaagtgt tgggattaca ggcgt                                          25

SEQ ID NO: 69             moltype = DNA  length = 25
FEATURE                   Location/Qualifiers
misc_feature              1..25
                          note = Synthetic Construct
source                    1..25
                          mol_type = other DNA
                          organism = synthetic construct
SEQUENCE: 69
cccctctga gaagctgatg caagt                                           25

SEQ ID NO: 70             moltype = DNA  length = 25
FEATURE                   Location/Qualifiers
misc_feature              1..25
                          note = Synthetic Construct
source                    1..25
                          mol_type = other DNA
                          organism = synthetic construct
SEQUENCE: 70
cccctctga gaagctgatg caagt                                           25

SEQ ID NO: 71             moltype = DNA  length = 25
```

```
FEATURE              Location/Qualifiers
misc_feature         1..25
                     note = Synthetic Construct
source               1..25
                     mol_type = other DNA
                     organism = synthetic construct
SEQUENCE: 71
ctttggtgtg ggctccgacc tctta                                              25

SEQ ID NO: 72        moltype = DNA  length = 28
FEATURE              Location/Qualifiers
misc_feature         1..28
                     note = Synthetic Construct
source               1..28
                     mol_type = other DNA
                     organism = synthetic construct
SEQUENCE: 72
aggacaaagt acaaacggca gaagctgg                                           28

SEQ ID NO: 73        moltype = DNA  length = 28
FEATURE              Location/Qualifiers
misc_feature         1..28
                     note = Synthetic Construct
source               1..28
                     mol_type = other DNA
                     organism = synthetic construct
SEQUENCE: 73
gggatcacta aactacagtg gtgcctgg                                           28

SEQ ID NO: 74        moltype = RNA  length = 46
FEATURE              Location/Qualifiers
misc_feature         1..46
                     note = Synthetic Construct
source               1..46
                     mol_type = other RNA
                     organism = synthetic construct
SEQUENCE: 74
agacatgtgt cctcagtgac actgtccccc caagttttgg acccct                       46

SEQ ID NO: 75        moltype = DNA  length = 24
FEATURE              Location/Qualifiers
misc_feature         1..24
                     note = Synthetic Construct
source               1..24
                     mol_type = other DNA
                     organism = synthetic construct
SEQUENCE: 75
tgtcccccca agttttggac ccct                                               24

SEQ ID NO: 76        moltype = RNA  length = 46
FEATURE              Location/Qualifiers
misc_feature         1..46
                     note = Synthetic Construct
source               1..46
                     mol_type = other RNA
                     organism = synthetic construct
SEQUENCE: 76
agacatgtgt cctcagtgac acgtgagaat ggtgcgtcct aggtgt                       46

SEQ ID NO: 77        moltype = DNA  length = 24
FEATURE              Location/Qualifiers
misc_feature         1..24
                     note = Synthetic Construct
source               1..24
                     mol_type = other DNA
                     organism = synthetic construct
SEQUENCE: 77
gtgagaatgg tgcgtcctag gtgt                                               24

SEQ ID NO: 78        moltype = RNA  length = 46
FEATURE              Location/Qualifiers
misc_feature         1..46
                     note = Synthetic Construct
source               1..46
                     mol_type = other RNA
                     organism = synthetic construct
SEQUENCE: 78
agacatgtgt cctcagtgac acaactggcc ctggctttgg cagcct                       46
```

-continued

```
SEQ ID NO: 79            moltype = DNA   length = 24
FEATURE                  Location/Qualifiers
misc_feature             1..24
                         note = Synthetic Construct
source                   1..24
                         mol_type = other DNA
                         organism = synthetic construct
SEQUENCE: 79
aactggccct ggctttggca gcct                                                24

SEQ ID NO: 80            moltype = RNA   length = 46
FEATURE                  Location/Qualifiers
misc_feature             1..46
                         note = Synthetic Construct
source                   1..46
                         mol_type = other RNA
                         organism = synthetic construct
SEQUENCE: 80
agacatgtgt cctcagtgac acgtagcctc tcccgctctg gttcag                        46

SEQ ID NO: 81            moltype = DNA   length = 24
FEATURE                  Location/Qualifiers
misc_feature             1..24
                         note = Synthetic Construct
source                   1..24
                         mol_type = other DNA
                         organism = synthetic construct
SEQUENCE: 81
gtagcctctc ccgctctggt tcag                                                24

SEQ ID NO: 82            moltype = RNA   length = 46
FEATURE                  Location/Qualifiers
misc_feature             1..46
                         note = Synthetic Construct
source                   1..46
                         mol_type = other RNA
                         organism = synthetic construct
SEQUENCE: 82
agacatgtgt cctcagtgac acgggaagtg gttggtcagc atggat                        46

SEQ ID NO: 83            moltype = DNA   length = 24
FEATURE                  Location/Qualifiers
misc_feature             1..24
                         note = Synthetic Construct
source                   1..24
                         mol_type = other DNA
                         organism = synthetic construct
SEQUENCE: 83
gggaagtggt tggtcagcat ggat                                                24

SEQ ID NO: 84            moltype = RNA   length = 46
FEATURE                  Location/Qualifiers
misc_feature             1..46
                         note = Synthetic Construct
source                   1..46
                         mol_type = other RNA
                         organism = synthetic construct
SEQUENCE: 84
agacatgtgt cctcagtgac acgggaagtg gttggtcagc atggat                        46

SEQ ID NO: 85            moltype = DNA   length = 24
FEATURE                  Location/Qualifiers
misc_feature             1..24
                         note = Synthetic Construct
source                   1..24
                         mol_type = other DNA
                         organism = synthetic construct
SEQUENCE: 85
gggcgcaggg ccacctggac cctg                                                24

SEQ ID NO: 86            moltype = RNA   length = 46
FEATURE                  Location/Qualifiers
misc_feature             1..46
                         note = Synthetic Construct
source                   1..46
                         mol_type = other RNA
                         organism = synthetic construct
SEQUENCE: 86
agacatgtgt cctcagtgac acggatggcg acttcaggca caggat                        46
```

```
SEQ ID NO: 87           moltype = DNA  length = 24
FEATURE                 Location/Qualifiers
misc_feature            1..24
                        note = Synthetic Construct
source                  1..24
                        mol_type = other DNA
                        organism = synthetic construct
SEQUENCE: 87
ggatggcgac ttcaggcaca ggat                                              24

SEQ ID NO: 88           moltype = RNA  length = 46
FEATURE                 Location/Qualifiers
misc_feature            1..46
                        note = Synthetic Construct
source                  1..46
                        mol_type = other RNA
                        organism = synthetic construct
SEQUENCE: 88
agacatgtgt cctcagtgac acggggaggc ctggagtcat ggcccc                      46

SEQ ID NO: 89           moltype = DNA  length = 24
FEATURE                 Location/Qualifiers
misc_feature            1..24
                        note = Synthetic Construct
source                  1..24
                        mol_type = other DNA
                        organism = synthetic construct
SEQUENCE: 89
ggggaggcct ggagtcatgg cccc                                              24

SEQ ID NO: 90           moltype = RNA  length = 46
FEATURE                 Location/Qualifiers
misc_feature            1..46
                        note = Synthetic Construct
source                  1..46
                        mol_type = other RNA
                        organism = synthetic construct
SEQUENCE: 90
agacatgtgt cctcagtgac acgagccagt gttgctagtc aagggc                      46

SEQ ID NO: 91           moltype = DNA  length = 24
FEATURE                 Location/Qualifiers
misc_feature            1..24
                        note = Synthetic Construct
source                  1..24
                        mol_type = other DNA
                        organism = synthetic construct
SEQUENCE: 91
gagccagtgt tgctagtcaa gggc                                              24

SEQ ID NO: 92           moltype = RNA  length = 46
FEATURE                 Location/Qualifiers
misc_feature            1..46
                        note = Synthetic Construct
source                  1..46
                        mol_type = other RNA
                        organism = synthetic construct
SEQUENCE: 92
agacatgtgt cctcagtgac acagcaaggg actattcagg gatgaa                      46

SEQ ID NO: 93           moltype = DNA  length = 24
FEATURE                 Location/Qualifiers
misc_feature            1..24
                        note = Synthetic Construct
source                  1..24
                        mol_type = other DNA
                        organism = synthetic construct
SEQUENCE: 93
agcaagggac tattcaggga tgaa                                              24

SEQ ID NO: 94           moltype = RNA  length = 46
FEATURE                 Location/Qualifiers
misc_feature            1..46
                        note = Synthetic Construct
source                  1..46
                        mol_type = other RNA
                        organism = synthetic construct
SEQUENCE: 94
```

```
agacatgtgt cctcagtgac acaaaattga gcaatctacc ctggtc          46

SEQ ID NO: 95           moltype = DNA  length = 24
FEATURE                 Location/Qualifiers
misc_feature            1..24
                        note = Synthetic Construct
source                  1..24
                        mol_type = other DNA
                        organism = synthetic construct
SEQUENCE: 95
aaaattgagc aatctaccct ggtc                                  24

SEQ ID NO: 96           moltype = RNA  length = 46
FEATURE                 Location/Qualifiers
misc_feature            1..46
                        note = Synthetic Construct
source                  1..46
                        mol_type = other RNA
                        organism = synthetic construct
SEQUENCE: 96
agacatgtgt cctcagtgac actggggtg accgccggag cgcggc           46

SEQ ID NO: 97           moltype = DNA  length = 24
FEATURE                 Location/Qualifiers
misc_feature            1..24
                        note = Synthetic Construct
source                  1..24
                        mol_type = other DNA
                        organism = synthetic construct
SEQUENCE: 97
tgggggtgac cgccggagcg cggc                                  24

SEQ ID NO: 98           moltype = RNA  length = 46
FEATURE                 Location/Qualifiers
misc_feature            1..46
                        note = Synthetic Construct
source                  1..46
                        mol_type = other RNA
                        organism = synthetic construct
SEQUENCE: 98
agacatgtgt cctcagtgac acaatcctcc accagtcatg gtgaca          46

SEQ ID NO: 99           moltype = DNA  length = 24
FEATURE                 Location/Qualifiers
misc_feature            1..24
                        note = Synthetic Construct
source                  1..24
                        mol_type = other DNA
                        organism = synthetic construct
SEQUENCE: 99
aatcctccac cagtcatggt gaca                                  24

SEQ ID NO: 100          moltype = RNA  length = 46
FEATURE                 Location/Qualifiers
misc_feature            1..46
                        note = Synthetic Construct
source                  1..46
                        mol_type = other RNA
                        organism = synthetic construct
SEQUENCE: 100
agacatgtgt cctcagtgac acgttgacat tgtccacacc tggaat          46

SEQ ID NO: 101          moltype = DNA  length = 24
FEATURE                 Location/Qualifiers
misc_feature            1..24
                        note = Synthetic Construct
source                  1..24
                        mol_type = other DNA
                        organism = synthetic construct
SEQUENCE: 101
gttgacattg tccacacctg gaat                                  24

SEQ ID NO: 102          moltype = RNA  length = 46
FEATURE                 Location/Qualifiers
misc_feature            1..46
                        note = Synthetic Construct
source                  1..46
                        mol_type = other RNA
                        organism = synthetic construct
```

```
SEQUENCE: 102
agacatgtgt cctcagtgac acttaaactc tccatggacc aggctc                    46

SEQ ID NO: 103          moltype = DNA  length = 24
FEATURE                 Location/Qualifiers
misc_feature            1..24
                        note = Synthetic Construct
source                  1..24
                        mol_type = other DNA
                        organism = synthetic construct
SEQUENCE: 103
ttaaactctc catggaccag gctc                                            24

SEQ ID NO: 104          moltype = RNA  length = 46
FEATURE                 Location/Qualifiers
misc_feature            1..46
                        note = Synthetic Construct
source                  1..46
                        mol_type = other RNA
                        organism = synthetic construct
SEQUENCE: 104
agacatgtgt cctcagtgac acgcccatac tggggaccaa ggaagt                    46

SEQ ID NO: 105          moltype = DNA  length = 24
FEATURE                 Location/Qualifiers
misc_feature            1..24
                        note = Synthetic Construct
source                  1..24
                        mol_type = other DNA
                        organism = synthetic construct
SEQUENCE: 105
gcccatactg gggaccaagg aagt                                            24

SEQ ID NO: 106          moltype = RNA  length = 46
FEATURE                 Location/Qualifiers
misc_feature            1..46
                        note = Synthetic Construct
source                  1..46
                        mol_type = other RNA
                        organism = synthetic construct
SEQUENCE: 106
agacatgtgt cctcagtgac acgccgtaac ccttcgtggg tagaga                    46

SEQ ID NO: 107          moltype = DNA  length = 24
FEATURE                 Location/Qualifiers
misc_feature            1..24
                        note = Synthetic Construct
source                  1..24
                        mol_type = other DNA
                        organism = synthetic construct
SEQUENCE: 107
gccgtaaccc ttcgtgggta gaga                                            24

SEQ ID NO: 108          moltype = RNA  length = 36
FEATURE                 Location/Qualifiers
misc_feature            1..36
                        note = Synthetic Construct
source                  1..36
                        mol_type = other RNA
                        organism = synthetic construct
SEQUENCE: 108
ttttaacaac actcaggcat gtgtccacag tgacac                               36

SEQ ID NO: 109          moltype = RNA  length = 36
FEATURE                 Location/Qualifiers
misc_feature            1..36
                        note = Synthetic Construct
source                  1..36
                        mol_type = other RNA
                        organism = synthetic construct
SEQUENCE: 109
ttgaacggat actcagacat gtgtttccag tgacac                               36

SEQ ID NO: 110          moltype = RNA  length = 36
FEATURE                 Location/Qualifiers
misc_feature            1..36
                        note = Synthetic Construct
source                  1..36
                        mol_type = other RNA
```

```
                        organism = synthetic construct
SEQUENCE: 110
tgccctcaat agtcagatgt gtgtccacag tgacac                                    36

SEQ ID NO: 111          moltype = RNA   length = 36
FEATURE                 Location/Qualifiers
misc_feature            1..36
                        note = Synthetic Construct
source                  1..36
                        mol_type = other RNA
                        organism = synthetic construct
SEQUENCE: 111
tctcaatgat acttagatac gtgtcctcag tgacac                                    36

SEQ ID NO: 112          moltype = RNA   length = 36
FEATURE                 Location/Qualifiers
misc_feature            1..36
                        note = Synthetic Construct
source                  1..36
                        mol_type = other RNA
                        organism = synthetic construct
SEQUENCE: 112
tctcaatgat actcagacat gtgtccccag tgacac                                    36

SEQ ID NO: 113          moltype = RNA   length = 36
FEATURE                 Location/Qualifiers
misc_feature            1..36
                        note = Synthetic Construct
source                  1..36
                        mol_type = other RNA
                        organism = synthetic construct
SEQUENCE: 113
tctcaatgat actaagacat gtgtcctcag tgacac                                    36

SEQ ID NO: 114          moltype = RNA   length = 36
FEATURE                 Location/Qualifiers
misc_feature            1..36
                        note = Synthetic Construct
source                  1..36
                        mol_type = other RNA
                        organism = synthetic construct
SEQUENCE: 114
tctcaactat actcagacat gtgtcctcag tgacac                                    36

SEQ ID NO: 115          moltype = RNA   length = 36
FEATURE                 Location/Qualifiers
misc_feature            1..36
                        note = Synthetic Construct
source                  1..36
                        mol_type = other RNA
                        organism = synthetic construct
SEQUENCE: 115
tctcaacgat actcagacat gtgtcctcag tgacac                                    36

SEQ ID NO: 116          moltype = RNA   length = 36
FEATURE                 Location/Qualifiers
misc_feature            1..36
                        note = Synthetic Construct
source                  1..36
                        mol_type = other RNA
                        organism = synthetic construct
SEQUENCE: 116
tctcaacgat actaagatat gtgtcctcag cgacac                                    36

SEQ ID NO: 117          moltype = RNA   length = 36
FEATURE                 Location/Qualifiers
misc_feature            1..36
                        note = Synthetic Construct
source                  1..36
                        mol_type = other RNA
                        organism = synthetic construct
SEQUENCE: 117
tctcaacgat actaagatat gtgtccccag tgacac                                    36

SEQ ID NO: 118          moltype = RNA   length = 36
FEATURE                 Location/Qualifiers
misc_feature            1..36
                        note = Synthetic Construct
source                  1..36
```

```
                           mol_type = other RNA
                           organism = synthetic construct
SEQUENCE: 118
tctcaacgat actaagatat gtgtccacag tgacac                                36

SEQ ID NO: 119             moltype = RNA   length = 36
FEATURE                    Location/Qualifiers
misc_feature               1..36
                           note = Synthetic Construct
source                     1..36
                           mol_type = other RNA
                           organism = synthetic construct
SEQUENCE: 119
tctcaacaat actcagacat gtgtccccag tgacac                                36

SEQ ID NO: 120             moltype = RNA   length = 36
FEATURE                    Location/Qualifiers
misc_feature               1..36
                           note = Synthetic Construct
source                     1..36
                           mol_type = other RNA
                           organism = synthetic construct
SEQUENCE: 120
tctcaacaat actaaggcat gtgtccccag tgaccc                                36

SEQ ID NO: 121             moltype = RNA   length = 36
FEATURE                    Location/Qualifiers
misc_feature               1..36
                           note = Synthetic Construct
source                     1..36
                           mol_type = other RNA
                           organism = synthetic construct
SEQUENCE: 121
tctcaaagat actcagacac gtgtccccag tgacac                                36

SEQ ID NO: 122             moltype = RNA   length = 36
FEATURE                    Location/Qualifiers
misc_feature               1..36
                           note = Synthetic Construct
source                     1..36
                           mol_type = other RNA
                           organism = synthetic construct
SEQUENCE: 122
tctcaaaaat actcagacat gtgtcctcag tgacac                                36

SEQ ID NO: 123             moltype = RNA   length = 36
FEATURE                    Location/Qualifiers
misc_feature               1..36
                           note = Synthetic Construct
source                     1..36
                           mol_type = other RNA
                           organism = synthetic construct
SEQUENCE: 123
gcgaaacaac agtcagacat gtgtccccag tgacac                                36

SEQ ID NO: 124             moltype = RNA   length = 36
FEATURE                    Location/Qualifiers
misc_feature               1..36
                           note = Synthetic Construct
source                     1..36
                           mol_type = other RNA
                           organism = synthetic construct
SEQUENCE: 124
cctcaacgat attaagacat gtgtccgcag tgacac                                36

SEQ ID NO: 125             moltype = RNA   length = 22
FEATURE                    Location/Qualifiers
misc_feature               1..22
                           note = Synthetic Construct
misc_feature               3
                           note = n is a or g
misc_feature               4
                           note = n is c or u
misc_feature               5
                           note = n is a or g
misc_feature               6
                           note = n is u or c
misc_feature               11
                           note = n is c or u
```

```
misc_feature            12
                        note = n is c or u
misc_feature            13
                        note = n is u, a, c, or g
misc_feature            17
                        note = n is u or c
misc_feature            21
                        note = n is a or c
source                  1..22
                        mol_type = other RNA
                        organism = synthetic construct
SEQUENCE: 125
agnnnngtgt nnncagngac nc                                              22

SEQ ID NO: 126          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 126
ctcattcttc ccttaggggt                                                 20

SEQ ID NO: 127          moltype = RNA  length = 42
FEATURE                 Location/Qualifiers
misc_feature            1..42
                        note = Synthetic Construct
source                  1..42
                        mol_type = other RNA
                        organism = synthetic construct
SEQUENCE: 127
agacatgtgt cctcagtgac acctcattct tcccttaggg gt                        42

SEQ ID NO: 128          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 128
cccccccaagt ccctcacctc                                                20

SEQ ID NO: 129          moltype = RNA  length = 42
FEATURE                 Location/Qualifiers
misc_feature            1..42
                        note = Synthetic Construct
source                  1..42
                        mol_type = other RNA
                        organism = synthetic construct
SEQUENCE: 129
agacatgtgt cctcagtgac acccccccaa gtccctcacc tc                        42

SEQ ID NO: 130          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 130
accaggtcgt ggccgcctct                                                 20

SEQ ID NO: 131          moltype = RNA  length = 42
FEATURE                 Location/Qualifiers
misc_feature            1..42
                        note = Synthetic Construct
source                  1..42
                        mol_type = other RNA
                        organism = synthetic construct
SEQUENCE: 131
agacatgtgt cctcagtgac acaccaggtc gtggccgcct ct                        42

SEQ ID NO: 132          moltype = DNA  length = 20
FEATURE                 Location/Qualifiers
misc_feature            1..20
                        note = Synthetic Construct
source                  1..20
```

```
                        mol_type = other DNA
                        organism = synthetic construct
SEQUENCE: 132
taggcctgca tcatcaccgt                                               20

SEQ ID NO: 133          moltype = RNA   length = 42
FEATURE                 Location/Qualifiers
misc_feature            1..42
                        note = Synthetic Construct
source                  1..42
                        mol_type = other RNA
                        organism = synthetic construct
SEQUENCE: 133
agacatgtgt cctcagtgac actaggcctg catcatcacc gt                      42

SEQ ID NO: 134          moltype = DNA   length = 20
FEATURE                 Location/Qualifiers
misc_feature            1..20
                        note = Synthetic Construct
source                  1..20
                        mol_type = other DNA
                        organism = synthetic construct
SEQUENCE: 134
actggccctg gctttggcag                                               20

SEQ ID NO: 135          moltype = RNA   length = 42
FEATURE                 Location/Qualifiers
misc_feature            1..42
                        note = Synthetic Construct
source                  1..42
                        mol_type = other RNA
                        organism = synthetic construct
SEQUENCE: 135
agacatgtgt cctcagtgac acactggccc tggctttggc ag                      42

SEQ ID NO: 136          moltype = DNA   length = 20
FEATURE                 Location/Qualifiers
misc_feature            1..20
                        note = Synthetic Construct
source                  1..20
                        mol_type = other DNA
                        organism = synthetic construct
SEQUENCE: 136
tagcctctcc cgctctggtt                                               20

SEQ ID NO: 137          moltype = RNA   length = 42
FEATURE                 Location/Qualifiers
misc_feature            1..42
                        note = Synthetic Construct
source                  1..42
                        mol_type = other RNA
                        organism = synthetic construct
SEQUENCE: 137
agacatgtgt cctcagtgac actagcctct cccgctctgg tt                      42

SEQ ID NO: 138          moltype = DNA   length = 20
FEATURE                 Location/Qualifiers
misc_feature            1..20
                        note = Synthetic Construct
source                  1..20
                        mol_type = other DNA
                        organism = synthetic construct
SEQUENCE: 138
tagccgaagg ccccagcttt                                               20

SEQ ID NO: 139          moltype = RNA   length = 42
FEATURE                 Location/Qualifiers
misc_feature            1..42
                        note = Synthetic Construct
source                  1..42
                        mol_type = other RNA
                        organism = synthetic construct
SEQUENCE: 139
agacatgtgt cctcagtgac actagccgaa ggccccagct tt                      42

SEQ ID NO: 140          moltype = DNA   length = 20
FEATURE                 Location/Qualifiers
misc_feature            1..20
                        note = Synthetic Construct
```

```
source              1..20
                    mol_type = other DNA
                    organism = synthetic construct
SEQUENCE: 140
gcgggtatgg gaagggcttt                                                   20

SEQ ID NO: 141      moltype = RNA  length = 42
FEATURE             Location/Qualifiers
misc_feature        1..42
                    note = Synthetic Construct
source              1..42
                    mol_type = other RNA
                    organism = synthetic construct
SEQUENCE: 141
agacatgtgt cctcagtgac acgcgggtat gggaagggct tt                          42

SEQ ID NO: 142      moltype = DNA  length = 20
FEATURE             Location/Qualifiers
misc_feature        1..20
                    note = Synthetic Construct
source              1..20
                    mol_type = other DNA
                    organism = synthetic construct
SEQUENCE: 142
acacgggcca ccgtttctca                                                   20

SEQ ID NO: 143      moltype = RNA  length = 42
FEATURE             Location/Qualifiers
misc_feature        1..42
                    note = Synthetic Construct
source              1..42
                    mol_type = other RNA
                    organism = synthetic construct
SEQUENCE: 143
agacatgtgt cctcagtgac acacgggc caccgtttct ca                            42

SEQ ID NO: 144      moltype = DNA  length = 20
FEATURE             Location/Qualifiers
misc_feature        1..20
                    note = Synthetic Construct
source              1..20
                    mol_type = other DNA
                    organism = synthetic construct
SEQUENCE: 144
acccccccaag tccctcacct                                                  20

SEQ ID NO: 145      moltype = RNA  length = 42
FEATURE             Location/Qualifiers
misc_feature        1..42
                    note = Synthetic Construct
source              1..42
                    mol_type = other RNA
                    organism = synthetic construct
SEQUENCE: 145
agacatgtgt cctcagtgac acaccccca agtccctcac ct                           42

SEQ ID NO: 146      moltype = DNA  length = 20
FEATURE             Location/Qualifiers
misc_feature        1..20
                    note = Synthetic Construct
source              1..20
                    mol_type = other DNA
                    organism = synthetic construct
SEQUENCE: 146
ggtgttcacc aggtcgtggc                                                   20

SEQ ID NO: 147      moltype = RNA  length = 42
FEATURE             Location/Qualifiers
misc_feature        1..42
                    note = Synthetic Construct
source              1..42
                    mol_type = other RNA
                    organism = synthetic construct
SEQUENCE: 147
agacatgtgt cctcagtgac acggtgttca ccaggtcgtg gc                          42

SEQ ID NO: 148      moltype = DNA  length = 20
FEATURE             Location/Qualifiers
misc_feature        1..20
```

```
                    note = Synthetic Construct
source              1..20
                    mol_type = other DNA
                    organism = synthetic construct
SEQUENCE: 148
ggcctgcatc atcaccgttt                                                    20

SEQ ID NO: 149      moltype = RNA   length = 42
FEATURE             Location/Qualifiers
misc_feature        1..42
                    note = Synthetic Construct
source              1..42
                    mol_type = other RNA
                    organism = synthetic construct
SEQUENCE: 149
agacatgtgt cctcagtgac acggcctgca tcatcaccgt tt                            42

SEQ ID NO: 150      moltype = DNA   length = 20
FEATURE             Location/Qualifiers
misc_feature        1..20
                    note = Synthetic Construct
source              1..20
                    mol_type = other DNA
                    organism = synthetic construct
SEQUENCE: 150
gccctggctt tggcagcctg                                                    20

SEQ ID NO: 151      moltype = RNA   length = 42
FEATURE             Location/Qualifiers
misc_feature        1..42
                    note = Synthetic Construct
source              1..42
                    mol_type = other RNA
                    organism = synthetic construct
SEQUENCE: 151
agacatgtgt cctcagtgac acgccctggc tttggcagcc tg                            42

SEQ ID NO: 152      moltype = DNA   length = 20
FEATURE             Location/Qualifiers
misc_feature        1..20
                    note = Synthetic Construct
source              1..20
                    mol_type = other DNA
                    organism = synthetic construct
SEQUENCE: 152
gcctctcccg ctctggttca                                                    20

SEQ ID NO: 153      moltype = RNA   length = 42
FEATURE             Location/Qualifiers
misc_feature        1..42
                    note = Synthetic Construct
source              1..42
                    mol_type = other RNA
                    organism = synthetic construct
SEQUENCE: 153
agacatgtgt cctcagtgac acgcctctcc cgctctggtt ca                            42

SEQ ID NO: 154      moltype = DNA   length = 20
FEATURE             Location/Qualifiers
misc_feature        1..20
                    note = Synthetic Construct
source              1..20
                    mol_type = other DNA
                    organism = synthetic construct
SEQUENCE: 154
attatagccg aaggccccag                                                    20

SEQ ID NO: 155      moltype = RNA   length = 42
FEATURE             Location/Qualifiers
misc_feature        1..42
                    note = Synthetic Construct
source              1..42
                    mol_type = other RNA
                    organism = synthetic construct
SEQUENCE: 155
agacatgtgt cctcagtgac acattatagc cgaaggcccc ag                            42

SEQ ID NO: 156      moltype = DNA   length = 20
FEATURE             Location/Qualifiers
```

```
misc_feature               1..20
                           note = Synthetic Construct
source                     1..20
                           mol_type = other DNA
                           organism = synthetic construct
SEQUENCE: 156
gtgcagaggg tgggccgggg                                                    20

SEQ ID NO: 157             moltype = RNA   length = 42
FEATURE                    Location/Qualifiers
misc_feature               1..42
                           note = Synthetic Construct
source                     1..42
                           mol_type = other RNA
                           organism = synthetic construct
SEQUENCE: 157
agacatgtgt cctcagtgac acgtgcagag ggtgggccgg gg                           42

SEQ ID NO: 158             moltype = DNA   length = 20
FEATURE                    Location/Qualifiers
misc_feature               1..20
                           note = Synthetic Construct
source                     1..20
                           mol_type = other DNA
                           organism = synthetic construct
SEQUENCE: 158
tgctgagaac cacccagggt                                                    20

SEQ ID NO: 159             moltype = RNA   length = 42
FEATURE                    Location/Qualifiers
misc_feature               1..42
                           note = Synthetic Construct
source                     1..42
                           mol_type = other RNA
                           organism = synthetic construct
SEQUENCE: 159
agacatgtgt cctcagtgac actgctgaga accacccagg gt                           42

SEQ ID NO: 160             moltype = DNA   length = 20
FEATURE                    Location/Qualifiers
misc_feature               1..20
                           note = Synthetic Construct
source                     1..20
                           mol_type = other DNA
                           organism = synthetic construct
SEQUENCE: 160
ggtgccctag gaagctgcct                                                    20

SEQ ID NO: 161             moltype = RNA   length = 42
FEATURE                    Location/Qualifiers
misc_feature               1..42
                           note = Synthetic Construct
source                     1..42
                           mol_type = other RNA
                           organism = synthetic construct
SEQUENCE: 161
agacatgtgt cctcagtgac acggtgccct aggaagctgc ct                           42

SEQ ID NO: 162             moltype = DNA   length = 20
FEATURE                    Location/Qualifiers
misc_feature               1..20
                           note = Synthetic Construct
source                     1..20
                           mol_type = other DNA
                           organism = synthetic construct
SEQUENCE: 162
atgcccaaag gtcagatgat                                                    20

SEQ ID NO: 163             moltype = RNA   length = 42
FEATURE                    Location/Qualifiers
misc_feature               1..42
                           note = Synthetic Construct
source                     1..42
                           mol_type = other RNA
                           organism = synthetic construct
SEQUENCE: 163
agacatgtgt cctcagtgac acatgcccaa aggtcagatg at                           42

SEQ ID NO: 164             moltype = DNA   length = 20
```

```
FEATURE              Location/Qualifiers
misc_feature         1..20
                     note = Synthetic Construct
source               1..20
                     mol_type = other DNA
                     organism = synthetic construct
SEQUENCE: 164
ggggaggcct ggagtcatgg                                                    20

SEQ ID NO: 165       moltype = RNA   length = 42
FEATURE              Location/Qualifiers
misc_feature         1..42
                     note = Synthetic Construct
source               1..42
                     mol_type = other RNA
                     organism = synthetic construct
SEQUENCE: 165
agacatgtgt cctcagtgac acggggaggc ctggagtcat gg                           42

SEQ ID NO: 166       moltype = DNA   length = 20
FEATURE              Location/Qualifiers
misc_feature         1..20
                     note = Synthetic Construct
source               1..20
                     mol_type = other DNA
                     organism = synthetic construct
SEQUENCE: 166
gcaccactgt agtttagtga                                                    20

SEQ ID NO: 167       moltype = RNA   length = 42
FEATURE              Location/Qualifiers
misc_feature         1..42
                     note = Synthetic Construct
source               1..42
                     mol_type = other RNA
                     organism = synthetic construct
SEQUENCE: 167
agacatgtgt cctcagtgac acgcaccact gtagtttagt ga                           42

SEQ ID NO: 168       moltype = DNA   length = 20
FEATURE              Location/Qualifiers
misc_feature         1..20
                     note = Synthetic Construct
source               1..20
                     mol_type = other DNA
                     organism = synthetic construct
SEQUENCE: 168
tttgagccag tgttgctagt                                                    20

SEQ ID NO: 169       moltype = RNA   length = 42
FEATURE              Location/Qualifiers
misc_feature         1..42
                     note = Synthetic Construct
source               1..42
                     mol_type = other RNA
                     organism = synthetic construct
SEQUENCE: 169
agacatgtgt cctcagtgac actttgagcc agtgttgcta gt                           42

SEQ ID NO: 170       moltype = DNA   length = 20
FEATURE              Location/Qualifiers
misc_feature         1..20
                     note = Synthetic Construct
source               1..20
                     mol_type = other DNA
                     organism = synthetic construct
SEQUENCE: 170
ctttagcaag ggactattca                                                    20

SEQ ID NO: 171       moltype = RNA   length = 42
FEATURE              Location/Qualifiers
misc_feature         1..42
                     note = Synthetic Construct
source               1..42
                     mol_type = other RNA
                     organism = synthetic construct
SEQUENCE: 171
agacatgtgt cctcagtgac accttagcaa aggactatt ca                            42
```

```
SEQ ID NO: 172          moltype = DNA    length = 20
FEATURE                 Location/Qualifiers
misc_feature            1..20
                        note = Synthetic Construct
source                  1..20
                        mol_type = other DNA
                        organism = synthetic construct
SEQUENCE: 172
agcaatctac cctggtcctc                                                   20

SEQ ID NO: 173          moltype = RNA    length = 42
FEATURE                 Location/Qualifiers
misc_feature            1..42
                        note = Synthetic Construct
source                  1..42
                        mol_type = other RNA
                        organism = synthetic construct
SEQUENCE: 173
agacatgtgt cctcagtgac acagcaatct accctggtcc tc                          42

SEQ ID NO: 174          moltype = DNA    length = 20
FEATURE                 Location/Qualifiers
misc_feature            1..20
                        note = Synthetic Construct
source                  1..20
                        mol_type = other DNA
                        organism = synthetic construct
SEQUENCE: 174
agaaccaccc agggtccagg                                                   20

SEQ ID NO: 175          moltype = RNA    length = 42
FEATURE                 Location/Qualifiers
misc_feature            1..42
                        note = Synthetic Construct
source                  1..42
                        mol_type = other RNA
                        organism = synthetic construct
SEQUENCE: 175
agacatgtgt cctcagtgac acagaaccac ccagggtcca gg                          42

SEQ ID NO: 176          moltype = DNA    length = 20
FEATURE                 Location/Qualifiers
misc_feature            1..20
                        note = Synthetic Construct
source                  1..20
                        mol_type = other DNA
                        organism = synthetic construct
SEQUENCE: 176
gggtgccsta ggaagctgcc                                                   20

SEQ ID NO: 177          moltype = RNA    length = 42
FEATURE                 Location/Qualifiers
misc_feature            1..42
                        note = Synthetic Construct
source                  1..42
                        mol_type = other RNA
                        organism = synthetic construct
SEQUENCE: 177
agacatgtgt cctcagtgac acgggtgccc taggaagctg cc                          42

SEQ ID NO: 178          moltype = DNA    length = 20
FEATURE                 Location/Qualifiers
misc_feature            1..20
                        note = Synthetic Construct
source                  1..20
                        mol_type = other DNA
                        organism = synthetic construct
SEQUENCE: 178
agatgatagc ataggtacac                                                   20

SEQ ID NO: 179          moltype = RNA    length = 42
FEATURE                 Location/Qualifiers
misc_feature            1..42
                        note = Synthetic Construct
source                  1..42
                        mol_type = other RNA
                        organism = synthetic construct
SEQUENCE: 179
agacatgtgt cctcagtgac acagatgata gcataggtac ac                          42
```

```
SEQ ID NO: 180            moltype = DNA  length = 20
FEATURE                   Location/Qualifiers
misc_feature              1..20
                          note = Synthetic Construct
source                    1..20
                          mol_type = other DNA
                          organism = synthetic construct
SEQUENCE: 180
actccaggcc tccccaaagc                                                     20

SEQ ID NO: 181            moltype = RNA  length = 42
FEATURE                   Location/Qualifiers
misc_feature              1..42
                          note = Synthetic Construct
source                    1..42
                          mol_type = other RNA
                          organism = synthetic construct
SEQUENCE: 181
agacatgtgt cctcagtgac acactccagg cctccccaaa gc                            42

SEQ ID NO: 182            moltype = DNA  length = 20
FEATURE                   Location/Qualifiers
misc_feature              1..20
                          note = Synthetic Construct
source                    1..20
                          mol_type = other DNA
                          organism = synthetic construct
SEQUENCE: 182
actaaactac agtggtgcct                                                     20

SEQ ID NO: 183            moltype = RNA  length = 42
FEATURE                   Location/Qualifiers
misc_feature              1..42
                          note = Synthetic Construct
source                    1..42
                          mol_type = other RNA
                          organism = synthetic construct
SEQUENCE: 183
agacatgtgt cctcagtgac acactaaact acagtggtgc ct                            42

SEQ ID NO: 184            moltype = DNA  length = 20
FEATURE                   Location/Qualifiers
misc_feature              1..20
                          note = Synthetic Construct
source                    1..20
                          mol_type = other DNA
                          organism = synthetic construct
SEQUENCE: 184
ctttgagcca gtgttgctag                                                     20

SEQ ID NO: 185            moltype = RNA  length = 42
FEATURE                   Location/Qualifiers
misc_feature              1..42
                          note = Synthetic Construct
source                    1..42
                          mol_type = other RNA
                          organism = synthetic construct
SEQUENCE: 185
agacatgtgt cctcagtgac acctttgagc cagtgttgct ag                            42

SEQ ID NO: 186            moltype = DNA  length = 20
FEATURE                   Location/Qualifiers
misc_feature              1..20
                          note = Synthetic Construct
source                    1..20
                          mol_type = other DNA
                          organism = synthetic construct
SEQUENCE: 186
ccttgctaaa gaaacatgtg                                                     20

SEQ ID NO: 187            moltype = RNA  length = 42
FEATURE                   Location/Qualifiers
misc_feature              1..42
                          note = Synthetic Construct
source                    1..42
                          mol_type = other RNA
                          organism = synthetic construct
SEQUENCE: 187
```

```
agacatgtgt cctcagtgac acccttgcta aagaaacatg tg                                42

SEQ ID NO: 188         moltype = DNA  length = 20
FEATURE                Location/Qualifiers
misc_feature           1..20
                       note = Synthetic Construct
source                 1..20
                       mol_type = other DNA
                       organism = synthetic construct
SEQUENCE: 188
gagcaatcta ccctggtcct                                                         20

SEQ ID NO: 189         moltype = RNA  length = 42
FEATURE                Location/Qualifiers
misc_feature           1..42
                       note = Synthetic Construct
source                 1..42
                       mol_type = other RNA
                       organism = synthetic construct
SEQUENCE: 189
agacatgtgt cctcagtgac acgagcaatc taccctggtc ct                                42

SEQ ID NO: 190         moltype = DNA  length = 20
FEATURE                Location/Qualifiers
misc_feature           1..20
                       note = Synthetic Construct
source                 1..20
                       mol_type = other DNA
                       organism = synthetic construct
SEQUENCE: 190
tgggggtgac cgccggagcg                                                         20

SEQ ID NO: 191         moltype = RNA  length = 42
FEATURE                Location/Qualifiers
misc_feature           1..42
                       note = Synthetic Construct
source                 1..42
                       mol_type = other RNA
                       organism = synthetic construct
SEQUENCE: 191
agacatgtgt cctcagtgac actgggggtg accgccggag cg                                42

SEQ ID NO: 192         moltype = DNA  length = 20
FEATURE                Location/Qualifiers
misc_feature           1..20
                       note = Synthetic Construct
source                 1..20
                       mol_type = other DNA
                       organism = synthetic construct
SEQUENCE: 192
tgggctgctt ggggttgtca                                                         20

SEQ ID NO: 193         moltype = RNA  length = 42
FEATURE                Location/Qualifiers
misc_feature           1..42
                       note = Synthetic Construct
source                 1..42
                       mol_type = other RNA
                       organism = synthetic construct
SEQUENCE: 193
agacatgtgt cctcagtgac actgggctgc ttggggttgt ca                                42

SEQ ID NO: 194         moltype = DNA  length = 20
FEATURE                Location/Qualifiers
misc_feature           1..20
                       note = Synthetic Construct
source                 1..20
                       mol_type = other DNA
                       organism = synthetic construct
SEQUENCE: 194
tccacacctg gaatcggctt                                                         20

SEQ ID NO: 195         moltype = RNA  length = 42
FEATURE                Location/Qualifiers
misc_feature           1..42
                       note = Synthetic Construct
source                 1..42
                       mol_type = other RNA
                       organism = synthetic construct
```

```
SEQUENCE: 195
agacatgtgt cctcagtgac actccacacc tggaatcggc tt                               42

SEQ ID NO: 196          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 196
gtgtagagag gaaaatgtgg                                                        20

SEQ ID NO: 197          moltype = RNA  length = 42
FEATURE                 Location/Qualifiers
misc_feature            1..42
                        note = Synthetic Construct
source                  1..42
                        mol_type = other RNA
                        organism = synthetic construct
SEQUENCE: 197
agacatgtgt cctcagtgac acgtgtagag aggaaaatgt gg                               42

SEQ ID NO: 198          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 198
ggggctttgt ttgggaagct                                                        20

SEQ ID NO: 199          moltype = RNA  length = 42
FEATURE                 Location/Qualifiers
misc_feature            1..42
                        note = Synthetic Construct
source                  1..42
                        mol_type = other RNA
                        organism = synthetic construct
SEQUENCE: 199
agacatgtgt cctcagtgac acggggcttt gtttgggaag ct                               42

SEQ ID NO: 200          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 200
acacttcctt ggtccccagt                                                        20

SEQ ID NO: 201          moltype = RNA  length = 42
FEATURE                 Location/Qualifiers
misc_feature            1..42
                        note = Synthetic Construct
source                  1..42
                        mol_type = other RNA
                        organism = synthetic construct
SEQUENCE: 201
agacatgtgt cctcagtgac acacacttcc ttggtcccca gt                               42

SEQ ID NO: 202          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 202
gtgggtagag aaggattctg                                                        20

SEQ ID NO: 203          moltype = RNA  length = 42
FEATURE                 Location/Qualifiers
misc_feature            1..42
                        note = Synthetic Construct
source                  1..42
                        mol_type = other RNA
```

```
                        organism = synthetic construct
SEQUENCE: 203
agacatgtgt cctcagtgac acgtgggtag agaaggattc tg                           42

SEQ ID NO: 204          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 204
aaatcctccc ttgacccacc                                                    20

SEQ ID NO: 205          moltype = RNA  length = 42
FEATURE                 Location/Qualifiers
misc_feature            1..42
                        note = Synthetic Construct
source                  1..42
                        mol_type = other RNA
                        organism = synthetic construct
SEQUENCE: 205
agacatgtgt cctcagtgac acaaatcctc ccttgaccca cc                           42

SEQ ID NO: 206          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 206
ccaaggggga gggctcacgc                                                    20

SEQ ID NO: 207          moltype = RNA  length = 42
FEATURE                 Location/Qualifiers
misc_feature            1..42
                        note = Synthetic Construct
source                  1..42
                        mol_type = other RNA
                        organism = synthetic construct
SEQUENCE: 207
agacatgtgt cctcagtgac acccaagggg gagggctcac gc                           42

SEQ ID NO: 208          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 208
acaaccccaa gcagcccaca                                                    20

SEQ ID NO: 209          moltype = RNA  length = 42
FEATURE                 Location/Qualifiers
misc_feature            1..42
                        note = Synthetic Construct
source                  1..42
                        mol_type = other RNA
                        organism = synthetic construct
SEQUENCE: 209
agacatgtgt cctcagtgac acacaacccc aagcagccca ca                           42

SEQ ID NO: 210          moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 210
aaagccgatt ccaggtgtgg                                                    20

SEQ ID NO: 211          moltype = RNA  length = 42
FEATURE                 Location/Qualifiers
misc_feature            1..42
                        note = Synthetic Construct
source                  1..42
```

```
                        mol_type = other RNA
                        organism = synthetic construct
SEQUENCE: 211
agacatgtgt cctcagtgac acaaagccga ttccaggtgt gg                           42

SEQ ID NO: 212          moltype = DNA   length = 20
FEATURE                 Location/Qualifiers
misc_feature            1..20
                        note = Synthetic Construct
source                  1..20
                        mol_type = other DNA
                        organism = synthetic construct
SEQUENCE: 212
tgtgtagaga ggaaaatgtg                                                    20

SEQ ID NO: 213          moltype = RNA   length = 42
FEATURE                 Location/Qualifiers
misc_feature            1..42
                        note = Synthetic Construct
source                  1..42
                        mol_type = other RNA
                        organism = synthetic construct
SEQUENCE: 213
agacatgtgt cctcagtgac actgtgtaga gaggaaaatg tg                           42

SEQ ID NO: 214          moltype = DNA   length = 20
FEATURE                 Location/Qualifiers
misc_feature            1..20
                        note = Synthetic Construct
source                  1..20
                        mol_type = other DNA
                        organism = synthetic construct
SEQUENCE: 214
atccagcttc ccaaacaaag                                                    20

SEQ ID NO: 215          moltype = RNA   length = 42
FEATURE                 Location/Qualifiers
misc_feature            1..42
                        note = Synthetic Construct
source                  1..42
                        mol_type = other RNA
                        organism = synthetic construct
SEQUENCE: 215
agacatgtgt cctcagtgac acatccagct tcccaaacaa ag                           42

SEQ ID NO: 216          moltype = DNA   length = 20
FEATURE                 Location/Qualifiers
misc_feature            1..20
                        note = Synthetic Construct
source                  1..20
                        mol_type = other DNA
                        organism = synthetic construct
SEQUENCE: 216
ctggggacca aggaagtgtc                                                    20

SEQ ID NO: 217          moltype = RNA   length = 42
FEATURE                 Location/Qualifiers
misc_feature            1..42
                        note = Synthetic Construct
source                  1..42
                        mol_type = other RNA
                        organism = synthetic construct
SEQUENCE: 217
agacatgtgt cctcagtgac acctggggac caaggaagtg tc                           42

SEQ ID NO: 218          moltype = DNA   length = 20
FEATURE                 Location/Qualifiers
misc_feature            1..20
                        note = Synthetic Construct
source                  1..20
                        mol_type = other DNA
                        organism = synthetic construct
SEQUENCE: 218
ggtagagaag gattctgtgc                                                    20

SEQ ID NO: 219          moltype = RNA   length = 42
FEATURE                 Location/Qualifiers
misc_feature            1..42
                        note = Synthetic Construct
```

```
source                    1..42
                          mol_type = other RNA
                          organism = synthetic construct
SEQUENCE: 219
agacatgtgt cctcagtgac acggtagaga aggattctgt gc                              42

SEQ ID NO: 220            moltype = DNA  length = 20
FEATURE                   Location/Qualifiers
misc_feature              1..20
                          note = Synthetic Construct
source                    1..20
                          mol_type = other DNA
                          organism = synthetic construct
SEQUENCE: 220
ttcaaatcct cccttgaccc                                                       20

SEQ ID NO: 221            moltype = RNA  length = 42
FEATURE                   Location/Qualifiers
misc_feature              1..42
                          note = Synthetic Construct
source                    1..42
                          mol_type = other RNA
                          organism = synthetic construct
SEQUENCE: 221
agacatgtgt cctcagtgac acttcaaatc ctcccttgac cc                              42

SEQ ID NO: 222            moltype = DNA  length = 3222
FEATURE                   Location/Qualifiers
misc_feature              1..3222
                          note = Synthetic Construct
source                    1..3222
                          mol_type = other DNA
                          organism = synthetic construct
SEQUENCE: 222
atggccagca tctcacgccc ctacgggacc aagctgcggc ctgatgcccg gaaaaaggaa           60
atgctggaca aattttttcaa cactctcacc aagggccaaa gggtatttgc cgatctggcg        120
ctgtgtatat acgggagcct gacactcgag atggccaaga gcctagagcc ggaatctgac         180
agcgagctcg tttgtgccat cgggtggttt agactcgtag acaaaaccat ttggagtaag         240
gatgggataa agcaggagaa tctcgtgaag caatatgagg cctattccgg aaaagaggcg         300
tcagaggtgg tgaagactta cctgaatagc ccctcatccg acaaatacgt atggattgat         360
tgccgacaaa agttttacg gttccagcgg gaacttggaa cgaggaacct gagcgaagat          420
tttgaatgta tgctgtttga gcagtatatc cggcttacca aaggcgagat tgaaggatac         480
gccgccattt ctaatatgtt tggtaatggc gagaaggagg acagatcaaa gaagaggatg         540
tacgctactc gtatgaagga ctggttggag gcaaatgaaa atattacctg ggagcagtac         600
cgagaagcgc tcaaaaacca gttgaacgca agaatctgg agcaagtggt ggccaactat          660
aagggcaatg ccggcggcgc cgatccattt ttcaagtata gttttctcgaa ggaaggtatg        720
gtgtccaaga aagagcacgc gcagcagctg gacaagttca aaacagtcct gaagaataaa         780
gcccgcgatt taaatttccc caacaaggag aagctcaagc agtacttaga agctgagatt         840
ggtatcccag ttgatgcaaa cgtatactca cagatgttct ctaacggggt gtcggaggtc         900
caaccaaaaa caacacgaaa catgtccttt agcaatgaga agctagatct gttgactgaa         960
ctgaaggact taaacaaggg cgatggattc gaatacgcca gagaagtgct taatgcttct        1020
ttcgatagtg aactccacac tacagaagat aaattcaaca ttactagtcg gtaccttggt        1080
ggggacaaat ccaacaggct cagcaagttg tataagattt ggaagaagga gggggttgat        1140
tgtgaagaag gaattcagca gttctgcgag gctgtgaagg ataaaatggg ccagatcccc        1200
atccgaaatg tcctcaaata tttatgcag tttagggaga ccgtcagtgc cgaggacttc         1260
gaagctgcag caaaggcaaa ccacctagag gagaaaataa gccgagtgaa agctcacccg        1320
attgtgattt ccaacaggta ttgggctttc ggcacaagcg ctctggttgg caacatcatg        1380
ccagctgaca agcgtcacca gggggagtat gccggacaga acttcaaaat gtggctgcgc        1440
gcagagctgc attatgatgg caagaaagcc aaacatcacc tcccgttcta tgccaagg          1500
tttttcgaag aagtctattg ttaccatcca tctgtcgctg aaatcactcc tttttaaaagg       1560
aaacaattcg gctgcgagat cgggaaggat attccggatt atgtctctgt ggctctgaag        1620
gacaatccct acaagaaggc gactaaaagg attctacggg ccatctacaa ccccgttgct        1680
aacactacac gagtggataa acaaccaat tgctccttca tgatcaaaag agagaacgac         1740
gagtataaac tggtcataaa taggaagatc tcgcgaagca gcctaagg gataagaagtc        1800
ggacgcacca tcatgggcta tgaccgaaac cagaccgcgt ctgacaccta ctggatcggt       1860
cggcttgtgc tcctgggac cagaggagct tacagaattg gggagtggag tgtgcagtat        1920
atcaaatccg gaccagtgct gtcttccaca cagggtgtta taactccac aaccgatcag         1980
ctcgtctaca acggtatgcc ttcaagtagc gagcgcttta aggcgtggaa gaaggccaga        2040
atggcattta tccgcaaact catcagacaa ctgaatgatg agggtttaga atcaaaaggg        2100
caggactata ttcctgaaaa tccaagttcc ttcgacgtga gggggaaac gttgtatgtg         2160
ttcaactcca attccttaa ggccctggta tcaaaacaca ggaaggctaa gaagcctgtg         2220
gaaggcatcc ttgacgagat cgaagcctgg acctccaaag acaaagattc ctgttcactg        2280
atgcggctct ctagcctgag tgatgcctcc atgcaaggta tagcctcact aaagagcctg        2340
attaactctt acttttaataa aaatggttgc aagacaatag aggataaaga aaaatttaac       2400
ccagtcttgt atgcaaaact ggtgaggtc gaacagagac gtacaaacaa acggagcgag         2460
aaagtgggaa gaatcgctgg atctctagag cagctggcgc tgcttaacgg cgtcgaagtg        2520
gttattggag aggcagatct gggagaagtt gagaaaggga gtctaagaa acagaatagc         2580
cgtaacatgg actggtgcgc caagcaggtg gcacagagat ggagtacaa gctggcttt         2640
cacggcatcg gttactttgg cgttaatccc atgtacacga gtcaccagga ccccttcgag        2700
```

```
catcgccgtg tagccgacca tatcgtgatg cgtgcaagat ttgaggaagt taacgtagag 2760
aacatcgctg aatggcatgt gagaaacttt agcaattacc tccgcgccga cagcggcacc 2820
ggcctttact acaagcaggc cacgatggac tttttgaagc attatggact ggaggagcac 2880
gccgagggct tggaaaacaa aaaaattaag ttctatgact tcaggaagat tcttgaagac 2940
aaaaacctga cgtctgtgat catacctaaa cgcggaggcg gcatttacat ggctacaaac 3000
cctgttactt ccgacagcac acccatcact tacgccggaa aaacctataa tcggtgcaat 3060
gcagacgagg tggcagctgc caatatagtg atctccgtcc tggcaccaag aagtaaaaag 3120
aatagggaac aagacgatat ccccctcata actaaaaagg cagagtcgaa gtctccccca 3180
aaggatcgca aacggtctaa gacctcacag ttgcccaaa ag 3222

SEQ ID NO: 223        moltype = DNA  length = 3222
FEATURE               Location/Qualifiers
misc_feature          1..3222
                      note = Synthetic Construct
source                1..3222
                      mol_type = other DNA
                      organism = synthetic construct
SEQUENCE: 223
atggctagca tcagcagacc ctacggcacc aagctgagac ccgacgctag aaagaaggag 60
atgctggaca agtttttcaa taccctgacc aaggggcagc gtgtgttcgc cgacctggcc 120
ctgtgcatct acgcagcct gaccctggag atggccaaga gcctggagcc cgagagcgac 180
agcgaactgg tgtgtgccat cggctggttc agactggtga taaaaccat ctggagcaag 240
gacggcatca agcaagaaa cctggtgaag cagtacgacg cctacagcgg caaggaggct 300
agcgaggtgg tgaagaccta cctgaacagc cctagcagcg acaagtacgt gtggatcgac 360
tgcagacaga agttcctgag atttcagaga gagctgggca agagaaaacct gagcgaggat 420
ttcgagtgca tgctgttcga gcagtacatc agactgacaa agggagagat cgagggctac 480
gccgccatca gcaacatgtt cggcaacggc gagaaggagg accggagcaa aagagaatg 540
tacgccacaa gaatgaagga ctggctggag gccaacgaga acatcacctg ggagcagtac 600
agagaggccc tgaagaatca gctgaacgcc aagaacctgg agcaagtggt ggccaactac 660
aagggcaacg ccggcggcgc cgaccccttc ttcaagtaca gcttcagcaa ggagggcgtg 720
gtgagcaaga aggagcacgc tcagcagctc gataagttca aaaccgtgct gaagaacaag 780
gctagagacc tgaacttccc caacaaggag aagctgaagc agtacctgga ggccgagatc 840
ggcatccccg tggacgccaa cgtgtactct cagatgttca gcaacggcgt gagcgaggtg 900
cagcccaaga ccacaagaaa catgagcttc agcaacgaga agctggacct gctgaccgag 960
ctgaaggacc tgaacaaggg cgacggcttc gagtacgcta gagaggtgct gaacggcttc 1020
ttcgatagcg aactgcatac aaccgaggac aagttcaaca ttacaagcag atacctgggc 1080
ggcgacaaga gcaacagact gagcaagctg tacaagatct ggaagaagga gggcgtggac 1140
tgcgaggagg gcattcagca gttctgcgag gccgtgaagg acaagatggg cagatcccc 1200
atcagaaacg tgctgaagta cctgtgcag ttcagagaa ccgtgagcgc cgaagactc 1260
gaggcagccg ccaaagccaa ccacctggag gagaaaatta gcagtgaa gcccaccc 1320
atcgtgatta gcaatagata ctgggccttc ggcacaagcg cctggtggg caacatcatg 1380
cccgccgaca agagacacca aggcgagtac gccgggcaga cttcaagat gtggctgaga 1440
gccgagtcg actacgacgg caagaaggcc aagcaccacc tgcccttcta caacgctaga 1500
ttcttcgaag aggtgtactg ctaccaccct agcgtggccg agatcacccc cttcaagacc 1560
aagcagttcg gctgcgagat cggcaaggac atccccgact acgtgagcgt ggccctgaag 1620
gacaaccccc acaagaaggc caccaagaga atcctgagag ccatctacaa ccccgtggcc 1680
aacaccacaa gagtcgataa gaccaccaac tgcagcttca tgatcaagag agagaacgac 1740
gagtataagc tggtaatcaa cagaaaaatt tcccgagaca gacccaagag aatcgaggtc 1800
ggcagaacca taatgggcta cgacagaaat cagaccgcta cgacaccta ctggatcggc 1860
agactggtgc ccccggcac aagaggcgcc tacagaatcg cgagtggag cgtgcagtac 1920
atcaagagcg gcccgtgct caagcacc caaggcgtga caacagcac caccgatcag 1980
ctggtgtaca cggcatgcc tagcagcagc gagagattca aggcctgaa gaaggctaga 2040
atggccttca tcagaaagct gatcagacag ctgaacgacg agggtctgga gagcaagggc 2100
caagactaca tcccgagaa ccctagcagc ttcgacgtga gaggcgagac cctgtacgtg 2160
ttcaactcca actatctgaa agctctggtg agcaaggcca gaaaggccaa gaagcccgtg 2220
gagggcatcc tggacgagat cgaggcctgg acaagcaagg acaagacag ctgcagcctg 2280
atgagactga gcagcctgag cgacgctagc atgcaaggca tcgctagcct gaagagcctg 2340
atcaacagct acttcaacaa gaacggctgc aagaccatcg aggacaagga aagttcaac 2400
cccgtgctgt acgccaagct ggtggaggtg gagcagagaa gaaccaacaa gagaagcgag 2460
aaggtaggaa gaatcgcgg cagcctggag cagctgccc tgctgaacg cgtggaggtg 2520
gtgatcggcg aggccgacct gggcgaggtg gagaagggca agagcaagaa gcagaacagc 2580
agaaacatga actggtgcgc caagcaagtg gctcagagac tggagtacaa gctgccttc 2640
cacggcatcg gctacttcgg cgtgaacccc atgtacacaa gccaccaaga ccccttcgag 2700
cacagaaagag tggccgacca catcgtgatg agactagat aaacgtggg 2760
aacatcgccg agtggcacgt gagaaacttc agcaactacc tgcgcgcgga cagcggcacc 2820
ggcctgtact acaagcaagc caccatggac ttcctgaagc actacggcct ggaggagcac 2880
gccgagggcc tggagaacaa gaagatcaag ttctacgact tcagaaagat cctggaggac 2940
aagaacctga agcgtgat catcccaag agagcggca gaattctat ggccaccaac 3000
cccgtgacaa gcgacgacga ccccatcacc tacgccgacca gactacaa cagatgccaa 3060
gccgacgagg tggcagccgc gaatatagtg atcagcgtgc tagccccccg aagcaagaag 3120
aacagagagc aagacgacat cccctgatcc accaagaagg ccgagagcaa gagcccccc 3180
aaggacagaa agaagagcaa gacatctcag ctgcctcaga ag 3222

SEQ ID NO: 224        moltype = DNA  length = 3222
FEATURE               Location/Qualifiers
misc_feature          1..3222
                      note = Synthetic Construct
source                1..3222
                      mol_type = other DNA
```

```
                         organism = synthetic construct
SEQUENCE: 224
atggccagca tcagccggcc ctacggcacc aagctgcggc ccgacgcccg gaagaaggag   60
atgctggaca agttcttcaa caccctgacc aagggccagg gggtgttcgc cgacctggcc  120
ctgtgcatct acggcagcct gaccctggag atggccaaga gcctggagcc cgagagcgac  180
agcgagctgg tgtgcgccat cggctggttc cggctggtgg acaagaccat ctggagcaag  240
gacggcatca agcaggagaa cctggtgaag cagtacgagg cctacagcgg caaggaggcc  300
agcgaggtgg tgaagaccta cctgaacagc cccagcagcg acaagtacgt gtggatcgac  360
tgccggcaga agttcctgcg gttccagcgg gagctgggca cccggaacct gagcgaggac  420
ttcgagtgca tgctgttcga gcagtacatc cggctgacca agggcgagat cgagggctac  480
gccgccatca gcaacatgtt cggcaacggc gagaaggagg accggagcaa gagcggatg  540
tacgccaccc ggatgaagga ctggctggag gccaacgaga acatcacctg ggagcagtac  600
cggggaggcc tgaagaacca gctgaacgcc aagaacctgg agcaggtggt ggccaactac  660
aagggcaacg ccggccggcg cgacccctc ttcaagtaca gcttcagcaa ggagggcatg  720
gtgagcaaga aggagcacgc ccagcagctg acaagttca agaccgtgct gaagaacaag  780
gcccgggacc tgaacttccc caacaaggag aagctgaagc agtacctgga ggccgagatc  840
ggcatccccg tggacgccaa cgtgtacagc cagatgttca gcaacggcgt gagcgaggtg  900
cagcccaaga ccaccggaa catgagcttc agcaacggaa agctggacct gctgaccgag  960
ctgaaggacc tgaacaaggg cgacggcttc gagtacgccc gggaggtgct gaacggcttc 1020
ttcgacagcg agctgcacac caccgaggac aagttcaaca tcaccagccg gtacctgggc 1080
ggcgacaaga gcaaccggct gagcaagctg tacaagatct ggaagaagga gggcgtggac 1140
tgcgagagg gcatccagca gttctgcgag gccgtgaagg acaagatgg ccagatcccc 1200
atccggaacg tgctgaagta cctgtgcag ttcggggaga ccgtgagcgc cgaggacttc 1260
gaggccgccg ccaaggccaa ccacctggag gagaagatca gccgggtgaa ggcccacccc 1320
atcgtgatca gcaaccggta ctgggccttc ggcaccagcg ccctggtggg caacatcatg 1380
cccgccgaca agcggcacca gggcgagtac gccggccaga acttcaagat gtggctgcgg 1440
gccgagctgc actacgacgg caagaaggcc aagcaccacc tgcccttcta caacgcccgg 1500
ttcttcgagg aggtgtactg ctaccacccc agcgtggccg agatcacccc cttcaagacc 1560
aagcagttcg gctgcgagat cggcaaggac atccccgact acgtgagcgt ggccctgaag 1620
gacaaccct acaagaaggc catcaagcgg atcctgcggg ccatctacaa ccccgtggcc 1680
aacaccaccc gggtggacaa gaccaccaac tgcagcttca tgatcaagcg ggagaacgac 1740
gagtacaagc tggtggatcaa ccggaagatc agccggacc ggcccaagcg gatcgaggtg 1800
ggccggacca tcatgggcta cgaccggaac cagaccgcca gcgacaccta ctggatcggc 1860
cggctggtgc ccccgggcac ccggggcgcc taccggatcg gcgagtggag cgtgcagtac 1920
atcaagagcg gcccgtgct gagcagcacc cagggcgtga acaacagcac caccgaccag 1980
ctggtgtaca acggcatgcc cagcagcagc gagcggttca aggcctggaa gaaggcccgg 2040
atggccttca tccggaagct gatccggcag ctgaacgacg agggcctgga gagcaagggc 2100
caggactaca tccccgagaa ccccagcagc ttcgacgtgc gggcgagac cctgtacgtg 2160
ttcaacagca actacctgaa ggccctggtg agcaagcacc ggaaggccaa gaagcccgtg 2220
gagggcatcc tggacgagat cgaggcctgg accagcaagg acaaggacag ctgcagcctg 2280
atgcggctga gcagcctgag cgacgccagc atgcagggca tcgccagcct gaagagcctg 2340
atcaacagct acttcaacaa gaacggctgc aagaccatcg aggacaagga agttcaac 2400
cccgtgctgt acgccaagct ggtggaggtg agcagcggc agcaacaa gcggagcgag 2460
aaggtgggcc ggatcgccgg cagcctggag cagctggccc tgctgaacgg cgtggaggtg 2520
gtgatcggcg aggccgacct gggcgaggtg gagaagggca agagcaagaa gcagaacagc 2580
cggaacatgg actggtgcgc caagcaggtg gcccagcggc tggagtacaa gctggccttc 2640
cacggcatcg gctacttcgg cgtgaacccc atgtacaacca gccaccagga cccttcgag 2700
caccggcggg tggccgacca catcgtgatg cgggcccggt tcgaggaggt gaacgtggag 2760
aacatcgccg agtggcacgt gcggaacttc agcaactacc tgcgggccga cagcggcacc 2820
ggcctgtact acaagcaggc caccatggac ttcctgaagc actacggcct ggaggagcac 2880
gccgaggcc tggagaacaa gaagatcaag ttctacgact tccggaagat cctggaggac 2940
aagaacctga ccagcgtgat catccccaag cggggcggcc ggatctacat ggccaccaac 3000
cccgtgacca gcgacagcac ccccatcacc tacgccggca agacctacaa ccggtgcaac 3060
gccgacgagg tggccgccgc caacatcgtg atcagcgtgc tggcccccg agcaagaag 3120
aaccgggagc aggacgacat cccctgatc accaagaagg ccgagagcaa gagcccccc 3180
aaggaccgga gcggagcaa gaccagccag ctgcccaga ag                       3222

SEQ ID NO: 225         moltype = DNA   length = 3222
FEATURE                Location/Qualifiers
misc_feature           1..3222
                       note = Synthetic Construct
source                 1..3222
                       mol_type = other DNA
                       organism = synthetic construct
SEQUENCE: 225
atggcctcaa taagtcggcc gtacggaaca aaactcagac cagatgccag gaaaaaggaa   60
atgctcgata aattcttcaa taccctgaca aaaggacagc gagtctttgc ggatcttgcg  120
ctctgtattt atggttcact gacactggag atggcgaagt cactcgagcc agaatcagat  180
agtgaacttg tatgtgccat cggctggttt agattggtgg acaagactat atggagcaag  240
gatggcatca agcaagaaaa cttggtcaag cagtacgagg cgtatagtgg taaagaggcg  300
tcagaggtcg tgaaaacgta tcttaacagt cctagttcag acaagtatgt ctggatagac  360
tgtcgccaaa agtttcttcg cttccagcgg gaactcggga cccgaaatct tagtgaggac  420
tttgagtgca tgttgttcga acaatatatc cggctgacta aggtgagat cgaggatac  480
gccgcaatta gtaacatgtt cggaaacgga gaaaaggagg ataggtctaa gaagcggatg  540
tacgcgacac gaatgaagga ttggctgaa gcaaatgaga acatcacctg ggagcagtat  600
agggaggctt tgaaaaatca actgaatgct aaaaacttgg agcaagtcgt cgcaaattat  660
aagggaaacg caggtggcgc cgacccattc tttaagtata gcttcagtaa ggaaggaatg  720
gtttcaaaga aagagcacgc ccagcagctt gataagttca gaccgtact gaaaaataaa  780
gcgcgggacc tcaatttccc taataaggaa aaattgaagc aatacttgga ggctgagatt  840
```

```
ggtataccgg tagatgcaaa tgtctatagc caaatgttta gtaacggtgt gagtgaggta    900
caaccaaaga caacgcgaaa tatgagtttt tcaaatgaga agttggatct tttgacggaa    960
ttgaaggatc ttaacaaggg tgacggcttc gagtacgctc gggaagtctt gaacggtttt   1020
tttgattccg agttgcacac cactgaggac aagtttaaca tcaccagtcg atacctgggg   1080
ggcgataaat ctaacaggct cagtaaaactc tacaagatat ggaagaaaga aggagtcgat   1140
tgcgaggaag gtatccaaca gttctgcgaa gctgtgaagg acaaaatggg acaaatcccc   1200
ataaggaatg tgcttaaata tctttggcag ttccgcgaaa cagtcagtgc agaagacttc   1260
gaagctgcga ccaaagccaa ccacctcgaa gagaaaatca gcagagtaaa agcgcatcct   1320
atcgtcataa gtaatcgcta ctgggcgttt ggtacttctg cgctcgttgg gaatatcatg   1380
ccggcagaca aaagcacaca aggggagtac gctgggcaaa atttcaaaat gtggctcagg   1440
gcggagctcc attatgatgg aaagaaagca aagcatcatc tgccttttta taacgcgcgg   1500
ttctttgaag aagtctactg ttatcatcca agcgtagctg aaataacgcc ctttaaaact   1560
aaacagtttg ggtgcgaaat agggaaagat attcccgatt atgtgtccgt ggcgctgaaa   1620
gataatccat acaaaaaggc tacgaacgg atcctgcgcg ccatttataa tcccgtcgcg   1680
aacaccaccc gcgtggataa acaactaat tgttccttta tgataaagcg cgaaaacgat   1740
gagtataaac tggtcattaa ccgcaagatc tctcgagaca ggccaaaacg catagaggta   1800
ggccgaacca ttatgggtta tgacaggaat cagaccgcct ctgatacata ttggattggg   1860
aggctcgtgc ctcctggtac gaggggcgct taccgcattg gagaatggtc agtgcagtac   1920
atcaagtccg ggcccgtgct tagttctacc caagggggtta ataactcaac tacggaccaa   1980
ctggtgtata acggaatgcc aagtagttcc gaacggttta aagcatggaa gaaggctaga   2040
atggcgttta tacggaaact catacgacaa ttgaatgatg agggacttga gagcaagggt   2100
caagattaca tcccagagaa tccaagctct tttgacgtca ggggtgagac actgtatgtt   2160
ttcaatagca actatttgaa agcactcgtt tctaaacacc ggaaggccaa aaaacctgtg   2220
gaagggatac tcgacgagat tgaagcctgg acttctaaag ataaagatag ttgttccctt   2280
atgcggctct ctagcttgag cgatgcgtca atgcaaggga ttgcctcttt gaaaagtctc   2340
atcaacagct acttcaataa gaacggttgc aagacgatcg aggataagga gaagttcaat   2400
cctgttttgt atgccaaatt ggtagaagtg gagcagagaa gaactaacaa gatctcgag   2460
aaggtaggca ggattgccgg atcccttgaa cagctggcac tccttaatgg ggtcgaagtg   2520
gtcattggtg aagccgacct tggcgaagtc gaaaagggca agtccaagaa gcagaacagt   2580
cgcaacagtg attggtgcgc aaaacaggta gcacaaaggc tcgaatataa gctcgccttc   2640
cacggcattg ggtacttcgg cgttaaccca atgtacacca gtcaccaaga cccctttgag   2700
catagaagag tagcagatca tatagtgatg agggccagat tcgaagaagt gaacgtcgag   2760
aatatcgcag aatggcacgt aaggaatttc tccaattatc tgcgcgctga ttctggtaca   2820
ggcctctact acaagcaggc caccatggat ttctgaaact acgggct cgaggagcac   2880
gccgaaggtc tggagaataa gaagattaag ttttatgact tccgaaagat tctgaggac   2940
aagaatctta cctccgtgat catcccaaag cgaggggac gcatctatat ggctaccaat   3000
cccgtgacta gcgacagcac tccaataacg tatgccggca aaacctacaa tcgctgtaac   3060
gctgacgagg tggctgccgc caatatagtc atatccgtgc ttgctcccg aagtaaaaag   3120
aatcgggagc aagacgatat tcctttgata acgaaaaaag ccgagagtaa atctccaccc   3180
aaagatcgga agagatcaaa gacctcacaa ctcccgcaaa ag                     3222

SEQ ID NO: 226         moltype = DNA length = 3222
FEATURE                Location/Qualifiers
misc_feature           1..3222
                       note = Synthetic Construct
source                 1..3222
                       mol_type = other DNA
                       organism = synthetic construct
SEQUENCE: 226
atggcatcta tcagcagacc atacggaacc aaactgagac cagatgctcg gaaaaaggag     60
atgctgaca agttcttcaa caccctgacc aaggggacaga gggtgttcgc cgatctgcgn    120
ctgtgcatct acggctctct gaccctggaa atggctaagt cgctcgaacc tgagagcgac    180
tccgagctgg tttgtgccat tggatggttc agactggtcg ataagaccat ctggagcaag    240
gacggcatca agcaggagaa cctggtgaaa cagtacgagg cctacagcgg caaggaggcg    300
tctgaagtcg tgaagaccta cctgaacagc ccttctagtc ataagtacgt gtggatcgac    360
tgtagacaga agttcctgag atttcagcgg gaactgggca ccagaaacct gagcgaggac    420
tttgaatgca tgctgttcga gcagtacatc agactgacca agggcgaaat cgagggatat    480
gccgccatta gcaacatgtt cggcaacggc gagaaagagg atagaagcaa gaagagaatg    540
tacgctacac ggatgaagga ctggctggag gccaacgaga acatcacctg ggagcagtat    600
agagaagccc tgaagaacca gctgaacgcc aagaacctcg agcaggtgg ggctaactac    660
aagggcaacg ccggcggcgc cgatcctttc ttcaagtact ccttcagcaa ggagggcatg    720
gtgtccaaga aggagcatgc ccagcaactg gacaaattca agacagtgct gaagaacaag    780
gcccgggatc tgaacttccc caacaaggag aagctcaaac agtacctgga agccgagatc    840
ggcatccccg tcgacgccaa tgtgtactct cagatgttct ccaacggcgt gtctgaagtg    900
caacctaaga caacaagaaa tatgagcttt agcaatgaaa agctggacct gctgacagaa    960
ctgaaagatc tgaacaaagg cgatgggttc gaatacgccc gcgaagtgct gaacgggttc   1020
tttgattctg agctgcacac gacagaagat aagttcaata tcacctcgcg gtaccctgga   1080
ggcgacaaga gcaatagact gagcaagctg tataagatct ggaagaagga gggcgtggac   1140
tgcgaggagg gcatccaaca gttctgcgag gctgtgaagg ataagatggg ccaaatccct   1200
atcaggaacg ttctcaagta cctgtggcag ttcagagaaa ccgtgagcgc cgaggatttc   1260
gaggccgccg ctaaggccaa ccacctggag gagaagatca gcagagtgaa gcccacccct   1320
atcgtgatca gcaacagata ctgggccttc ggcacctctg ctctggtcgg aaatatcatg   1380
cccgccgata agcggcacca gggcgagtac gccggccaga acttcaagat gtggctgcgg   1440
gccgaactic attacgacgg caaaaaggct aaacaccacc tgccttttca caacgccaga   1500
ttcttcgagg aggtgtactg ctaccacccc agcgtggccg aaatcacacc tttcaagact   1560
aagcagtttg gatgtgaaat cggtaaggat atccccgact acgtcagcgt ggcactgaaa   1620
gacaacccttt acaaaaagc taccaaacgg attctgagag ccatctacaa ccccgttgcc   1680
aataccacaa gagtggacaa aacaaccaac tgctctttca tgatcaaaag agagaatgac   1740
gaatacaagc tggtaataaa cagaaagatc agcagagacc ggcctaagcg catcgagtg   1800
```

```
ggaagaacca ttatgggcta cgatagaaac cagaccgcca gcgatacota ctggatcggc  1860
agactggtgc cccctggcac aagaggcgcg tacagaatcg gcgaatggtc cgtgcagtac  1920
atcaagagcg gccctgtgct gagctctacc cagggagtga acaacagcac caccgatcag  1980
ctggtgtaca acgtatgcc tagcagcagc gagcggttca aggcatggaa gaaggcccgg  2040
atggccttca tccggaagct gatcagacag ctgaatgacg agggcctgga agcaagggga  2100
caggactaca tcccagagaa ccctagcagc ttcgacgtgc ggggcgagac gctgtacgtg  2160
ttcaacagca actatctgaa agccctggtc agcaagcaca gaaaggccaa gaagcccgtg  2220
gaaggtatcc tggatgagat cgaggcctgg accagcaagg acaaggacag ctgcagcctg  2280
atgcggctgt cttctctgag cgacgcctcc atgcagggga tcgccagcct gaaaagcta  2340
atcaacagct actttaacaa gaaccgctgc aagacaatcg aggacaagga aaagtttaac  2400
cctgtgctgt atgccaaact ggtggaggtg aacagcggc ggaccaacaa gcggagcgaa  2460
aaagtgggca gaatcgccgg aagcctggag cagcttgccc tgctgaatgg cgtggaagtg  2520
gtgataggcg aggccgacct gggcgaagtg gagaagggca agagccaagaa gcagaactcc  2580
agaaacatgg actggtcgc caaacaggtg gcccagaagc tggaatataa gctggctttt  2640
cacggcatcg gctacttcgg cgttaatcct atgtacacca gccaccagga ccccttcgag  2700
caccggagag tggccgacca catagtgatg agagcccggt tcgaggaagt gaacgtggag  2760
aacatcgccg agtggcacgt gcggaatttt tctaattacc tgagagccga cagcggaaca  2820
ggcctgtact acaagcaggc cacaatggac ttcctgaagc tacggcct ggaagagcac  2880
gccgagggcc tggaaaacaa gaagatcaag ttctacgact tccggaaaat cctgggagat  2940
aagaacctca cctctgtcat catccctaag cgaggcggaa gaatctacat ggccacaaac  3000
ccagtgacca gcgactccac ccctatcacc tacgccggca agacatacaa caggtgtaac  3060
gccgacgaag tggccgctgc caacatcgtg atctctgtgc tggtcctag atcaaagaag  3120
aatagagaac aagacgacat tcccctgatc acaaagaaag cagagagcaa gtccccacct  3180
aaggacagaa agagaagcaa aacctcccag ttgcctcaaa aa  3222

SEQ ID NO: 227           moltype = DNA    length = 3222
FEATURE                  Location/Qualifiers
misc_feature             1..3222
                         note = Synthetic Construct
source                   1..3222
                         mol_type = other DNA
                         organism = synthetic construct SEQUENCE: 227
atggcctcaa tctctaggcc atatgggacc aaattgagac ctgatgctcg aaaaaaggag  60
atgctggata agttttttcaa cacacttacc aaaggccaga gagtattcgc tgacctggct  120
ctgtgtatct atggctctct gaccctggag atggccaaat ctctggagcc tgagagcgat  180
tccgaacttg tgtgcgctat tggttggttc aagctggttg acaaaacaat ctggtctaaa  240
gatggaatta agcaggaaaa cctggtgaag caatatgagg catattcagg aaaagaggct  300
tccgagctgg ttaagactta ccttaactca ccatcaagtg ataagtacgt ctggatcgac  360
tgtaggcaga aatttctgcg cttttcagagg gaactcggca ctcgcaatct gtccgaagat  420
tttgagtgca tgctgtttga acagtatatc cgcctcacaa agggcgaaat tgagggttac  480
gctgcaatct ccaacatgtt cggtaatggc gagaaggaag ataggtccaa gaagcgcatg  540
tacgcaacac gaatgaaaga ctggctcgaa gccaacgaga atattacatg gacgcagtac  600
cgggaagctc tgaagaatca actcaatgcg aaaaaactgg aacaggtggt tgcgaattac  660
aaagggaatg ctggtggtgc tgaccccttc tttaaatact ccttctcaaa ggagggtatg  720
gtttcaaaga aagagcatgc tcagcagctc gacaagttca gacagtgtt gaagaataag  780
gccaggagatt tgaacttccc aaacaaagaa aagctcaaca aatacctgga agctgagatt  840
ggcattcccg ttgatgctaa cgtgtacagc caaatgttct ccaatggcgt cagtgaggtc  900
caaccgaaaa caacaagaaa catgtccttc tctaacgaga agctcgatt gttgactgaa  960
ttgaaggatc tgaacaaagg agacggcttc gaatatgctc gggaagtgtt gaacggcttt  1020
ttcgacagcg agttgcacac tactgaagat aaattcaaca tcacctctag gtatctcggc  1080
ggggataaga gcaatagact ctctaagttg tacaagatat ggaaaaagga gggcgttgat  1140
tgtgaggagg aatccagca gttcctgtgag gccgtgaagg acaagatggg tcaaatccct  1200
atccggaacg tgctgaagta cctgtggcaa ttccagaga cggtgtccgc tgaagatttt  1260
gaggccgctg ccaaagcaaa tcacctggag gagaagtata gtagggtgaa ggcacaccct  1320
atcgtgatta gtaacagata ttgggcattt ggaacctcag cgttggttgg aaacattatg  1380
cccgctgata aagacatca aggagagtat gccgggcaga atttcaaaat gtggctccgc  1440
gcagaactcc actatgacgg gaaaaaggcc aagcatcact tgccatttta caacgcccgc  1500
ttcttcgagg aggtctattg ctaccacccc tccgtcgcag agatcacacc atttaaacc  1560
aaacagtttg gttgcgagat cgggaaggac attccagatt acgtaagcgt cgcacttaaa  1620
gacaatcctt acaagaaggc gacaaaaagg atcctcagag ccatttataa ccccgtggcc  1680
aacaccacaa gggtggacaa gactaccaac tgttccttca tgattaagcg ggagaacgac  1740
gagtacaaat tggtgattaa ccgcaagatt agcagagaca gaccaaaaag gattgaagta  1800
ggacggacca tcatggggta tgatcggaat cagactgcga gcgatacata ctggatcgga  1860
agattggtgc cacctggtac caggggagca taccggatcg agagtggtc tgtacagtac  1920
attaaatctg gccccgtgct ttcctctacc cagggcgtta caactctac tacagaccag  1980
ctcgtttaca acggaatgcc aagttcttcc gaaagattta aggcctggaa aaaggcccgg  2040
atggccttca tccgaaagct gatcgcgcag ctgaatgacg aagggttgga atctaagggc  2100
caggactaca ttcctgagaa tcctagcagt tttgatgctc gcggagagac gctgtacgtg  2160
ttaattcta actatcttaa agccctcgtg agtaagcata ggaaggctaa aaaaccagtc  2220
gaaggtatat tggacgaaat cgaagcatgg accagcaagg acaaagactc ttgttctctg  2280
atgcgactgt ccagcttgag cgatgcttcc atgcagggca ttgcaagcct gaaaagtctt  2340
attaacagct acttcaacaa aaatgggtgc aaaactatcg aggacaaaga gaagtttaac  2400
cccgtgctct atgcaaagtt ggttgaagtg agcagcgac ggaacaaataa acggagtgag  2460
aaggtcggac ggattgctgg gagcctcgaa caattggccc tgttgaatgg ggtgaaggtg  2520
gtgatcgggg aagcagacct ggagaagta gagaagggca aaagtaaaaa gcagaattcc  2580
cgaaatatcg attggtgtgc caaacaggtg gctcagaggc tggagtataa actgccttt  2640
catggtatcg ggtatttcgg cgtgaatcct atgtacacca gtcatcagga cccgtttgaa  2700
cacaggaggg tcgctgacca tattgtgatg agagccaggt ttgaagaagt caatgtagag  2760
```

```
aacatcgccg aatggcacgt gcgaaatttc tcaaactatc tccgggccga ctccggaacg  2820
ggtctttatt acaaacaagc taccatggat ttcctgaagc attacggcct ggaagagcat  2880
gccgagggtc tggaaaacaa gaagataaaa ttctacgatt tccggaagat cctcgaggac  2940
aagaacctga cctccgtcat cattcccaaa cggggtggac gaatctacat ggccacaaat  3000
cccgttacgt ccgacagcac ccctattaca tacgccggca agacctataa ccggtgcaac  3060
gcagatgaag tcgccgctgc aaatatagtt atctccgttc tggccccgag gtccaagaaa  3120
aacagagaac aggacgacat ccccctgatt accaaaaaag ctgagtcaaa atctccgccc  3180
aaagacagga agcggagcaa gacctcccag ctgccccaga ag                    3222

SEQ ID NO: 228          moltype = DNA   length = 3222
FEATURE                 Location/Qualifiers
misc_feature            1..3222
                        note = Synthetic Construct
source                  1..3222
                        mol_type = other DNA
                        organism = synthetic construct
SEQUENCE: 228
atggcttcaa tttcccgccc ctatggcact aagctgcgcc ctgacgcccg gaaaaaggag    60
atgctggaca gttttttaa tacactgacc aagggacagc gcgtgttcgc cgacctggcc   120
ctgtgtatct acggctctct gacgctggag atggctaagt ccctggagcc cgagtctgac   180
tctgagctgg tgtgcgctat cgggtggttc agactggtgg ataagaccat ctggtctaaa   240
gatggcatta gcaggagaa cctggtgaag caatacgagg cctactcagg gaaggaggcc    300
agcgaagtgg tgaaaaccta cctcaatagc ccaagcagcg acaagtacgt gtggattgat   360
tgccgccaga agtttctccg cttccagcgg gagctgggga ctaggaatct gacgaagat    420
tttgagtgca tgctgtttga acagtacatc cggctgacta aagggagat cgagggctat    480
gccgccatca gcaacatgtt tggcaacggg gagaaagagg acagaagtaa aaaacggatg   540
tatgcaaccc gcatgaagga ctggctggaa gccaatgaga acatcacctg gaacagtat    600
cgcgaagctc tgaagaacca gctgaatgcc aagaatctgg aacaggtggt ggccaattac   660
aaagggaacc ccggcgggc cgatcccttc ttcaaatact ctttcagtaa ggaaggcatg    720
gtgagtaaga aggagcacgc ccagcagctg gataagttta aaacggtgct caagaacaag   780
gccagggacc tgaactttcc caataaggag aagctgaagc agtacctgga ggccgagatc   840
ggcatccccg tggacgcgaa cgtgtactcc cagatgttca gcaatggagt gagcgaggtg   900
cagcccaaga ccacccggaa catgagcttt ctctaacgaaa aactggacct gctgaccgag   960
ctgaaggacc tgaataaggg cgacggattt gagtacgcac gggaagtgct gaatggcttc  1020
tttgatagca agctgcacac cacagaggat aagttcaata tcacctccag gtacctggga  1080
ggcgataaga gcaacagact ctctaagctg tataagattt ggaagaagga aggggtggac  1140
tgcgaggagc gcatccagca gttctgcgag gccgtgaagg acaagatggg ccagatccct  1200
atcagaaacg tgctgaagta tctgtgcag ttccgcaaga ccgtgagcgc cgagactttt  1260
gaggccgccg ctaaggctaa ccacctgaaa gaaaagatct cccgggtgaa agcccacccct  1320
attgtgatct ccaatagata ctgggccttc ggaacttctg ccctggtggg aaatatcatg  1380
cccgccgaca aaagacacca gggggagtat gctggccaga acttcaagat gtggcttagg  1440
gccgagctgc actatgatgg caagaaggcc aagcatcacc tgcctttcta caatgctaga  1500
ttctttgaag aggtgtactg ttaccaccct agcgtggccg agatcacccc ctttaagact  1560
aaacagtttg gctgtgagat tggcaaggac atccccgatt acgtgagcgt ggctctgaag  1620
gacaacccat ataagaaagc caccaaacgc atcctccggg ctatctataa ccccgtggcc  1680
aatactaccc gggtgaacaa gacaaccaac tgtagcttca tgatcaaaag agagaacgac  1740
gagtataagc tggtgatcaa cagaaaaatc tcccgggacc gccccaaaag gattgaggtg  1800
ggacgcacca ttatgggata cgataggaac cagaccgcct cagacaccta ctggatcggc  1860
cggctggtgc tcctggcac tagggggcc taccgcatcg cgaatggtc cgtgcagtac     1920
attaaatccg gccccgtgct gagctccaca cagggagtga ataattccac caccgaccag  1980
ctggtgtaca acggcatgcc cagcagcgc gagcggttca aggcctggaa gaaggcccag  2040
atggcttta tacgaagct gatccgccaa ctgaacgatg agggcctgga atccaagggc     2100
caggactaca ttcccgaaaa cccttcatcc ttcgacgtga gaggcgaaac tctgtacgtg  2160
ttcaattcca actacctcaa ggccctggtg tctaagcaca ggaaggccaa gaagcccgtg  2220
gaaggcatcc tggacgagat tgaggcatgg accagcaagg acaaggatag ctgttctctc  2280
atgagactga gcagcctgtc cgatgcaagc atgcagggga tcgcctccct gaagagcctg  2340
attaactctt actttaacaa aaatggctgc aagaccatcg aggataaaga gaagtttaat  2400
cccgtgctgt acgcaaaact cgtggaggtg gagcagagcc gcaccaacaa gaggacgagg  2460
aaagtgggc ggatcgctgg aagtctggaa cagctggccc tgctgaacgg cgtggaggtc    2520
gtgattggcg aagcggacct gggcgaggtg gagaagggga gtctaagaa gcagaactct   2580
aggaatatgg actggtgcgc caagcaggtg gcccagagac tggaatacaa actgccttt   2640
catggcattg gatacttcgg cgtgaatcct atgtacacat cacccaggga tccattcgag  2700
cacaggagag tggccgacca catcgtgatg agagccagat tcgaggaggt gaacgtggag  2760
aacatcgcag agtggcacgt gaggaacttt tccaactatc tgcgggccga ctctgggact  2820
ggactgtatt acaagcaggc caccatggac ttcctgaagc actatggcct gggaggagcc  2880
gctgaagggc tggaaaacaa gaaaataaag ttttacgact tccggaagat tctggaggat  2940
aagaacctga cctctgttat catcccaaag cggggcggca gaatctacat ggccaccaac  3000
cccgtgacct ccgacagcac ccccattacc tacgccggaa agacataaa cagatgcaat  3060
gctgacgagg tggccgccgc caacatagtg atttccgtgc tggccccaag gagtaagaag  3120
aaccgagagc aggacgacat tccactgatt accaagaagg ctgaatccaa atccccacca  3180
aaggacagga gaggagcaa gacctctcag ctgcctcaga ag                     3222
```

COMPOSITIONS COMPRISING A VARIANT CAS12I4 POLYPEPTIDE AND USES THEREOF

RELATED APPLICATIONS

The instant application is a continuation of International Patent Application No. PCT/US2022/016214 filed Feb. 11, 2022, which claims priority to U.S. Ser. No. 63/148,421, filed Feb. 11, 2021, and U.S. Ser. No. 63/154,437, filed Feb. 26, 2021. The contents of each of these prior applications are incorporated herein by reference in their entireties.

SEQUENCE LISTING

The instant application contains a Sequence Listing which has been submitted electronically in XML format and is hereby incorporated by reference in its entirety. Said XML copy, created on Dec. 29, 2022, is named A2186-706120FT_SL.xml, and is 382,906 bytes in size.

BACKGROUND

Clustered Regularly Interspaced Short Palindromic Repeats (CRISPR) and CRISPR-associated (Cas) genes, collectively known as CRISPR-Cas or CRISPR/Cas systems, are adaptive immune systems in archaea and bacteria that defend particular species against foreign genetic elements.

SUMMARY OF THE INVENTION

It is against the above background that the present invention provides certain advantages and advancements over the prior art. Although this invention disclosed herein is not limited to specific advantages or functionalities, the invention a variant Cas12i4 polypeptide comprising a sequence having at least 95% identity to a sequence set forth in any one of SEQ ID NOs: 3-59.

In one aspect of the variant, the variant Cas12i4 polypeptide is a variant of a parent polypeptide of SEQ ID NO: 2.

In another aspect of the variant, the variant Cas12i4 polypeptide comprises a substitution of Table 2.

In another aspect of the variant, the variant comprises the sequence set forth in any one of SEQ ID NOs: 3-59.

In another aspect of the variant, the variant comprises the sequence set forth in SEQ ID NO: 3.

In another aspect of the variant, the variant comprises the sequence set forth in SEQ ID NO: 4.

In another aspect of the variant, the variant Cas12i4 polypeptide exhibits increased binary complex formation with an RNA guide, relative to a parent polypeptide.

In another aspect of the variant, a binary complex comprising the variant Cas12i4 polypeptide exhibits increased stability, relative to a parent binary complex.

In another aspect of the variant, the variant Cas12i4 polypeptide exhibits increased nuclease activity, relative to a parent polypeptide.

In another aspect of the variant, the variant Cas12i4 polypeptide further comprises a substitution of Table 4.

In another aspect of the variant, the substitution of Table 4 increases binary complex formation with an RNA guide, relative to a parent polypeptide.

In another aspect of the variant, the substitution of Table 4 increases stability of a binary complex comprising the variant Cas12i4 polypeptide, relative to a parent binary complex.

In another aspect of the variant, the variant Cas12i4 polypeptide further comprises a substitution that increases ternary complex formation with an RNA guide and a target nucleic acid, relative to a parent polypeptide.

In another aspect of the variant, the variant Cas12i4 polypeptide further comprises a substitution that increases ternary complex stability, relative to a parent polypeptide.

In another aspect of the variant, the substitution is a substitution of Table 5, Table 6, Table 7, Table 8, Table 9, and/or Table 10.

In another aspect of the variant, the variant Cas12i4 polypeptide further comprises a substitution that increases on-target binding to a target nucleic acid, relative to a parent polypeptide.

In another aspect of the variant, the substitution is a substitution of Table 11.

The invention yet further provides a composition comprising a variant Cas12i4 polypeptide as described herein, wherein the composition further comprises an RNA guide or a nucleic acid encoding the RNA guide, wherein the RNA guide comprises a direct repeat sequence and a spacer sequence.

In one aspect of the composition, the direct repeat sequence comprises:
a. nucleotide 1 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
b. nucleotide 2 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
c. nucleotide 3 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
d. nucleotide 4 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
e. nucleotide 5 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
f. nucleotide 6 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
g. nucleotide 7 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
h. nucleotide 8 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
i. nucleotide 9 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
j. nucleotide 10 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
k. nucleotide 11 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
l. nucleotide 12 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
m. nucleotide 13 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
n. nucleotide 14 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124; or
o. a sequence that is at least 90% identical to a sequence of SEQ ID NO: 61 or a portion thereof. In another aspect of the composition, the direct repeat sequence comprises:
a. nucleotide 1 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
b. nucleotide 2 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
c. nucleotide 3 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
d. nucleotide 4 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
e. nucleotide 5 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
f. nucleotide 6 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
g. nucleotide 7 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
h. nucleotide 8 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
i. nucleotide 9 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
j. nucleotide 10 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
k. nucleotide 11 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
l. nucleotide 12 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
m. nucleotide 13 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
n. nucleotide 14 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124; or
o. a sequence that is at least 95% identical to a sequence of SEQ ID NO: 61 or a portion thereof. In another aspect of the composition, the direct repeat comprises:
a. nucleotide 1 through nucleotide 36 of any one of SEQ ID NOs: 60, 108, 109, 110, 111, 112, 113, 114, 115, 116, 117, 118, 119, 120, 121, 122, 123, or 124;
b. nucleotide 2 through nucleotide 36 of any one of SEQ ID NOs: 60, 108, 109, 110, 111, 112, 113, 114, 115, 116, 117, 118, 119, 120, 121, 122, 123, or 124;
c. nucleotide 3 through nucleotide 36 of any one of SEQ ID NOs: 60, 108, 109, 110, 111, 112, 113, 114, 115, 116, 117, 118, 119, 120, 121, 122, 123, or 124;
d. nucleotide 4 through nucleotide 36 of any one of SEQ ID NOs: 60, 108, 109, 110, 111, 112, 113, 114, 115, 116, 117, 118, 119, 120, 121, 122, 123, or 124;
e. nucleotide 5 through nucleotide 36 of any one of SEQ ID NOs: 60, 108, 109, 110, 111, 112, 113, 114, 115, 116, 117, 118, 119, 120, 121, 122, 123, or 124;
f. nucleotide 6 through nucleotide 36 of any one of SEQ ID NOs: 60, 108, 109, 110, 111, 112, 113, 114, 115, 116, 117, 118, 119, 120, 121, 122, 123, or 124;
g. nucleotide 7 through nucleotide 36 of any one of SEQ ID NOs: 60, 108, 109, 110, 111, 112, 113, 114, 115, 116, 117, 118, 119, 120, 121, 122, 123, or 124;
h. nucleotide 8 through nucleotide 36 of any one of SEQ ID NOs: 60, 108, 109, 110, 111, 112, 113, 114, 115, 116, 117, 118, 119, 120, 121, 122, 123, or 124;
i. nucleotide 9 through nucleotide 36 of any one of SEQ ID NOs: 60, 108, 109, 110, 111, 112, 113, 114, 115, 116, 117, 118, 119, 120, 121, 122, 123, or 124;
j. nucleotide 10 through nucleotide 36 of any one of SEQ ID NOs: 60, 108, 109, 110, 111, 112, 113, 114, 115, 116, 117, 118, 119, 120, 121, 122, 123, or 124;
k. nucleotide 11 through nucleotide 36 of any one of SEQ ID NOs: 60, 108, 109, 110, 111, 112, 113, 114, 115, 116, 117, 118, 119, 120, 121, 122, 123, or 124;
l. nucleotide 12 through nucleotide 36 of any one of SEQ ID NOs: 60, 108, 109, 110, 111, 112, 113, 114, 115, 116, 117, 118, 119, 120, 121, 122, 123, or 124;
m. nucleotide 13 through nucleotide 36 of any one of SEQ ID NOs: 60, 108, 109, 110, 111, 112, 113, 114, 115, 116, 117, 118, 119, 120, 121, 122, 123, or 124;
n. nucleotide 14 through nucleotide 36 of any one of SEQ ID NOs: 60, 108, 109, 110, 111, 112, 113, 114, 115, 116, 117, 118, 119, 120, 121, 122, 123, or 124; or
o. SEQ ID NO: 61 or a portion thereof.

In another aspect of the composition, the direct repeat sequence comprises $AGN_1N_2N_3N_4GUGUN_5N_6N_7CAGN_8GACN_9C$ (SEQ ID NO: 125), wherein $N_1$ is A or G, $N_2$ is C or U, $N_3$ is A or G, $N_4$ is U or C, $N_5$ is C or U, $N_6$ is C or U, $N_7$ is U, A, C, or G, $N_8$ is U or C, and $N_9$ is A or C.

In another aspect of the composition, the spacer sequence comprises about 15 nucleotides to about 35 nucleotides in length.

In another aspect of the composition, the spacer sequence binds to a target strand sequence of a target nucleic acid, and a non-target strand sequence of the target nucleic acid sequence is adjacent to a protospacer adjacent motif (PAM) sequence.

In another aspect of the composition, the PAM sequence is 5'-TTN-3', 5'-NTTN-3', 5'-NTN'-3', 5'-NNTN-3', 5'-VTN-3', or 5'-NVTN-3', wherein N is any nucleotide and V is A, G, or C.

In another aspect of the variant or the composition, the variant Cas12i4 polypeptide further comprises a nuclear localization signal (NLS).

In another aspect of the variant or the composition, the variant Cas12i4 polypeptide further comprises a peptide tag, a fluorescent protein, a base-editing domain, a DNA methylation domain, a histone residue modification domain, a localization factor, a transcription modification factor, a light-gated control factor, a chemically inducible factor, or a chromatin visualization factor.

The invention yet further provides a nucleic acid that encodes a Cas12i4 polypeptide or a composition as described herein.

In one aspect of the composition, the nucleic acid is codon-optimized for expression in a cell.

In another aspect of the composition, the nucleic acid is operably linked to a promoter.

In another aspect of the composition, the nucleic acid is in a vector.

In another aspect of the composition, the vector comprises a retroviral vector, a lentiviral vector, a phage vector, an adenoviral vector, an adeno-associated vector, or a herpes simplex vector.

In another aspect of the variant or the composition, the variant Cas12i4 polypeptide is present in a delivery system comprising a nanoparticle (e.g., a lipid nanoparticle), a liposome, an exosome, a microvesicle, or a gene-gun.

The invention yet further provides a cell comprising a variant Cas12i4 polypeptide or a composition as described herein.

In one aspect of the cell, the cell is a eukaryotic cell.

In another aspect of the cell, the cell is a mammalian cell or a plant cell.

In another aspect of the cell, the cell is a human cell.

The invention yet further provides a composition comprising a variant Cas12i4 polypeptide or a complex comprising the variant Cas12i4 polypeptide, wherein the variant Cas12i4 polypeptide comprises a sequence having at least 95% identity to a sequence set forth in any one of SEQ ID NOs: 3-59, and wherein the variant Cas12i4 polypeptide or the complex exhibits enhanced enzymatic activity, enhanced binding activity, enhanced binding specificity, and/or enhanced stability, relative to a parent polypeptide or a complex comprising the parent polypeptide.

In one aspect of the composition, the variant Cas12i4 polypeptide comprises a substitution of Table 2, Table 4, Table 5, Table 6, Table 7, Table 8, Table 9, Table 10, and/or Table 11.

In another aspect of the composition, the variant Cas12i4 polypeptide comprises the sequence set forth in any one of SEQ ID NOs: 3-59.

In another aspect of the composition, the variant Cas12i4 polypeptide comprises the sequence set forth in SEQ ID NO: 3.

In another aspect of the composition, the variant Cas12i4 polypeptide comprises the sequence set forth in SEQ ID NO: 4.

In another aspect of the composition, the enhanced enzymatic activity is enhanced nuclease activity.

In another aspect of the composition, the variant Cas12i4 polypeptide exhibits enhanced binding activity to an RNA guide, relative to the parent polypeptide.

In another aspect of the composition, the variant Cas12i4 polypeptide exhibits enhanced binding specificity to an RNA guide, relative to the parent polypeptide.

In another aspect of the composition, the complex comprising the variant Cas12i4 polypeptide is a variant binary complex that further comprises an RNA guide, and the variant binary complex exhibits enhanced binding activity to a target nucleic acid (e.g., on-target binding activity), relative to a parent binary complex.

In another aspect of the composition, the complex comprising the variant Cas12i4 polypeptide is a variant binary complex that further comprises an RNA guide, and the variant binary complex exhibits enhanced binding specificity to a target nucleic acid (e.g., on-target binding specificity), relative to a parent binary complex.

In another aspect of the composition, the complex comprising the variant Cas12i4 polypeptide is a variant binary complex that further comprises an RNA guide, and the variant binary complex exhibits enhanced stability, relative to a parent binary complex.

In another aspect of the composition, the variant binary complex and a target nucleic acid form a variant ternary complex, and the variant ternary complex exhibits increased stability, relative to a parent ternary complex.

In another aspect of the composition, the variant Cas12i4 polypeptide further exhibits enhanced binary complex formation, enhanced protein-RNA interactions, and/or decreased dissociation from an RNA guide, relative to the parent polypeptide.

In another aspect of the composition, the variant binary complex further exhibits decreased dissociation from a target nucleic acid, and/or decreased off-target binding to a non-target nucleic acid, relative to the parent binary complex.

In another aspect of the composition, the enhanced enzymatic activity, enhanced binding activity, enhanced binding specificity, and/or enhanced stability occur over a range of temperatures, e.g., 20° C. to 65° C.

In another aspect of the composition, the enhanced enzymatic activity, enhanced binding activity, enhanced binding specificity, and/or enhanced stability occur over a range of incubation times.

In another aspect of the composition, the enhanced enzymatic activity, enhanced binding activity, enhanced binding specificity, and/or enhanced stability occur in a buffer having a pH in a range of about 7.3 to about 8.6.

In another aspect of the composition, the enhanced enzymatic activity, enhanced binding activity, enhanced binding specificity, and/or enhanced stability occurs when a $T_m$ value of the variant Cas12i4 polypeptide, variant binary complex, or variant ternary complex is at least 8° C. greater than the $T_m$ value of the parent polypeptide, parent binary complex, or parent ternary complex.

In another aspect of the composition, the variant Cas12i4 polypeptide comprises a RuvC domain or a split RuvC domain.

In another aspect of the composition, the parent polypeptide comprises the sequence of SEQ ID NO: 2.

In another aspect of the composition, the RNA guide comprises a direct repeat sequence and a spacer sequence.

In another aspect of the composition, the direct repeat comprises:
  a. nucleotide 1 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
b. nucleotide 2 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
c. nucleotide 3 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
d. nucleotide 4 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
e. nucleotide 5 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
f. nucleotide 6 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
g. nucleotide 7 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
h. nucleotide 8 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
i. nucleotide 9 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
j. nucleotide 10 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
k. nucleotide 11 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
l. nucleotide 12 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
m. nucleotide 13 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
n. nucleotide 14 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124; or
o. a sequence that is at least 90% identical to a sequence of SEQ ID NO: 61 or a portion thereof.

In another aspect of the composition, the direct repeat comprises:
a. nucleotide 1 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
b. nucleotide 2 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
c. nucleotide 3 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
d. nucleotide 4 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
e. nucleotide 5 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
f. nucleotide 6 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
g. nucleotide 7 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
h. nucleotide 8 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
i. nucleotide 9 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
j. nucleotide 10 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
k. nucleotide 11 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
l. nucleotide 12 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
m. nucleotide 13 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
n. nucleotide 14 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124; or
o. a sequence that is at least 95% identical to a sequence of SEQ ID NO: 61 or a portion thereof.

In another aspect of the composition, the direct repeat comprises:
a. nucleotide 1 through nucleotide 36 of any one of SEQ ID NOs: 60, 108, 109, 110, 111, 112, 113, 114, 115, 116, 117, 118, 119, 120, 121, 122, 123, or 124;
b. nucleotide 2 through nucleotide 36 of any one of SEQ ID NOs: 60, 108, 109, 110, 111, 112, 113, 114, 115, 116, 117, 118, 119, 120, 121, 122, 123, or 124;
c. nucleotide 3 through nucleotide 36 of any one of SEQ ID NOs: 60, 108, 109, 110, 111, 112, 113, 114, 115, 116, 117, 118, 119, 120, 121, 122, 123, or 124;
d. nucleotide 4 through nucleotide 36 of any one of SEQ ID NOs: 60, 108, 109, 110, 111, 112, 113, 114, 115, 116, 117, 118, 119, 120, 121, 122, 123, or 124;
e. nucleotide 5 through nucleotide 36 of any one of SEQ ID NOs: 60, 108, 109, 110, 111, 112, 113, 114, 115, 116, 117, 118, 119, 120, 121, 122, 123, or 124;

f. nucleotide 6 through nucleotide 36 of any one of SEQ ID NOs: 60, 108, 109, 110, 111, 112, 113, 114, 115, 116, 117, 118, 119, 120, 121, 122, 123, or 124;
g. nucleotide 7 through nucleotide 36 of any one of SEQ ID NOs: 60, 108, 109, 110, 111, 112, 113, 114, 115, 116, 117, 118, 119, 120, 121, 122, 123, or 124;
h. nucleotide 8 through nucleotide 36 of any one of SEQ ID NOs: 60, 108, 109, 110, 111, 112, 113, 114, 115, 116, 117, 118, 119, 120, 121, 122, 123, or 124;
i. nucleotide 9 through nucleotide 36 of any one of SEQ ID NOs: 60, 108, 109, 110, 111, 112, 113, 114, 115, 116, 117, 118, 119, 120, 121, 122, 123, or 124;
j. nucleotide 10 through nucleotide 36 of any one of SEQ ID NOs: 60, 108, 109, 110, 111, 112, 113, 114, 115, 116, 117, 118, 119, 120, 121, 122, 123, or 124;
k. nucleotide 11 through nucleotide 36 of any one of SEQ ID NOs: 60, 108, 109, 110, 111, 112, 113, 114, 115, 116, 117, 118, 119, 120, 121, 122, 123, or 124;
l. nucleotide 12 through nucleotide 36 of any one of SEQ ID NOs: 60, 108, 109, 110, 111, 112, 113, 114, 115, 116, 117, 118, 119, 120, 121, 122, 123, or 124;
m. nucleotide 13 through nucleotide 36 of any one of SEQ ID NOs: 60, 108, 109, 110, 111, 112, 113, 114, 115, 116, 117, 118, 119, 120, 121, 122, 123, or 124;
n. nucleotide 14 through nucleotide 36 of any one of SEQ ID NOs: 60, 108, 109, 110, 111, 112, 113, 114, 115, 116, 117, 118, 119, 120, 121, 122, 123, or 124; or
o. SEQ ID NO: 61 or a portion thereof.

In another aspect of the composition, the direct repeat sequence comprises $AGN_1N_2N_3N_4GUGUN_5N_6N_7CAGN_8GACN_9C$ (SEQ ID NO: 125), wherein $N_1$ is A or G, $N_2$ is C or U, $N_3$ is A or G, $N_4$ is U or C, $N_5$ is C or U, $N_6$ is C or U, $N_7$ is U, A, C, or G, $N_8$ is U or C, and $N_9$ is A or C.

In another aspect of the composition, the spacer sequence comprises between 15 and 35 nucleotides in length.

In another aspect of the composition, the spacer sequence comprises complementarity to a target strand sequence of a target nucleic acid.

In another aspect of the composition, the target nucleic acid comprises a non-target strand sequence adjacent to a protospacer adjacent motif (PAM) sequence.

In another aspect of the composition, the PAM sequence is a 5'-TTN-3', 5'-NTTN-3', 5'-NTN'-3', 5'-NNTN-3', 5'-VTN-3', or 5'-NVTN-3', wherein N is any nucleotide (e.g., A, G, T, or C) and V is A, G, or C.

In another aspect of the composition, the variant Cas12i4 polypeptide further comprises a peptide tag, a fluorescent protein, a base-editing domain, a DNA methylation domain, a histone residue modification domain, a localization factor, a transcription modification factor, a light-gated control factor, a chemically inducible factor, or a chromatin visualization factor.

The invention yet further provides a composition comprising a nucleic acid that encodes a Cas12i4 polypeptide as described herein, wherein optionally the nucleic acid is codon-optimized for expression in a cell.

In one aspect of the composition, the cell is a eukaryotic cell.

In another aspect of the composition, the cell is a mammalian cell or a plant cell.

In another aspect of the composition, the cell is a human cell.

In another aspect of the composition, the nucleic acid encoding the variant Cas12i4 polypeptide is operably linked to a promoter.

In another aspect of the composition, the nucleic acid encoding the variant Cas12i4 polypeptide is in a vector.

In another aspect of the composition, the vector comprises a retroviral vector, a lentiviral vector, a phage vector, an adenoviral vector, an adeno-associated vector, or a herpes simplex vector.

In another aspect of the composition, the composition is present in a delivery composition comprising a nanoparticle (e.g., a lipid nanoparticle), a liposome, an exosome, a microvesicle, or a gene-gun.

The invention yet further provides an RNA guide or a nucleic acid encoding the RNA guide, wherein the RNA guide comprises a direct repeat sequence comprising:
a. nucleotide 1 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
b. nucleotide 2 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
c. nucleotide 3 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
d. nucleotide 4 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
e. nucleotide 5 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
f. nucleotide 6 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
g. nucleotide 7 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
h. nucleotide 8 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
i. nucleotide 9 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
j. nucleotide 10 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
k. nucleotide 11 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
l. nucleotide 12 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
m. nucleotide 13 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
n. nucleotide 14 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124; or
o. a sequence that is at least 90% identical to a sequence of SEQ ID NO: 61 or a portion thereof.

In one aspect of the RNA guide or the nucleic acid encoding the RNA guide, the direct repeat comprises:
a. nucleotide 1 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
b. nucleotide 2 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
c. nucleotide 3 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
d. nucleotide 4 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
e. nucleotide 5 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
f. nucleotide 6 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
g. nucleotide 7 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
h. nucleotide 8 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
i. nucleotide 9 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
j. nucleotide 10 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
k. nucleotide 11 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
l. nucleotide 12 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
m. nucleotide 13 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124;
n. nucleotide 14 through nucleotide 36 of a sequence that is at least 95% identical to a sequence of any one of SEQ ID NOs: 60, 108, 109, 110, 111, 112, 113, 114, 115, 116, 117, 118, 119, 120, 121, 122, 123, or 124; or
o. a sequence that is at least 95% identical to a sequence of SEQ ID NO: 61 or a portion thereof.

In another aspect of the RNA guide or the nucleic acid encoding the RNA guide, the direct repeat comprises:
a. nucleotide 1 through nucleotide 36 of any one of SEQ ID NOs: 60, 108, 109, 110, 111, 112, 113, 114, 115, 116, 117, 118, 119, 120, 121, 122, 123, or 124;
b. nucleotide 2 through nucleotide 36 of any one of SEQ ID NOs: 60, 108, 109, 110, 111, 112, 113, 114, 115, 116, 117, 118, 119, 120, 121, 122, 123, or 124;
c. nucleotide 3 through nucleotide 36 of any one of SEQ ID NOs: 60, 108, 109, 110, 111, 112, 113, 114, 115, 116, 117, 118, 119, 120, 121, 122, 123, or 124;
d. nucleotide 4 through nucleotide 36 of any one of SEQ ID NOs: 60, 108, 109, 110, 111, 112, 113, 114, 115, 116, 117, 118, 119, 120, 121, 122, 123, or 124;
e. nucleotide 5 through nucleotide 36 of any one of SEQ ID NOs: 60, 108, 109, 110, 111, 112, 113, 114, 115, 116, 117, 118, 119, 120, 121, 122, 123, or 124;
f. nucleotide 6 through nucleotide 36 of any one of SEQ ID NOs: 60, 108, 109, 110, 111, 112, 113, 114, 115, 116, 117, 118, 119, 120, 121, 122, 123, or 124;
g. nucleotide 7 through nucleotide 36 of any one of SEQ ID NOs: 60, 108, 109, 110, 111, 112, 113, 114, 115, 116, 117, 118, 119, 120, 121, 122, 123, or 124;
h. nucleotide 8 through nucleotide 36 of any one of SEQ ID NOs: 60, 108, 109, 110, 111, 112, 113, 114, 115, 116, 117, 118, 119, 120, 121, 122, 123, or 124;
i. nucleotide 9 through nucleotide 36 of any one of SEQ ID NOs: 60, 108, 109, 110, 111, 112, 113, 114, 115, 116, 117, 118, 119, 120, 121, 122, 123, or 124;
j. nucleotide 10 through nucleotide 36 of any one of SEQ ID NOs: 60, 108, 109, 110, 111, 112, 113, 114, 115, 116, 117, 118, 119, 120, 121, 122, 123, or 124;
k. nucleotide 11 through nucleotide 36 of any one of SEQ ID NOs: 60, 108, 109, 110, 111, 112, 113, 114, 115, 116, 117, 118, 119, 120, 121, 122, 123, or 124;
l. nucleotide 12 through nucleotide 36 of any one of SEQ ID NOs: 60, 108, 109, 110, 111, 112, 113, 114, 115, 116, 117, 118, 119, 120, 121, 122, 123, or 124;
m. nucleotide 13 through nucleotide 36 of any one of SEQ ID NOs: 60, 108, 109, 110, 111, 112, 113, 114, 115, 116, 117, 118, 119, 120, 121, 122, 123, or 124;
n. nucleotide 14 through nucleotide 36 of any one of SEQ ID NOs: 60, 108, 109, 110, 111, 112, 113, 114, 115, 116, 117, 118, 119, 120, 121, 122, 123, or 124; or
o. SEQ ID NO: 61 or a portion thereof.

In another aspect of the RNA guide or the nucleic acid encoding the RNA guide, the direct repeat sequence comprises AGN$_1$N$_2$N$_3$N$_4$GUGUN$_5$N$_6$N$_7$CAGN$_8$GACN$_9$C (SEQ ID NO: 125), N$_1$ is A or G, N$_2$ is C or U, N$_3$ is A or G, N$_4$ is U or C, N$_5$ is C or U, N$_6$ is C or U, N$_7$ is U, A, C, or G, N$_8$ is U or C, and N$_9$ is A or C.

In another aspect of the RNA guide or the nucleic acid encoding the RNA guide, the RNA guide further comprises a spacer sequence.

In another aspect of the RNA guide or the nucleic acid encoding the RNA guide, the spacer sequence comprises about 15 to about 35 nucleotides in length.

In another aspect of the RNA guide or the nucleic acid encoding the RNA guide, the spacer sequence recognizes a target nucleic acid.

In another aspect of the RNA guide or the nucleic acid encoding the RNA guide, the target nucleic acid comprises a target sequence adjacent to a protospacer adjacent motif (PAM) sequence, wherein the PAM sequence comprises a nucleotide sequence set forth as 5'-TTN-3', 5'-NTTN-3', 5'-NTN'-3', 5'-NNTN-3', 5'-VTN-3', or 5'-NVTN-3', wherein N is any nucleotide (e.g., A, G, T, or C) and V is A, G, or C.

The invention yet further provides a composition comprising an RNA guide or a nucleic acid encoding the RNA guide as described herein.

In one aspect of the composition, the composition is a delivery composition comprising a nanoparticle (e.g., a lipid nanoparticle), a liposome, an exosome, a microvesicle, or a gene-gun.

In another aspect of the RNA guide or the nucleic acid encoding the RNA guide described herein, the nucleic acid encoding the RNA guide is operably linked to a promoter.

In another aspect of the RNA guide or the nucleic acid encoding the RNA guide, the nucleic acid encoding the RNA guide is in a vector.

In another aspect of the RNA guide or the nucleic acid encoding the RNA guide, the vector comprises a retroviral vector, a lentiviral vector, a phage vector, an adenoviral vector, an adeno-associated vector, or a herpes simplex vector.

The invention yet further provides a cell comprising the RNA guide or the nucleic acid encoding the RNA guide described herein.

In one aspect of the cell, the cell is a eukaryotic cell.

In another aspect of the cell, the cell is a mammalian cell or a plant cell.

In another aspect of the cell, the cell is a human cell.

The invention yet further provides a method for editing a gene in a cell, the method comprising contacting the cell with a variant, a composition, an RNA guide, or a nucleic acid molecule as described herein.

The invention yet further provides a nucleic acid molecule encoding a Cas12i4 variant of SEQ ID NO: 4, wherein the sequence of the nucleic acid molecule is 95% identical to the selected from the group consisting of SEQ ID NOs: 222-228.

In one embodiment, the sequence of the nucleic acid molecule comprises a sequence selected from the group consisting of SEQ ID NOs: 222-228

Definitions

The present invention will be described with respect to particular embodiments and with reference to certain Figures, but the invention is not limited thereto but only by the claims. Terms as set forth hereinafter are generally to be understood in their common sense unless indicated otherwise.

As used herein, the term "activity" refers to a biological activity. In some embodiments, nuclease activity includes enzymatic activity, e.g., catalytic ability of a nuclease. For example, nuclease activity can include nuclease activity. In some embodiments, nuclease activity includes binding activity, e.g., binding activity of a nuclease to an RNA guide and/or target nucleic acid.

As used herein, the term "complex" refers to a grouping of two or more molecules. In some embodiments, the complex comprises a polypeptide and a nucleic acid molecule interacting with (e.g. binding to, coming into contact with, adhering to) one another.

As used herein, the term "binary complex" refers to a grouping of two molecules (e.g., a polypeptide and a nucleic acid molecule). In some embodiments, a binary complex refers to a grouping of a polypeptide and a targeting moiety (e.g., an RNA guide). In some embodiments, a binary complex refers to a ribonucleoprotein (RNP). As used herein, the term "variant binary complex" refers to the grouping of a variant Cas12i4 polypeptide and RNA guide. As used herein, the term "parent binary complex" refers to the grouping of a parent polypeptide and RNA guide or a reference polypeptide and RNA guide.

As used herein, the term "ternary complex" refers to a grouping of three molecules (e.g., a polypeptide and two nucleic acid molecules). In some embodiments, a "ternary complex" refers to a grouping of a polypeptide, an RNA molecule, and a DNA molecule. In some embodiments, a ternary complex refers to a grouping of a polypeptide, a targeting moiety (e.g., an RNA guide), and a target nucleic acid (e.g., a target DNA molecule). In some embodiments, a "ternary complex" refers to a grouping of a binary complex (e.g., a ribonucleoprotein) and a third molecule (e.g., a target nucleic acid).

As used herein, the term "domain" refers to a distinct functional and/or structural unit of a polypeptide. In some embodiments, a domain may comprise a conserved amino acid sequence.

As used herein, the term "interface" refers to one or more residues of a variant Cas12i4 polypeptide (e.g., a domain/motif or a portion of a domain/motif) in contact with (e.g., that interact with or are adjacent to) a nucleic acid molecule or a distinct domain/motif or a portion of a distinct domain/motif of the variant Cas12i4 polypeptide. In some aspects, an interface is a buried surface area between adjacent domains or motifs. In some aspects, an interface is a surface area between the a polypeptide and a ligand (e.g., DNA or RNA) where the polypeptide and ligand make contact. As used herein, the term "nucleic acid interface" refers to residues of the variant Cas12i4 polypeptide that are in close proximity to (e.g., are adjacent to) or interact with a nucleic acid sequence (e.g., a DNA sequence or an RNA sequence). As used herein, the term "RNA binding interface" refers to the residues of the variant Cas12i4 polypeptide that are in close proximity to (e.g., are adjacent to) or interact with an RNA guide (e.g., the direct repeat of the RNA guide). As used herein, the term "double-stranded DNA binding interface" refers to the residues of the variant Cas12i4 polypeptide that are in close proximity to (e.g., are adjacent to) and/or interact with double-stranded DNA.

As used herein, the term "single-stranded DNA binding interface" refers to the residues of the variant Cas12i4 polypeptide that are in close proximity to (e.g., are adjacent to) and/or interact with single-stranded DNA. As used herein, the term "domain-domain interface" refers to a domain in close-proximity to (e.g., adjacent to) a separate domain. In some embodiments, a domain-domain interface (e.g., a Helical II domain-Nuc domain interface) forms upon complex formation (e.g., ternary complex formation).

As used herein, the terms "parent," "parent polypeptide," and "parent sequence" refer to an original polypeptide (e.g., starting polypeptide) to which an alteration is made to produce a variant Cas12i4 polypeptide of the present invention. In some embodiments, the parent is a polypeptide having an identical amino acid sequence of the variant at one or more of specified positions. The parent may be a naturally occurring (wild-type) polypeptide. In a particular embodiment, the parent is a polypeptide with at least 60%, at least 61%, at least 62%, at least 63%, at least 64%, at least 65%, at least 70%, at least 72%, at least 73%, at least 74%, at least 75%, at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99% or 100% identity to a polypeptide of SEQ ID NO: 2.

As used herein, the term "protospacer adjacent motif" or "PAM" refers to a DNA sequence adjacent to a "target sequence" to which a complex comprising a Cas12i4 polypeptide and an RNA guide binds. The "target nucleic acid" is a double-stranded molecule: one strand comprises the target sequence adjacent to the PAM and is referred to as the "PAM strand" (e.g., the non-target strand or the non-spacer-complementary strand), and the other complementary strand is referred to as the "non-PAM strand" (e.g., the target strand or the spacer-complementary strand). As used herein, the term "adjacent" includes instances in which an RNA guide of the complex specifically binds, interacts, or associates with a target sequence that is immediately adjacent to a PAM. In such instances, there are no nucleotides between the target sequence and the PAM. The term "adjacent" also includes instances in which there are a small number (e.g., 1, 2, 3, 4, or 5) of nucleotides between the target sequence, to which the targeting moiety binds, and the PAM.

As used herein, the terms "reference composition," "reference molecule," "reference sequence," and "reference" refer to a control, such as a negative control or a parent (e.g., a parent sequence, a parent protein, or a wild-type protein). For example, a reference molecule refers to a polypeptide to which a variant Cas12i4 polypeptide is compared. Likewise, a reference RNA guide refers to a targeting moiety to which a modified RNA guide is compared. The variant or modified molecule may be compared to the reference molecule on the basis of sequence (e.g., the variant or modified molecule may have X % sequence identity or homology with the reference molecule), thermostability, or activity (e.g., the variant or modified molecule may have X % of the activity of the reference molecule). For example, a variant or modified molecule may be characterized as having no more than 10% of an activity of the reference polypeptide or may be characterized as having at least 10% greater of an activity of the reference polypeptide. Examples of reference polypeptides include naturally occurring unmodified polypeptides, e.g., naturally occurring polypeptides from archaea or bacterial species. In certain embodiments, the reference polypeptide is a naturally occurring polypeptide having the closest sequence identity or homology with the variant Cas12i4 polypeptide to which it is being compared. In certain embodiments, the reference polypeptide is a parental molecule having a naturally occurring or known sequence on which a mutation has been made to arrive at the variant Cas12i4 polypeptide.

As used herein, the terms "RNA guide" or "RNA guide sequence" refer to any RNA molecule that facilitates the targeting of a Cas12i4 polypeptide described herein to a target nucleic acid. For example, an RNA guide can be a molecule that recognizes (e.g., binds to) a target nucleic acid. An RNA guide may be designed to be complementary to a target strand (e.g., the non-PAM strand) of a target nucleic acid sequence. An RNA guide comprises a DNA targeting sequence and a direct repeat (DR) sequence. The terms CRISPR RNA (crRNA), pre-crRNA, mature crRNA, and gRNA are also used herein to refer to an RNA guide. As used herein, the term "pre-crRNA" refers to an unprocessed RNA molecule comprising a DR-spacer-DR sequence. As used herein, the term "mature crRNA" refers to a processed form of a pre-crRNA; a mature crRNA may comprise a DR-spacer sequence, wherein the DR is a truncated form of the DR of a pre-crRNA and/or the spacer is a truncated form of the spacer of a pre-crRNA.

As used herein, the term "substantially identical" refers to a sequence, polynucleotide, or polypeptide, that has a certain degree of identity to a reference sequence.

As used herein, the terms "target nucleic acid," "target sequence," and "target substrate" refer to a nucleic acid to which an RNA guide specifically binds. In some embodiments, the DNA targeting sequence of an RNA guide binds to a target nucleic acid.

As used herein, the terms "variant Cas12i4 polypeptide" and "variant nuclease polypeptide" refer to a polypeptide comprising an alteration, e.g., a substitution, insertion, deletion and/or fusion, at one or more residue positions, compared to a parent polypeptide. As used herein, the terms "variant Cas12i4 polypeptide" and "variant nuclease polypeptide" refer to a polypeptide comprising an alteration as compared to the polypeptide of SEQ ID NO: 2.

DETAILED DESCRIPTION

Figure 1A:
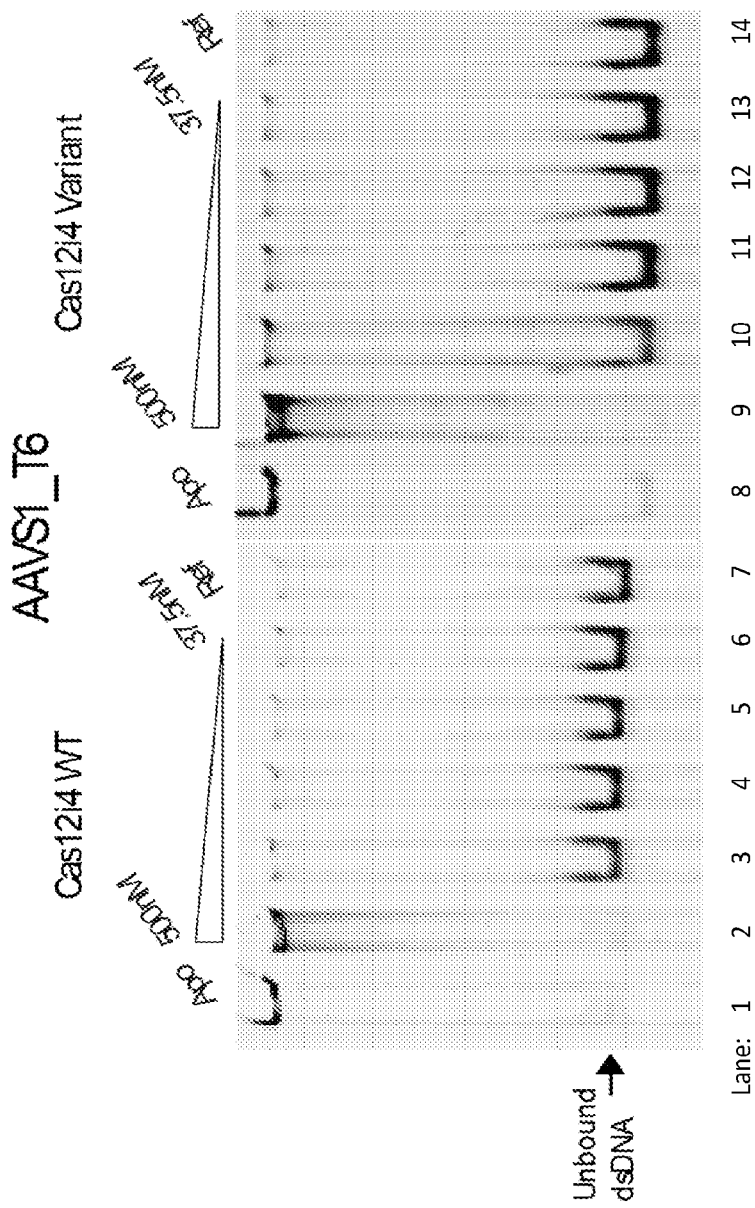
FIG. 1A is a DNA EMSA gel showing the ability of RNPs prepared with a) wild-type Cas12i4 (SEQ ID NO: 2) or variant Cas12i4 of SEQ ID NO: 4 and b) an RNA guide of SEQ ID NO: 62 to bind an AAVS1 dsDNA target (SEQ ID NO: 65). Unbound dsDNA bands are indicated.

The present disclosure relates to novel variants of the polypeptide of SEQ ID NO: 2 and methods of production and use thereof. The present disclosure further relates to complexes comprising a variant of the polypeptide of SEQ ID NO: 2 and methods of production and use thereof. In some aspects, a composition comprising a complex having one or more characteristics is described herein. In some aspects, a method of delivering a composition comprising the complex is described.

Compositions

In some embodiments, a composition of the invention includes a variant Cas12i4 polypeptide that exhibits enhanced enzymatic activity, enhanced binding activity, enhanced binding specificity, and/or enhanced stability, relative to a parent polypeptide. In some embodiments, a composition of the invention includes a complex comprising a variant Cas12i4 polypeptide that exhibits enhanced enzymatic activity, enhanced binding activity, enhanced binding specificity, and/or enhanced stability relative to a parent complex.

In some embodiments, a composition of the invention includes a variant Cas12i4 polypeptide and an RNA guide. In some embodiments, a composition of the invention includes a variant binary complex comprising a variant Cas12i4 polypeptide and an RNA guide.

In some aspects of the composition, the variant Cas12i4 polypeptide has increased complex formation (e.g., increased binary complex formation) with the RNA guide as compared to a parent polypeptide. In some aspects of the composition, the variant Cas12i4 polypeptide and the RNA guide have a greater binding affinity, as compared to a parent polypeptide and the RNA guide. In some aspects of the composition, the variant Cas12i4 polypeptide and the RNA guide have stronger protein-RNA interactions (e.g., ionic interactions), as compared to a parent polypeptide and the RNA guide. In some aspects of the composition, the variant binary complex is more stable than a parent binary complex.

In some embodiments, a composition of the invention includes a variant Cas12i4 polypeptide, an RNA guide, and a target nucleic acid. In some embodiments, a composition of the invention includes a variant ternary complex comprising a variant Cas12i4 polypeptide, an RNA guide, and a target nucleic acid.

In some aspects of the composition, the variant Cas12i4 polypeptide has increased complex formation (e.g., increased ternary complex formation) with the RNA guide and target nucleic acid as compared to a parent polypeptide. In some aspects of the composition, the variant Cas12i4 polypeptide and the RNA guide (e.g., the variant binary complex) have a greater binding affinity to a target nucleic acid, as compared to a parent polypeptide and the RNA guide (e.g., a parent binary complex). In some aspects of the composition, the variant ternary complex is more stable than a parent ternary complex.

Variant Cas12i4 Polypeptide

In some embodiments, the composition of the present invention includes a variant Cas12i4 polypeptide described herein.

In some embodiments, the polypeptide of the present invention is a variant of a parent polypeptide, wherein the parent is encoded by a polynucleotide that comprises a nucleotide sequence such as SEQ ID NO: 1 or comprises an amino acid sequence such as SEQ ID NO: 2.

TABLE 1

Parent sequences.

| Sequence identifier | Sequence | Description |
| --- | --- | --- |
| SEQ ID NO: 1 | ATGGCTTCCATCTCTAGGCCATACGGCACCAAGCTGCGACCGGA CGCACGGAAGAAGGAGATGCTCGATAAGTTCTTTAATACACTGA CTAAGGGTCAGCGCGTGTTCGCAGACCTGGCCCTGTGCATCTAT GGCTCCCTGACCCTGGAGATGGCCAAGTCTCTGGAGCCAGAAAG TGATTCAGAACTGGTGTGCGCTATTGGGTGGTTTCGGCTGGTGG ACAAGACCATCTGGTCCAAGGATGGCATCAAGCAGGAGAATCTG GTGAAACAGTACGAAGCCTATTCCGGAAAGGAGGCTTCTGAAGT GGTCAAAACATACCTGAACAGCCCCAGCTCCGACAAGTACGTGT GGATCGATTGCAGGCAGAAATTCCTGAGGTTTCAGCGCGAGCTC GGCACTCGCAACCTGTCCGAGGACTTCGAATGTATGCTCTTTGA ACAGTACATTAGACTGACCAAGGGCGAGATCGAAGGGTATGCCG CTATTTCAAATATGTTCGGAAACGGCGAGAAGGAAGACCGGAGC AAGAAAAGAATGTACGCTACACGGATGAAAGATTGGCTGGAGGC AAACGAAAATATCACTTGGGAGCAGTATAGAGAGGCCCTGAAGA ACCAGCTGAATGCTAAAAACCTGGAGCAGGTTGTGGCCAATTAC AAGGGGAACGCTGGCGGGCAGACCCCTTCTTTAAGTATAGCTT CTCCAAAGAGGGAATGGTGAGCAAGAAAGAACATGCACAGCAGC TCGACAAGTTCAAAACCGTCCTGAAGAACAAAGCCCGGGACCTG AATTTTCCAAACAAGGAGAAGCTGAAGCAGTACCTGGAGGCCGA AATCGGCATTCCGGTCGACGCTAACGTGTACTCCCAGATGTTCT CTAACGGGGTGAGTGAGGTCCAGCCTAAGACCACACGGAATATG TCTTTTAGTAACGAGAAACTGGATCTGCTCACTGAACTGAAGGA CCTGAACAAGGGCGATGGGTTCGAGTACGCCAGAGAAGTGCTGA ACGGGTTCTTTGACTCCGAGCTCCACACTACCGAGGATAAGTTT | Nucleotide sequence encoding parent polypeptide |

TABLE 1-continued

Parent sequences.

| Sequence identifier | Sequence | Description |
|---|---|---|
| | AATATCACCTCTAGGTACCTGGGAGGCGACAAATCAAACCGCCT GAGCAAACTCTATAAGATCTGGAAGAAAGAGGGTGTGGACTGCG AGGAAGGCATTCAGCAGTTCTGTGAAGCCGTCAAAGATAAGATG GGCCAGATCCCCATTCGAAATGTGCTGAAGTACCTGTGGCAGTT CCGGGAGACAGTCAGTGCCGAGGATTTTGAAGCAGCCGCTAAGG CTAACCATCTGGAGGAAAAGATCAGCCGGGTGAAAGCCCACCCA ATCGTGATTAGCAATAGGTACTGGGCTTTTGGGACTTCCGCACT GGTGGGAAACATTATGCCCGCAGACAAGAGGCATCAGGGAGAGT ATGCCGGTCAGAATTTCAAAATGTGGCTGGAGGCTGAACTGCAC TACGATGGCAAGAAAGCAAAGCACCATCTGCCTTTTTATAACGC CCGCTTCTTTGAGGAAGTGTACTGCTATCACCCCTCTGTCGCCG AGATCACTCCTTTCAAAACCAAGCAGTTTGGCTGTGAAATCGGG AAGGACATTCCAGATTACGTGAGCGTCGCTCTGAAGGACAATCC GTATAAGAAAGCAACCAAACGAATCCTGCGTGCAATCTACAATC CCGTCGCCAACACAACTGGCGTTGATAAGACCACAAACTGCAGC TTCATGATCAAACGCGAGAATGACGAATATAAGCTGGTCATCAA CCGAAAAATTTCCGTGGATCGGCCTAAGAGAATCGAAGTGGGCA GGACAATTATGGGGTACGACCGCAATCAGACAGCTAGCGATACT TATTGGATTGGCCGGCTGGTGCCACCTGGAACCCGGGGCGCATA CCGCATCGGAGAGTGGAGCGTCCAGTATATTAAGTCCGGGCCTG TCCTGTCTAGTACTCAGGGAGTTAACAATTCCACTACCGACCAG CTGGTGTACAACGGCATGCCATCAAGCTCCGAGCGGTTCAAGGC CTGGAAGAAAGCCAGAATGGCTTTTATCCGAAAACTCATTCGTC AGCTGAATGACGAGGGACTGGAATCTAAGGGTCAGGATTATATC CCCGAGAACCCTTCTAGTTTCGATGTGCGGGGCGAAACCCTGTA CGTCTTTAACAGTAATTATCTGAAGGCCCTGGTGAGCAAACACA GAAAGGCCAAGAAACCTGTTGAGGGGATCCTGGACGAGATTGAA GCCTGGACATCTAAAGACAAGGATTCATGCAGCCTGATGCGGCT GAGCAGCCTGAGCGATGCTTCCATGCAGGGAATCGCCAGCCTGA AGAGTCTGATTAACAGCTACTTCAACAAGAATGGCTGTAAAACC ATCGAGGACAAAGAAAAGTTTAATCCCGTGCTGTATGCCAAGCT GGTTGAGGTGGAACAGCGGAGAACAAACAAGCGGTCTGAGAAAG TGGGAAGAATCGCAGGTAGTCTGGAGCAGCTGGCCCTGCTGAAC GGGGTTGAGGTGGTCATCGGCGAAGCTGACCTGGGGGAGGTCGA AAAAGGAAAGAGTAAGAAACAGAATTCACGGAACATGGATTGGT GCGCAAAGCAGGTGGCACAGCGGCTGGAGTACAAACTGGCCTTC CATGGAATCGGTTACTTTGGAGTGAACCCCATGTATACCAGCCA CCAGGACCCTTTCGAACATAGGCGCGTGGCTGATCACATCGTCA TGCGAGCACGTTTTGAGGAAGTCAACGTGGAGAACATTGCCGAA TGGCACGTGCGAAATTTCTCAAACTACCTGCGTGCAGACAGCGG CACTGGGCTGTACTATAAGCAGGCCACCATGGACTTCCTGAAAC ATTACGGTCTGGAGGAACACGCTGAGGGCCTGGAAAATAAGAAA ATCAAGTTCTATGACTTTAGAAAGATCCTGGAGGATAAAAACCT GACAAGCGTGATCATTCCAAAGAGGGGGGGGCGCATCTACATGG CCACCAACCCAGTGACATCCGACTCTACCCCCGATTACATACGCC GGCAAGACTTATAATAGGTGTAACGCTGATGAGGTGGCAGCCGC TAATATCGTTATTTCTGTGCTGGCTCCCCGCAGTAAGAAAAACG AGGAACAGGACGATATCCCTCTGATTACCAAGAAAGCCGAGAGT AAGTCACCACCGAAAGACCGGAAGAGATCAAAAACAAGCCAGCT GCCTCAGAAA | |
| SEQ ID NO: 2 | MASISRPYGTKLRPDARKKEMLDKFFNTLTKGQRVFADLALCIY GSLTLEMAKSLEPESDSELVCAIGWFRLVDKTIWSKDGIKQENL VKQYEAYSGKEASEVVKTYLNSPSSDKYVWIDCRQKFLRFQREL GTRNLSEDFECMLFEQYIRLTKGEIEGYAAISNMFGNGEKEDRS KKRMYATRMKDWLEANENITWEQYREALKNQLNAKNLEQVVANY KGNAGGADPFFKYSFSKEGMVSKKEHAQQLDKFKTVLKNKARDL NFPNKEKLKQYLEAEIGIPVDANVYSQMFSNGVSEVQPKTTRNM SFSNEKLDLLTELKDLNKGDGFEYAREVLNGFFDSELHTTEDKF NITSRYLGGDKSNRLSKLYKIWKKEGVDCEEGIQQFCEAVKDKM GQIPIRNVLKYLWQFRETVSAEDFEAAAKANHLEEKISRVKAHP IVISNRYWAFGTSALVGNIMPADKRHQGEYAGQNFKMWLEAELH YDGKKAKHHLPFYNARFFEEVYCYHPSVAEITPFKTKQFGCEIG KDIPDYVSVALKDNPYKKATKRILRAIYNPVANTTGVDKTTNCS FMIKRENDEYKLVINRKISVDRPKRIEVGRTIMGYDRNQTASDT YWIGRLVPPGTRGAYRIGEWSVQYIKSGPVLSSTQGVNNSTTDQ LVYNGMPSSSERFKAWKKARMAFIRKLIRQLNDEGLESKGQDYI PENPSSFDVRGETLYVFNSNYLKALVSKHRKAKKPVEGILDEIE AWTSKDKDSCSLMRLSSLSDASMQGIASLKSLINSYFNKNGCKT IEDKEKFNPVLYAKLVEVEQRRTNKRSEKVGRIAGSLEQLALLN GVEVVIGEADLGEVEKGKSKKQNSRNMDWCAKQVAQRLEYKLAF HGIGYFGVNPMYTSHQDPFEHRRVADHIVMRARFEEVNVENIAE | Parent polypeptide |

TABLE 1-continued

Parent sequences.

| Sequence identifier | Sequence | Description |
|---|---|---|
| | WHVRNFSNYLRADSGTGLYYKQATMDFLKHYGLEEHAEGLENKK IKFYDFRKILEDKNLTSVIIPKRGGRIYMATNPVTSDSTPITYA GKTYNRCNADEVAAANIVISVLAPRSKKNEEQDDIPLITKKAES KSPPKDRKRSKTSQLPQK | |

A nucleic acid sequence encoding the parent polypeptide described herein may be substantially identical to a reference nucleic acid sequence, e.g., SEQ ID NO: 1. In some embodiments, the variant Cas12i4 polypeptide is encoded by a nucleic acid comprising a sequence having least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the reference nucleic acid sequence, e.g., nucleic acid sequence encoding the parent polypeptide, e.g., SEQ ID NO: 1. The percent identity between two such nucleic acids can be determined manually by inspection of the two optimally aligned nucleic acid sequences or by using software programs or algorithms (e.g., BLAST, ALIGN, CLUSTAL) using standard parameters. One indication that two nucleic acid sequences are substantially identical is that the nucleic acid molecules hybridize to the complementary sequence of the other under stringent conditions (e.g., within a range of medium to high stringency).

In some embodiments, the variant Cas12i4 polypeptide is encoded by a nucleic acid sequence having at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more sequence identity, but not 100% sequence identity, to a reference nucleic acid sequence, e.g., nucleic acid sequence encoding the parent polypeptide, e.g., SEQ ID NO: 1.

In some embodiments, the variant Cas12i4 polypeptide of the present invention comprises a polypeptide sequence having 50%, 60%, 65%, 70%, 75%, 80%, 85%, 90%, 91%, 92%, 93%, 94%, 95%, 96%, 97%, 98%, or 99%, but not 100%, identity to SEQ ID NO: 2. In some embodiments, the variant Cas12i4 polypeptide of the present invention comprises a polypeptide sequence having greater than 50%, 60%, 65%, 70%, 75%, 80%, 85%, 90%, 91%, 92%, 93%, 94%, 95%, 96%, 97%, 98%, or 99%, but not 100%, identity to SEQ ID NO: 2. In some embodiments, the variant Cas12i4 polypeptide maintains the amino acid changes (or at least 1, 2, 3, 4, 5 etc. of these changes) that differentiate the polypeptide from its respective parent/reference sequence.

In some embodiments, the present invention describes a variant Cas12i4 polypeptide having a specified degree of amino acid sequence identity to one or more reference polypeptides, e.g., a parent polypeptide, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99%, but not 100%, sequence identity to the amino acid sequence of SEQ ID NO: 2. Homology or identity can be determined by amino acid sequence alignment, e.g., using a program such as BLAST, ALIGN, or CLUSTAL, as described herein. In some embodiments, the variant Cas12i4 polypeptide maintains the amino acid changes (or at least 1, 2, 3, 4, 5 etc. of these changes) that differentiate the polypeptide from its respective parent/reference sequence.

In some embodiments, the variant Cas12i4 polypeptide comprises an alteration at one or more (e.g., several) amino acids of a parent polypeptide, wherein at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 162, 164, 164, 165, 166, 167, 168, 169, 170, 171, 172, 173, 174, 175, 176, 177, 178, 179, 180, 181, 182, 183, 184, 185, 186, 187, 188, 189, 190, 191, 193, 194, 195, 196, 197, 198, 199, 200, or more are altered. In some embodiments, the variant Cas12i4 polypeptide maintains the amino acid changes (or at least 1, 2, 3, 4, 5 etc. of these changes) that differentiate the polypeptide from its respective parent/reference sequence.

In some embodiments, the variant Cas12i4 polypeptide comprises one or more of the amino acid substitutions listed in Table 2.

TABLE 2

Single amino acid substitutions in variant Cas12i4 polypeptide.

| Position | Wild-Type Residue | Substitution(s) |
|---|---|---|
| 1 | M | R, G, A, K, Q, N, H |
| 2 | A | R, G, K, Q, N, H |
| 3 | S | R, G, A, K, Q, N, H |
| 4 | I | R, G, A, K, Q, N, H |
| 5 | S | R, G, A, K, Q, N, H |
| 6 | R | G, A, K, Q, N, H |
| 7 | P | R, G, A, K, Q, N, H |
| 8 | Y | R, G, A, K, Q, N, H |
| 9 | G | R, A, K, Q, N, H |
| 10 | T | R, G, A, K, Q, N, H |
| 11 | K | R, G, A, Q, N, H |
| 12 | L | R, G, A, K, Q, N, H |
| 13 | R | G, A, K, Q, N, H |
| 14 | P | R, G, A, K, Q, N, H |
| 15 | D | R, G, A, K, Q, N, H |
| 16 | A | R, G, K, Q, N, H |
| 17 | R | G, A, K, Q, N, H |
| 18 | K | R, G, A, Q, N, H |
| 19 | K | R, G, A, Q, N, H |

TABLE 2-continued

Single amino acid substitutions in variant Cas12i4 polypeptide.

| Position | Wild-Type Residue | Substitution(s) |
|---|---|---|
| 20 | E | R, G, A, K, Q, N, H |
| 21 | M | R, G, A, K, Q, N, H |
| 22 | L | R, G, A, K, Q, N, H |
| 23 | D | R, G, A, K, Q, N, H |
| 24 | K | R, G, A, Q, N, H |
| 25 | F | R, G, A, K, Q, N, H |
| 26 | F | R, G, A, K, Q, N, H |
| 27 | N | R, G, A, K, Q, H |
| 28 | T | R, G, A, K, Q, N, H |
| 29 | L | R, G, A, K, Q, N, H |
| 30 | T | R, G, A, K, Q, N, H |
| 31 | K | R, G, A, Q, N, H |
| 32 | G | R, A, K, Q, N, H |
| 33 | Q | R, G, A, K, N, H |
| 34 | R | G, A, K, Q, N, H |
| 35 | V | R, G, A, K, Q, N, H |
| 36 | F | R, G, A, K, Q, N, H |
| 37 | A | R, G, K, Q, N, H |
| 38 | D | R, G, A, K, Q, N, H |
| 39 | L | R, G, A, K, Q, N, H |
| 40 | A | R, G, K, Q, N, H |
| 41 | L | R, G, A, K, Q, N, H |
| 42 | C | R, G, A, K, Q, N, H |
| 43 | I | R, G, A, K, Q, N, H |
| 44 | Y | R, G, A, K, Q, N, H |
| 45 | G | R, A, K, Q, N, H |
| 46 | S | R, G, A, K, Q, N, H |
| 47 | L | R, G, A, K, Q, N, H |
| 48 | T | R, G, A, K, Q, N, H |
| 49 | L | R, G, A, K, Q, N, H |
| 50 | E | R, G, A, K, Q, N, H |
| 51 | M | R, G, A, K, Q, N, H |
| 52 | A | R, G, K, Q, N, H |
| 53 | K | R, G, A, Q, N, H |
| 54 | S | R, G, A, K, Q, N, H |
| 55 | L | R, G, A, K, Q, N, H |
| 56 | E | R, G, A, K, Q, N, H |
| 57 | P | R, G, A, K, Q, N, H |
| 58 | E | R, G, A, K, Q, N, H |
| 59 | S | R, G, A, K, Q, N, H |
| 60 | D | R, G, A, K, Q, N, H |
| 61 | S | R, G, A, K, Q, N, H |
| 62 | E | R, G, A, K, Q, N, H |
| 63 | L | R, G, A, K, Q, N, H |
| 64 | V | R, G, A, K, Q, N, H |
| 65 | C | R, G, A, K, Q, N, H |
| 66 | A | R, G, K, Q, N, H |
| 67 | I | R, G, A, K, Q, N, H |
| 68 | G | R, A, K, Q, N, H |
| 69 | W | R, G, A, K, Q, N, H |
| 70 | F | R, G, A, K, Q, N, H |
| 71 | R | G, A, K, Q, N, H |
| 72 | L | R, G, A, K, Q, N, H |
| 73 | V | R, G, A, K, Q, N, H |
| 74 | D | R, G, A, K, Q, N, H |
| 75 | K | R, G, A, Q, N, H |
| 76 | T | R, G, A, K, Q, N, H |
| 77 | I | R, G, A, K, Q, N, H |
| 78 | W | R, G, A, K, Q, N, H |
| 79 | S | R, G, A, K, Q, N, H |
| 80 | K | R, G, A, Q, N, H |
| 81 | D | R, G, A, K, Q, N, H |
| 82 | G | R, A, K, Q, N, H |
| 83 | I | R, G, A, K, Q, N, H |
| 84 | K | R, G, A, Q, N, H |
| 85 | Q | R, G, A, K, N, H |
| 86 | E | R, G, A, K, Q, N, H |
| 87 | N | R, G, A, K, Q, H |
| 88 | L | R, G, A, K, Q, N, H |
| 89 | V | R, G, A, K, Q, N, H |
| 90 | K | R, G, A, Q, N, H |
| 91 | Q | R, G, A, K, N, H |
| 92 | Y | R, G, A, K, Q, N, H |
| 93 | E | R, G, A, K, Q, N, H |
| 94 | A | R, G, K, Q, N, H |
| 95 | Y | R, G, A, K, Q, N, H |
| 96 | S | R, G, A, K, Q, N, H |
| 97 | G | R, A, K, Q, N, H |
| 98 | K | R, G, A, Q, N, H |
| 99 | E | R, G, A, K, Q, N, H |
| 100 | A | R, G, K, Q, N, H |
| 101 | S | R, G, A, K, Q, N, H |
| 102 | E | R, G, A, K, Q, N, H |
| 103 | V | R, G, A, K, Q, N, H |
| 104 | V | R, G, A, K, Q, N, H |
| 105 | K | R, G, A, Q, N, H |
| 106 | T | R, G, A, K, Q, N, H |
| 107 | Y | R, G, A, K, Q, N, H |
| 108 | L | R, G, A, K, Q, N, H |
| 109 | N | R, G, A, K, Q, H |
| 110 | S | R, G, A, K, Q, N, H |
| 111 | P | R, G, A, K, Q, N, H |
| 112 | S | R, G, A, K, Q, N, H |
| 113 | S | R, G, A, K, Q, N, H |
| 114 | D | R, G, A, K, Q, N, H |
| 115 | K | R, G, A, Q, N, H |
| 116 | Y | R, G, A, K, Q, N, H |
| 117 | V | R, G, A, K, Q, N, H |
| 118 | W | R, G, A, K, Q, N, H |
| 119 | I | R, G, A, K, Q, N, H |
| 120 | D | R, G, A, K, Q, N, H |
| 121 | C | R, G, A, K, Q, N, H |
| 122 | R | G, A, K, Q, N, H |
| 123 | Q | R, G, A, K, N, H |
| 124 | K | R, G, A, Q, N, H |
| 125 | F | R, G, A, K, Q, N, H |
| 126 | L | R, G, A, K, Q, N, H |
| 127 | R | G, A, K, Q, N, H |
| 128 | F | R, G, A, K, Q, N, H |
| 129 | Q | R, G, A, K, N, H |
| 130 | R | G, A, K, Q, N, H |
| 131 | E | R, G, A, K, Q, N, H |
| 132 | L | R, G, A, K, Q, N, H |
| 133 | G | R, A, K, Q, N, H |
| 134 | T | R, G, A, K, Q, N, H |
| 135 | R | G, A, K, Q, N, H |
| 136 | N | R, G, A, K, Q, H |
| 137 | L | R, G, A, K, Q, N, H |
| 138 | S | R, G, A, K, Q, N, H |
| 139 | E | R, G, A, K, Q, N, H |
| 140 | D | R, G, A, K, Q, N, H |
| 141 | F | R, G, A, K, Q, N, H |
| 142 | E | R, G, A, K, Q, N, H |
| 143 | C | R, G, A, K, Q, N, H |
| 144 | M | R, G, A, K, Q, N, H |
| 145 | L | R, G, A, K, Q, N, H |
| 146 | F | R, G, A, K, Q, N, H |
| 147 | E | R, G, A, K, Q, N, H |
| 148 | Q | R, G, A, K, N, H |
| 149 | Y | R, G, A, K, Q, N, H |
| 150 | I | R, G, A, K, Q, N, H |
| 151 | R | G, A, K, Q, N, H |
| 152 | L | R, G, A, K, Q, N, H |
| 153 | T | R, G, A, K, Q, N, H |
| 154 | K | R, G, A, Q, N, H |
| 155 | G | R, A, K, Q, N, H |
| 156 | E | R, G, A, K, Q, N, H |
| 157 | I | R, G, A, K, Q, N, H |
| 158 | E | R, G, A, K, Q, N, H |
| 159 | G | R, A, K, Q, N, H |
| 160 | Y | R, G, A, K, Q, N, H |
| 161 | A | R, G, K, Q, N, H |
| 162 | A | R, G, K, Q, N, H |
| 163 | I | R, G, A, K, Q, N, H |
| 164 | S | R, G, A, K, Q, N, H |
| 165 | N | R, G, A, K, Q, H |
| 166 | M | R, G, A, K, Q, N, H |
| 167 | F | R, G, A, K, Q, N, H |
| 168 | G | R, A, K, Q, N, H |
| 169 | N | R, G, A, K, Q, H |

TABLE 2-continued

Single amino acid substitutions in variant Cas12i4 polypeptide.

| Position | Wild-Type Residue | Substitution(s) |
|---|---|---|
| 170 | G | R, A, K, Q, N, H |
| 171 | E | R, G, A, K, Q, N, H |
| 172 | K | R, G, A, Q, N, H |
| 173 | E | R, G, A, K, Q, N, H |
| 174 | D | R, G, A, K, Q, N, H |
| 175 | R | G, A, K, Q, N, H |
| 176 | S | R, G, A, K, Q, N, H |
| 177 | K | R, G, A, Q, N, H |
| 178 | K | R, G, A, Q, N, H |
| 179 | R | G, A, K, Q, N, H |
| 180 | M | R, G, A, K, Q, N, H |
| 181 | Y | R, G, A, K, Q, N, H |
| 182 | A | R, G, K, Q, N, H |
| 183 | T | R, G, A, K, Q, N, H |
| 184 | R | G, A, K, Q, N, H |
| 185 | M | R, G, A, K, Q, N, H |
| 186 | K | R, G, A, Q, N, H |
| 187 | D | R, G, A, K, Q, N, H |
| 188 | W | R, G, A, K, Q, N, H |
| 189 | L | R, G, A, K, Q, N, H |
| 190 | E | R, G, A, K, Q, N, H |
| 191 | A | R, G, K, Q, N, H |
| 192 | N | R, G, A, K, Q, H |
| 193 | E | R, G, A, K, Q, N, H |
| 194 | N | R, G, A, K, Q, H |
| 195 | I | R, G, A, K, Q, N, H |
| 196 | T | R, G, A, K, Q, N, H |
| 197 | W | R, G, A, K, Q, N, H |
| 198 | E | R, G, A, K, Q, N, H |
| 199 | Q | R, G, A, K, N, H |
| 200 | Y | R, G, A, K, Q, N, H |
| 201 | R | G, A, K, Q, N, H |
| 202 | E | R, G, A, K, Q, N, H |
| 203 | A | R, G, K, Q, N, H |
| 204 | L | R, G, A, K, Q, N, H |
| 205 | K | R, G, A, Q, N, H |
| 206 | N | R, G, A, K, Q, H |
| 207 | Q | R, G, A, K, N, H |
| 208 | L | R, G, A, K, Q, N, H |
| 209 | N | R, G, A, K, Q, H |
| 210 | A | R, G, K, Q, N, H |
| 211 | K | R, G, A, Q, N, H |
| 212 | N | R, G, A, K, Q, H |
| 213 | L | R, G, A, K, Q, N, H |
| 214 | E | R, G, A, K, Q, N, H |
| 215 | Q | R, G, A, K, N, H |
| 216 | V | R, G, A, K, Q, N, H |
| 217 | V | R, G, A, K, Q, N, H |
| 218 | A | R, G, K, Q, N, H |
| 219 | N | R, G, A, K, Q, H |
| 220 | Y | R, G, A, K, Q, N, H |
| 221 | K | R, G, A, Q, N, H |
| 222 | G | R, A, K, Q, N, H |
| 223 | N | R, G, A, K, Q, H |
| 224 | A | R, G, K, Q, N, H |
| 225 | G | R, A, K, Q, N, H |
| 226 | G | R, A, K, Q, N, H |
| 227 | A | R, G, K, Q, N, H |
| 228 | D | R, G, A, K, Q, N, H |
| 229 | P | R, G, A, K, Q, N, H |
| 230 | F | R, G, A, K, Q, N, H |
| 231 | F | R, G, A, K, Q, N, H |
| 232 | K | R, G, A, Q, N, H |
| 233 | Y | R, G, A, K, Q, N, H |
| 234 | S | R, G, A, K, Q, N, H |
| 235 | F | R, G, A, K, Q, N, H |
| 236 | S | R, G, A, K, Q, N, H |
| 237 | K | R, G, A, Q, N, H |
| 238 | E | R, G, A, K, Q, N, H |
| 239 | G | R, A, K, Q, N, H |
| 240 | M | R, G, A, K, Q, N, H |
| 241 | V | R, G, A, K, Q, N, H |
| 242 | S | R, G, A, K, Q, N, H |
| 243 | K | R, G, A, Q, N, H |
| 244 | K | R, G, A, Q, N, H |
| 245 | E | R, G, A, K, Q, N, H |
| 246 | H | R, G, A, K, Q, N |
| 247 | A | R, G, K, Q, N, H |
| 248 | Q | R, G, A, K, N, H |
| 249 | Q | R, G, A, K, N, H |
| 250 | L | R, G, A, K, Q, N, H |
| 251 | D | R, G, A, K, Q, N, H |
| 252 | K | R, G, A, Q, N, H |
| 253 | F | R, G, A, K, Q, N, H |
| 254 | K | R, G, A, Q, N, H |
| 255 | T | R, G, A, K, Q, N, H |
| 256 | V | R, G, A, K, Q, N, H |
| 257 | L | R, G, A, K, Q, N, H |
| 258 | K | R, G, A, Q, N, H |
| 259 | N | R, G, A, K, Q, H |
| 260 | K | R, G, A, Q, N, H |
| 261 | A | R, G, K, Q, N, H |
| 262 | R | G, A, K, Q, N, H |
| 263 | D | R, G, A, K, Q, N, H |
| 264 | L | R, G, A, K, Q, N, H |
| 265 | N | R, G, A, K, Q, H |
| 266 | F | R, G, A, K, Q, N, H |
| 267 | P | R, G, A, K, Q, N, H |
| 268 | N | R, G, A, K, Q, H |
| 269 | K | R, G, A, Q, N, H |
| 270 | E | R, G, A, K, Q, N, H |
| 271 | K | R, G, A, Q, N, H |
| 272 | L | R, G, A, K, Q, N, H |
| 273 | K | R, G, A, Q, N, H |
| 274 | Q | R, G, A, K, N, H |
| 275 | W | R, G, A, K, Q, N, H |
| 276 | L | R, G, A, K, Q, N, H |
| 277 | E | R, G, A, K, Q, N, H |
| 278 | A | R, G, K, Q, N, H |
| 279 | E | R, G, A, K, Q, N, H |
| 280 | I | R, G, A, K, Q, N, H |
| 281 | G | R, A, K, Q, N, H |
| 282 | I | R, G, A, K, Q, N, H |
| 283 | P | R, G, A, K, Q, N, H |
| 284 | V | R, G, A, K, Q, N, H |
| 285 | D | R, G, A, K, Q, N, H |
| 286 | A | R, G, K, Q, N, H |
| 287 | N | R, G, A, K, Q, H |
| 288 | V | R, G, A, K, Q, N, H |
| 289 | Y | R, G, A, K, Q, N, H |
| 290 | S | R, G, A, K, Q, N, H |
| 291 | Q | R, G, A, K, N, H |
| 292 | M | R, G, A, K, Q, N, H |
| 293 | F | R, G, A, K, Q, N, H |
| 294 | S | R, G, A, K, Q, N, H |
| 295 | N | R, G, A, K, Q, H |
| 296 | G | R, A, K, Q, N, H |
| 297 | V | R, G, A, K, Q, N, H |
| 298 | S | R, G, A, K, Q, N, H |
| 299 | E | R, G, A, K, Q, N, H |
| 300 | V | R, G, A, K, Q, N, H |
| 301 | Q | R, G, A, K, N, H |
| 302 | P | R, G, A, K, Q, N, H |
| 303 | K | R, G, A, Q, N, H |
| 304 | T | R, G, A, K, Q, N, H |
| 305 | T | R, G, A, K, Q, N, H |
| 306 | R | G, A, K, Q, N, H |
| 307 | N | R, G, A, K, Q, H |
| 308 | M | R, G, A, K, Q, N, H |
| 309 | S | R, G, A, K, Q, N, H |
| 310 | F | R, G, A, K, Q, N, H |
| 311 | S | R, G, A, K, Q, N, H |
| 312 | N | R, G, A, K, Q, H |
| 313 | E | R, G, A, K, Q, N, H |
| 314 | K | R, G, A, Q, N, H |
| 315 | L | R, G, A, K, Q, N, H |
| 316 | D | R, G, A, K, Q, N, H |
| 317 | L | R, G, A, K, Q, N, H |
| 318 | L | R, G, A, K, Q, N, H |
| 319 | T | R, G, A, K, Q, N, H |

TABLE 2-continued

Single amino acid substitutions in variant Cas12i4 polypeptide.

| Position | Wild-Type Residue | Substitution(s) |
|---|---|---|
| 320 | E | R, G, A, K, Q, N, H |
| 321 | L | R, G, A, K, Q, N, H |
| 322 | K | R, G, A, Q, N, H |
| 323 | D | R, G, A, K, Q, N, H |
| 324 | L | R, G, A, K, Q, N, H |
| 325 | N | R, G, A, K, Q, H |
| 326 | K | R, G, A, Q, N, H |
| 327 | G | R, A, K, Q, N, H |
| 328 | D | R, G, A, K, Q, N, H |
| 329 | G | R, A, K, Q, N, H |
| 330 | F | R, G, A, K, Q, N, H |
| 331 | E | R, G, A, K, Q, N, H |
| 332 | Y | R, G, A, K, Q, N, H |
| 333 | A | R, G, K, Q, N, H |
| 334 | R | G, A, K, Q, N, H |
| 335 | E | R, G, A, K, N, H |
| 336 | V | R, G, A, K, Q, N, H |
| 337 | L | R, G, A, K, Q, N, H |
| 338 | N | R, G, A, K, Q, H |
| 339 | G | R, A, K, Q, N, H |
| 340 | F | R, G, A, K, Q, N, H |
| 341 | F | R, G, A, K, Q, N, H |
| 342 | D | R, G, A, K, Q, N, H |
| 343 | S | R, G, A, K, Q, N, H |
| 344 | E | R, G, A, K, Q, N, H |
| 345 | L | R, G, A, K, Q, N, H |
| 346 | H | R, G, A, K, Q, N |
| 347 | T | R, G, A, K, Q, N, H |
| 348 | T | R, G, A, K, Q, N, H |
| 349 | E | R, G, A, K, Q, N, H |
| 350 | D | R, G, A, K, Q, N, H |
| 351 | K | R, G, A, Q, N, H |
| 352 | F | R, G, A, K, Q, N, H |
| 353 | N | R, G, A, K, Q, H |
| 354 | I | R, G, A, K, Q, N, H |
| 355 | T | R, G, A, K, Q, N, H |
| 356 | S | R, G, A, K, Q, N, H |
| 357 | R | G, A, K, Q, N, H |
| 358 | Y | R, G, A, K, Q, N, H |
| 359 | L | R, G, A, K, Q, N, H |
| 360 | G | R, A, K, Q, N, H |
| 361 | G | R, A, K, Q, N, H |
| 362 | D | R, G, A, K, Q, N, H |
| 363 | K | R, G, A, Q, N, H |
| 364 | S | R, G, A, K, Q, N, H |
| 365 | N | R, G, A, K, Q, H |
| 366 | R | G, A, K, Q, N, H |
| 367 | L | R, G, A, K, Q, N, H |
| 368 | S | R, G, A, K, Q, N, H |
| 369 | K | R, G, A, Q, N, H |
| 370 | L | R, G, A, K, Q, N, H |
| 371 | Y | R, G, A, K, Q, N, H |
| 372 | K | R, G, A, Q, N, H |
| 373 | I | R, G, A, K, Q, N, H |
| 374 | W | R, G, A, K, Q, N, H |
| 375 | K | R, G, A, Q, N, H |
| 376 | K | R, G, A, Q, N, H |
| 377 | E | R, G, A, K, Q, N, H |
| 378 | G | R, A, K, Q, N, H |
| 379 | V | R, G, A, K, Q, N, H |
| 380 | D | R, G, A, K, Q, N, H |
| 381 | C | R, G, A, K, Q, N, H |
| 382 | E | R, G, A, K, Q, N, H |
| 383 | E | R, G, A, K, Q, N, H |
| 384 | G | R, A, K, Q, N, H |
| 385 | I | R, G, A, K, Q, N, H |
| 386 | Q | R, G, A, K, N, H |
| 387 | Q | R, G, A, K, N, H |
| 388 | F | R, G, A, K, Q, N, H |
| 389 | C | R, G, A, K, Q, N, H |
| 390 | E | R, G, A, K, Q, N, H |
| 391 | A | R, G, K, Q, N, H |
| 392 | V | R, G, A, K, Q, N, H |
| 393 | K | R, G, A, Q, N, H |
| 394 | D | R, G, A, K, Q, N, H |
| 395 | K | R, G, A, K, Q, N, H |
| 396 | M | R, G, A, K, Q, N, H |
| 397 | G | R, A, K, Q, N, H |
| 398 | Q | R, G, A, K, N, H |
| 399 | I | R, G, A, K, Q, N, H |
| 400 | P | R, G, A, K, Q, N, H |
| 401 | I | R, G, A, K, Q, N, H |
| 402 | R | G, A, K, Q, N, H |
| 403 | N | R, G, A, K, Q, H |
| 404 | V | R, G, A, K, Q, N, H |
| 405 | L | R, G, A, K, Q, N, H |
| 406 | K | R, G, A, Q, N, H |
| 407 | Y | R, G, A, K, Q, N, H |
| 408 | L | R, G, A, K, Q, N, H |
| 409 | W | R, G, A, K, Q, N, H |
| 410 | Q | R, G, A, K, N, H |
| 411 | F | R, G, A, K, Q, N, H |
| 412 | R | G, A, K, Q, N, H |
| 413 | E | R, G, A, K, Q, N, H |
| 414 | T | R, G, A, K, Q, N, H |
| 415 | V | R, G, A, K, Q, N, H |
| 416 | S | R, G, A, K, Q, N, H |
| 417 | A | R, G, K, Q, N, H |
| 418 | E | R, G, A, K, Q, N, H |
| 419 | D | R, G, A, K, Q, N, H |
| 420 | F | R, G, A, K, Q, N, H |
| 421 | E | R, G, A, K, Q, N, H |
| 422 | A | R, G, K, Q, N, H |
| 423 | A | R, G, K, Q, N, H |
| 424 | A | R, G, K, Q, N, H |
| 425 | K | R, G, A, Q, N, H |
| 426 | A | R, G, K, Q, N, H |
| 427 | N | R, G, A, K, Q, H |
| 428 | H | R, G, A, K, Q, N |
| 429 | L | R, G, A, K, Q, N, H |
| 430 | E | R, G, A, K, Q, N, H |
| 431 | E | R, G, A, K, Q, N, H |
| 432 | K | R, G, A, Q, N, H |
| 433 | I | R, G, A, K, Q, N, H |
| 434 | S | R, G, A, K, Q, N, H |
| 435 | R | G, A, K, Q, N, H |
| 436 | V | R, G, A, K, Q, N, H |
| 437 | K | R, G, A, Q, N, H |
| 438 | A | R, G, K, Q, N, H |
| 439 | H | R, G, A, K, Q, N |
| 440 | P | R, G, A, K, Q, N, H |
| 441 | I | R, G, A, K, Q, N, H |
| 442 | V | R, G, A, K, Q, N, H |
| 443 | I | R, G, A, K, Q, N, H |
| 444 | S | R, G, A, K, Q, N, H |
| 445 | N | R, G, A, K, Q, H |
| 446 | R | G, A, K, Q, N, H |
| 447 | Y | R, G, A, K, Q, N, H |
| 448 | W | R, G, A, K, Q, N, H |
| 449 | A | R, G, K, Q, N, H |
| 450 | F | R, G, A, K, Q, N, H |
| 451 | G | R, A, K, Q, N, H |
| 452 | T | R, G, A, K, Q, N, H |
| 453 | S | R, G, A, K, Q, N, H |
| 454 | A | R, G, K, Q, N, H |
| 455 | L | R, G, A, K, Q, N, H |
| 456 | V | R, G, A, K, Q, N, H |
| 457 | G | R, A, K, Q, N, H |
| 458 | N | R, G, A, K, Q, H |
| 459 | I | R, G, A, K, Q, N, H |
| 460 | M | R, G, A, K, Q, N, H |
| 461 | P | R, G, A, K, Q, N, H |
| 462 | A | R, G, K, Q, N, H |
| 463 | D | R, G, A, K, Q, N, H |
| 464 | K | R, G, A, Q, N, H |
| 465 | R | G, A, K, Q, N, H |
| 466 | H | R, G, A, K, Q, N |
| 467 | Q | R, G, A, K, N, H |
| 468 | G | R, A, K, Q, N, H |
| 469 | E | R, G, A, K, Q, N, H |

TABLE 2-continued

Single amino acid substitutions in variant Cas12i4 polypeptide.

| Position | Wild-Type Residue | Substitution(s) |
|---|---|---|
| 470 | Y | R, G, A, K, Q, N, H |
| 471 | A | R, G, K, Q, N, H |
| 472 | G | R, A, K, Q, N, H |
| 473 | Q | R, G, A, K, N, H |
| 474 | N | R, G, A, K, Q, H |
| 475 | F | R, G, A, K, Q, N, H |
| 476 | K | R, G, A, Q, N, H |
| 477 | M | R, G, A, K, Q, N, H |
| 478 | W | R, G, A, K, Q, N, H |
| 479 | L | R, G, A, K, Q, N, H |
| 480 | E | R, G, A, K, Q, N, H |
| 481 | A | R, G, K, Q, N, H |
| 482 | E | R, G, A, K, Q, N, H |
| 483 | L | R, G, A, K, Q, N, H |
| 484 | H | R, G, A, K, Q, N |
| 485 | Y | R, G, A, K, Q, N, H |
| 486 | D | R, G, A, K, Q, N, H |
| 487 | G | R, A, K, Q, N, H |
| 488 | K | R, G, A, Q, N, H |
| 489 | K | R, G, A, Q, N, H |
| 490 | A | R, G, K, Q, N, H |
| 491 | K | R, G, A, Q, N, H |
| 492 | H | R, G, A, K, Q, N |
| 493 | H | R, G, A, K, Q, N |
| 494 | L | R, G, A, K, Q, N, H |
| 495 | P | R, G, A, K, Q, N, H |
| 496 | F | R, G, A, K, Q, N, H |
| 497 | Y | R, G, A, K, Q, N, H |
| 498 | N | R, G, A, K, Q, H |
| 499 | A | R, G, K, Q, N, H |
| 500 | R | G, A, K, Q, N, H |
| 501 | F | R, G, A, K, Q, N, H |
| 502 | F | R, G, A, K, Q, N, H |
| 503 | E | R, G, A, K, Q, N, H |
| 504 | E | R, G, A, K, Q, N, H |
| 505 | V | R, G, A, K, Q, N, H |
| 506 | Y | R, G, A, K, Q, N, H |
| 507 | C | R, G, A, K, Q, N, H |
| 508 | Y | R, G, A, K, Q, N, H |
| 509 | H | R, G, A, K, Q, N |
| 510 | P | R, G, A, K, Q, N, H |
| 511 | S | R, G, A, K, Q, N, H |
| 512 | V | R, G, A, K, Q, N, H |
| 513 | A | R, G, K, Q, N, H |
| 514 | E | R, G, A, K, Q, N, H |
| 515 | I | R, G, A, K, Q, N, H |
| 516 | T | R, G, A, K, Q, N, H |
| 517 | P | R, G, A, K, Q, N, H |
| 518 | F | R, G, A, K, Q, N, H |
| 519 | K | R, G, A, Q, N, H |
| 520 | T | R, G, A, K, Q, N, H |
| 521 | K | R, G, A, Q, N, H |
| 522 | Q | R, G, A, K, N, H |
| 523 | F | R, G, A, K, Q, N, H |
| 524 | G | R, A, K, Q, N, H |
| 525 | C | R, G, A, K, Q, N, H |
| 526 | E | R, G, A, K, Q, N, H |
| 527 | I | R, G, A, K, Q, N, H |
| 528 | G | R, A, K, Q, N, H |
| 529 | K | R, G, A, Q, N, H |
| 530 | D | R, G, A, K, Q, N, H |
| 531 | I | R, A, K, Q, N, H |
| 532 | P | R, G, A, K, Q, N, H |
| 533 | D | R, G, A, K, Q, N, H |
| 534 | Y | R, G, A, K, Q, N, H |
| 535 | V | R, G, A, K, Q, N, H |
| 536 | S | R, G, A, K, Q, N, H |
| 537 | V | R, G, A, K, Q, N, H |
| 538 | A | R, G, K, Q, N, H |
| 539 | L | R, G, A, K, Q, N, H |
| 540 | K | R, G, A, Q, N, H |
| 541 | D | R, G, A, K, Q, N, H |
| 542 | N | R, G, A, K, Q, H |
| 543 | P | R, G, A, K, Q, N, H |
| 544 | Y | R, G, A, K, Q, N, H |
| 545 | K | R, G, A, Q, N, H |
| 546 | K | R, G, A, Q, N, H |
| 547 | A | R, G, K, Q, N, H |
| 548 | T | R, G, A, K, Q, N, H |
| 549 | K | R, G, A, Q, N, H |
| 550 | R | G, A, K, Q, N, H |
| 551 | I | R, G, A, K, Q, N, H |
| 552 | L | R, G, A, K, Q, N, H |
| 553 | R | G, A, K, Q, N, H |
| 554 | A | R, G, K, Q, N, H |
| 555 | I | R, G, A, K, Q, N, H |
| 556 | Y | R, G, A, K, Q, N, H |
| 557 | N | R, G, A, K, Q, H |
| 558 | P | R, G, A, K, Q, N, H |
| 559 | V | R, G, A, K, Q, N, H |
| 560 | A | R, G, K, Q, N, H |
| 561 | N | R, G, A, K, Q, H |
| 562 | T | R, G, A, K, Q, N, H |
| 563 | T | R, G, A, K, Q, N, H |
| 564 | G | R, A, K, Q, N, H |
| 565 | V | R, G, A, K, Q, N, H |
| 566 | D | R, G, A, K, Q, N, H |
| 567 | K | R, G, A, Q, N, H |
| 568 | T | R, G, A, K, Q, N, H |
| 569 | T | R, G, A, K, Q, N, H |
| 570 | N | R, G, A, K, Q, H |
| 571 | C | R, G, A, K, Q, N, H |
| 572 | S | R, G, A, K, Q, N, H |
| 573 | F | R, G, A, K, Q, N, H |
| 574 | M | R, G, A, K, Q, N, H |
| 575 | I | R, G, A, K, Q, N, H |
| 576 | K | R, G, A, Q, N, H |
| 577 | R | G, A, K, Q, N, H |
| 578 | E | R, G, A, K, Q, N, H |
| 579 | N | R, G, A, K, Q, H |
| 580 | D | R, G, A, K, Q, N, H |
| 581 | E | R, G, A, K, Q, N, H |
| 582 | Y | R, G, A, K, Q, N, H |
| 583 | K | R, G, A, Q, N, H |
| 584 | L | R, G, A, K, Q, N, H |
| 585 | V | R, G, A, K, Q, N, H |
| 586 | I | R, G, A, K, Q, N, H |
| 587 | N | R, G, A, K, Q, H |
| 588 | R | G, A, K, Q, N, H |
| 589 | K | R, G, A, Q, N, H |
| 590 | I | R, G, A, K, Q, N, H |
| 591 | S | R, G, A, K, Q, N, H |
| 592 | V | R, G, A, K, Q, N, H |
| 593 | D | R, G, A, K, Q, N, H |
| 594 | R | G, A, K, Q, N, H |
| 595 | P | R, G, A, K, Q, N, H |
| 596 | K | R, G, A, Q, N, H |
| 597 | R | G, A, K, Q, N, H |
| 598 | I | R, G, A, K, Q, N, H |
| 599 | E | R, G, A, K, Q, N, H |
| 600 | V | R, G, A, K, Q, N, H |
| 601 | G | R, A, K, Q, N, H |
| 602 | R | G, A, K, Q, N, H |
| 603 | T | R, G, A, K, Q, N, H |
| 604 | I | R, G, A, K, Q, N, H |
| 605 | M | R, G, A, K, Q, N, H |
| 606 | G | R, A, K, Q, N, H |
| 607 | Y | R, G, A, K, Q, N, H |
| 608 | D | A, C, E, F, G, H, I, K, L, M, N, P, Q, R, S, T, V, W, Y |
| 609 | R | G, A, K, Q, N, H |
| 610 | N | R, G, A, K, Q, H |
| 611 | Q | R, G, A, K, N, H |
| 612 | V | R, G, A, K, Q, N, H |
| 613 | A | R, G, K, Q, N, H |
| 614 | S | R, G, A, K, Q, N, H |
| 615 | D | R, G, A, K, Q, N, H |
| 616 | T | R, G, A, K, Q, N, H |
| 617 | Y | R, G, A, K, Q, N, H |

TABLE 2-continued

Single amino acid substitutions in variant Cas12i4 polypeptide.

| Position | Wild-Type Residue | Substitution(s) |
|---|---|---|
| 618 | W | R, G, A, K, Q, N, H |
| 619 | I | R, G, A, K, Q, N, H |
| 620 | G | R, A, K, Q, N, H |
| 621 | R | G, A, K, Q, N, H |
| 622 | L | R, G, A, K, Q, N, H |
| 623 | V | R, G, A, K, Q, N, H |
| 624 | P | R, G, A, K, Q, N, H |
| 625 | P | R, G, A, K, Q, N, H |
| 626 | G | R, A, K, Q, N, H |
| 627 | T | R, G, A, K, Q, N, H |
| 628 | R | G, A, K, Q, N, H |
| 629 | G | R, A, K, Q, N, H |
| 630 | A | R, G, K, Q, N, H |
| 631 | Y | R, G, A, K, Q, N, H |
| 632 | R | G, A, K, Q, N, H |
| 633 | I | R, G, A, K, Q, N, H |
| 634 | G | R, A, K, Q, N, H |
| 635 | E | R, G, A, K, Q, N, H |
| 636 | W | R, G, A, K, Q, N, H |
| 637 | S | R, G, A, K, Q, N, H |
| 638 | V | R, G, A, K, Q, N, H |
| 639 | Q | R, G, A, K, N, H |
| 640 | Y | R, G, A, K, Q, N, H |
| 641 | I | R, A, K, Q, N, H |
| 642 | K | R, G, A, Q, N, H |
| 643 | S | R, G, A, K, Q, N, H |
| 644 | G | R, A, K, Q, N, H |
| 645 | P | R, G, A, K, Q, N, H |
| 646 | V | R, G, A, K, Q, N, H |
| 647 | L | R, G, A, K, Q, N, H |
| 648 | S | R, G, A, K, Q, N, H |
| 649 | S | R, G, A, K, Q, N, H |
| 650 | T | R, G, A, K, Q, N, H |
| 651 | Q | R, G, A, K, N, H |
| 652 | G | R, A, K, Q, N, H |
| 653 | V | R, G, A, K, Q, N, H |
| 654 | N | R, G, A, K, Q, H |
| 655 | N | R, G, A, K, Q, H |
| 656 | S | R, G, A, K, Q, N, H |
| 657 | T | R, G, A, K, Q, N, H |
| 658 | T | R, G, A, K, Q, N, H |
| 659 | D | R, G, A, K, Q, N, H |
| 660 | Q | R, G, A, K, N, H |
| 661 | L | R, G, A, K, Q, N, H |
| 662 | V | R, G, A, K, Q, N, H |
| 663 | Y | R, G, A, K, Q, N, H |
| 664 | N | R, G, A, K, Q, H |
| 665 | G | R, A, K, Q, N, H |
| 666 | M | R, G, A, K, Q, N, H |
| 667 | P | R, G, A, K, Q, N, H |
| 668 | S | R, G, A, K, Q, N, H |
| 669 | S | R, G, A, K, Q, N, H |
| 670 | S | R, G, A, K, Q, N, H |
| 671 | E | R, G, A, K, Q, N, H |
| 672 | R | G, A, K, Q, N, H |
| 673 | F | R, G, A, K, Q, N, H |
| 674 | K | R, G, A, Q, N, H |
| 675 | A | R, G, K, Q, N, H |
| 676 | W | R, G, A, K, Q, N, H |
| 677 | K | R, G, A, Q, N, H |
| 678 | K | R, G, A, Q, N, H |
| 679 | A | R, G, K, Q, N, H |
| 680 | R | G, A, K, Q, N, H |
| 681 | M | R, G, A, K, Q, N, H |
| 682 | A | R, G, K, Q, N, H |
| 683 | F | R, G, A, K, Q, N, H |
| 684 | I | R, G, A, K, Q, N, H |
| 685 | R | G, A, K, Q, N, H |
| 686 | K | R, G, A, Q, N, H |
| 687 | L | R, G, A, K, Q, N, H |
| 688 | I | R, G, A, K, Q, N, H |
| 689 | R | G, A, K, Q, N, H |
| 690 | Q | R, G, A, K, N, H |
| 691 | L | R, G, A, K, Q, N, H |
| 692 | N | R, G, A, K, Q, H |
| 693 | D | R, G, A, K, Q, N, H |
| 694 | E | R, G, A, K, Q, N, H |
| 695 | G | R, A, K, Q, N, H |
| 696 | L | R, G, A, K, Q, N, H |
| 697 | E | R, G, A, K, Q, N, H |
| 698 | S | R, G, A, K, Q, N, H |
| 699 | K | R, G, A, Q, N, H |
| 700 | G | R, A, K, Q, N, H |
| 701 | Q | R, G, A, K, N, H |
| 702 | D | R, G, A, K, Q, N, H |
| 703 | Y | R, G, A, K, Q, N, H |
| 704 | I | R, G, A, K, Q, N, H |
| 705 | P | R, G, A, K, Q, N, H |
| 706 | E | R, G, A, K, Q, N, H |
| 707 | N | R, G, A, K, Q, H |
| 708 | P | R, G, A, K, Q, N, H |
| 709 | S | R, G, A, K, Q, N, H |
| 710 | S | R, G, A, K, Q, N, H |
| 711 | F | R, G, A, K, Q, N, H |
| 712 | D | R, G, A, K, Q, N, H |
| 713 | V | R, G, A, K, Q, N, H |
| 714 | D | R, G, A, K, Q, N, H |
| 715 | R | G, A, K, Q, N, H |
| 716 | G | R, A, K, Q, N, H |
| 717 | T | R, G, A, K, Q, N, H |
| 718 | L | R, G, A, K, Q, N, H |
| 719 | Y | R, G, A, K, Q, N, H |
| 720 | V | R, G, A, K, Q, N, H |
| 721 | F | R, G, A, K, Q, N, H |
| 722 | N | R, G, A, K, Q, H |
| 723 | S | R, G, A, K, Q, N, H |
| 724 | N | R, G, A, K, Q, H |
| 725 | Y | R, G, A, K, Q, N, H |
| 726 | L | R, G, A, K, Q, N, H |
| 727 | K | R, G, A, Q, N, H |
| 728 | A | R, G, K, Q, N, H |
| 729 | L | R, G, A, K, Q, N, H |
| 730 | V | R, G, A, K, Q, N, H |
| 731 | S | R, G, A, K, Q, N, H |
| 732 | K | R, G, A, Q, N, H |
| 733 | H | R, G, A, K, Q, N |
| 734 | R | G, A, K, Q, N, H |
| 735 | K | R, G, A, Q, N, H |
| 736 | A | R, G, K, Q, N, H |
| 737 | K | R, G, A, Q, N, H |
| 738 | K | R, G, A, Q, N, H |
| 739 | P | R, G, A, K, Q, N, H |
| 740 | V | R, G, A, K, Q, N, H |
| 741 | E | R, G, A, K, Q, N, H |
| 742 | G | R, A, K, Q, N, H |
| 743 | I | R, G, A, K, Q, N, H |
| 744 | L | R, G, A, K, Q, N, H |
| 745 | D | R, G, A, K, Q, N, H |
| 746 | E | R, G, A, K, Q, N, H |
| 747 | I | R, G, A, K, Q, N, H |
| 748 | F | R, G, A, K, Q, N, H |
| 749 | A | R, G, K, Q, N, H |
| 750 | W | R, G, A, K, Q, N, H |
| 751 | T | R, G, A, K, Q, N, H |
| 752 | S | R, G, A, K, Q, N, H |
| 753 | K | R, G, A, Q, N, H |
| 754 | D | R, G, A, K, Q, N, H |
| 755 | K | R, G, A, Q, N, H |
| 756 | D | R, G, A, K, Q, N, H |
| 757 | S | R, G, A, K, Q, N, H |
| 758 | C | R, G, A, K, Q, N, H |
| 759 | S | R, G, A, K, Q, N, H |
| 760 | L | R, G, A, K, Q, N, H |
| 761 | M | R, G, A, K, Q, N, H |
| 762 | R | G, A, K, Q, N, H |
| 763 | L | R, G, A, K, Q, N, H |
| 764 | S | R, G, A, K, Q, N, H |
| 765 | S | R, G, A, K, Q, N, H |
| 766 | L | R, G, A, K, Q, N, H |
| 767 | S | R, G, A, K, Q, N, H |

TABLE 2-continued

Single amino acid substitutions in variant Cas12i4 polypeptide.

| Position | Wild-Type Residue | Substitution(s) |
|---|---|---|
| 768 | D | R, G, A, K, Q, N, H |
| 769 | A | R, G, K, Q, N, H |
| 770 | S | R, G, A, K, Q, N, H |
| 771 | M | R, G, A, K, Q, N, H |
| 772 | Q | R, G, A, K, Q, N, H |
| 773 | G | R, A, K, Q, N, H |
| 774 | I | R, G, A, K, Q, N, H |
| 775 | A | R, G, K, Q, N, H |
| 776 | S | R, G, A, K, Q, N, H |
| 777 | L | R, G, A, K, Q, N, H |
| 778 | K | R, G, A, Q, N, H |
| 779 | S | R, G, A, K, Q, N, H |
| 780 | L | R, G, A, K, Q, N, H |
| 781 | I | R, G, A, K, Q, N, H |
| 782 | N | R, G, A, K, Q, H |
| 783 | S | R, G, A, K, Q, N, H |
| 784 | Y | R, G, A, K, Q, N, H |
| 785 | F | R, G, A, K, Q, N, H |
| 786 | N | R, G, A, K, Q, H |
| 787 | K | R, G, A, Q, N, H |
| 788 | N | R, G, A, K, Q, H |
| 789 | G | R, A, K, Q, N, H |
| 790 | C | R, G, A, K, Q, N, H |
| 791 | K | R, G, A, Q, N, H |
| 792 | T | R, G, A, K, Q, N, H |
| 793 | I | R, G, A, K, Q, N, H |
| 794 | E | R, G, A, K, Q, N, H |
| 795 | D | R, G, A, K, Q, N, H |
| 796 | K | R, G, A, Q, N, H |
| 797 | E | R, G, A, K, Q, N, H |
| 798 | K | R, G, A, Q, N, H |
| 799 | F | R, G, A, K, Q, N, H |
| 800 | N | R, G, A, K, Q, H |
| 801 | P | R, G, A, K, Q, N, H |
| 802 | V | R, G, A, K, Q, N, H |
| 803 | L | R, G, A, K, Q, N, H |
| 804 | Y | R, G, A, K, Q, N, H |
| 805 | A | R, G, K, Q, N, H |
| 806 | K | R, G, A, Q, N, H |
| 807 | L | R, G, A, K, Q, N, H |
| 808 | V | R, G, A, K, Q, N, H |
| 809 | E | R, G, A, K, Q, N, H |
| 810 | V | R, G, A, K, Q, N, H |
| 811 | E | R, G, A, K, Q, N, H |
| 812 | Q | R, G, A, K, N, H |
| 813 | R | G, A, K, Q, N, H |
| 814 | R | G, A, K, Q, N, H |
| 815 | T | R, G, A, K, Q, N, H |
| 816 | N | R, G, A, K, Q, H |
| 817 | K | R, G, A, Q, N, H |
| 818 | R | G, A, K, Q, N, H |
| 819 | S | R, G, A, K, Q, N, H |
| 820 | E | R, G, A, K, Q, N, H |
| 821 | K | R, G, A, Q, N, H |
| 822 | V | R, G, A, K, Q, N, H |
| 823 | G | R, A, K, Q, N, H |
| 824 | R | G, A, K, Q, N, H |
| 825 | I | R, G, A, K, Q, N, H |
| 826 | A | R, G, K, Q, N, H |
| 827 | G | R, A, K, Q, N, H |
| 828 | S | R, G, A, K, Q, N, H |
| 829 | L | R, G, A, K, Q, N, H |
| 830 | E | R, G, A, K, Q, N, H |
| 831 | Q | R, G, A, K, N, H |
| 832 | L | R, G, A, K, Q, N, H |
| 833 | A | R, G, K, Q, N, H |
| 834 | L | R, G, A, K, Q, N, H |
| 835 | L | R, G, A, K, Q, N, H |
| 836 | N | R, G, A, K, Q, H |
| 837 | G | R, A, K, Q, N, H |
| 838 | V | R, G, A, K, Q, N, H |
| 839 | E | R, G, A, K, Q, N, H |
| 840 | V | R, G, A, K, Q, N, H |
| 841 | V | R, G, A, K, Q, N, H |
| 842 | I | R, G, A, K, Q, N, H |
| 843 | G | R, A, K, Q, N, H |
| 844 | E | A, C, D, F, G, H, I, K, L, M, N, P, Q, R, S, T, V, W, Y |
| 845 | A | R, G, K, Q, N, H |
| 846 | D | R, G, A, K, Q, N, H |
| 847 | L | R, G, A, K, Q, N, H |
| 848 | G | R, A, K, Q, N, H |
| 849 | E | R, G, A, K, Q, N, H |
| 850 | V | R, G, A, K, Q, N, H |
| 851 | E | R, G, A, K, Q, N, H |
| 852 | K | R, G, A, Q, N, H |
| 853 | G | R, A, K, Q, N, H |
| 854 | K | R, G, A, Q, N, H |
| 855 | S | R, G, A, K, Q, N, H |
| 856 | K | R, G, A, Q, N, H |
| 857 | K | R, G, A, Q, N, H |
| 858 | Q | R, G, A, K, N, H |
| 859 | N | R, G, A, K, Q, H |
| 860 | S | R, G, A, K, Q, N, H |
| 861 | R | G, A, K, Q, N, H |
| 862 | N | R, G, A, K, Q, H |
| 863 | M | R, G, A, K, Q, N, H |
| 864 | D | R, G, A, K, Q, N, H |
| 865 | W | R, G, A, K, Q, N, H |
| 866 | C | R, G, A, K, Q, N, H |
| 867 | A | R, G, K, Q, N, H |
| 868 | K | R, G, A, Q, N, H |
| 869 | Q | R, G, A, K, N, H |
| 870 | V | R, G, A, K, Q, N, H |
| 871 | A | R, G, K, Q, N, H |
| 872 | Q | R, G, A, K, N, H |
| 873 | R | G, A, K, Q, N, H |
| 874 | L | R, G, A, K, Q, N, H |
| 875 | E | R, G, A, K, Q, N, H |
| 876 | Y | R, G, A, K, Q, N, H |
| 877 | K | R, G, A, Q, N, H |
| 878 | L | R, G, A, K, Q, N, H |
| 879 | A | R, G, K, Q, N, H |
| 880 | F | R, G, A, K, Q, N, H |
| 881 | H | R, G, A, K, Q, N |
| 882 | G | R, A, K, Q, N, H |
| 883 | I | R, G, A, K, Q, N, H |
| 884 | G | R, A, K, Q, N, H |
| 885 | Y | R, G, A, K, Q, N, H |
| 886 | F | R, G, A, K, Q, N, H |
| 887 | G | R, A, K, Q, N, H |
| 888 | C | R, G, A, K, Q, N, H |
| 889 | N | R, G, A, K, Q, H |
| 890 | P | R, G, A, K, Q, N, H |
| 891 | M | R, G, A, K, Q, N, H |
| 892 | Y | R, G, A, K, Q, N, H |
| 893 | T | R, G, A, K, Q, N, H |
| 894 | S | R, G, A, K, Q, N, H |
| 895 | H | R, G, A, K, Q, N |
| 896 | Q | R, G, A, K, N, H |
| 897 | D | R, G, A, K, Q, N, H |
| 898 | P | R, G, A, K, Q, N, H |
| 899 | F | R, G, A, K, Q, N, H |
| 900 | E | R, G, A, K, Q, N, H |
| 901 | H | R, G, A, K, Q, N |
| 902 | R | G, A, K, Q, N, H |
| 903 | R | G, A, K, Q, N, H |
| 904 | V | R, G, A, K, Q, N, H |
| 905 | A | R, G, K, Q, N, H |
| 906 | D | R, G, A, K, Q, N, H |
| 907 | H | R, G, A, K, Q, N |
| 908 | I | R, G, A, K, Q, N, H |
| 909 | V | R, G, A, K, Q, N, H |
| 910 | M | R, G, A, K, Q, N, H |
| 911 | R | G, A, K, Q, N, H |
| 912 | A | R, G, K, Q, N, H |
| 913 | R | G, A, K, Q, N, H |
| 914 | F | R, G, A, K, Q, N, H |
| 915 | E | R, G, A, K, Q, N, H |

TABLE 2-continued

Single amino acid substitutions in variant Cas12i4 polypeptide.

| Position | Wild-Type Residue | Substitution(s) |
|---|---|---|
| 916 | E | R, G, A, K, Q, N, H |
| 917 | V | R, G, A, K, Q, N, H |
| 918 | N | R, G, A, K, Q, H |
| 919 | V | R, G, A, K, Q, N, H |
| 920 | E | R, G, A, K, Q, N, H |
| 921 | N | R, G, A, K, Q, H |
| 922 | I | R, G, A, K, Q, N, H |
| 923 | A | R, G, K, Q, N, H |
| 924 | E | R, G, A, K, Q, N, H |
| 925 | W | R, G, A, K, Q, N, H |
| 926 | H | R, G, A, K, Q, N |
| 927 | V | R, G, A, K, Q, N, H |
| 928 | R | G, A, K, Q, N, H |
| 929 | N | R, G, A, K, Q, H |
| 930 | F | R, G, A, K, Q, N, H |
| 931 | S | R, G, A, K, Q, N, H |
| 932 | N | R, G, A, K, Q, H |
| 933 | Y | R, G, A, K, Q, N, H |
| 934 | L | R, G, A, K, Q, N, H |
| 935 | R | G, A, K, Q, N, H |
| 936 | A | R, G, K, Q, N, H |
| 937 | D | R, G, A, K, Q, N, H |
| 938 | S | R, G, A, K, Q, N, H |
| 939 | G | R, A, K, Q, N, H |
| 940 | T | R, G, A, K, Q, N, H |
| 941 | G | R, A, K, Q, N, H |
| 942 | L | R, G, A, K, Q, N, H |
| 943 | Y | R, G, A, K, Q, N, H |
| 944 | Y | R, G, A, K, Q, N, H |
| 945 | K | R, G, A, Q, N, H |
| 946 | Q | R, G, A, K, N, H |
| 947 | A | R, G, K, Q, N, H |
| 948 | T | R, G, A, K, Q, N, H |
| 949 | M | R, G, A, K, Q, N, H |
| 950 | D | R, G, A, K, Q, N, H |
| 951 | F | R, G, A, K, Q, N, H |
| 952 | L | R, G, A, K, Q, N, H |
| 953 | K | R, G, A, Q, N, H |
| 954 | H | R, G, A, K, Q, N |
| 955 | Y | R, G, A, K, Q, N, H |
| 956 | G | R, A, K, Q, N, H |
| 957 | L | R, G, A, K, Q, N, H |
| 958 | E | R, G, A, K, Q, N, H |
| 959 | E | R, G, A, K, Q, N, H |
| 960 | H | R, G, A, K, Q, N |
| 961 | A | R, G, K, Q, N, H |
| 962 | E | R, G, A, K, Q, N, H |
| 963 | G | R, A, K, Q, N, H |
| 964 | L | R, G, A, K, Q, N, H |
| 965 | E | R, G, A, K, Q, N, H |
| 966 | N | R, G, A, K, Q, H |
| 967 | K | R, G, A, Q, N, H |
| 968 | K | R, G, A, Q, N, H |
| 969 | I | R, G, A, K, Q, N, H |
| 970 | K | R, G, A, Q, N, H |
| 971 | F | R, G, A, K, Q, N, H |
| 972 | Y | R, G, A, K, Q, N, H |
| 973 | D | R, G, A, K, Q, N, H |
| 974 | F | R, G, A, K, Q, N, H |
| 975 | R | G, A, K, Q, N, H |
| 976 | K | R, G, A, Q, N, H |
| 977 | I | R, G, A, K, Q, N, H |
| 978 | L | R, G, A, K, Q, N, H |
| 979 | E | R, G, A, K, Q, N, H |
| 980 | D | R, G, A, K, Q, N, H |
| 981 | K | R, G, A, Q, N, H |
| 982 | N | R, G, A, K, Q, H |
| 983 | L | R, G, A, K, Q, N, H |
| 984 | T | R, G, A, K, Q, N, H |
| 985 | S | R, G, A, K, Q, N, H |
| 986 | V | R, G, A, K, Q, N, H |
| 987 | I | R, G, A, K, Q, N, H |
| 988 | I | R, G, A, K, Q, N, H |
| 989 | P | R, G, A, K, Q, N, H |
| 990 | K | R, G, A, Q, N, H |
| 991 | R | G, A, K, Q, N, H |
| 992 | G | R, A, K, Q, N, H |
| 993 | G | R, A, K, Q, N, H |
| 994 | R | G, A, K, Q, N, H |
| 995 | I | R, G, A, K, Q, N, H |
| 996 | Y | R, G, A, K, Q, N, H |
| 997 | M | R, G, A, K, Q, N, H |
| 998 | A | R, G, K, Q, N, H |
| 999 | T | R, G, A, K, Q, N, H |
| 1000 | N | R, G, A, K, Q, H |
| 1001 | P | R, G, A, K, Q, N, H |
| 1002 | V | R, G, A, K, Q, N, H |
| 1003 | T | R, G, A, K, Q, N, H |
| 1004 | S | R, G, A, K, Q, N, H |
| 1005 | D | R, G, A, K, Q, N, H |
| 1006 | S | R, G, A, K, Q, N, H |
| 1007 | T | R, G, A, K, Q, N, H |
| 1008 | P | R, G, A, K, Q, N, H |
| 1009 | I | R, G, A, K, Q, N, H |
| 1010 | T | R, G, A, K, Q, N, H |
| 1011 | Y | R, G, A, K, Q, N, H |
| 1012 | A | R, G, K, Q, N, H |
| 1013 | G | R, A, K, Q, N, H |
| 1014 | K | R, G, A, Q, N, H |
| 1015 | T | R, G, A, K, Q, N, H |
| 1016 | Y | R, G, A, K, Q, N, H |
| 1017 | N | R, G, A, K, Q, H |
| 1018 | R | G, A, K, Q, N, H |
| 1019 | C | R, G, A, K, Q, N, H |
| 1020 | N | R, G, A, K, Q, H |
| 1021 | A | R, G, K, Q, N, H |
| 1022 | D | A, C, E, F, G, H, I, K, L, M, N, P, Q, R, S, T, V, W, Y |
| 1023 | E | R, G, A, K, Q, N, H |
| 1024 | V | R, G, A, K, Q, N, H |
| 1025 | A | R, G, K, Q, N, H |
| 1026 | A | R, G, K, Q, N, H |
| 1027 | A | R, G, K, Q, N, H |
| 1028 | N | R, G, A, K, Q, H |
| 1029 | I | R, G, A, K, Q, N, H |
| 1030 | V | R, G, A, K, Q, N, H |
| 1031 | I | R, G, A, K, Q, N, H |
| 1032 | S | R, G, A, K, Q, N, H |
| 1033 | V | R, G, A, K, Q, N, H |
| 1034 | L | R, G, A, K, Q, N, H |
| 1035 | A | R, G, K, Q, N, H |
| 1036 | P | R, G, A, K, Q, N, H |
| 1037 | R | G, A, K, Q, N, H |
| 1038 | S | R, G, A, K, Q, N, H |
| 1039 | K | R, G, A, Q, N, H |
| 1040 | K | R, G, A, Q, N, H |
| 1041 | N | R, G, A, K, Q, H |
| 1042 | E | R, G, A, K, Q, N, H |
| 1043 | E | R, G, A, K, Q, N, H |
| 1044 | Q | R, G, A, K, N, H |
| 1045 | D | R, G, A, K, Q, N, H |
| 1046 | D | R, G, A, K, Q, N, H |
| 1047 | I | R, G, A, K, Q, N, H |
| 1048 | P | R, G, A, K, Q, N, H |
| 1049 | L | R, G, A, K, Q, N, H |
| 1050 | I | R, G, A, K, Q, N, H |
| 1051 | T | R, G, A, K, Q, N, H |
| 1052 | K | R, G, A, Q, N, H |
| 1053 | K | R, G, A, Q, N, H |
| 1054 | A | R, G, K, Q, N, H |
| 1055 | E | R, G, A, K, Q, N, H |
| 1056 | S | R, G, A, K, Q, N, H |
| 1057 | K | R, G, A, Q, N, H |
| 1058 | S | R, G, A, K, Q, N, H |
| 1059 | P | R, G, A, K, Q, N, H |
| 1060 | P | R, G, A, K, Q, N, H |
| 1061 | K | R, G, A, Q, N, H |
| 1062 | D | R, G, A, K, Q, N, H |
| 1063 | R | G, A, K, Q, N, H |

TABLE 2-continued

Single amino acid substitutions in variant Cas12i4 polypeptide.

| Position | Wild-Type Residue | Substitution(s) |
|---|---|---|
| 1064 | K | R, G, A, Q, N, H |
| 1065 | R | G, A, K, Q, N, H |
| 1066 | S | R, G, A, K, Q, N, H |
| 1067 | K | R, G, A, Q, N, H |
| 1068 | T | R, G, A, K, Q, N, H |
| 1069 | S | R, G, A, K, Q, N, H |
| 1070 | Q | R, G, A, K, N, H |
| 1071 | L | R, G, A, K, Q, N, H |
| 1072 | P | R, G, A, K, Q, N, H |
| 1073 | Q | R, G, A, K, N, H |
| 1074 | K | R, G, A, Q, N, H |

In some embodiments, the variant Cas12i4 polypeptide comprises an alteration that increases interactions of the variant Cas12i4 polypeptide to the RNA guide. In some embodiments, the alteration that increases interactions with the RNA guide is an arginine, lysine, glutamine, asparagine, or histidine substitution. In some embodiments, the variant Cas12i4 polypeptide comprises an alteration that increases interactions of the variant Cas12i4 polypeptide to the target nucleic acid. In some embodiments, the alteration that increases interactions with the target nucleic acid is an arginine, lysine, glutamine, asparagine, or histidine substitution. In some embodiments, the variant Cas12i4 polypeptide comprises an alanine substitution.

In some embodiments, the variant Cas12i4 polypeptide comprises an arginine substitution relative to the parent polypeptide of SEQ ID NO: 2. For example, in some embodiments, the variant Cas12i4 polypeptide comprises an arginine substitution at residue 480, 482, 484, 486, 487, 490, 503, 545, 564, 566, 568, 569, 570, 587, 591, 592, 595, 598, 599, 612, 625, 629, 633, 635, 641, 668, 679, 713, 727, 735, 753, 754, 812, 825, 826, 831, 845, 846, 863, 865, 867, 870, 875, 886, 906, 945, 1028, 1032, 1042, 1049, 1055, 1058, 1059, 1071 of SEQ ID NO: 2.

In some embodiments, the variant Cas12i4 polypeptide comprises a glycine substitution relative to the parent polypeptide of SEQ ID NO: 2. For example, in some embodiments, the variant Cas12i4 polypeptide comprises a glycine substitution at residue 480, 482, 484, 486, 490, 503, 545, 566, 568, 569, 570, 587, 591, 592, 595, 598, 599, 612, 621, 625, 633, 635, 641, 668, 679, 689, 713, 727, 735, 753, 754, 812, 818, 825, 826, 831, 845, 846, 863, 865, 867, 870, 875, 886, 906, 945, 1028, 1032, 1042, 1049, 1055, 1058, 1059, 1071 of SEQ ID NO: 2.

In some embodiments, the variant Cas12i4 polypeptide comprises two or more substitutions relative to the parent polypeptide of SEQ ID NO: 2. For example, the variant polypeptide may comprise two, three, four, five, six, seven, eight, nine, ten, or more substitutions compared to SEQ ID NO: 2. Non-limiting examples of the two or more substitutions are shown in Table 3. In some embodiments, a variant Cas12i4 polypeptide comprises the two or more substitutions listed in Table 3 and further comprises a substitution listed in Table 2.

TABLE 3

Multi amino acid substitutions in variant Cas12i4 polypeptide.

| Sequence identifier | Sequence | Substitutions |
|---|---|---|
| SEQ ID NO: 3 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF PKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLE AELHYDGKKA KHHLPFYNAR FFEEVYCYHP SVAEITPFKT KQFGCEIGKD IPDYVSVALK DNPYKKATKR ILRAIYNPVA NTTGVDKTTN CSFMIKREND EYKLVINRKI SRDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL MRLSSLSDAS MQGIASLKSL INSYFNKNGC KTIEDKEKFN PVLYAKLVEV EQRRTNKRSE KVGRIAGSLE QLALLNGVEV VIGEADLGEV EKGKSKKQNS RNMDWCAKQV AQRLEYKLAF HGIGYFGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NREQDDIPLI TKKAESKSPP KDRKRSKTSQ LPQK | V592R E1042R |
| SEQ ID NO: 4 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF PKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG | E480R G564R V592R E1042R |

TABLE 3-continued

Multi amino acid substitutions in variant Cas12i4 polypeptide.

| Sequence identifier | Sequence | Substitutions |
|---|---|---|
| | GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLR AELHYDGKKA KHHLPFYNAR FFEEVYCYHP SVAEITPFKT KQFGCEIGKD IPDYVSVALK DNPYKKATKR ILRAIYNPVA NTTRVDKTTN CSFMIKREND EYKLVINRKI SRDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL MRLSSLSDAS MQGIASLKSL INSYFNKNGC KTIEDKEKFN PVLYAKLVEV EQRRTNKRSE KVGRIAGSLE QLALLNGVEV VIGEADLGEV EKGKSKKQNS RNMDWCAKQV AQRLEYKLAF HGIGYFGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NREQDDIPLI TKKAESKSPP KDRKRSKTSQ LPQK | |
| SEQ ID NO: 5 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLR AELHYDGKKA KHHLPFYNAR FFEEVYCYHP SVAEITPFKT KQFGCEIGKD IPDYVSVALK DNPYKKATKR ILRAIYNPVA NTTRVDKTTN CSFMIKREND EYKLVINRKI SVDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL MRLSSLSDAS MQGIASLKSL INSYFNKNGC KTIEDKEKFN PVLYAKLVEV EQRRTNKRSE KVGRIAGSLE QLALLNGVEV VIGEADLGEV EKGKSKKQNS RNMDWCAKQV AQRLEYKLAF HGIGYFGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NEEQDDIPLI TKKAESKSPP KDRKRSKTSQ LPQK | E480R G564R |
| SEQ ID NO: 6 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLR AELHYDGKKA KHHLPFYNAR FFEEVYCYHP SVAEITPFKT KQFGCEIGKD IPDYVSVALK DNPYKKATKR ILRAIYNPVA NTTGVDKTTN CSFMIKREND EYKLVINRKI SRDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL MRLSSLSDAS MQGIASLKSL INSYFNKNGC KTIEDKEKFN PVLYAKLVEV EQRRTNKRSE KVGRIAGSLE QLALLNGVEV VIGEADLGEV EKGKSKKQNS RNMDWCAKQV AQRLEYKLAF HGIGYFGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NEEQDDIPLI TKKAESKSPP KDRKRSKTSQ LPQK | E480R V592R |

TABLE 3-continued

Multi amino acid substitutions in variant Cas12i4 polypeptide.

| Sequence identifier | Sequence | Substitutions |
|---|---|---|
| SEQ ID NO: 7 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLR AELHYDGKKA KHHLPFYNAR FFEEVYCYHP SVAEITPFKT KQFGCEIGKD IPDYVSVALK DNPYKKATKR ILRAIYNPVA NTTGVDKTTN CSFMIKREND EYKLVINRKI SVDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL MRLSSLSDAS MQGIASLKSL INSYFNKNGC KTIEDKEKFN PVLYAKLVEV EQRRTNKRSE KVGRIAGSLE QLALLNGVEV VIGEADLGEV EKGKSKKQNS RNMDWCAKQV AQRLEYKLAF HGIGYFGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NREQDDIPLI TKKAESKSPP KDRKRSKTSQ LPQK | E480R E1042R |
| SEQ ID NO: 8 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLR AGLHYDGKKA KHHLPFYNAR FFEEVYCYHP SVAEITPFKT KQFGCEIGKD IPDYVSVALK DNPYKKATKR ILRAIYNPVA NTTGVDKTTN CSFMIKREND EYKLVINRKI SVDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL MRLSSLSDAS MQGIASLKSL INSYFNKNGC KTIEDKEKFN PVLYAKLVEV EQRRTNKRSE KVGRIAGSLE QLALLNGVEV VIGEADLGEV EKGKSKKQNS RNMDWCAKQV AQRLEYKLAF HGIGYFGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NEEQDDIPLI TKKAESKSPP KDRKRSKTSQ LPQK | E480R E482G |
| SEQ ID NO: 9 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLE AELHYDGKKA KHHLPFYNAR FFEEVYCYHP SVAEITPFKT KQFGCEIGKD IPDYVSVALK DNPYKKATKR ILRAIYNPVA NTTRVDKTTN CSFMIKREND EYKLVINRKI SRDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL | G564R V592R |

TABLE 3-continued

Multi amino acid substitutions in variant Cas12i4 polypeptide.

| Sequence identifier | Sequence | Substitutions |
|---|---|---|
| | MRLSSLSDAS MQGIASLKSL INSYFNKNGC KTIEDKEKFN PVLYAKLVEV EQRRTNKRSE KVGRIAGSLE QLALLNGVEV VIGEADLGEV EKGKSKKQNS RNMDWCAKQV AQRLEYKLAF HGIGYFGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NEEQDDIPLI TKKAESKSPP KDRKRSKTSQ LPQK | |
| SEQ ID NO: 10 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLE AELHYDGKKA KHHLPFYNAR FFEEVYCYHP SVAEITPFKT KQFGCEIGKD IPDYVSVALK DNPYKKATKR ILRAIYNPVA NTTRVDKTTN CSFMIKREND EYKLVINRKI SVDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL MRLSSLSDAS MQGIASLKSL INSYFNKNGC KTIEDKEKFN PVLYAKLVEV EQRRTNKRSE KVGRIAGSLE QLALLNGVEV VIGEADLGEV EKGKSKKQNS RNMDWCAKQV AQRLEYKLAF HGIGYFGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NREQDDIPLI TKKAESKSPP KDRKRSKTSQ LPQK | G564R E1042R |
| SEQ ID NO: 11 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLE AGLHYDGKKA KHHLPFYNAR FFEEVYCYHP SVAEITPFKT KQFGCEIGKD IPDYVSVALK DNPYKKATKR ILRAIYNPVA NTTRVDKTTN CSFMIKREND EYKLVINRKI SVDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL MRLSSLSDAS MQGIASLKSL INSYFNKNGC KTIEDKEKFN PVLYAKLVEV EQRRTNKRSE KVGRIAGSLE QLALLNGVEV VIGEADLGEV EKGKSKKQNS RNMDWCAKQV AQRLEYKLAF HGIGYFGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NEEQDDIPLI TKKAESKSPP KDRKRSKTSQ LPQK | G564R E482G |
| SEQ ID NO: 12 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP | V592R E482G |

TABLE 3-continued

Multi amino acid substitutions in variant Cas12i4 polypeptide.

| Sequence identifier | Sequence | Substitutions |
|---|---|---|
| | IRNVLKYLWQ FRETVSAEDF EAAAKANHLE EKISRVKAHP<br>IVISNRYWAF GTSALVGNIM PADKRHQGEY AGQNFKMWLE<br>AGLHYDGKKA KHHLPFYNAR FFEEVYCYHP SVAEITPFKT<br>KQFGCEIGKD IPDYVSVALK DNPYKKATKR ILRAIYNPVA<br>NTTGVDKTTN CSFMIKREND EYKLVINRKI SRDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV<br>FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEADLGEV EKGKSKKQNS RNMDWCAKQV AQRLEYKLAF<br>HGIGYFGVNP MYTSHQDPFE HRRVADHIVM RARFEEVNVE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NEEQDDIPLI TKKAESKSPP KDRKRSKTSQ LPQK | |
| SEQ ID NO: 13 | MASISRPYGT KLRPDARKKE MLDKFFNTLT KGQRVFADLA<br>LCIYGSLTLE MAKSLEPESD SELVCAIGWF RLVDKTIWSK<br>DGIKQENLVK QYEAYSGKEA SEVVKTYLNS PSSDKYVWID<br>CRQKFLRFQR ELGTRNLSED FECMLFEQYI RLTKGEIEGY<br>AAISNMFGNG EKEDRSKKRM YATRMKDWLE ANENITWEQY<br>REALKNQLNA KNLEQVVANY KGNAGGADPF FKYSFSKEGM<br>VSKKEHAQQL DKFKTVLKNK ARDLNFPNKE KLKQYLEAEI<br>GIPVDANVYS QMFSNGVSEV QPKTTRNMSF SNEKLDLLTE<br>LKDLNKGDGF EYAREVLNGF FDSELHTTED KFNITSRYLG<br>GDKSNRLSKL YKIWKKEGVD CEEGIQQFCE AVKDKMGQIP<br>IRNVLKYLWQ FRETVSAEDF EAAAKANHLE EKISRVKAHP<br>IVISNRYWAF GTSALVGNIM PADKRHQGEY AGQNFKMWLE<br>AGLHYDGKKA KHHLPFYNAR FFEEVYCYHP SVAEITPFKT<br>KQFGCEIGKD IPDYVSVALK DNPYKKATKR ILRAIYNPVA<br>NTTGVDKTTN CSFMIKREND EYKLVINRKI SVDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV<br>FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEADLGEV EKGKSKKQNS RNMDWCAKQV AQRLEYKLAF<br>HGIGYFGVNP MYTSHQDPFE HRRVADHIVM RARFEEVNVE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NREQDDIPLI TKKAESKSPP KDRKRSKTSQ LPQK | E1042R<br>E482G |
| SEQ ID NO: 14 | MASISRPYGT KLRPDARKKE MLDKFFNTLT KGQRVFADLA<br>LCIYGSLTLE MAKSLEPESD SELVCAIGWF RLVDKTIWSK<br>DGIKQENLVK QYEAYSGKEA SEVVKTYLNS PSSDKYVWID<br>CRQKFLRFQR ELGTRNLSED FECMLFEQYI RLTKGEIEGY<br>AAISNMFGNG EKEDRSKKRM YATRMKDWLE ANENITWEQY<br>REALKNQLNA KNLEQVVANY KGNAGGADPF FKYSFSKEGM<br>VSKKEHAQQL DKFKTVLKNK ARDLNFPNKE KLKQYLEAEI<br>GIPVDANVYS QMFSNGVSEV QPKTTRNMSF SNEKLDLLTE<br>LKDLNKGDGF EYAREVLNGF FDSELHTTED KFNITSRYLG<br>GDKSNRLSKL YKIWKKEGVD CEEGIQQFCE AVKDKMGQIP<br>IRNVLKYLWQ FRETVSAEDF EAAAKANHLE EKISRVKAHP<br>IVISNRYWAF GTSALVGNIM PADKRHQGEY AGQNFKMWLR<br>AELHYDGKKA KHHLPFYNAR FFEEVYCYHP SVAEITPFKT<br>KQFGCEIGKD IPDYVSVALK DNPYKKATKR ILRAIYNPVA<br>NTTRVDKTTN CSFMIKREND EYKLVINRKI SRDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV<br>FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEADLGEV EKGKSKKQNS RNMDWCAKQV AQRLEYKLAF<br>HGIGYFGVNP MYTSHQDPFE HRRVADHIVM RARFEEVNVE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NEEQDDIPLI TKKAESKSPP KDRKRSKTSQ LPQK | E480R<br>G564R<br>V592R |

TABLE 3-continued

Multi amino acid substitutions in variant Cas12i4 polypeptide.

| Sequence identifier | Sequence | Substitutions |
|---|---|---|
| SEQ ID NO: 15 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLR AELHYDGKKA KHHLPFYNAR FFEEVYCYHP SVAEITPFKT KQFGCEIGKD IPDYVSVALK DNPYKKATKR ILRAIYNPVA NTTRVDKTTN CSFMIKREND EYKLVINRKI SVDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL MRLSSLSDAS MQGIASLKSL INSYFNKNGC KTIEDKEKFN PVLYAKLVEV EQRRTNKRSE KVGRIAGSLE QLALLNGVEV VIGEADLGEV EKGKSKKQNS RNMDWCAKQV AQRLEYKLAF HGIGYFGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NREQDDIPLI TKKAESKSPP KDRKRSKTSQ LPQK | E480R G564R E1042R |
| SEQ ID NO: 16 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLR AGLHYDGKKA KHHLPFYNAR FFEEVYCYHP SVAEITPFKT KQFGCEIGKD IPDYVSVALK DNPYKKATKR ILRAIYNPVA NTTRVDKTTN CSFMIKREND EYKLVINRKI SVDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL MRLSSLSDAS MQGIASLKSL INSYFNKNGC KTIEDKEKFN PVLYAKLVEV EQRRTNKRSE KVGRIAGSLE QLALLNGVEV VIGEADLGEV EKGKSKKQNS RNMDWCAKQV AQRLEYKLAF HGIGYFGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NEEQDDIPLI TKKAESKSPP KDRKRSKTSQ LPQK | E480R E482G G564R |
| SEQ ID NO: 17 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLR AELHYDGKKA KHHLPFYNAR FFEEVYCYHP SVAEITPFKT KQFGCEIGKD IPDYVSVALK DNPYKKATKR ILRAIYNPVA NTTGVDKTTN CSFMIKREND EYKLVINRKI SRDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV | E480R V592R E1042R |

TABLE 3-continued

Multi amino acid substitutions in variant Cas12i4 polypeptide.

| Sequence identifier | Sequence | Substitutions |
|---|---|---|
| | FNSNYLKALV SKHRKAKKPV EGILDEIEAW TSKDKDSCSL MRLSSLSDAS MQGIASLKSL INSYFNKNGC KTIEDKEKFN PVLYAKLVEV EQRRTNKRSE KVGRIAGSLE QLALLNGVEV VIGEADLGEV EKGKSKKQNS RNMDWCAKQV AQRLEYKLAF HGIGYFGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NREQDDIPLI TKKAESKSPP KDRKRSKTSQ LPQK | |
| SEQ ID NO: 18 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLR AGLHYDGKKA KHHLPFYNAR FFEEVYCYHP SVAEITPFKT KQFGCEIGKD IPDYVSVALK DNPYKKATKR ILRAIYNPVA NTTGVDKTTN CSFMIKREND EYKLVINRKI SRDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL MRLSSLSDAS MQGIASLKSL INSYFNKNGC KTIEDKEKFN PVLYAKLVEV EQRRTNKRSE KVGRIAGSLE QLALLNGVEV VIGEADLGEV EKGKSKKQNS RNMDWCAKQV AQRLEYKLAF HGIGYFGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NEEQDDIPLI TKKAESKSPP KDRKRSKTSQ LPQK | E480R E482G V592R |
| SEQ ID NO: 19 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLR AGLHYDGKKA KHHLPFYNAR FFEEVYCYHP SVAEITPFKT KQFGCEIGKD IPDYVSVALK DNPYKKATKR ILRAIYNPVA NTTGVDKTTN CSFMIKREND EYKLVINRKI SVDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL MRLSSLSDAS MQGIASLKSL INSYFNKNGC KTIEDKEKFN PVLYAKLVEV EQRRTNKRSE KVGRIAGSLE QLALLNGVEV VIGEADLGEV EKGKSKKQNS RNMDWCAKQV AQRLEYKLAF HGIGYFGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NREQDDIPLI TKKAESKSPP KDRKRSKTSQ LPQK | E480R E482G E1042R |
| SEQ ID NO: 20 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG | G564R V592R E1042R |

TABLE 3-continued

Multi amino acid substitutions in variant Cas12i4 polypeptide.

| Sequence identifier | Sequence | Substitutions |
|---|---|---|
| | GDKSNRLSKL YKIWKKEGVD CEEGIQQFCE AVKDKMGQIP<br>IRNVLKYLWQ FRETVSAEDF EAAAKANHLE EKISRVKAHP<br>IVISNRYWAF GTSALVGNIM PADKRHQGEY AGQNFKMWLE<br>AELHYDGKKA KHHLPFYNAR FFEEVYCYHP SVAEITPFKT<br>KQFGCEIGKD IPDYVSVALK DNPYKKATKR ILRAIYNPVA<br>NTTRVDKTTN CSFMIKREND EYKLVINRKI SRDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV<br>FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEADLGEV EKGKSKKQNS RNMDWCAKQV AQRLEYKLAF<br>HGIGYFGVNP MYTSHQDPFE HRRVADHIVM RARFEEVNVE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NREQDDIPLI TKKAESKSPP KDRKRSKTSQ LPQK | |
| SEQ ID NO: 21 | MASISRPYGT KLRPDARKKE MLDKFFNTLT KGQRVFADLA<br>LCIYGSLTLE MAKSLEPESD SELVCAIGWF RLVDKTIWSK<br>DGIKQENLVK QYEAYSGKEA SEVVKTYLNS PSSDKYVWID<br>CRQKFLRFQR ELGTRNLSED FECMLFEQYI RLTKGEIEGY<br>AAISNMFGNG EKEDRSKKRM YATRMKDWLE ANENITWEQY<br>REALKNQLNA KNLEQVVANY KGNAGGADPF FKYSFSKEGM<br>VSKKEHAQQL DKFKTVLKNK ARDLNFPNKE KLKQYLEAEI<br>GIPVDANVYS QMFSNGVSEV QPKTTRNMSF SNEKLDLLTE<br>LKDLNKGDGF EYAREVLNGF FDSELHTTED KFNITSRYLG<br>GDKSNRLSKL YKIWKKEGVD CEEGIQQFCE AVKDKMGQIP<br>IRNVLKYLWQ FRETVSAEDF EAAAKANHLE EKISRVKAHP<br>IVISNRYWAF GTSALVGNIM PADKRHQGEY AGQNFKMWLE<br>AGLHYDGKKA KHHLPFYNAR FFEEVYCYHP SVAEITPFKT<br>KQFGCEIGKD IPDYVSVALK DNPYKKATKR ILRAIYNPVA<br>NTTRVDKTTN CSFMIKREND EYKLVINRKI SRDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV<br>FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEADLGEV EKGKSKKQNS RNMDWCAKQV AQRLEYKLAF<br>HGIGYFGVNP MYTSHQDPFE HRRVADHIVM RARFEEVNVE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NEEQDDIPLI TKKAESKSPP KDRKRSKTSQ LPQK | E482G<br>G564R<br>V592R |
| SEQ ID NO: 22 | MASISRPYGT KLRPDARKKE MLDKFFNTLT KGQRVFADLA<br>LCIYGSLTLE MAKSLEPESD SELVCAIGWF RLVDKTIWSK<br>DGIKQENLVK QYEAYSGKEA SEVVKTYLNS PSSDKYVWID<br>CRQKFLRFQR ELGTRNLSED FECMLFEQYI RLTKGEIEGY<br>AAISNMFGNG EKEDRSKKRM YATRMKDWLE ANENITWEQY<br>REALKNQLNA KNLEQVVANY KGNAGGADPF FKYSFSKEGM<br>VSKKEHAQQL DKFKTVLKNK ARDLNFPNKE KLKQYLEAEI<br>GIPVDANVYS QMFSNGVSEV QPKTTRNMSF SNEKLDLLTE<br>LKDLNKGDGF EYAREVLNGF FDSELHTTED KFNITSRYLG<br>GDKSNRLSKL YKIWKKEGVD CEEGIQQFCE AVKDKMGQIP<br>IRNVLKYLWQ FRETVSAEDF EAAAKANHLE EKISRVKAHP<br>IVISNRYWAF GTSALVGNIM PADKRHQGEY AGQNFKMWLE<br>AGLHYDGKKA KHHLPFYNAR FFEEVYCYHP SVAEITPFKT<br>KQFGCEIGKD IPDYVSVALK DNPYKKATKR ILRAIYNPVA<br>NTTRVDKTTN CSFMIKREND EYKLVINRKI SVDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV<br>FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEADLGEV EKGKSKKQNS RNMDWCAKQV AQRLEYKLAF<br>HGIGYFGVNP MYTSHQDPFE HRRVADHIVM RARFEEVNVE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NREQDDIPLI TKKAESKSPP KDRKRSKTSQ LPQK | E482G<br>G564R<br>E1042R |

TABLE 3-continued

Multi amino acid substitutions in variant Cas12i4 polypeptide.

| Sequence identifier | Sequence | Substitutions |
|---|---|---|
| SEQ ID NO: 23 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLE AGLHYDGKKA KHHLPFYNAR FFEEVYCYHP SVAEITPFKT KQFGCEIGKD IPDYVSVALK DNPYKKATKR ILRAIYNPVA NTTGVDKTTN CSFMIKREND EYKLVINRKI SRDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL MRLSSLSDAS MQGIASLKSL INSYFNKNGC KTIEDKEKFN PVLYAKLVEV EQRRTNKRSE KVGRIAGSLE QLALLNGVEV VIGEADLGEV EKGKSKKQNS RNMDWCAKQV AQRLEYKLAF HGIGYFGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NREQDDIPLI TKKAESKSPP KDRKRSKTSQ LPQK | E482G V592R E1042R |
| SEQ ID NO: 24 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLR AGLHYDGKKA KHHLPFYNAR FFEEVYCYHP SVAEITPFKT KQFGCEIGKD IPDYVSVALK DNPYKKATKR ILRAIYNPVA NTTRVDKTTN CSFMIKREND EYKLVINRKI SRDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL MRLSSLSDAS MQGIASLKSL INSYFNKNGC KTIEDKEKFN PVLYAKLVEV EQRRTNKRSE KVGRIAGSLE QLALLNGVEV VIGEADLGEV EKGKSKKQNS RNMDWCAKQV AQRLEYKLAF HGIGYFGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NEEQDDIPLI TKKAESKSPP KDRKRSKTSQ LPQK | E480R E482G G564R V592R |
| SEQ ID NO: 25 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLR AGLHYDGKKA KHHLPFYNAR FFEEVYCYHP SVAEITPFKT KQFGCEIGKD IPDYVSVALK DNPYKKATKR ILRAIYNPVA NTTRVDKTTN CSFMIKREND EYKLVINRKI SVDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL | E480R E482G G564R E1042R |

TABLE 3-continued

Multi amino acid substitutions in variant Cas12i4 polypeptide.

| Sequence identifier | Sequence | Substitutions |
|---|---|---|
|  | MRLSSLSDAS MQGIASLKSL INSYFNKNGC KTIEDKEKFN PVLYAKLVEV EQRRTNKRSE KVGRIAGSLE QLALLNGVEV VIGEADLGEV EKGKSKKQNS RNMDWCAKQV AQRLEYKLAF HGIGYFGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NREQDDIPLI TKKAESKSPP KDRKRSKTSQ LPQK |  |
| SEQ ID NO: 26 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLR AGLHYDGKKA KHHLPFYNAR FFEEVYCYHP SVAEITPFKT KQFGCEIGKD IPDYVSVALK DNPYKKATKR ILRAIYNPVA NTTGVDKTTN CSFMIKREND EYKLVINRKI SRDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL MRLSSLSDAS MQGIASLKSL INSYFNKNGC KTIEDKEKFN PVLYAKLVEV EQRRTNKRSE KVGRIAGSLE QLALLNGVEV VIGEADLGEV EKGKSKKQNS RNMDWCAKQV AQRLEYKLAF HGIGYFGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NREQDDIPLI TKKAESKSPP KDRKRSKTSQ LPQK | E480R E482G V592R E1042R |
| SEQ ID NO: 27 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLR AGLHYDGKKA KHHLPFYNAR FFEEVYCYHP SVAEITPFKT KQFGCEIGKD IPDYVSVALK DNPYKKATKR ILRAIYNPVA NTTRVDKTTN CSFMIKREND EYKLVINRKI SRDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL MRLSSLSDAS MQGIASLKSL INSYFNKNGC KTIEDKEKFN PVLYAKLVEV EQRRTNKRSE KVGRIAGSLE QLALLNGVEV VIGEADLGEV EKGKSKKQNS RNMDWCAKQV AQRLEYKLAF HGIGYFGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NREQDDIPLI TKKAESKSPP KDRKRSKTSQ LPQK | E482G G564R V592R E1042R |
| SEQ ID NO: 28 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP | E480R E482G G564R V592R E1042R |

TABLE 3-continued

Multi amino acid substitutions in variant Cas12i4 polypeptide.

| Sequence identifier | Sequence | Substitutions |
|---|---|---|
| | IRNVLKYLWQ FRETVSAEDF EAAAKANHLE EKISRVKAHP<br>IVISNRYWAF GTSALVGNIM PADKRHQGEY AGQNFKMWLR<br>AGLHYDGKKA KHHLPFYNAR FFEEVYCYHP SVAEITPFKT<br>KQFGCEIGKD IPDYVSVALK DNPYKKATKR ILRAIYNPVA<br>NTTRVDKTTN CSFMIKREND EYKLVINRKI SRDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV<br>FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEADLGEV EKGKSKKQNS RNMDWCAKQV AQRLEYKLAF<br>HGIGYFGVNP MYTSHQDPFE HRRVADHIVM RARFEEVNVE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NREQDDIPLI TKKAESKSPP KDRKRSKTSQ LPQK | |
| SEQ ID NO: 29 | MASISRPYGT KLRPDARKKE MLDKFFNTLT KGQRVFADLA<br>LCIYGSLTLE MAKSLEPESD SELVCAIGWF RLVDKTIWSK<br>DGIKQENLVK QYEAYSGKEA SEVVKTYLNS PSSDKYVWID<br>CRQKFLRFQR ELGTRNLSED FECMLFEQYI RLTKGEIEGY<br>AAISNMFGNG EKEDRSKKRM YATRMKDWLE ANENITWEQY<br>REALKNQLNA KNLEQVVANY KGNAGGADPF FKYSFSKEGM<br>VSKKEHAQQL DKFKTVLKNK ARDLNFPNKE KLKQYLEAEI<br>GIPVDANVYS QMFSNGVSEV QPKTTRNMSF SNEKLDLLTE<br>LKDLNKGDGF EYAREVLNGF FDSELHTTED KFNITSRYLG<br>GDKSNRLSKL YKIWKKEGVD CEEGIQQFCE AVKDKMGQIP<br>IRNVLKYLWQ FRETVSAEDF EAAAKANHLE EKISRVKAHP<br>IVISNRYWAF GTSALVGNIM PADKRHQGEY AGQNFKMWLR<br>AELHYDGKKA KHHLPFYNAR FFEEVYCYHP SVAEITPFKT<br>KQFGCEIGKD IPDYVSVALK DNPYKKATKR ILRAIYNPVA<br>NTTRVDKRTN CSFMIKREND EYKLVINRKI SRDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV<br>FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEADLGEV EKGKSKKQNS RNMDWCAKQV AQRLEYKLAF<br>HGIGYFGVNP MYTSHQDPFE HRRVADHIVM RARFEEVNVE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NREQDDIPLI TKKAESKSPP KDRKRSKTSQ LPQK | E480R<br>G564R<br>V592R<br>E1042R<br>T568R |
| SEQ ID NO: 30 | MASISRPYGT KLRPDARKKE MLDKFFNTLT KGQRVFADLA<br>LCIYGSLTLE MAKSLEPESD SELVCAIGWF RLVDKTIWSK<br>DGIKQENLVK QYEAYSGKEA SEVVKTYLNS PSSDKYVWID<br>CRQKFLRFQR ELGTRNLSED FECMLFEQYI RLTKGEIEGY<br>AAISNMFGNG EKEDRSKKRM YATRMKDWLE ANENITWEQY<br>REALKNQLNA KNLEQVVANY KGNAGGADPF FKYSFSKEGM<br>VSKKEHAQQL DKFKTVLKNK ARDLNFPNKE KLKQYLEAEI<br>GIPVDANVYS QMFSNGVSEV QPKTTRNMSF SNEKLDLLTE<br>LKDLNKGDGF EYAREVLNGF FDSELHTTED KFNITSRYLG<br>GDKSNRLSKL YKIWKKEGVD CEEGIQQFCE AVKDKMGQIP<br>IRNVLKYLWQ FRETVSAEDF EAAAKANHLE EKISRVKAHP<br>IVISNRYWAF GTSALVGNIM PADKRHQGEY AGQNFKMWLR<br>AELHYDGKKA KHHLPFYNAR FFEEVYCYHP SVAEITPFKT<br>KQFGCEIGKD IPDYVSVALK DNPYKKATKR ILRAIYNPVA<br>NTTRVDKTTN CSFMIKREND EYKLVINRKI RRDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV<br>FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEADLGEV EKGKSKKQNS RNMDWCAKQV AQRLEYKLAF<br>HGIGYFGVNP MYTSHQDPFE HRRVADHIVM RARFEEVNVE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NREQDDIPLI TKKAESKSPP KDRKRSKTSQ LPQK | E480R<br>G564R<br>V592R<br>E1042R<br>S591R |

TABLE 3-continued

Multi amino acid substitutions in variant Cas12i4 polypeptide.

| Sequence identifier | Sequence | Substitutions |
|---|---|---|
| SEQ ID NO: 31 | MASISRPYGT KLRPDARKKE MLDKFFNTLT KGQRVFADLA<br>LCIYGSLTLE MAKSLEPESD SELVCAIGWF RLVDKTIWSK<br>DGIKQENLVK QYEAYSGKEA SEVVKTYLNS PSSDKYVWID<br>CRQKFLRFQR ELGTRNLSED FECMLFEQYI RLTKGEIEGY<br>AAISNMFGNG EKEDRSKKRM YATRMKDWLE ANENITWEQY<br>REALKNQLNA KNLEQVVANY KGNAGGADPF FKYSFSKEGM<br>VSKKEHAQQL DKFKTVLKNK ARDLNFPNKE KLKQYLEAEI<br>GIPVDANVYS QMFSNGVSEV QPKTTRNMSF SNEKLDLLTE<br>LKDLNKGDGF EYAREVLNGF FDSELHTTED KFNITSRYLG<br>GDKSNRLSKL YKIWKKEGVD CEEGIQQFCE AVKDKMGQIP<br>IRNVLKYLWQ FRETVSAEDF EAAAKANHLE EKISRVKAHP<br>IVISNRYWAF GTSALVGNIM PADKRHQGEY AGQNFKMWLR<br>AELHYDGKKA KHHLPFYNAR FFEEVYCYHP SVAEITPFKT<br>KQFGCEIGKD IPDYVSVALK DNPYKKATKR ILRAIYNPVA<br>NTTRVDKTTN CSFMIKREND EYKLVINRKI SRDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV<br>FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEAGLGEV EKGKSKKQNS RNMDWCAKQV AQRLEYKLAF<br>HGIGYFGVNP MYTSHQDPFE HRRVADHIVM RARFEEVNVE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NREQDDIPLI TKKAESKSPP KDRKRSKTSQ LPQK | E480R<br>G564R<br>V592R<br>E1042R<br>D846G |
| SEQ ID NO: 32 | MASISRPYGT KLRPDARKKE MLDKFFNTLT KGQRVFADLA<br>LCIYGSLTLE MAKSLEPESD SELVCAIGWF RLVDKTIWSK<br>DGIKQENLVK QYEAYSGKEA SEVVKTYLNS PSSDKYVWID<br>CRQKFLRFQR ELGTRNLSED FECMLFEQYI RLTKGEIEGY<br>AAISNMFGNG EKEDRSKKRM YATRMKDWLE ANENITWEQY<br>REALKNQLNA KNLEQVVANY KGNAGGADPF FKYSFSKEGM<br>VSKKEHAQQL DKFKTVLKNK ARDLNFPNKE KLKQYLEAEI<br>GIPVDANVYS QMFSNGVSEV QPKTTRNMSF SNEKLDLLTE<br>LKDLNKGDGF EYAREVLNGF FDSELHTTED KFNITSRYLG<br>GDKSNRLSKL YKIWKKEGVD CEEGIQQFCE AVKDKMGQIP<br>IRNVLKYLWQ FRETVSAEDF EAAAKANHLE EKISRVKAHP<br>IVISNRYWAF GTSALVGNIM PADKRHQGEY AGQNFKMWLR<br>AELHYDGKKA KHHLPFYNAR FFEEVYCYHP SVAEITPFKT<br>KQFGCEIGKD IPDYVSVALK DNPYKKATKR ILRAIYNPVA<br>NTTRVDKTTN CSFMIKREND EYKLVINRKI SRDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV<br>FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEADLGEV EKGKSKKQNS RNMDWCAKQV AQRLEYKLAF<br>HGIGYRGVNP MYTSHQDPFE HRRVADHIVM RARFEEVNVE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NREQDDIPLI TKKAESKSPP KDRKRSKTSQ LPQK | E480R<br>G564R<br>V592R<br>E1042R<br>F886R |
| SEQ ID NO: 33 | MASISRPYGT KLRPDARKKE MLDKFFNTLT KGQRVFADLA<br>LCIYGSLTLE MAKSLEPESD SELVCAIGWF RLVDKTIWSK<br>DGIKQENLVK QYEAYSGKEA SEVVKTYLNS PSSDKYVWID<br>CRQKFLRFQR ELGTRNLSED FECMLFEQYI RLTKGEIEGY<br>AAISNMFGNG EKEDRSKKRM YATRMKDWLE ANENITWEQY<br>REALKNQLNA KNLEQVVANY KGNAGGADPF FKYSFSKEGM<br>VSKKEHAQQL DKFKTVLKNK ARDLNFPNKE KLKQYLEAEI<br>GIPVDANVYS QMFSNGVSEV QPKTTRNMSF SNEKLDLLTE<br>LKDLNKGDGF EYAREVLNGF FDSELHTTED KFNITSRYLG<br>GDKSNRLSKL YKIWKKEGVD CEEGIQQFCE AVKDKMGQIP<br>IRNVLKYLWQ FRETVSAEDF EAAAKANHLE EKISRVKAHP<br>IVISNRYWAF GTSALVGNIM PADKRHQGEY AGQNFKMWLR<br>AELHYDGKKA KHHLPFYNAR FFEEVYCYHP SVAEITPFKT<br>KQFGCEIGKD IPDYVSVALK DNPYKKATKR ILRAIYNPVA<br>NTTRVDKTRN CSFMIKREND EYKLVINRKI RRDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV | E480R<br>G564R<br>V592R<br>E1042R<br>T568R<br>S591R |

TABLE 3-continued

Multi amino acid substitutions in variant Cas12i4 polypeptide.

| Sequence identifier | Sequence | Substitutions |
|---|---|---|
| | FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEADLGEV EKGKSKKQNS RNMDWCAKQV AQRLEYKLAF<br>HGIGYFGVNP MYTSHQDPFE HRRVADHIVM RARFEEVNVE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NREQDDIPLI TKKAESKSPP KDRKRSKTSQ LPQK | |
| SEQ ID NO: 34 | MASISRPYGT KLRPDARKKE MLDKFFNTLT KGQRVFADLA<br>LCIYGSLTLE MAKSLEPESD SELVCAIGWF RLVDKTIWSK<br>DGIKQENLVK QYEAYSGKEA SEVVKTYLNS PSSDKYVWID<br>CRQKFLRFQR ELGTRNLSED FECMLFEQYI RLTKGEIEGY<br>AAISNMFGNG EKEDRSKKRM YATRMKDWLE ANENITWEQY<br>REALKNQLNA KNLEQVVANY KGNAGGADPF FKYSFSKEGM<br>VSKKEHAQQL DKFKTVLKNK ARDLNFPNKE KLKQYLEAEI<br>GIPVDANVYS QMFSNGVSEV QPKTTRNMSF SNEKLDLLTE<br>LKDLNKGDGF EYAREVLNGF FDSELHTTED KFNITSRYLG<br>GDKSNRLSKL YKIWKKEGVD CEEGIQQFCE AVKDKMGQIP<br>IRNVLKYLWQ FRETVSAEDF EAAAKANHLE EKISRVKAHP<br>IVISNRYWAF GTSALVGNIM PADKRHQGEY AGQNFKMWLR<br>AELHYDGKKA KHHLPFYNAR FFEEVYCYHP SVAEITPFKT<br>KQFGCEIGKD IPDYVSVALK DNPYKKATKR ILRAIYNPVA<br>NTTRVDKRTN CSFMIKREND EYKLVINRKI SRDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV<br>FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEADLGEV EKGKSKKQNS RNMDWCAKQV AQRLEYKLAF<br>HGIGYFGVNP MYTSHQDPFE HRRVADHIVM RARFEEVNVE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NREQDDIPLI TKKAESKSPP KDRKRSKTSQ LPQK | E480R<br>G564R<br>V592R<br>E1042R<br>T568R<br>D846G |
| SEQ ID NO: 35 | MASISRPYGT KLRPDARKKE MLDKFFNTLT KGQRVFADLA<br>LCIYGSLTLE MAKSLEPESD SELVCAIGWF RLVDKTIWSK<br>DGIKQENLVK QYEAYSGKEA SEVVKTYLNS PSSDKYVWID<br>CRQKFLRFQR ELGTRNLSED FECMLFEQYI RLTKGEIEGY<br>AAISNMFGNG EKEDRSKKRM YATRMKDWLE ANENITWEQY<br>REALKNQLNA KNLEQVVANY KGNAGGADPF FKYSFSKEGM<br>VSKKEHAQQL DKFKTVLKNK ARDLNFPNKE KLKQYLEAEI<br>GIPVDANVYS QMFSNGVSEV QPKTTRNMSF SNEKLDLLTE<br>LKDLNKGDGF EYAREVLNGF FDSELHTTED KFNITSRYLG<br>GDKSNRLSKL YKIWKKEGVD CEEGIQQFCE AVKDKMGQIP<br>IRNVLKYLWQ FRETVSAEDF EAAAKANHLE EKISRVKAHP<br>IVISNRYWAF GTSALVGNIM PADKRHQGEY AGQNFKMWLR<br>AELHYDGKKA KHHLPFYNAR FFEEVYCYHP SVAEITPFKT<br>KQFGCEIGKD IPDYVSVALK DNPYKKATKR ILRAIYNPVA<br>NTTRVDKRTN CSFMIKREND EYKLVINRKI SRDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV<br>FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEADLGEV EKGKSKKQNS RNMDWCAKQV AQRLEYKLAF<br>HGIGYRGVNP MYTSHQDPFE HRRVADHIVM RARFEEVNVE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NREQDDIPLI TKKAESKSPP KDRKRSKTSQ LPQK | E480R<br>G564R<br>V592R<br>E1042R<br>T568R<br>F886R |
| SEQ ID NO: 36 | MASISRPYGT KLRPDARKKE MLDKFFNTLT KGQRVFADLA<br>LCIYGSLTLE MAKSLEPESD SELVCAIGWF RLVDKTIWSK<br>DGIKQENLVK QYEAYSGKEA SEVVKTYLNS PSSDKYVWID<br>CRQKFLRFQR ELGTRNLSED FECMLFEQYI RLTKGEIEGY<br>AAISNMFGNG EKEDRSKKRM YATRMKDWLE ANENITWEQY<br>REALKNQLNA KNLEQVVANY KGNAGGADPF FKYSFSKEGM<br>VSKKEHAQQL DKFKTVLKNK ARDLNFPNKE KLKQYLEAEI<br>GIPVDANVYS QMFSNGVSEV QPKTTRNMSF SNEKLDLLTE<br>LKDLNKGDGF EYAREVLNGF FDSELHTTED KFNITSRYLG | E480R<br>G564R<br>V592R<br>E1042R<br>S591R<br>D846G |

TABLE 3-continued

Multi amino acid substitutions in variant Cas12i4 polypeptide.

| Sequence identifier | Sequence | Substitutions |
|---|---|---|
|  | GDKSNRLSKL YKIWKKEGVD CEEGIQQFCE AVKDKMGQIP<br>IRNVLKYLWQ FRETVSAEDF EAAAKANHLE EKISRVKAHP<br>IVISNRYWAF GTSALVGNIM PADKRHQGEY AGQNFKMWLR<br>AELHYDGKKA KHHLPFYNAR FFEEVYCYHP SVAEITPFKT<br>KQFGCEIGKD IPDYVSVALK DNPYKKATKR ILRAIYNPVA<br>NTTRVDKTTN CSFMIKREND EYKLVINRKI RRDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV<br>FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEAGLGEV EKGKSKKQNS RNMDWCAKQV AQRLEYKLAF<br>HGIGYFGVNP MYTSHQDPFE HRRVADHIVM RARFEEVNVE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NREQDDIPLI TKKAESKSPP KDRKRSKTSQ LPQK |  |
| SEQ ID NO: 37 | MASISRPYGT KLRPDARKKE MLDKFFNTLT KGQRVFADLA<br>LCIYGSLTLE MAKSLEPESD SELVCAIGWF RLVDKTIWSK<br>DGIKQENLVK QYEAYSGKEA SEVVKTYLNS PSSDKYVWID<br>CRQKFLRFQR ELGTRNLSED FECMLFEQYI RLTKGEIEGY<br>AAISNMFGNG EKEDRSKKRM YATRMKDWLE ANENITWEQY<br>REALKNQLNA KNLEQVVANY KGNAGGADPF FKYSFSKEGM<br>VSKKEHAQQL DKFKTVLKNK ARDLNFPNKE KLKQYLEAEI<br>GIPVDANVYS QMFSNGVSEV QPKTTRNMSF SNEKLDLLTE<br>LKDLNKGDGF EYAREVLNGF FDSELHTTED KFNITSRYLG<br>GDKSNRLSKL YKIWKKEGVD CEEGIQQFCE AVKDKMGQIP<br>IRNVLKYLWQ FRETVSAEDF EAAAKANHLE EKISRVKAHP<br>IVISNRYWAF GTSALVGNIM PADKRHQGEY AGQNFKMWLR<br>AELHYDGKKA KHHLPFYNAR FFEEVYCYHP SVAEITPFKT<br>KQFGCEIGKD IPDYVSVALK DNPYKKATKR ILRAIYNPVA<br>NTTRVDKTTN CSFMIKREND EYKLVINRKI RRDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV<br>FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEADLGEV EKGKSKKQNS RNMDWCAKQV AQRLEYKLAF<br>HGIGYRGVNP MYTSHQDPFE HRRVADHIVM RARFEEVNVE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NREQDDIPLI TKKAESKSPP KDRKRSKTSQ LPQK | E480R<br>G564R<br>V592R<br>E1042R<br>S591R<br>F886R |
| SEQ ID NO: 38 | MASISRPYGT KLRPDARKKE MLDKFFNTLT KGQRVFADLA<br>LCIYGSLTLE MAKSLEPESD SELVCAIGWF RLVDKTIWSK<br>DGIKQENLVK QYEAYSGKEA SEVVKTYLNS PSSDKYVWID<br>CRQKFLRFQR ELGTRNLSED FECMLFEQYI RLTKGEIEGY<br>AAISNMFGNG EKEDRSKKRM YATRMKDWLE ANENITWEQY<br>REALKNQLNA KNLEQVVANY KGNAGGADPF FKYSFSKEGM<br>VSKKEHAQQL DKFKTVLKNK ARDLNFPNKE KLKQYLEAEI<br>GIPVDANVYS QMFSNGVSEV QPKTTRNMSF SNEKLDLLTE<br>LKDLNKGDGF EYAREVLNGF FDSELHTTED KFNITSRYLG<br>GDKSNRLSKL YKIWKKEGVD CEEGIQQFCE AVKDKMGQIP<br>IRNVLKYLWQ FRETVSAEDF EAAAKANHLE EKISRVKAHP<br>IVISNRYWAF GTSALVGNIM PADKRHQGEY AGQNFKMWLR<br>AELHYDGKKA KHHLPFYNAR FFEEVYCYHP SVAEITPFKT<br>KQFGCEIGKD IPDYVSVALK DNPYKKATKR ILRAIYNPVA<br>NTTRVDKTTN CSFMIKREND EYKLVINRKI SRDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV<br>FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEAGLGEV EKGKSKKQNS RNMDWCAKQV AQRLEYKLAF<br>HGIGYRGVNP MYTSHQDPFE HRRVADHIVM RARFEEVNVE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NREQDDIPLI TKKAESKSPP KDRKRSKTSQ LPQK | E480R<br>G564R<br>V592R<br>E1042R<br>D846G<br>F886R |

TABLE 3-continued

Multi amino acid substitutions in variant Cas12i4 polypeptide.

| Sequence identifier | Sequence | Substitutions |
|---|---|---|
| SEQ ID NO: 39 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLR AELHYDGKKA KHHLPFYNAR FFEEVYCYHP SVAEITPFKT KQFGCEIGKD IPDYVSVALK DNPYKKATKR ILRAIYNPVA NTTRVDKRTN CSFMIKREND EYKLVINRKI RRDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL MRLSSLSDAS MQGIASLKSL INSYFNKNGC KTIEDKEKFN PVLYAKLVEV EQRRTNKRSE KVGRIAGSLE QLALLNGVEV VIGEAGLGEV EKGKSKKQNS RNMDWCAKQV AQRLEYKLAF HGIGYFGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NREQDDIPLI TKKAESKSPP KDRKRSKTSQ LPQK | E480R G564R V592R E1042R T568R S591R D846G |
| SEQ ID NO: 40 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLR AELHYDGKKA KHHLPFYNAR FFEEVYCYHP SVAEITPFKT KQFGCEIGKD IPDYVSVALK DNPYKKATKR ILRAIYNPVA NTTRVDKRTN CSFMIKREND EYKLVINRKI RRDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL MRLSSLSDAS MQGIASLKSL INSYFNKNGC KTIEDKEKFN PVLYAKLVEV EQRRTNKRSE KVGRIAGSLE QLALLNGVEV VIGEADLGEV EKGKSKKQNS RNMDWCAKQV AQRLEYKLAF HGIGYRGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NREQDDIPLI TKKAESKSPP KDRKRSKTSQ LPQK | E480R G564R V592R E1042R T568R S591R F886R |
| SEQ ID NO: 41 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLR AELHYDGKKA KHHLPFYNAR FFEEVYCYHP SVAEITPFKT KQFGCEIGKD IPDYVSVALK DNPYKKATKR ILRAIYNPVA NTTRVDKRTN CSFMIKREND EYKLVINRKI SRDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL | E480R G564R V592R E1042R T568R D846G F886R |

TABLE 3-continued

Multi amino acid substitutions in variant Cas12i4 polypeptide.

| Sequence identifier | Sequence | Substitutions |
|---|---|---|
| | MRLSSLSDAS MQGIASLKSL INSYFNKNGC KTIEDKEKFN PVLYAKLVEV EQRRTNKRSE KVGRIAGSLE QLALLNGVEV VIGEAGLGEV EKGKSKKQNS RNMDWCAKQV AQRLEYKLAF HGIGYRGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NREQDDIPLI TKKAESKSPP KDRKRSKTSQ LPQK | |
| SEQ ID NO: 42 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLR AELHYDGKKA KHHLPFYNAR FFEEVYCYHP SVAEITPFKT KQFGCEIGKD IPDYVSVALK DNPYKKATKR ILRAIYNPVA NTTRVDKTTN CSFMIKREND EYKLVINRKI RRDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL MRLSSLSDAS MQGIASLKSL INSYFNKNGC KTIEDKEKFN PVLYAKLVEV EQRRTNKRSE KVGRIAGSLE QLALLNGVEV VIGEAGLGEV EKGKSKKQNS RNMDWCAKQV AQRLEYKLAF HGIGYRGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NREQDDIPLI TKKAESKSPP KDRKRSKTSQ LPQK | E480R G564R V592R E1042R S591R D846G F886R |
| SEQ ID NO: 43 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLR AELHYDGKKA KHHLPFYNAR FFEEVYCYHP SVAEITPFKT KQFGCEIGKD IPDYVSVALK DNPYKKATKR ILRAIYNPVA NTTRVDKRTN CSFMIKREND EYKLVINRKI RRDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL MRLSSLSDAS MQGIASLKSL INSYFNKNGC KTIEDKEKFN PVLYAKLVEV EQRRTNKRSE KVGRIAGSLE QLALLNGVEV VIGEAGLGEV EKGKSKKQNS RNMDWCAKQV AQRLEYKLAF HGIGYRGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NREQDDIPLI TKKAESKSPP KDRKRSKTSQ LPQK | E480R G564R V592R E1042R T568R S591R D846G F886R |
| SEQ ID NO: 44 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP | E480R T568R V592R |

TABLE 3-continued

Multi amino acid substitutions in variant Cas12i4 polypeptide.

| Sequence identifier | Sequence | Substitutions |
|---|---|---|
| | IRNVLKYLWQ FRETVSAEDF EAAAKANHLE EKISRVKAHP<br>IVISNRYWAF GTSALVGNIM PADKRHQGEY AGQNFKMWLR<br>AELHYDGKKA KHHLPFYNAR FFEEVYCYHP SVAEITPFKT<br>KQFGCEIGKD IPDYVSVALK DNPYKKATKR ILRAIYNPVA<br>NTTGVDKRTN CSFMIKREND EYKLVINRKI SRDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV<br>FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEADLGEV EKGKSKKQNS RNMDWCAKQV AQRLEYKLAF<br>HGIGYFGVNP MYTSHQDPFE HRRVADHIVM RARFEEVNVE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NEEQDDIPLI TKKAESKSPP KDRKRSKTSQ LPQK | |
| SEQ ID NO: 45 | MASISRPYGT KLRPDARKKE MLDKFFNTLT KGQRVFADLA<br>LCIYGSLTLE MAKSLEPESD SELVCAIGWF RLVDKTIWSK<br>DGIKQENLVK QYEAYSGKEA SEVVKTYLNS PSSDKYVWID<br>CRQKFLRFQR ELGTRNLSED FECMLFEQYI RLTKGEIEGY<br>AAISNMFGNG EKEDRSKKRM YATRMKDWLE ANENITWEQY<br>REALKNQLNA KNLEQVVANY KGNAGGADPF FKYSFSKEGM<br>VSKKEHAQQL DKFKTVLKNK ARDLNFPNKE KLKQYLEAEI<br>GIPVDANVYS QMFSNGVSEV QPKTTRNMSF SNEKLDLLTE<br>LKDLNKGDGF EYAREVLNGF FDSELHTTED KFNITSRYLG<br>GDKSNRLSKL YKIWKKEGVD CEEGIQQFCE AVKDKMGQIP<br>IRNVLKYLWQ FRETVSAEDF EAAAKANHLE EKISRVKAHP<br>IVISNRYWAF GTSALVGNIM PADKRHQGEY AGQNFKMWLR<br>AELHYDGKKA KHHLPFYNAR FFEEVYCYHP SVAEITPFKT<br>KQFGCEIGKD IPDYVSVALK DNPYKKATKR ILRAIYNPVA<br>NTTGVDKRTN CSFMIKREND EYKLVINRKI SVDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV<br>FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEAGLGEV EKGKSKKQNS RNMDWCAKQV AQRLEYKLAF<br>HGIGYFGVNP MYTSHQDPFE HRRVADHIVM RARFEEVNVE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NEEQDDIPLI TKKAESKSPP KDRKRSKTSQ LPQK | E480R<br>T568R<br>D846G |
| SEQ ID NO: 46 | MASISRPYGT KLRPDARKKE MLDKFFNTLT KGQRVFADLA<br>LCIYGSLTLE MAKSLEPESD SELVCAIGWF RLVDKTIWSK<br>DGIKQENLVK QYEAYSGKEA SEVVKTYLNS PSSDKYVWID<br>CRQKFLRFQR ELGTRNLSED FECMLFEQYI RLTKGEIEGY<br>AAISNMFGNG EKEDRSKKRM YATRMKDWLE ANENITWEQY<br>REALKNQLNA KNLEQVVANY KGNAGGADPF FKYSFSKEGM<br>VSKKEHAQQL DKFKTVLKNK ARDLNFPNKE KLKQYLEAEI<br>GIPVDANVYS QMFSNGVSEV QPKTTRNMSF SNEKLDLLTE<br>LKDLNKGDGF EYAREVLNGF FDSELHTTED KFNITSRYLG<br>GDKSNRLSKL YKIWKKEGVD CEEGIQQFCE AVKDKMGQIP<br>IRNVLKYLWQ FRETVSAEDF EAAAKANHLE EKISRVKAHP<br>IVISNRYWAF GTSALVGNIM PADKRHQGEY AGQNFKMWLR<br>AELHYDGKKA KHHLPFYNAR FFEEVYCYHP SVAEITPFKT<br>KQFGCEIGKD IPDYVSVALK DNPYKKATKR ILRAIYNPVA<br>NTTGVDKRTN CSFMIKREND EYKLVINRKI SVDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV<br>FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEADLGEV EKGKSKKQNS RNMDWCAKQV AQRLEYKLAF<br>HGIGYRGVNP MYTSHQDPFE HRRVADHIVM RARFEEVNVE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NEEQDDIPLI TKKAESKSPP KDRKRSKTSQ LPQK | E480R<br>T568R<br>F886R |

TABLE 3-continued

Multi amino acid substitutions in variant Cas12i4 polypeptide.

| Sequence identifier | Sequence | Substitutions |
|---|---|---|
| SEQ ID NO: 47 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLR AELHYDGKKA KHHLPFYNAR FFEEVYCYHP SVAEITPFKT KQFGCEIGKD IPDYVSVALK DNPYKKATKR ILRAIYNPVA NTTGVDKTTN CSFMIKREND EYKLVINRKI SRDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL MRLSSLSDAS MQGIASLKSL INSYFNKNGC KTIEDKEKFN PVLYAKLVEV EQRRTNKRSE KVGRIAGSLE QLALLNGVEV VIGEAGLGEV EKGKSKKQNS RNMDWCAKQV AQRLEYKLAF HGIGYFGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NEEQDDIPLI TKKAESKSPP KDRKRSKTSQ LPQK | E480R V592R D846G |
| SEQ ID NO: 48 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLR AELHYDGKKA KHHLPFYNAR FFEEVYCYHP SVAEITPFKT KQFGCEIGKD IPDYVSVALK DNPYKKATKR ILRAIYNPVA NTTGVDKTTN CSFMIKREND EYKLVINRKI SRDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL MRLSSLSDAS MQGIASLKSL INSYFNKNGC KTIEDKEKFN PVLYAKLVEV EQRRTNKRSE KVGRIAGSLE QLALLNGVEV VIGEADLGEV EKGKSKKQNS RNMDWCAKQV AQRLEYKLAF HGIGYRGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NEEQDDIPLI TKKAESKSPP KDRKRSKTSQ LPQK | E480R V592R F886R |
| SEQ ID NO: 49 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLR AELHYDGKKA KHHLPFYNAR FFEEVYCYHP SVAEITPFKT KQFGCEIGKD IPDYVSVALK DNPYKKATKR ILRAIYNPVA NTTGVDKTTN CSFMIKREND EYKLVINRKI SVDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV | E480R D846G F886R |

TABLE 3-continued

Multi amino acid substitutions in variant Cas12i4 polypeptide.

| Sequence identifier | Sequence | Substitutions |
|---|---|---|
| | FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEAGLGEV EKGKSKKQNS RNMDWCAKQV AQRLEYKLAF<br>HGIGYRGVNP MYTSHQDPFE HRRVADHIVM RARFEEVVNE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NEEQDDIPLI TKKAESKSPP KDRKRSKTSQ LPQK | |
| SEQ ID NO: 50 | MASISRPYGT KLRPDARKKE MLDKFFNTLT KGQRVFADLA<br>LCIYGSLTLE MAKSLEPESD SELVCAIGWF RLVDKTIWSK<br>DGIKQENLVK QYEAYSGKEA SEVVKTYLNS PSSDKYVWID<br>CRQKFLRFQR ELGTRNLSED FECMLFEQYI RLTKGEIEGY<br>AAISNMFGNG EKEDRSKKRM YATRMKDWLE ANENITWEQY<br>REALKNQLNA KNLEQVVANY KGNAGGADPF FKYSFSKEGM<br>VSKKEHAQQL DKFKTVLKNK ARDLNFPNKE KLKQYLEAEI<br>GIPVDANVYS QMFSNGVSEV QPKTTRNMSF SNEKLDLLTE<br>LKDLNKGDGF EYAREVLNGF FDSELHTTED KFNITSRYLG<br>GDKSNRLSKL YKIWKKEGVD CEEGIQQFCE AVKDKMGQIP<br>IRNVLKYLWQ FRETVSAEDF EAAAKANHLE EKISRVKAHP<br>IVISNRYWAF GTSALVGNIM PADKRHQGEY AGQNFKMWLE<br>AELHYDGKKA KHHLPFYNAR FFEEVYCYHP SVAEITPFKT<br>KQFGCEIGKD IPDYVSVALK DNPYKKATKR ILRAIYNPVA<br>NTTGVDKRTN CSFMIKREND EYKLVINRKI SRDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV<br>FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEAGLGEV EKGKSKKQNS RNMDWCAKQV AQRLEYKLAF<br>HGIGYFGVNP MYTSHQDPFE HRRVADHIVM RARFEEVVNE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NEEQDDIPLI TKKAESKSPP KDRKRSKTSQ LPQK | T568R<br>V592R<br>D846G |
| SEQ ID NO: 51 | MASISRPYGT KLRPDARKKE MLDKFFNTLT KGQRVFADLA<br>LCIYGSLTLE MAKSLEPESD SELVCAIGWF RLVDKTIWSK<br>DGIKQENLVK QYEAYSGKEA SEVVKTYLNS PSSDKYVWID<br>CRQKFLRFQR ELGTRNLSED FECMLFEQYI RLTKGEIEGY<br>AAISNMFGNG EKEDRSKKRM YATRMKDWLE ANENITWEQY<br>REALKNQLNA KNLEQVVANY KGNAGGADPF FKYSFSKEGM<br>VSKKEHAQQL DKFKTVLKNK ARDLNFPNKE KLKQYLEAEI<br>GIPVDANVYS QMFSNGVSEV QPKTTRNMSF SNEKLDLLTE<br>LKDLNKGDGF EYAREVLNGF FDSELHTTED KFNITSRYLG<br>GDKSNRLSKL YKIWKKEGVD CEEGIQQFCE AVKDKMGQIP<br>IRNVLKYLWQ FRETVSAEDF EAAAKANHLE EKISRVKAHP<br>IVISNRYWAF GTSALVGNIM PADKRHQGEY AGQNFKMWLE<br>AELHYDGKKA KHHLPFYNAR FFEEVYCYHP SVAEITPFKT<br>KQFGCEIGKD IPDYVSVALK DNPYKKATKR ILRAIYNPVA<br>NTTGVDKRTN CSFMIKREND EYKLVINRKI SRDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV<br>FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEADLGEV EKGKSKKQNS RNMDWCAKQV AQRLEYKLAF<br>HGIGYRGVNP MYTSHQDPFE HRRVADHIVM RARFEEVVNE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NEEQDDIPLI TKKAESKSPP KDRKRSKTSQ LPQK | T568R<br>V592R<br>F886R |
| SEQ ID NO: 52 | MASISRPYGT KLRPDARKKE MLDKFFNTLT KGQRVFADLA<br>LCIYGSLTLE MAKSLEPESD SELVCAIGWF RLVDKTIWSK<br>DGIKQENLVK QYEAYSGKEA SEVVKTYLNS PSSDKYVWID<br>CRQKFLRFQR ELGTRNLSED FECMLFEQYI RLTKGEIEGY<br>AAISNMFGNG EKEDRSKKRM YATRMKDWLE ANENITWEQY<br>REALKNQLNA KNLEQVVANY KGNAGGADPF FKYSFSKEGM<br>VSKKEHAQQL DKFKTVLKNK ARDLNFPNKE KLKQYLEAEI<br>GIPVDANVYS QMFSNGVSEV QPKTTRNMSF SNEKLDLLTE<br>LKDLNKGDGF EYAREVLNGF FDSELHTTED KFNITSRYLG | T568R<br>D846G<br>F886R |

TABLE 3-continued

Multi amino acid substitutions in variant Cas12i4 polypeptide.

| Sequence identifier | Sequence | Substitutions |
|---|---|---|
| | GDKSNRLSKL YKIWKKEGVD CEEGIQQFCE AVKDKMGQIP<br>IRNVLKYLWQ FRETVSAEDF EAAAKANHLE EKISRVKAHP<br>IVISNRYWAF GTSALVGNIM PADKRHQGEY AGQNFKMWLE<br>AELHYDGKKA KHHLPFYNAR FFEEVYCYHP SVAEITPFKT<br>KQFGCEIGKD IPDYVSVALK DNPYKKATKR ILRAIYNPVA<br>NTTGVDKRTN CSFMIKREND EYKLVINRKI SVDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV<br>FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEAGLGEV EKGKSKKQNS RNMDWCAKQV AQRLEYKLAF<br>HGIGYRGVNP MYTSHQDPFE HRRVADHIVM RARFEEVNVE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NEEQDDIPLI TKKAESKSPP KDRKRSKTSQ LPQK | |
| SEQ ID NO: 53 | MASISRPYGT KLRPDARKKE MLDKFFNTLT KGQRVFADLA<br>LCIYGSLTLE MAKSLEPESD SELVCAIGWF RLVDKTIWSK<br>DGIKQENLVK QYEAYSGKEA SEVVKTYLNS PSSDKYVWID<br>CRQKFLRFQR ELGTRNLSED FECMLFEQYI RLTKGEIEGY<br>AAISNMFGNG EKEDRSKKRM YATRMKDWLE ANENITWEQY<br>REALKNQLNA KNLEQVVANY KGNAGGADPF FKYSFSKEGM<br>VSKKEHAQQL DKFKTVLKNK ARDLNFPNKE KLKQYLEAEI<br>GIPVDANVYS QMFSNGVSEV QPKTTRNMSF SNEKLDLLTE<br>LKDLNKGDGF EYAREVLNGF FDSELHTTED KFNITSRYLG<br>GDKSNRLSKL YKIWKKEGVD CEEGIQQFCE AVKDKMGQIP<br>IRNVLKYLWQ FRETVSAEDF EAAAKANHLE EKISRVKAHP<br>IVISNRYWAF GTSALVGNIM PADKRHQGEY AGQNFKMWLE<br>AELHYDGKKA KHHLPFYNAR FFEEVYCYHP SVAEITPFKT<br>KQFGCEIGKD IPDYVSVALK DNPYKKATKR ILRAIYNPVA<br>NTTGVDKTTN CSFMIKREND EYKLVINRKI SRDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV<br>FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEAGLGEV EKGKSKKQNS RNMDWCAKQV AQRLEYKLAF<br>HGIGYRGVNP MYTSHQDPFE HRRVADHIVM RARFEEVNVE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NEEQDDIPLI TKKAESKSPP KDRKRSKTSQ LPQK | V592R<br>D846G<br>F886R |
| SEQ ID NO: 54 | MASISRPYGT KLRPDARKKE MLDKFFNTLT KGQRVFADLA<br>LCIYGSLTLE MAKSLEPESD SELVCAIGWF RLVDKTIWSK<br>DGIKQENLVK QYEAYSGKEA SEVVKTYLNS PSSDKYVWID<br>CRQKFLRFQR ELGTRNLSED FECMLFEQYI RLTKGEIEGY<br>AAISNMFGNG EKEDRSKKRM YATRMKDWLE ANENITWEQY<br>REALKNQLNA KNLEQVVANY KGNAGGADPF FKYSFSKEGM<br>VSKKEHAQQL DKFKTVLKNK ARDLNFPNKE KLKQYLEAEI<br>GIPVDANVYS QMFSNGVSEV QPKTTRNMSF SNEKLDLLTE<br>LKDLNKGDGF EYAREVLNGF FDSELHTTED KFNITSRYLG<br>GDKSNRLSKL YKIWKKEGVD CEEGIQQFCE AVKDKMGQIP<br>IRNVLKYLWQ FRETVSAEDF EAAAKANHLE EKISRVKAHP<br>IVISNRYWAF GTSALVGNIM PADKRHQGEY AGQNFKMWLR<br>AELHYDGKKA KHHLPFYNAR FFEEVYCYHP SVAEITPFKT<br>KQFGCEIGKD IPDYVSVALK DNPYKKATKR ILRAIYNPVA<br>NTTGVDKRTN CSFMIKREND EYKLVINRKI SRDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV<br>FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEAGLGEV EKGKSKKQNS RNMDWCAKQV AQRLEYKLAF<br>HGIGYFGVNP MYTSHQDPFE HRRVADHIVM RARFEEVNVE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NEEQDDIPLI TKKAESKSPP KDRKRSKTSQ LPQK | E480R<br>T568R<br>V592R<br>D846G |

TABLE 3-continued

Multi amino acid substitutions in variant Cas12i4 polypeptide.

| Sequence identifier | Sequence | Substitutions |
|---|---|---|
| SEQ ID NO: 55 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLR AELHYDGKKA KHHLPFYNAR FFEEVYCYHP SVAEITPFKT KQFGCEIGKD IPDYVSVALK DNPYKKATKR ILRAIYNPVA NTTGVDKRTN CSFMIKREND EYKLVINRKI SRDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL MRLSSLSDAS MQGIASLKSL INSYFNKNGC KTIEDKEKFN PVLYAKLVEV EQRRTNKRSE KVGRIAGSLE QLALLNGVEV VIGEADLGEV EKGKSKKQNS RNMDWCAKQV AQRLEYKLAF HGIGYRGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NEEQDDIPLI TKKAESKSPP KDRKRSKTSQ LPQK | E480R T568R V592R F886R |
| SEQ ID NO: 56 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLR AELHYDGKKA KHHLPFYNAR FFEEVYCYHP SVAEITPFKT KQFGCEIGKD IPDYVSVALK DNPYKKATKR ILRAIYNPVA NTTGVDKRTN CSFMIKREND EYKLVINRKI SVDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL MRLSSLSDAS MQGIASLKSL INSYFNKNGC KTIEDKEKFN PVLYAKLVEV EQRRTNKRSE KVGRIAGSLE QLALLNGVEV VIGEAGLGEV EKGKSKKQNS RNMDWCAKQV AQRLEYKLAF HGIGYRGVNP MYTSHQDPFE HRRVADHIVM RARFEEVNVE NIAEWHVRNF SNYLRADSGT GLYYKQATMD FLKHYGLEEH AEGLENKKIK FYDFRKILED KNLTSVIIPK RGGRIYMATN PVTSDSTPIT YAGKTYNRCN ADEVAAANIV ISVLAPRSKK NEEQDDIPLI TKKAESKSPP KDRKRSKTSQ LPQK | E480R T568R D846G F886R |
| SEQ ID NO: 57 | MASISRPYGT KLRPDARKKE MLDKFFNTLT KGQRVFADLA LCIYGSLTLE MAKSLEPESD SELVCAIGWF RLVDKTIWSK DGIKQENLVK QYEAYSGKEA SEVVKTYLNS PSSDKYVWID CRQKFLRFQR ELGTRNLSED FECMLFEQYI RLTKGEIEGY AAISNMFGNG EKEDRSKKRM YATRMKDWLE ANENITWEQY REALKNQLNA KNLEQVVANY KGNAGGADPF FKYSFSKEGM VSKKEHAQQL DKFKTVLKNK ARDLNFPNKE KLKQYLEAEI GIPVDANVYS QMFSNGVSEV QPKTTRNMSF SNEKLDLLTE LKDLNKGDGF EYAREVLNGF FDSELHTTED KFNITSRYLG GDKSNRLSKL YKIWKKEGVD CEEGIQQFCE AVKDKMGQIP IRNVLKYLWQ FRETVSAEDF EAAAKANHLE EKISRVKAHP IVISNRYWAF GTSALVGNIM PADKRHQGEY AGQNFKMWLR AELHYDGKKA KHHLPFYNAR FFEEVYCYHP SVAEITPFKT KQFGCEIGKD IPDYVSVALK DNPYKKATKR ILRAIYNPVA NTTGVDKTTN CSFMIKREND EYKLVINRKI SRDRPKRIEV GRTIMGYDRN QTASDTYWIG RLVPPGTRGA YRIGEWSVQY IKSGPVLSST QGVNNSTTDQ LVYNGMPSSS ERFKAWKKAR MAFIRKLIRQ LNDEGLESKG QDYIPENPSS FDVRGETLYV FNSNYLKALV SKHRKAKKPV EGILDEIEAW TSKDKDSCSL | E480R V592R D846G F886R |

TABLE 3-continued

Multi amino acid substitutions in variant Cas12i4 polypeptide.

| Sequence identifier | Sequence | Substitutions |
|---|---|---|
| | MRLSSLSDAS MQGIASLKSL INSYFNKNGC KTIEDKEKFN<br>PVLYAKLVEV EQRRTNKRSE KVGRIAGSLE QLALLNGVEV<br>VIGEAGLGEV EKGKSKKQNS RNMDWCAKQV AQRLEYKLAF<br>HGIGYRGVNP MYTSHQDPFE HRRVADHIVM RARFEEVNVE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NEEQDDIPLI TKKAESKSPP KDRKRSKTSQ LPQK | |
| SEQ ID NO: 58 | MASISRPYGT KLRPDARKKE MLDKFFNTLT KGQRVFADLA<br>LCIYGSLTLE MAKSLEPESD SELVCAIGWF RLVDKTIWSK<br>DGIKQENLVK QYEAYSGKEA SEVVKTYLNS PSSDKYVWID<br>CRQKFLRFQR ELGTRNLSED FECMLFEQYI RLTKGEIEGY<br>AAISNMFGNG EKEDRSKKRM YATRMKDWLE ANENITWEQY<br>REALKNQLNA KNLEQVVANY KGNAGGADPF FKYSFSKEGM<br>VSKKEHAQQL DKFKTVLKNK ARDLNFPNKE KLKQYLEAEI<br>GIPVDANVYS QMFSNGVSEV QPKTTRNMSF SNEKLDLLTE<br>LKDLNKGDGF EYAREVLNGF FDSELHTTED KFNITSRYLG<br>GDKSNRLSKL YKIWKKEGVD CEEGIQQFCE AVKDKMGQIP<br>IRNVLKYLWQ FRETVSAEDF EAAAKANHLE EKISRVKAHP<br>IVISNRYWAF GTSALVGNIM PADKRHQGEY AGQNFKMWLE<br>AELHYDGKKA KHHLPFYNAR FFEEVYCYHP SVAEITPFKT<br>KQFGCEIGKD IPDYVSVALK DNPYKKATKR ILRAIYNPVA<br>NTTGVDKRTN CSFMIKREND EYKLVINRKI SRDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV<br>FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEAGLGEV EKGKSKKQNS RNMDWCAKQV AQRLEYKLAF<br>HGIGYRGVNP MYTSHQDPFE HRRVADHIVM RARFEEVNVE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NEEQDDIPLI TKKAESKSPP KDRKRSKTSQ LPQK | T568R<br>V592R<br>D846G<br>F886R |
| SEQ ID NO: 59 | MASISRPYGT KLRPDARKKE MLDKFFNTLT KGQRVFADLA<br>LCIYGSLTLE MAKSLEPESD SELVCAIGWF RLVDKTIWSK<br>DGIKQENLVK QYEAYSGKEA SEVVKTYLNS PSSDKYVWID<br>CRQKFLRFQR ELGTRNLSED FECMLFEQYI RLTKGEIEGY<br>AAISNMFGNG EKEDRSKKRM YATRMKDWLE ANENITWEQY<br>REALKNQLNA KNLEQVVANY KGNAGGADPF FKYSFSKEGM<br>VSKKEHAQQL DKFKTVLKNK ARDLNFPNKE KLKQYLEAEI<br>GIPVDANVYS QMFSNGVSEV QPKTTRNMSF SNEKLDLLTE<br>LKDLNKGDGF EYAREVLNGF FDSELHTTED KFNITSRYLG<br>GDKSNRLSKL YKIWKKEGVD CEEGIQQFCE AVKDKMGQIP<br>IRNVLKYLWQ FRETVSAEDF EAAAKANHLE EKISRVKAHP<br>IVISNRYWAF GTSALVGNIM PADKRHQGEY AGQNFKMWLR<br>AELHYDGKKA KHHLPFYNAR FFEEVYCYHP SVAEITPFKT<br>KQFGCEIGKD IPDYVSVALK DNPYKKATKR ILRAIYNPVA<br>NTTGVDKRTN CSFMIKREND EYKLVINRKI SRDRPKRIEV<br>GRTIMGYDRN QTASDTYWIG RLVPPGTRGA YRIGEWSVQY<br>IKSGPVLSST QGVNNSTTDQ LVYNGMPSSS ERFKAWKKAR<br>MAFIRKLIRQ LNDEGLESKG QDYIPENPSS FDVRGETLYV<br>FNSNYLKALV SKHRKAKKPV EGILDEIEAW TSKDKDSCSL<br>MRLSSLSDAS MQGIASLKSL INSYFNKNGC KTIEDKEKFN<br>PVLYAKLVEV EQRRTNKRSE KVGRIAGSLE QLALLNGVEV<br>VIGEAGLGEV EKGKSKKQNS RNMDWCAKQV AQRLEYKLAF<br>HGIGYRGVNP MYTSHQDPFE HRRVADHIVM RARFEEVNVE<br>NIAEWHVRNF SNYLRADSGT GLYYKQATMD FLKHYGLEEH<br>AEGLENKKIK FYDFRKILED KNLTSVIIPK RGGRIYMATN<br>PVTSDSTPIT YAGKTYNRCN ADEVAAANIV ISVLAPRSKK<br>NEEQDDIPLI TKKAESKSPP KDRKRSKTSQ LPQK | E480R<br>T568R<br>V592R<br>D846G<br>F886R |

In some embodiments, the variant Cas12i4 polypeptide comprises one or more additional substitutions on top of the sequence of SEQ ID NO: 3 (e.g., the variant Cas12i4 polypeptide comprises a V592R substitution and an E1042R substitution and further comprises one or more substitutions shown in Table 2 or Table 3). In some embodiments, the variant Cas12i4 polypeptide comprises one or more additional substitutions on top of the sequence of SEQ ID NO: 4 (e.g., the variant Cas12i4 polypeptide comprises an E480R substitution, a G564R substitution, a V592R substitution, an E1042R substitution and further comprises one or more substitutions shown in Table 2 or Table 3). In some embodiments, the variant Cas12i4 polypeptide comprises one or more additional substitutions on top of any one of the sequences of SEQ ID NOs: 5-59 (e.g., the variant Cas12i4 polypeptide further comprises one or more substitutions shown in Table 2 or Table 3). As noted above, in some embodiments, the variant Cas12i4 polypeptide maintains the amino acid changes (or at least 1, 2, 3, 4, 5 etc. of these changes) that differentiate the polypeptide from its respective parent/reference sequence.

In some embodiments, the variant Cas12i4 polypeptide comprises at least one RuvC motif or a RuvC domain.

Figure 5:
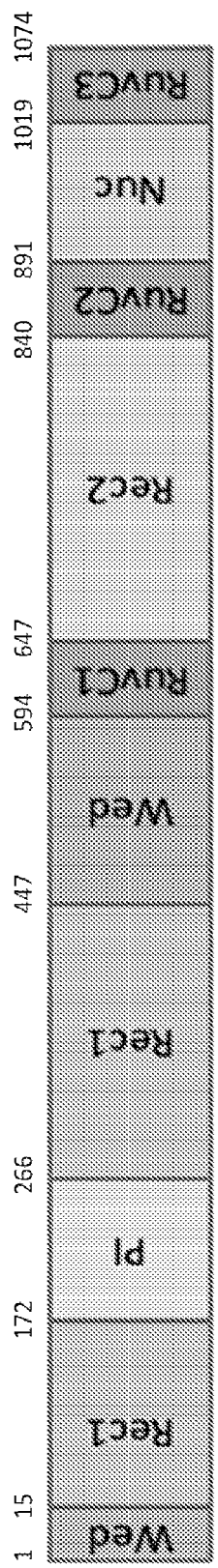
FIG. 5 is a schematic showing the domain structure of the Cas12i4 polypeptide.

The domains of Cas12i4 polypeptides disclosed herein are depicted in FIG. 5. The Wedge domain comprises residues 1-14 and 447-593 of the Cas12i4 polypeptide. The Rec1 domain comprises residues 15-171 and 266-446 of the Cas12i4 polypeptide. The PI domain comprises residues 172-265 of the Cas12i4 polypeptide. The Rec2 domain comprises residues 647-839 of the Cas12i4 polypeptide. The Nuc domain comprises residues 891-11018 of the Cas12i4 polypeptide. The RuvC domain comprises residues 594-646 (RuvC1 motif), residues 840-890 (RuvC2 motif), and residues 1019-1074 (RuvC3 motif) of the Cas12i4 polypeptide.

Although the changes described herein may be one or more amino acid changes, changes to the variant Cas12i4 polypeptide may also be of a substantive nature, such as fusion of polypeptides as amino- and/or carboxyl-terminal extensions. For example, variant Cas12i4 polypeptide may contain additional peptides, e.g., one or more peptides. Examples of additional peptides may include epitope peptides for labelling, such as a polyhistidine tag (His-tag), Myc, and FLAG. In some embodiments, the variant Cas12i4 polypeptide described herein can be fused to a detectable moiety such as a fluorescent protein (e.g., green fluorescent protein (GFP) or yellow fluorescent protein (YFP)).

In some embodiments, the variant Cas12i4 polypeptide comprises at least one (e.g., two, three, four, five, six, or more) nuclear localization signal (NLS). In some embodiments, the variant Cas12i4 polypeptide comprises at least one (e.g., two, three, four, five, six, or more) nuclear export signal (NES).

In some embodiments, the variant Cas12i4 polypeptide comprises at least one (e.g., two, three, four, five, six, or more) NLS and at least one (e.g., two, three, four, five, six, or more) NES.

In some embodiments, the variant Cas12i4 polypeptide described herein can be self-inactivating. See, Epstein et al., "Engineering a Self-Inactivating CRISPR System for AAV Vectors," *Mol. Ther.*, 24 (2016): S50, which is incorporated by reference in its entirety.

In some embodiments, the nucleotide sequence encoding the variant Cas12i4 polypeptide described herein can be codon-optimized for use in a particular host cell or organism. For example, the nucleic acid can be codon-optimized for any non-human eukaryote including mice, rats, rabbits, dogs, livestock, or non-human primates. Codon usage tables are readily available, for example, at the "Codon Usage Database" available at www.kazusa.orjp/codon/and these tables can be adapted in a number of ways. See Nakamura et al. *Nucl. Acids Res.* 28:292 (2000), which is incorporated herein by reference in its entirety. Computer algorithms for codon optimizing a particular sequence for expression in a particular host cell are also available, such as Gene Forge (Aptagen; Jacobus, PA).

Functionality of Variant Polypeptides

As used herein, a "biologically active portion" is a portion that retains at least one function (e.g. completely, partially, minimally) of the parent polypeptide (e.g., a "minimal" or "core" domain). In some embodiments, the variant Cas12i4 polypeptide retains enzymatic activity at least as active as the parent polypeptide. Accordingly, in some embodiments, a variant Cas12i4 polypeptide has enzymatic activity greater than the parent polypeptide.

Also provided is a variant Cas12i4 polypeptide of the present invention having enzymatic activity, e.g., nuclease or endonuclease activity, and comprising an amino acid sequence which differs from the amino acid sequences of any one of a parent polypeptide and SEQ ID NO: 2 by 50, 40, 35, 30, 25, 20, 19, 18, 17, 16, 15, 14, 13, 12, 11, 10, 9, 8, 7, 6, 5, 4, 3, 2, or 1 amino acid residue(s), when aligned using any of the previously described alignment methods.

Figure 6A:
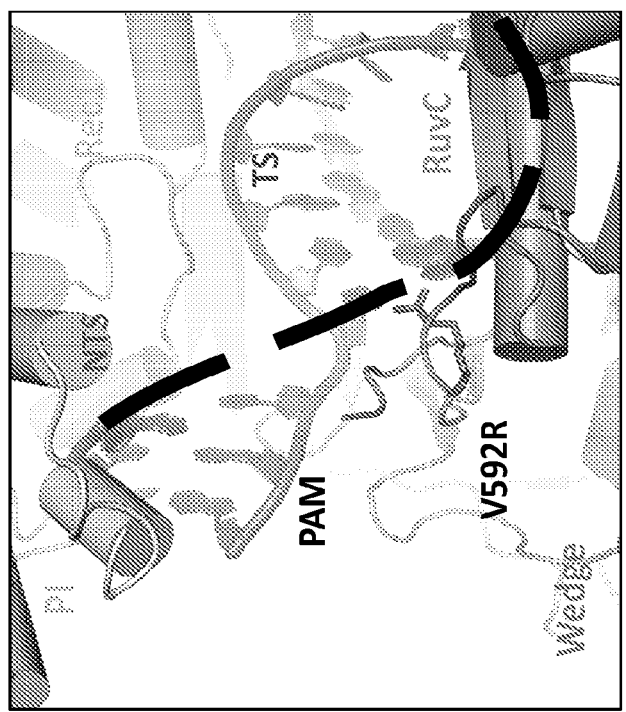
FIG. 6A depicts the location of the V592R substitution in the Cas12i4 structure. The V592R substitution can interact with the single-stranded non-target strand.

In some embodiments, a variant Cas12i4 polypeptide comprising a V592R substitution exhibits enhanced enzymatic activity. In some embodiments, the V592R residue interacts with the NTS. In some embodiments, the V592R residue contacts the NTS near the PAM sequence. See FIG. 6A.

Figure 6B:
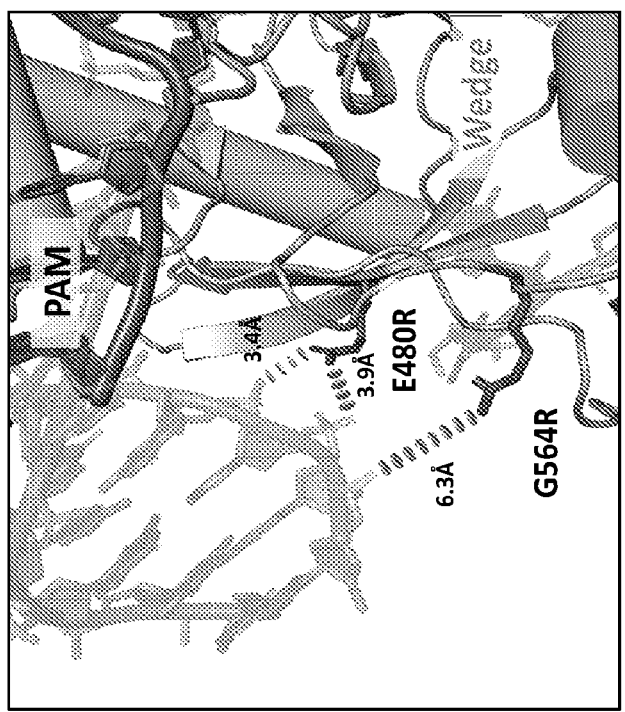
FIG. 6B depicts the locations of the E480R and G564R substitutions in the Cas12i4 structure, which are close to the PAM sequence of double-stranded DNA. The E480R and G564R substitutions can stabilize interactions with double-stranded DNA.

In some embodiments, a variant Cas12i4 polypeptide comprising an E480R substitution exhibits enhanced enzymatic activity. In some embodiments, the E480R substitution interacts with double-stranded DNA. In some embodiments, the E480R substitution interacts with double-stranded DNA upstream of the PAM sequence. In some embodiments, the E480R substitution stabilizes interactions of the variant Cas12i4 polypeptide with a target nucleic acid. See FIG. 6B.

In some embodiments, a variant Cas12i4 polypeptide comprising a G564R substitution exhibits enhanced enzymatic activity. In some embodiments, the G564R substitution interacts with double-stranded DNA. In some embodiments, the G564R substitution interacts with double-stranded DNA upstream of the PAM sequence. In some embodiments, the G564R substitution stabilizes interactions of the variant Cas12i4 polypeptide with a target nucleic acid. See FIG. 6B.

In some embodiments, a variant Cas12i4 polypeptide comprising an E1042R substitution exhibits enhanced enzymatic activity.

In some embodiments, the variant Cas12i4 polypeptide has reduced nuclease activity or is a nuclease dead polypeptide. As used herein, the catalytic residues of a polypeptide disclosed herein are D608, E844, and D1022. In some embodiments, a variant Cas12i4 polypeptide comprising a substitution at one or more of D608, E844, and D1022 (e.g., D608A, E844A, and D1022A) exhibits reduced nuclease activity or no nuclease activity relative to a parent polypeptide.

In some embodiments, the variant Cas12i4 polypeptide of the present invention has enzymatic activity equivalent to or greater than the parent polypeptide. In some embodiments, the variant Cas12i4 polypeptide of the present invention has enzymatic activity at a temperature range from about 20° C. to about 90° C. In some embodiments, the variant Cas12i4 polypeptide of the present invention has enzymatic activity at a temperature of about 20° C. to about 25° C. or at a temperature of about 37° C.

In some embodiments, the variant Cas12i4 polypeptide comprises at least one alteration that enhances affinity to RNA (e.g., RNA affinity), as compared to a parent polypeptide. In some embodiments, the variant Cas12i4 polypeptide exhibits enhanced RNA affinity, as compared to a parent polypeptide, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43°

C., 44° C., 45° C., 50° C., 51° C., 52° C., 53° C., 54° C., 55° C., 56° C., 57° C., 58° C., 59° C., 60° C. or 65° C. In some embodiments, the variant Cas12i4 polypeptide exhibits enhanced RNA affinity, as compared to a parent polypeptide, in a buffer having a pH in a range of about 7.3 to about 8.6. In some embodiments, the variant Cas12i4 polypeptide exhibits enhanced RNA affinity, as compared to a parent polypeptide, when the $T_m$ value of the variant Cas12i4 polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent polypeptide. In one embodiment, the variant Cas12i4 polypeptide exhibits enhanced RNA affinity when the $T_m$ value of the variant Cas12i4 polypeptide is at least 8° C. greater than the $T_m$ value of the parent polypeptide.

In some embodiments, at least one alteration is introduced into the parent polypeptide of SEQ ID NO: 2 to produce a variant Cas12i4 polypeptide that exhibits (a) decreased enzymatic activity and (b) enhanced RNA affinity relative to the parent polypeptide of SEQ ID NO: 2. In some embodiments, at least one alteration is introduced into the parent polypeptide of SEQ ID NO: 2 to produce a variant Cas12i4 polypeptide that exhibits (a) increased enzymatic activity and (b) enhanced RNA affinity, relative to the parent polypeptide of SEQ ID NO: 2. In some embodiments, at least one alteration is introduced into the parent polypeptide of SEQ ID NO: 2 to produce a variant Cas12i4 polypeptide that exhibits (a) retained enzymatic activity and (b) enhanced RNA affinity, relative to the parent polypeptide of SEQ ID NO: 2.

In some embodiments, the variant Cas12i4 polypeptide comprises at least one alteration that enhances complex formation with an RNA guide (e.g., binary complex formation), as compared to a parent polypeptide. In some embodiments, the variant Cas12i4 polypeptide exhibits enhanced binary complex formation, as compared to a parent polypeptide, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant Cas12i4 polypeptide exhibits enhanced binary complex formation, as compared to a parent polypeptide, in a buffer having a pH in a range of about 7.3 to about 8.6. In some embodiments, the variant Cas12i4 polypeptide exhibits enhanced binary complex formation, as compared to a parent polypeptide, when the $T_m$ value of the variant Cas12i4 polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent polypeptide. In one embodiment, the variant Cas12i4 polypeptide exhibits enhanced binary complex formation when the $T_m$ value of the variant Cas12i4 polypeptide is at least 8° C. greater than the $T_m$ value of the parent polypeptide.

In some embodiments, at least one alteration is introduced into the parent polypeptide of SEQ ID NO: 2 to produce a variant Cas12i4 polypeptide that exhibits (a) decreased enzymatic activity and (b) enhanced binary complex formation relative to the parent polypeptide of SEQ ID NO: 2. In some embodiments, at least one alteration is introduced into the parent polypeptide of SEQ ID NO: 2 to produce a variant Cas12i4 polypeptide that exhibits (a) increased enzymatic activity and (b) enhanced binary complex formation, relative to the parent polypeptide of SEQ ID NO: 2. In some embodiments, at least one alteration is introduced into the parent polypeptide of SEQ ID NO: 2 to produce a variant Cas12i4 polypeptide that exhibits (a) retained enzymatic activity and (b) enhanced binary complex formation, relative to the parent polypeptide of SEQ ID NO: 2.

In some embodiments, the variant Cas12i4 polypeptide comprises at least one alteration that enhances binding activity to an RNA guide, as compared to a parent polypeptide. In some embodiments, the variant Cas12i4 polypeptide exhibits enhanced RNA guide binding activity, as compared to a parent polypeptide, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant Cas12i4 polypeptide exhibits enhanced RNA guide binding activity, as compared to a parent polypeptide, in a buffer having a pH in a range of about 7.3 to about 8.6. In some embodiments, the variant Cas12i4 polypeptide exhibits enhanced RNA guide binding activity, as compared to a parent polypeptide, when the $T_m$ value of the variant Cas12i4 polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent polypeptide. In one embodiment, the variant Cas12i4 polypeptide exhibits enhanced RNA guide binding activity when the $T_m$ value of the variant Cas12i4 polypeptide is at least 8° C. greater than the $T_m$ value of the parent polypeptide.

In some embodiments, at least one alteration is introduced into the parent polypeptide of SEQ ID NO: 2 to produce a variant Cas12i4 polypeptide that exhibits (a) decreased enzymatic activity and (b) enhanced RNA guide binding activity relative to the parent polypeptide of SEQ ID NO: 2. In some embodiments, at least one alteration is introduced into the parent polypeptide of SEQ ID NO: 2 to produce a variant Cas12i4 polypeptide that exhibits (a) increased enzymatic activity and (b) enhanced RNA guide binding activity, relative to the parent polypeptide of SEQ ID NO: 2. In some embodiments, at least one alteration is introduced into the parent polypeptide of SEQ ID NO: 2 to produce a variant Cas12i4 polypeptide that exhibits (a) retained enzymatic activity and (b) enhanced RNA guide binding activity, relative to the parent polypeptide of SEQ ID NO: 2.

In some embodiments, the variant Cas12i4 polypeptide comprises at least one alteration that enhances binding specificity to an RNA guide, as compared to a parent polypeptide. In some embodiments, the variant Cas12i4 polypeptide exhibits enhanced RNA guide binding specificity, as compared to a parent polypeptide, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant Cas12i4 polypeptide exhibits enhanced RNA guide binding specificity, as compared to a parent polypeptide, in a buffer having a pH in a range of about 7.3 to about 8.6. In some embodiments, the variant Cas12i4 polypeptide exhibits enhanced RNA guide binding specificity, as compared to a parent polypeptide, when the $T_m$ value of the variant Cas12i4 polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent polypeptide. In one embodiment, the variant Cas12i4 polypeptide exhibits enhanced RNA guide binding specificity when the $T_m$ value of the variant Cas12i4 polypeptide is at least 8° C. greater than the $T_m$ value of the parent polypeptide.

In some embodiments, at least one alteration is introduced into the parent polypeptide of SEQ ID NO: 2 to produce a variant Cas12i4 polypeptide that exhibits (a) decreased enzymatic activity and (b) enhanced RNA guide binding specificity relative to the parent polypeptide of SEQ ID NO: 2. In some embodiments, at least one alteration is introduced into the parent polypeptide of SEQ ID NO: 2 to produce a variant Cas12i4 polypeptide that exhibits (a) increased enzymatic activity and (b) enhanced RNA guide binding specificity, relative to the parent polypeptide of SEQ ID NO: 2. In some embodiments, at least one alteration is introduced into the parent polypeptide of SEQ ID NO: 2 to produce a variant Cas12i4 polypeptide that exhibits (a) retained enzymatic activity and (b) enhanced RNA guide binding specificity, relative to the parent polypeptide of SEQ ID NO: 2.

In some embodiments, the variant Cas12i4 polypeptide comprises at least one alteration that enhances protein-RNA interactions, as compared to a parent polypeptide. In some embodiments, the variant Cas12i4 polypeptide exhibits enhanced protein-RNA interactions, as compared to a parent polypeptide, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant Cas12i4 polypeptide exhibits enhanced protein-RNA interactions, as compared to a parent polypeptide, in a buffer having a pH in a range of about 7.3 to about 8.6. In some embodiments, the variant Cas12i4 polypeptide exhibits enhanced protein-RNA interactions, as compared to a parent polypeptide, when the $T_m$ value of the variant Cas12i4 polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent polypeptide. In one embodiment, the variant Cas12i4 polypeptide exhibits enhanced protein-RNA interactions when the $T_m$ value of the variant Cas12i4 polypeptide is at least 8° C. greater than the $T_m$ value of the parent polypeptide.

In some embodiments, at least one alteration is introduced into the parent polypeptide of SEQ ID NO: 2 to produce a variant Cas12i4 polypeptide that exhibits (a) decreased enzymatic activity and (b) enhanced protein-RNA interactions relative to the parent polypeptide of SEQ ID NO: 2. In some embodiments, at least one alteration is introduced into the parent polypeptide of SEQ ID NO: 2 to produce a variant Cas12i4 polypeptide that exhibits (a) increased enzymatic activity and (b) enhanced protein-RNA interactions, relative to the parent polypeptide of SEQ ID NO: 2. In some embodiments, at least one alteration is introduced into the parent polypeptide of SEQ ID NO: 2 to produce a variant Cas12i4 polypeptide that exhibits (a) retained enzymatic activity and (b) enhanced protein-RNA interactions, relative to the parent polypeptide of SEQ ID NO: 2.

In some embodiments, the variant Cas12i4 polypeptide comprises at least one alteration that enhances protein stability, as compared to a parent polypeptide. In some embodiments, the variant Cas12i4 polypeptide exhibits enhanced protein stability, as compared to a parent polypeptide, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant Cas12i4 polypeptide exhibits enhanced protein stability, as compared to a parent polypeptide, in a buffer having a pH in a range of about 7.3 to about 8.6. In some embodiments, the variant Cas12i4 polypeptide exhibits enhanced protein stability, as compared to a parent polypeptide, when the $T_m$ value of the variant Cas12i4 polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent polypeptide. In one embodiment, the variant Cas12i4 polypeptide exhibits enhanced protein stability when the $T_m$ value of the variant Cas12i4 polypeptide is at least 8° C. greater than the $T_m$ value of the parent polypeptide.

In some embodiments, at least one alteration is introduced into the parent polypeptide of SEQ ID NO: 2 to produce a variant Cas12i4 polypeptide that exhibits (a) decreased enzymatic activity and (b) enhanced protein stability relative to the parent polypeptide of SEQ ID NO: 2. In some embodiments, at least one alteration is introduced into the parent polypeptide of SEQ ID NO: 2 to produce a variant Cas12i4 polypeptide that exhibits (a) increased enzymatic activity and (b) enhanced protein stability, relative to the parent polypeptide of SEQ ID NO: 2. In some embodiments, at least one alteration is introduced into the parent polypeptide of SEQ ID NO: 2 to produce a variant Cas12i4 polypeptide that exhibits (a) retained enzymatic activity and (b) enhanced protein stability, relative to the parent polypeptide of SEQ ID NO: 2.

In some embodiments, the variant Cas12i4 polypeptide comprises at least one alteration that decreases dissociation from an RNA guide (e.g., binary complex dissociation), as compared to a parent polypeptide. In some embodiments, the variant Cas12i4 polypeptide exhibits decreased dissociation from an RNA guide, as compared to a parent polypeptide, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant Cas12i4 polypeptide exhibits decreased dissociation from an RNA guide, as compared to a parent polypeptide, in a buffer having a pH in a range of about 7.3 to about 8.6. In some embodiments, the variant Cas12i4 polypeptide exhibits decreased dissociation from an RNA guide, as compared to a parent polypeptide, when the $T_m$ value of the variant Cas12i4 polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent polypeptide. In one embodiment, the variant Cas12i4 polypeptide exhibits decreased dissociation from an RNA guide when the $T_m$ value of the variant Cas12i4 polypeptide is at least 8° C. greater than the $T_m$ value of the parent polypeptide. In some embodiments, the variant Cas12i4 polypeptide exhibits decreased dissociation from an RNA guide, as compared to a parent polypeptide, over an incubation period of at least about any one of 10 mins, 15 mins, 20 mins, 25 mins, 30 mins, 35 mins, 40 mins, 45 mins, 50 mins, 55 mins, 1 hr, 2 hr, 3 hr, 4 hr, or more hours.

In some embodiments, a variant ribonucleoprotein (RNP) complex does not exchange the RNA guide with a different RNA.

In some embodiments, at least one alteration is introduced into the parent polypeptide of SEQ ID NO: 2 to produce a variant Cas12i4 polypeptide that exhibits (a) decreased enzymatic activity and (b) decreased dissociation from an RNA guide relative to the parent polypeptide of SEQ ID NO: 2. In some embodiments, at least one alteration is introduced into the parent polypeptide of SEQ ID NO: 2 to produce a variant Cas12i4 polypeptide that exhibits (a) increased enzymatic activity and (b) decreased dissociation from an RNA guide, relative to the parent polypeptide of SEQ ID NO: 2. In some embodiments, at least one alteration is introduced into the parent polypeptide of SEQ ID NO: 2 to produce a variant Cas12i4 polypeptide that exhibits (a) retained enzymatic activity and (b) decreased dissociation from an RNA guide, relative to the parent polypeptide of SEQ ID NO: 2.

In some embodiments, the variant Cas12i4 polypeptide comprises at least one alteration that enhances ternary complex formation with an RNA guide and a target nucleic acid, as compared to a parent polypeptide. In some embodiments, the variant Cas12i4 polypeptide exhibits enhanced ternary complex formation, as compared to a parent polypeptide, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant Cas12i4 polypeptide exhibits enhanced ternary complex formation, as compared to a parent polypeptide, in a buffer having a pH in a range of about 7.3 to about 8.6. In some embodiments, the variant Cas12i4 polypeptide exhibits enhanced ternary complex formation, as compared to a parent polypeptide, when the $T_m$ value of the variant Cas12i4 polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent polypeptide. In one embodiment, the variant Cas12i4 polypeptide exhibits enhanced ternary complex formation when the $T_m$ value of the variant Cas12i4 polypeptide is at least 8° C. greater than the $T_m$ value of the parent polypeptide.

In some embodiments, at least one alteration is introduced into the parent polypeptide of SEQ ID NO: 2 to produce a variant Cas12i4 polypeptide that exhibits (a) decreased enzymatic activity and (b) enhanced ternary complex formation relative to the parent polypeptide of SEQ ID NO: 2. In some embodiments, at least one alteration is introduced into the parent polypeptide of SEQ ID NO: 2 to produce a variant Cas12i4 polypeptide that exhibits (a) increased enzymatic activity and (b) enhanced ternary complex formation, relative to the parent polypeptide of SEQ ID NO: 2. In some embodiments, at least one alteration is introduced into the parent polypeptide of SEQ ID NO: 2 to produce a variant Cas12i4 polypeptide that exhibits (a) retained enzymatic activity and (b) enhanced ternary complex formation, relative to the parent polypeptide of SEQ ID NO: 2.

In some embodiments, the variant Cas12i4 polypeptide comprises at least one alteration such that a binary complex comprising the variant Cas12i4 polypeptide (e.g., a variant binary complex) exhibits enhanced binding affinity to a target nucleic acid, as compared to a parent binary complex. In some embodiments, the variant binary complex exhibits enhanced binding affinity to a target nucleic acid, as compared to a parent binary complex, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant binary complex exhibits enhanced binding affinity to a target nucleic acid, as compared to a parent binary complex, in a buffer having a pH in a range of about 7.3 to about 8.6. In some embodiments, the variant binary complex exhibits enhanced binding affinity to a target nucleic acid, as compared to a parent binary complex, when the $T_m$ value of the variant binary complex is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent binary complex. In one embodiment, the variant binary complex exhibits enhanced binding affinity to a target nucleic acid when the $T_m$ value of the variant binary complex is at least 8° C. greater than the $T_m$ value of the parent binary complex.

In some embodiments, at least one alteration is introduced into the parent polypeptide of SEQ ID NO: 2 to produce a variant Cas12i4 polypeptide that forms a variant binary complex exhibiting (a) decreased enzymatic activity and (b) enhanced binding affinity to a target nucleic acid, relative to a parent binary complex comprising the polypeptide of SEQ ID NO: 2. In some embodiments, at least one alteration is introduced into the parent polypeptide of SEQ ID NO: 2 to produce a variant Cas12i4 polypeptide that forms a variant binary complex exhibiting (a) increased enzymatic activity and (b) enhanced binding affinity to a target nucleic acid, relative to a parent binary complex comprising the polypeptide of SEQ ID NO: 2. In some embodiments, at least one alteration is introduced into the parent polypeptide of SEQ ID NO: 2 to produce a variant Cas12i4 polypeptide that forms a variant binary complex that exhibits (a) retained enzymatic activity and (b) enhanced binding affinity to a target nucleic acid, relative to a parent binary complex comprising the polypeptide of SEQ ID NO: 2.

In some embodiments, the variant Cas12i4 polypeptide comprises at least one alteration such that a binary complex comprising the variant Cas12i4 polypeptide (e.g., a variant binary complex) exhibits enhanced on-target binding activity, as compared to a parent binary complex. In some embodiments, the variant binary complex exhibits enhanced on-target binding activity, as compared to a parent binary complex, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant binary complex exhibits enhanced on-target binding activity, as compared to a parent binary complex, in a buffer having a pH in a range of about 7.3 to about 8.6. In some embodiments, the variant binary complex exhibits enhanced on-target binding activity, as compared to a parent binary complex, when the $T_m$ value of the variant binary complex is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent binary complex. In one embodiment, the variant binary complex exhibits enhanced on-target binding activity when the $T_m$ value of the variant binary complex is at least 8° C. greater than the $T_m$ value of the parent binary complex.

In some embodiments, at least one alteration is introduced into the parent polypeptide of SEQ ID NO: 2 to produce a variant Cas12i4 polypeptide that forms a variant binary complex exhibiting (a) decreased enzymatic activity and (b)

enhanced on-target binding activity, relative to a parent binary complex comprising the polypeptide of SEQ ID NO: 2. In some embodiments, at least one alteration is introduced into the parent polypeptide of SEQ ID NO: 2 to produce a variant Cas12i4 polypeptide that forms a variant binary complex exhibiting (a) increased enzymatic activity and (b) enhanced on-target binding activity, relative to a parent binary complex comprising the polypeptide of SEQ ID NO: 2. In some embodiments, at least one alteration is introduced into the parent polypeptide of SEQ ID NO: 2 to produce a variant Cas12i4 polypeptide that forms a variant binary complex that exhibits (a) retained enzymatic activity and (b) enhanced on-target binding activity, relative to a parent binary complex comprising the polypeptide of SEQ ID NO: 2.

In some embodiments, the variant Cas12i4 polypeptide comprises at least one alteration such that a binary complex comprising the variant Cas12i4 polypeptide (e.g., a variant binary complex) exhibits enhanced on-target binding specificity, as compared to a parent binary complex. In some embodiments, the variant binary complex exhibits enhanced on-target binding specificity, as compared to a parent binary complex, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant binary complex exhibits enhanced on-target binding specificity, as compared to a parent binary complex, in a buffer having a pH in a range of about 7.3 to about 8.6. In some embodiments, the variant binary complex exhibits enhanced on-target binding specificity, as compared to a parent binary complex, when the $T_m$ value of the variant binary complex is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent binary complex. In one embodiment, the variant binary complex exhibits enhanced on-target binding specificity when the $T_m$ value of the variant binary complex is at least 8° C. greater than the $T_m$ value of the parent binary complex.

In some embodiments, at least one alteration is introduced into the parent polypeptide of SEQ ID NO: 2 to produce a variant Cas12i4 polypeptide that forms a variant binary complex exhibiting (a) decreased enzymatic activity and (b) enhanced on-target binding specificity, relative to a parent binary complex comprising the polypeptide of SEQ ID NO: 2. In some embodiments, at least one alteration is introduced into the parent polypeptide of SEQ ID NO: 2 to produce a variant Cas12i4 polypeptide that forms a variant binary complex exhibiting (a) increased enzymatic activity and (b) enhanced on-target binding specificity, relative to a parent binary complex comprising the polypeptide of SEQ ID NO: 2.

In some embodiments, at least one alteration is introduced into the parent polypeptide of SEQ ID NO: 2 to produce a variant Cas12i4 polypeptide that forms a variant binary complex that exhibits (a) retained enzymatic activity and (b) enhanced on-target binding specificity, relative to a parent binary complex comprising the polypeptide of SEQ ID NO: 2.

In some embodiments, the variant Cas12i4 polypeptide comprises at least one alteration such that a binary complex comprising the variant Cas12i4 polypeptide (e.g., a variant binary complex) exhibits decreased off-target binding to a non-target nucleic acid, as compared to a parent binary complex. In some embodiments, the variant binary complex exhibits decreased off-target binding to a non-target nucleic acid, as compared to a parent binary complex, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant binary complex exhibits decreased off-target binding to a non-target nucleic acid, as compared to a parent binary complex, in a buffer having a pH in a range of about 7.3 to about 8.6. In some embodiments, the variant binary complex exhibits decreased off-target binding to a non-target nucleic acid, as compared to a parent binary complex, when the $T_m$ value of the variant Cas12i4 polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent polypeptide. In one embodiment, the variant binary complex exhibits decreased off-target binding to a non-target nucleic acid when the $T_m$ value of the variant binary complex is at least 8° C. greater than the $T_m$ value of the parent polypeptide.

In some embodiments, at least one alteration is introduced into the parent polypeptide of SEQ ID NO: 2 to produce a variant Cas12i4 polypeptide that forms a variant binary complex exhibiting (a) decreased enzymatic activity and (b) decreased off-target binding to a non-target nucleic acid, relative to a parent binary complex comprising the polypeptide of SEQ ID NO: 2. In some embodiments, at least one alteration is introduced into the parent polypeptide of SEQ ID NO: 2 to produce a variant Cas12i4 polypeptide that forms a variant binary complex exhibiting (a) increased enzymatic activity and (b) decreased off-target binding to a non-target nucleic acid, relative to a parent binary complex comprising the polypeptide of SEQ ID NO: 2. In some embodiments, at least one alteration is introduced into the parent polypeptide of SEQ ID NO: 2 to produce a variant Cas12i4 polypeptide that forms a variant binary complex exhibiting (a) retained enzymatic activity and (b) decreased off-target binding to a non-target nucleic acid, relative to a parent binary complex comprising the polypeptide of SEQ ID NO: 2.

In some embodiments, the variant Cas12i4 polypeptide comprises at least one alteration such that a binary complex comprising the variant Cas12i4 polypeptide (e.g., a variant binary complex) exhibits decreased dissociation from the target nucleic acid, as compared to a parent binary complex. In some embodiments, the variant binary complex exhibits decreased dissociation from the target nucleic acid, as compared to a parent binary complex, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant binary complex exhibits decreased dissociation from the target nucleic acid, as compared to a parent binary complex, in a buffer having a pH in a range of about 7.3 to about 8.6. In some embodiments, the variant binary complex exhibits decreased dissociation from the target nucleic acid, as compared to a parent binary complex, when the $T_m$ value of the variant Cas12i4 polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent polypeptide. In one embodiment, the variant binary complex exhibits decreased dissociation from the target nucleic acid when the $T_m$ value of the variant binary complex is at least 8° C. greater than the $T_m$ value of the parent polypeptide.

In some embodiments, at least one alteration is introduced into the parent polypeptide of SEQ ID NO: 2 to produce a variant Cas12i4 polypeptide that forms a variant binary complex exhibiting (a) decreased enzymatic activity and (b) decreased dissociation from the target nucleic acid, relative to a parent binary complex comprising the polypeptide of SEQ ID NO: 2. In some embodiments, at least one alteration is introduced into the parent polypeptide of SEQ ID NO: 2 to produce a variant Cas12i4 polypeptide that forms a variant binary complex exhibiting (a) increased enzymatic activity and (b) decreased dissociation from the target nucleic acid, relative to a parent binary complex comprising the polypeptide of SEQ ID NO: 2. In some embodiments, at least one alteration is introduced into the parent polypeptide of SEQ ID NO: 2 to produce a variant Cas12i4 polypeptide that forms a variant binary complex exhibiting (a) retained enzymatic activity and (b) decreased dissociation from the target nucleic acid, relative to a parent binary complex comprising the polypeptide of SEQ ID NO: 2.

In some embodiments, the variant Cas12i4 polypeptide comprises at least one alteration such that a ternary complex comprising the variant Cas12i4 polypeptide (e.g., a variant ternary complex) exhibits enhanced stability, as compared to a parent ternary complex. In some embodiments, the variant ternary complex exhibits enhanced stability, as compared to a parent ternary complex, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant ternary complex exhibits enhanced stability, as compared to a parent ternary complex, in a buffer having a pH in a range of about 7.3 to about 8.6. In some embodiments, the variant ternary complex exhibits enhanced stability, as compared to a parent ternary complex, when the $T_m$ value of the variant ternary complex is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent ternary complex. In one embodiment, the variant ternary complex exhibits enhanced stability when the $T_m$ value of the variant ternary complex is at least 8° C. greater than the $T_m$ value of the parent ternary complex.

Increased RNA Guide Interactions

In some embodiments, the variant Cas12i4 polypeptide comprises an alteration that increases interactions and/or affinity between the variant Cas12i4 polypeptide and the RNA guide, as compared to a parent polypeptide. In some embodiments, the alteration that increases interactions and/or affinity between the variant Cas12i4 polypeptide and the RNA guide is substituting one or more amino acids to an arginine, lysine, glutamine, asparagine, histidine, serine, or tyrosine residue. In some embodiments, the variant Cas12i4 polypeptide comprises a substitution of one or more amino acids in the RNA binding interface to an arginine, lysine, glutamine, asparagine, histidine, serine, tyrosine, phenylalanine, glutamic acid, or methionine residue. In some embodiments, the variant Cas12i4 polypeptide comprises an alteration of one or more amino acids in at least one domain (e.g., the Wedge domain, RuvC1 motif, RuvC2 motif, or Rec2 domain). In some embodiments, the RNA binding interface substitution(s) increases RNA guide binding or RNA guide binding affinity by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween, as compared to a parent polypeptide.

In some embodiments, the substitution increases RNA guide complex (binary complex) formation relative to a parent polypeptide. Non-limiting examples of substitutions that can alter the ability of a variant Cas12i4 polypeptide to interact with the direct repeat sequence of an RNA guide are shown in Table 4. In some embodiments, a variant Cas12i4 polypeptide comprising one or more substitutions listed in Table 4 exhibits enhanced RNA guide complex (binary complex) formation relative to a parent polypeptide. In some embodiments, a variant Cas12i4 polypeptide comprising one or more substitutions listed in Table 4 forms a more stable binary complex with an RNA guide, as compared to a binary complex comprising a parent polypeptide.

TABLE 4

Substitutions increasing direct repeat sequence contact.

| Residue | Substitution(s) |
| --- | --- |
| K11 | R |
| D15 | H, Q, Y, F, M, E |
| N474 | Q, E |
| E469 | R, W |
| F475 | Y |
| F476 | M |
| Y497 | K |
| T520 | K, R |
| Q522 | K |
| Y544 | R, K |
| K545 | R, |
| K546 | R |
| T612 | K, R |
| Q651 | R, K |
| N654 | R, K |
| T657 | K, R |
| T658 | K |
| Y633 | R, K |
| N654 | R |
| Y719 | K |
| C757 | T |
| V808 | K, R |
| E809 | R, K, Q |
| Q812 | H, R, K |
| N816 | K |
| E830 | N |
| Q831 | K |

In some embodiments, a variant Cas12i4 polypeptide of any one of SEQ ID NOs: 2-59 further comprises one or more substitutions listed in Table 4. In some embodiments, a variant Cas12i4 polypeptide comprises one or more substitutions listed in Table 2 and Table 4.

In some embodiments, a variant Cas12i4 polypeptide exhibiting enhanced RNA guide complex (binary complex) formation comprises two or more substitutions. In some embodiments a variant Cas12i4 polypeptide further comprises K545R and K546R. In some embodiments a variant Cas12i4 polypeptide further comprises K545R and K546R and N654R.

In some embodiments, the variant Cas12i4 polypeptide of any one of SEQ ID NOs: 2-59 further comprising one or more substitutions listed in Table 4 exhibits increased enzymatic activity. In some embodiments, the variant Cas12i4 polypeptide comprising one or more substitutions listed in Table 4 exhibits increased enzymatic activity. In some embodiments, the variant Cas12i4 polypeptide of any one of SEQ ID NOs: 2-59 that further comprises one or more substitutions listed in Table 4 exhibits increased enzymatic activity. In some embodiments, the variant Cas12i4 polypeptide exhibits increased enzymatic activity (e.g., by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween) as compared to a parent polypeptide.

Increased Double-Stranded DNA Interactions

In some aspects, a variant Cas12i4 polypeptide comprises an alteration that increases interactions with double-stranded DNA relative to a parent polypeptide. In some embodiments, increased interactions with double-stranded DNA are increased electrostatic interactions. In some embodiments, the variant Cas12i4 polypeptide comprises an alteration that increases affinity between the variant Cas12i4 polypeptide and double-stranded DNA relative to a parent polypeptide. In some embodiments, the alteration that increases interactions and/or affinity between the variant Cas12i4 polypeptide and double-stranded DNA increases binding of the variant Cas12i4 polypeptide to a PAM sequence.

In some embodiments, the alteration that increases interactions and/or affinity between the variant Cas12i4 polypeptide and the double-stranded DNA is substituting one or more amino acids. In some embodiments, the variant Cas12i4 polypeptide comprises a substitution of one or more amino acids in the double-stranded DNA binding interface. In some embodiments, the variant Cas12i4 polypeptide comprises an alteration of one or more amino acids in at least one domain (e.g., the Rec1 domain, PI domain, or Wedge domain) to an arginine, lysine, glutamine, asparagine, histidine, tryptophan, glycine, leucine, alanine, or serine residue. In some embodiments, the double-stranded DNA binding interface substitution(s) increase double-stranded DNA interactions and/or affinity by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween, as compared to a parent polypeptide. In some embodiments, the double-stranded DNA binding interface substitution(s) increase binding of the variant Cas12i4 polypeptide to a PAM sequence by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween, as compared to a parent polypeptide.

In some embodiments, the substitution that increases double-stranded DNA interactions increases ternary complex formation relative to a parent polypeptide. Non-limiting examples of substitutions that can alter the ability of a variant Cas12i4 polypeptide to interact with double-stranded DNA are shown in Table 5. In some embodiments, a variant Cas12i4 polypeptide comprising one or more substitutions listed in Table 5 exhibits increased double-stranded DNA interactions (ternary complex formation) relative to a parent polypeptide. In some embodiments, a variant Cas12i4 polypeptide comprising one or more substitutions listed in Table 5 forms a more stable ternary complex, as compared to a parent polypeptide.

TABLE 5

Substitutions altering double-stranded interactions.

| Residue | Substitution(s) |
|---|---|
| S3 | R, K |
| T568 | K, H |
| N165 | R, K |
| E173 | S |
| Y233 | R, K, Q, W |
| D285 | K, R, N |
| T568 | R |
| V456 | K, A, R |
| V458 | R, K |
| A227 | R, K |
| D228 | K, N, A |
| Q248 | R, K |
| K252 | R |
| T255 | N, K, R |
| N259 | Q, S, H, G |
| K260 | R |
| K264 | R, K |
| P461 | R, K |
| S5 | K, R |
| A161 | R, K |
| A449 | N |
| R175 | K |
| A218 | R, K |
| Y220 | K, R |
| K221 | R |
| N297 | K |
| N570 | K, R |
| V217 | R, K |
| K232 | R |
| K178 | R |
| N287 | K |
| A286 | R |
| Y160 | L |

In some embodiments, a variant Cas12i4 polypeptide of any one of SEQ ID NOs: 2-59 further comprises one or more substitutions listed in Table 5. In some embodiments, a variant Cas12i4 polypeptide comprises one or more substitutions listed in Table 2 and Table 5.

In some embodiments, a variant Cas12i4 polypeptide exhibiting increased double-stranded DNA interactions comprises two or more substitutions listed in Table 5. In some embodiments, a variant Cas12i4 polypeptide exhibiting increased double-stranded DNA interactions comprises K232R and D228A. In some embodiments, a variant Cas12i4 polypeptide exhibiting increased double-stranded DNA interactions comprises A286R and Y160L. In some embodiments, a variant Cas12i4 polypeptide exhibiting increased double-stranded DNA interactions comprises N287K and V456A. In some embodiments, a variant Cas12i4 polypeptide exhibiting increased double-stranded DNA interactions comprises K178R and E173S.

In some embodiments, the variant Cas12i4 polypeptide comprises any one or more substitutions in Table 4 and/or Table 5. In some embodiments, the variant Cas12i4 polypeptide with one or more of the substitutions in Table 4 and/or Table 5 exhibits increased double-stranded DNA interactions and/or affinity (e.g., by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween) as compared to a parent polypeptide. In some embodiments, the variant Cas12i4 polypeptide with one or more of the substitutions in Table 4 and/or Table 5 exhibits increased ternary complex formation and/or ternary complex stability (e.g., by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween) as compared to a parent polypeptide.

In some embodiments, the variant Cas12i4 polypeptide of any one of SEQ ID NOs: 2-59 comprising one or more substitutions listed in Table 4 and/or Table 5 exhibits increased enzymatic activity. In some embodiments, the variant Cas12i4 polypeptide comprising one or more substitutions listed in Table 4 and/or Table 5 exhibits increased enzymatic activity. In some embodiments, the variant Cas12i4 polypeptide exhibits increased enzymatic activity (e.g., by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween) as compared to a parent polypeptide.

Increased Single-Stranded DNA Interactions

In some embodiments, a variant Cas12i4 polypeptide comprises an alteration that increases interactions with single-stranded DNA relative to a parent polypeptide. In some embodiments, the variant Cas12i4 polypeptide comprises an alteration that increases affinity between the variant Cas12i4 polypeptide and double-stranded DNA relative to a parent polypeptide. In some embodiments, the single-stranded DNA comprises the non-target strand (NTS). In some embodiments, increased interactions with the single-stranded DNA (e.g., the NTS) are interactions between the PAM sequence and the active site of the variant Cas12i4 polypeptide. In some embodiments, the single-stranded DNA comprises single-stranded DNA that interacts with the variant Cas12i4 polypeptide at or near the active site of the variant Cas12i4 polypeptide.

In some embodiments, an alteration that increases interactions and/or affinity between the variant Cas12i4 polypeptide and the single-stranded DNA stabilizes the R-loop. As used herein, the "R-loop" refers to a nucleic acid comprising an RNA guide paired with the target strand (TS) and the single-stranded non-target strand (NTS).

In some embodiments, the alteration that increases interactions and/or affinity between the variant Cas12i4 polypeptide and the single-stranded DNA is substituting one or more amino acids. In some embodiments, the variant Cas12i4 polypeptide comprises a substitution of one or more amino acids in the single-stranded DNA binding interface. In some embodiments, the variant Cas12i4 polypeptide comprises an alteration of one or more amino acids in at least one domain/motif (e.g., the PI domain, Rec1 domain, RuvC1 motif, Rec2 domain, RuvC2 motif, Nuc domain, or RuvC3 motif) to an arginine, lysine, or alanine.

In some embodiments, the single-stranded DNA binding interface substitution(s) increase single-stranded DNA interactions and/or affinity by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween, as compared to a parent polypeptide.

In some embodiments, the substitution that increases single-stranded DNA interactions increases ternary complex formation relative to a parent polypeptide. Non-limiting examples of substitutions that can alter the ability of a variant Cas12i4 polypeptide to interact with single-stranded DNA are shown in Table 6. In some embodiments, a variant Cas12i4 polypeptide comprising one or more substitutions listed in Table 6 exhibits increased single-stranded DNA interactions (ternary complex formation) relative to a parent polypeptide. In some embodiments, a variant Cas12i4 polypeptide comprising one or more substitutions listed in Table 6 forms a more stable ternary complex, as compared to a parent polypeptide.

TABLE 6

Substitutions altering single-stranded interactions.

| Residue | Substitution(s) | |
|---|---|---|
| Y233 | R | in NTS of ssDNA |
| P625 | R, K | |
| E635 | R, K | |
| W636 | R, K | |
| P1036 | R, K | |
| T612 | R, K | Near the Active Site |
| D362 | R, K | |
| N724 | K | |
| A728 | R, K | |
| D768 | N, A | |
| Q772 | R, K | |
| S938 | R, K | |
| L942 | R, K | |
| V720 | R, K | |
| Q858 | K | |
| Y892 | R, K | |
| D937 | R, K | |
| G939 | K | |
| E962 | R, K | |
| E965 | R, K | |

In some embodiments, a variant Cas12i4 polypeptide of any one of SEQ ID NOs: 2-59 further comprises one or more substitutions listed in Table 6. In some embodiments, a variant Cas12i4 polypeptide comprises one or more substitutions listed in Table 2 and Table 6.

In some embodiments, a variant Cas12i4 polypeptide exhibiting increased single-stranded DNA interactions comprises two or more substitutions listed in Table 6. In some embodiments, a variant Cas12i4 polypeptide exhibiting increased ternary complex formation/stability comprises two or more substitutions listed in Table 6. In some embodiments, the variant Cas12i4 polypeptide comprises any one or more substitutions in Table 4 and/or Table 5 and/or Table 6. In some embodiments, the variant Cas12i4 polypeptide with one or more of the substitutions in Table 4 and/or Table 5 and/or Table 6 exhibits increased single-stranded DNA interactions and/or affinity (e.g., by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween) as compared to a parent polypeptide. In some embodiments, the variant Cas12i4 polypeptide with one or more of the substitutions in Table 4 and/or Table 5 and/or Table 6 exhibits increased ternary complex formation and/or ternary complex stability (e.g., by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween) as compared to a parent polypeptide.

In some embodiments, a variant Cas12i4 polypeptide comprises a substitution that increases single-stranded DNA stability (e.g., the substitution increases electrostatic interactions between single-stranded DNA and the active site of the variant Cas12i4 polypeptide). In some embodiments, the variant Cas12i4 polypeptide increases single-stranded DNA stability by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween, as compared to a parent polypeptide. Non-limiting examples of substitutions that can alter the ability of a variant Cas12i4 polypeptide to stabilize single-stranded DNA are shown in Table 6. In some embodiments, a variant Cas12i4 polypeptide comprising one or more substitutions listed in Table 6 exhibits increased single-stranded DNA stability relative to a parent polypeptide.

In some embodiments, the variant Cas12i4 polypeptide of any one of SEQ ID NOs: 2-59 comprising one or more substitutions listed in Table 4 and/or Table 5 and/or Table 6 exhibits increased enzymatic activity. In some embodiments, the variant Cas12i4 polypeptide comprising one or more substitutions listed in Table 4 and/or Table 5 and/or Table 6 exhibits increased enzymatic activity. In some embodiments, the variant Cas12i4 polypeptide of any one of SEQ ID NOs: 2-59 comprises one or more substitutions listed in Table 4 and/or Table 5 and/or Table 6 exhibits increased enzymatic activity. In some embodiments, the variant Cas12i4 polypeptide exhibits increased enzymatic activity (e.g., by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween) as compared to a parent polypeptide.

Increased Heteroduplex Interactions

In some embodiments, a variant Cas12i4 polypeptide comprises a substitution that increases interactions with a DNA/RNA hybrid molecule relative to a parent polypeptide. In some embodiments, the variant Cas12i4 polypeptide comprises an alteration that increases affinity between the variant Cas12i4 polypeptide and a DNA/RNA hybrid relative to a parent polypeptide. In some embodiments, the DNA/RNA hybrid molecule is a heteroduplex. As used herein, the "heteroduplex" refers to a double helix formed by the spacer of an RNA guide and the target strand (TS). As used herein, the term "seed region" refers to the TS part of the heteroduplex that is immediately downstream of the PAM sequence. The seed region comprises the first bases that pair with the RNA guide in the heteroduplex and are required for RNA-DNA binding and displacement of the TS. In some embodiments, an alteration that increases interactions and/or affinity between the variant Cas12i4 polypeptide and the heteroduplex increase non-specific nucleic acid contacts. In some embodiments, an alteration that increases interactions and/or affinity between the variant Cas12i4 polypeptide and the heteroduplex increases ternary complex formation/stability relative to a parent polypeptide.

In some embodiments, the alteration that increases interactions and/or affinity between the variant Cas12i4 polypeptide and the heteroduplex is substituting one or more amino acids. In some embodiments, the variant Cas12i4 polypeptide comprises a substitution of one or more amino acids contacting the heteroduplex. In some embodiments, the variant Cas12i4 polypeptide comprises an alteration of one or more amino acids in at least one domain/motif (e.g., the Wedge domain, Rec1 domain, Rec2 domain, or RuvC2 motif) to a lysine, arginine, histidine, serine, glutamine, or asparagine. In some embodiments, the nucleic acid interface substitution(s) increase heteroduplex interactions and/or affinity by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween, as compared to a parent polypeptide.

In some embodiments, the substitution that increases heteroduplex interactions increases ternary complex formation/stability relative to a parent polypeptide. Non-limiting examples of substitutions that can alter the ability of a variant Cas12i4 polypeptide to interact with the heteroduplex are shown in Table 7. In some embodiments, a variant Cas12i4 polypeptide comprising one or more substitutions listed in Table 7 exhibits increased heteroduplex interactions (ternary complex formation) relative to a parent polypeptide. In some embodiments, a variant Cas12i4 polypeptide comprising one or more substitutions listed in Table 7 forms a more stable ternary complex, as compared to a parent polypeptide.

TABLE 7

Substitutions altering heteroduplex interactions.

| Residue | Substitution(s) |
|---------|-----------------|
| S294*   | K, Q, R         |
| T355    | R, K            |
| T792    | R, K            |
| I793    | R, K, Q         |
| E811    | K, R, Q         |
| T815    | R, K, H, N      |
| S819    | R, K            |
| Q872    | R, K            |
| G9*     | R, K            |
| E156*   | R, K, Q         |
| T347    | R, K, H         |
| E349    | R, K, Q         |
| Y447*   | R, K, S         |
| V585*   | R, K            |
| S731    | R, K            |

TABLE 7-continued

Substitutions altering heteroduplex interactions.

| Residue | Substitution(s) |
|---------|-----------------|
| A775    | R, K            |
| S779    | R, K            |
| E794    | R, K, Q         |
| S855    | R, K, Q         |
| D74*    | R, K, N         |
| V442*   | A, K            |
| S113    | R, K            |
| N353    | R, K, H         |
| I401    | R, K            |
| E578*   | R, K            |
| D846*   | R, K, N         |
| S860    | K, Q            |
| Q869    | R, K            |
| Y116*   | R, K            |
| E313*   | R, K            |
| H428    | R, K            |
| S776    | R, K            |
| P7*     | N               |
| D114    | R               |
| Q301*   | H               |
| V730    | K               |
| S309*   | K               |
| V436    | K               |
| N445*   | R, K            |
| C866    | S               |
| G789    | R, K            |

*Substitution in seed region

In some embodiments, a variant Cas12i4 polypeptide of any one of SEQ ID NOs: 2-59 further comprises one or more substitutions listed in Table 7. In some embodiments, a variant Cas12i4 polypeptide comprises one or more substitutions listed in Table 2 and Table 7.

In some embodiments, a variant Cas12i4 polypeptide exhibiting increased heteroduplex interactions comprises two or more substitutions listed in Table 7. In some embodiments, a variant Cas12i4 polypeptide exhibiting increased ternary complex formation/stability comprises two or more substitutions listed in Table 7. In some embodiments, a variant Cas12i4 polypeptide comprises V585R and Y447S. In some embodiments, a variant Cas12i4 polypeptide comprises V585K and Y447S. In some embodiments, a variant Cas12i4 polypeptide comprises V585R and Y447K. In some embodiments, a variant Cas12i4 polypeptide comprises V585K and Y447K. In some embodiments, a variant Cas12i4 polypeptide of any one of SEQ ID NOs: 2-59 further comprises one or more substitutions listed in Table 7. In some embodiments, a variant Cas12i4 polypeptide of any one of SEQ ID NOs: 2-59 further comprises V585R and Y447S, V585K and Y447S, V585R and Y447K, or V585K and Y447K. In some embodiments, the variant Cas12i4 polypeptide comprises any one or more substitutions in Table 4 and/or Table 5 and/or Table 6 and/or Table 7. In some embodiments, the variant Cas12i4 polypeptide with one or more of the substitutions in Table 4 and/or Table 5 and/or Table 6 and/or Table 7 exhibits increased heteroduplex interactions and/or affinity (e.g., by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween) as compared to a parent polypeptide. In some embodiments, the variant Cas12i4 polypeptide with one or more of the substitutions in Table 4 and/or Table 5 and/or Table 6 and/or Table 7 exhibits increased ternary complex formation and/or ternary complex stability (e.g., by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween) as compared to a parent polypeptide.

In some embodiments, the variant Cas12i4 polypeptide of any one of SEQ ID NOs: 2-59 comprising one or more substitutions listed in Table 4 and/or Table 5 and/or Table 6 and/or Table 7 exhibits increased enzymatic activity. In some embodiments, the variant Cas12i4 polypeptide comprising one or more substitutions listed in Table 4 and/or Table 5 and/or Table 6 and/or Table 7 exhibits increased enzymatic activity. In some embodiments, the variant Cas12i4 polypeptide exhibits increased enzymatic activity (e.g., by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween) as compared to a parent polypeptide.

Increased Double-Stranded DNA Duplex and Heteroduplex Stability

During ternary complex formation, double-stranded DNA downstream of the PAM sequence melts (e.g., unwinds) into a target strand (TS) and a non-target strand (NTS). The spacer of an RNA guide binds to the TS, forming a double helix that is referred to as the heteroduplex. The PAM sequence does not melt and remains as intact double-stranded DNA. This results in partial exposure of these terminal PAM dsDNA base pair to the environment and protein, which may be energetically unfavorable. Similarly, the terminal base pair of the heteroduplex is exposed and may be energetically unfavorable. In some embodiments, an alteration that increases aromatic, hydrophobic, Van der Waals, and/or cation-pi interactions between the variant Cas12i4 polypeptide and the exposed terminal PAM bases of the double-stranded DNA duplex or terminal bases of the heteroduplex increases stability of DNA melting during ternary complex formation.

In some embodiments, an alteration that increases aromatic, hydrophobic, Van der Waals, and/or cation-pi interactions between the variant Cas12i4 polypeptide and exposed bases of the double-stranded DNA duplex or heteroduplex increases R-loop stability during ternary complex formation. In some embodiments, an alteration that increases aromatic, hydrophobic, Van der Waals, and/or cation-pi interactions between the variant Cas12i4 polypeptide and exposed bases of the double-stranded DNA duplex or heteroduplex increases ternary complex formation. In some embodiments, an alteration that increases aromatic, hydrophobic, Van der Waals, and/or cation-pi interactions between the variant Cas12i4 polypeptide and exposed bases of the double-stranded DNA duplex or heteroduplex increases ternary complex stability.

In some embodiments, the alteration that increases aromatic, hydrophobic, Van der Waals, and/or cation-pi interactions is substituting one or more residues. In some embodiments, the alteration that increases aromatic, hydrophobic, Van der Waals, and/or cation-pi interactions is substituting one or more residues contacting the double-stranded DNA duplex and/or heteroduplex. In some embodiments, the alteration that increases aromatic, hydrophobic, Van der Waals, and/or cation-pi interactions is a substitution listed in Table 8. In some embodiments, a variant Cas12i4 polypeptide comprising a substitution listed in Table 8 exhibits increased aromatic, hydrophobic, Van der Waals, and/or cation-pi interactions between the variant Cas12i4 polypeptide and exposed bases of the double-stranded DNA duplex or heteroduplex as compared to a parent polypeptide. In some embodiments, the alteration includes substituting amino acids adjacent to the terminal duplex base pairs with a positively charged, aromatic, hydrophobic, or branched-chain amino acids to create energetically more favorable conditions for the double-stranded DNA and heteroduplex.

TABLE 8

Substitutions stabilizing the R-loop.

| Residues | Substitution(s) |
|---|---|
| I4 | A |
| S5 | Q, I, M |
| Y876 | W, H |
| E156 | R |
| E158 | Q, K, R |
| A161 | M, R, Y |

In some embodiments, a variant Cas12i4 polypeptide of any one of SEQ ID NOs: 2-59 further comprises one or more substitutions listed in Table 8. In some embodiments, a variant Cas12i4 polypeptide comprises one or more substitutions listed in Table 2 and Table 8.

In some embodiments, a variant Cas12i4 polypeptide exhibiting increased ternary complex formation and/or ternary complex stability (e.g., by stabilizing melting of DNA and/or the R-loop) comprises two or more substitutions listed in Table 8. In some embodiments, a variant Cas12i4 polypeptide comprises I4A and Y876W. In some embodiments, a variant Cas12i4 polypeptide comprises E156R and E158Q. In some embodiments, a variant Cas12i4 polypeptide of any one of SEQ ID NOs: 2-59 further comprises one or more substitutions listed in Table 8. In some embodiments, the variant Cas12i4 polypeptide comprises any one or more substitutions in Table 4, Table 5, Table 6, Table 7, and/or Table 8. In some embodiments, the variant Cas12i4 polypeptide with one or more of the substitutions in Table 4, Table 5, Table 6, Table 7, and/or Table 8 exhibits increased ternary complex formation and/or ternary complex stability (e.g., by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween) as compared to a parent polypeptide.

In some embodiments, the variant Cas12i4 polypeptide of any one of SEQ ID NOs: 2-59 comprising one or more substitutions listed in Table 4, Table 5, Table 6, Table 7, and/or Table 8 exhibits increased enzymatic activity. In some embodiments, the variant Cas12i4 polypeptide comprising one or more substitutions listed in Table 4, Table 5, Table 6, Table 7, and/or Table 8 exhibits increased enzymatic activity. In some embodiments, the variant Cas12i4 polypeptide exhibits increased enzymatic activity (e.g., by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween) as compared to a parent polypeptide.

Increased Conformational Changes

Conformational changes, e.g., upon binding RNA guide or target DNA, impact the function of a variant Cas12i4 polypeptide, e.g., conformational changes may alter kinetics of the variant Cas12i4 polypeptide. The Rec1 (Helical II) domain of Cas12i4 moves and rotates to accommodate DNA binding during ternary complex formation. In some embodiments, an alteration that increases movement (e.g., flexibility or conformational changes) of the Helical II domain increases DNA binding/DNA binding affinity. In some embodiments, a substitution to increase flexibility, e.g., a substitution of a bulky amino acid to an amino acid with a small or smaller side chain (alanine, valine, glycine, or serine residue), in the Helical II domain increases ternary complex formation. In some embodiments, an alteration that increases movement (e.g., flexibility or conformational changes) of the Helical II domain increases ternary complex stability. In some embodiments, the alteration that increases conformational changes of the Helical II domain is substituting one or more residues with an alanine, valine, glycine, or serine residue. In some embodiments, the alteration that increases flexibility of the Helical II domain is substituting one or more residues. In some embodiments, a variant Cas12i4 polypeptide comprises an alteration of one or more amino acids near the Helical II domain. In some embodiments, the variant Cas12i4 polypeptide comprises an alteration of one or more amino acids near the Helical II domain. In some embodiments, a variant Cas12i4 polypeptide comprises a substitution set forth in Table 9.

TABLE 9

Substitutions altering flexibility of the Helical II domain.
Amino Acid Substitutions

| |
|---|
| D328G + F330V |
| D328G + F330N |
| D328A + F330V |
| D328A + F330N |
| D328G |
| D328A |
| F330V |
| F330N |
| P440A |
| P440G |
| L324A |
| A437G |
| K326G |
| K326S |

In some embodiments, a variant Cas12i4 polypeptide of any one of SEQ ID NOs: 2-59 further comprises one or more substitutions listed in Table 9. In some embodiments, a variant Cas12i4 polypeptide comprises one or more substitutions listed in Table 2 and Table 9.

In some embodiments, the alteration that increases Helical II domain flexibility is a substitution listed in Table 9. In some embodiments, the variant Cas12i4 polypeptide with one or more of the substitutions listed in Table 9 exhibits increased Helical II domain flexibility by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween, as compared to a parent polypeptide. In some embodiments, the alteration that increases DNA binding/DNA affinity is a substitution listed in Table 9. In some embodiments, the variant Cas12i4 polypeptide with one or more of the substitutions listed in Table 9 exhibits increased DNA binding/DNA affinity by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween, as compared to a parent polypeptide.

In some embodiments, a variant Cas12i4 polypeptide comprising a substitution listed in Table 9 exhibits increased ternary complex formation and/or ternary complex stability (e.g., by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween) as compared to a parent polypeptide.

In some embodiments, a variant Cas12i4 polypeptide exhibiting increased Helical II domain flexibility comprises two or more substitutions listed in Table 9. In some embodiments, a variant Cas12i4 polypeptide exhibiting increased DNA binding/affinity comprises two or more substitutions listed in Table 9. In some embodiments, a variant Cas12i4 polypeptide exhibiting increased ternary complex formation/stability comprises two or more substitutions listed in Table 9. In some embodiments, a variant Cas12i4 polypeptide of any one of SEQ ID NOs: 2-59 further comprises one or more substitutions listed in Table 9. In some embodiments, the variant Cas12i4 polypeptide comprises any one or more substitutions in Table 4 and/or Table 5 and/or Table 6 and/or Table 7 and/or Table 8 and/or Table 9. In some embodiments, the variant Cas12i4 polypeptide with one or more of the substitutions in Table 4 and/or Table 5 and/or Table 6 and/or Table 7 and/or Table 8 and/or Table 9 exhibits increased DNA binding/affinity (e.g., by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween) as compared to a parent polypeptide. In some embodiments, the variant Cas12i4 polypeptide with one or more of the substitutions in Table 4 and/or Table 5 and/or Table 6 and/or Table 7 and/or Table 8 and/or Table 9 exhibits increased ternary complex formation and/or ternary complex stability (e.g., by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween) as compared to a parent polypeptide.

In some embodiments, the variant Cas12i4 polypeptide of any one of SEQ ID NOs: 2-59 comprising one or more substitutions listed in Table 4 and/or Table 5 and/or Table 6 and/or Table 7 and/or Table 8 and/or Table 9 exhibits increased enzymatic activity. In some embodiments, the variant Cas12i4 polypeptide comprising one or more substitutions listed in Table 4 and/or Table 5 and/or Table 6 and/or Table 7 and/or Table 8 and/or Table 9 exhibits increased enzymatic activity. In some embodiments, the variant Cas12i4 polypeptide exhibits increased enzymatic activity (e.g., by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween) as compared to a parent polypeptide.

In some embodiments, an alteration that increases connections between the Nuc and Helical II interface, which forms when target single-stranded DNA is in the active site of a Cas12i4 polypeptide, increases the transition from binary complex to ternary complex. In some embodiments, an alteration that increases connections between the Nuc and Helical II interface increases ternary complex formation. In some embodiments, an alteration that increases connections between the Nuc and Helical II interface increases ternary complex stability. In some embodiments, the alteration that increases connections between the Nuc and Helical II interface is substituting one or more residues with an aspartic acid, glutamic acid, arginine, or lysine residue. In some embodiments, a variant Cas12i4 polypeptide comprises a substitution set forth in Table 10.

TABLE 10

Substitutions increasing connections at the Nuc and Helical II interface.
Amino Acid Substitutions

| |
| --- |
| Q386E + Q387D + N966R |
| Q386E + Q387E + N966R |
| Q386E + N966R |
| Q386E + Q387D + A936K + N966R |
| Q386E + Q387E + A936K + N966R |
| Q387D |
| A936K |
| Q387E |
| S931K |
| N932K |

In some embodiments, a variant Cas12i4 polypeptide of any one of SEQ ID NOs: 2-59 further comprises one or more substitutions listed in Table 10. In some embodiments, a variant Cas12i4 polypeptide comprises one or more substitutions listed in Table 2 and Table 10.

In some embodiments, a substitution in Table 10 increases connections between the Nuc and Helical II interface. In some embodiments, the variant Cas12i4 polypeptide with one or more of the substitutions in Table 10 increases connections between the Nuc and Helical II interface by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween, as compared to a parent polypeptide. In some embodiments, a variant Cas12i4 polypeptide comprising a substitution listed in Table 10 exhibits increased ternary complex formation and/or ternary complex stability (e.g., by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween) as compared to a parent polypeptide.

In some embodiments, a variant Cas12i4 polypeptide exhibiting increased connections between the Nuc and Helical II interface comprises two or more substitutions listed in Table 10. In some embodiments, a variant Cas12i4 polypeptide exhibiting increased ternary complex formation/stability comprises two or more substitutions listed in Table 10. In some embodiments, a variant Cas12i4 polypeptide of any one of SEQ ID NOs: 2-59 further comprises one or more substitutions listed in Table 10. In some embodiments, the variant Cas12i4 polypeptide comprises any one or more substitutions in Table 4 and/or Table 5 and/or Table 6 and/or Table 7 and/or Table 8 and/or Table 9 and/or Table 10. In some embodiments, the variant Cas12i4 polypeptide with one or more of the substitutions in Table 4 and/or Table 5 and/or Table 6 and/or Table 7 and/or Table 8 and/or Table 9 and/or Table 10 exhibits increased connections between the Nuc and Helical II interface (e.g., by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween) as compared to a parent polypeptide.

In some embodiments, the variant Cas12i4 polypeptide with one or more of the substitutions in Table 4 and/or Table 5 and/or Table 6 and/or Table 7 and/or Table 8 and/or Table 9 and/or Table 10 exhibits increased ternary complex formation and/or ternary complex stability (e.g., by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween) as compared to a parent polypeptide.

In some embodiments, the variant Cas12i4 polypeptide of any one of SEQ ID NOs: 2-59 comprising one or more substitutions listed in Table 4 and/or Table 5 and/or Table 6 and/or Table 7 and/or Table 8 and/or Table 9 and/or Table 10 exhibits increased enzymatic activity. In some embodiments, the variant Cas12i4 polypeptide comprising one or more substitutions listed in Table 4 and/or Table 5 and/or Table 6 and/or Table 7 and/or Table 8 and/or Table 9 and/or Table 10 exhibits increased enzymatic activity.

In some embodiments, the variant Cas12i4 polypeptide exhibits increased enzymatic activity (e.g., by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween) as compared to a parent polypeptide.

In some embodiments, an alteration decreases connections between the Nuc and Helical II interface. In some embodiments, an alteration that decreases connections between the Nuc and Helical II interface increases ternary complex formation. In some embodiments, an alteration that decreases connections between the Nuc and Helical II interface is substituting one or more residues. In some embodiments, the variant Cas12i4 polypeptide comprises of any one of SEQ ID NOs: 2-59 further comprises one or more substitutions listed in Table 10.

Increased Fidelity

In some aspects, a variant Cas12i4 polypeptide comprises an alteration that increases on-target specificity relative to a parent polypeptide. In some aspects, a variant Cas12i4 polypeptide comprises an alteration that increases on-target binding relative to a parent polypeptide. In some embodiments, the variant Cas12i4 polypeptide comprises an alteration that increases interactions (e.g., affinity) between the variant Cas12i4 polypeptide and on-target DNA relative to a parent polypeptide.

In some embodiments, the alteration that increases on-target specificity is substituting one or more amino acids. In some aspects, the alteration that increases on-target specificity is truncating a residue that contacts the spacer sequence of an RNA guide (e.g., substituting a residue that contacts the spacer sequence with a residue having a smaller side chain). In some aspects, the alteration that increases on-target specificity is truncating a residue that contacts the spacer sequence of an RNA guide.

In some embodiments, the variant Cas12i4 polypeptide comprises a substitution of one or more amino acids that contact the spacer sequence of an RNA guide. In some embodiments, the variant Cas12i4 polypeptide comprises an alteration of one or more amino acids in at least one domain/motif (e.g., the Wedge domain, Rec1 domain, Rec2 domain, or RuvC2 motif). In some embodiments, a truncating substitution in the Helical II domain results in a variant Cas12i4 polypeptide exhibiting increased on-target binding specificity.

In some embodiments, the substitution(s) increase on-target specificity with the variant Cas12i4 polypeptide by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween, as compared to a parent polypeptide.

In some embodiments, the substitution(s) increase on-target binding of the variant Cas12i4 polypeptide by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween, as compared to a parent polypeptide.

In some embodiments, the substitution(s) increase on-target binding affinity of the variant Cas12i4 polypeptide by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween, as compared to a parent polypeptide.

Non-limiting examples of alterations that can alter the ability of a variant Cas12i4 polypeptide to selectively bind to on-target DNA are substitutions listed in Table 11. In some embodiments, a variant Cas12i4 polypeptide comprising one or more substitutions listed in Table 11 exhibits increased on-target specificity relative to a parent polypeptide. In some embodiments, a variant Cas12i4 polypeptide comprising one or more substitutions listed in Table 11 exhibits increased on-target binding relative to a parent polypeptide. In some embodiments, a variant Cas12i4 polypeptide comprising one or more substitutions listed in Table 11 exhibits increased on-target binding affinity relative to a parent polypeptide.

TABLE 11

| Substitutions increasing on-target specificity. Substitution(s) |
|---|
| E349A |
| D350A |
| E349A + E350A |
| R446A |
| R306A |
| T348A |
| H439A |
| N786A |
| M863A |
| K303A |
| T305A |
| K437A |
| M574A |
| E811A |
| V850A |
| K852A |
| S855A |

TABLE 11-continued

| Substitutions increasing on-target specificity. Substitution(s) |
|---|
| K856A |
| K857A |
| N859A |
| S860A |
| F352A |
| R357A |
| K393A |
| Q398A |
| P302A |
| S309A |
| K432A |
| R435A |
| Y447A |
| R734A |
| S779A |
| T815A |
| R818A |
| K868A |
| R873A |
| K115A |
| K154A |
| T347A |
| Y358A |
| V442A |
| K576A |
| S783A |
| K787A |
| K791A |
| I793A |
| Q872A |
| Y116A |
| P400A |
| N445A |
| N782A |
| C866A |
| Q869A |

In some embodiments, the alteration that increases on-target specificity (e.g., a substitution listed in Table 11) further increases on-target ternary complex formation and/or on-target ternary complex stability (e.g., on-target ternary complex formation/stability). In some embodiments, the alteration that increases on-target specificity increases on-ternary complex formation and/or on-target ternary complex stability by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween as compared to a parent polypeptide.

In some aspects, a variant Cas12i4 polypeptide comprises an alteration that decreases off-target specificity relative to a parent polypeptide. In some aspects, a variant Cas12i4 polypeptide comprises an alteration that decreases off-target binding relative to a parent polypeptide. In some embodiments, the variant Cas12i4 polypeptide comprises an alteration that decreases interactions (e.g., affinity) between the variant Cas12i4 polypeptide and off-target DNA relative to a parent polypeptide.

Methods of detecting off-target activity are known in the art. In some embodiments, off-target activity is detected by tagmentation-based tag integration site sequencing (TTISS)

or genome-wide, unbiased identification of DSBs enabled by sequencing (GUIDE-Seq). For example, in some embodiments, TTISS is performed using a Cas12i4 polypeptide or a variant Cas12i4 polypeptide using the TTISS method described in PCT/US2021/025257, which is incorporated by reference in its entirety.

In some embodiments, the alteration that decreases off-target specificity is substituting one or more amino acids to an alanine, serine, valine, glutamine, or asparagine residue. In some aspects, the alteration that decreases off-target specificity is truncating a residue that contacts the spacer sequence of an RNA guide (e.g., substituting a residue that contacts the spacer sequence with a residue having a smaller side chain). In some aspects, the alteration that decreases off-target specificity is truncating a residue, e.g., substitution to alanine, serine, or valine, that contact the spacer sequence of an RNA guide. In some embodiments, the variant Cas12i4 polypeptide comprises an alteration of one or more amino acids in at least one domain/motif (e.g., the Wedge domain, Rec domain, Rec2 domain, or RuvC2 motif) to an alanine. In some embodiments, a truncating substitution in the Helical II domain results in a variant Cas12i4 polypeptide exhibiting decreased off-target binding specificity. In some embodiments, the substitution(s) decrease off-target specificity with the variant Cas12i4 polypeptide by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, as compared to a parent polypeptide. In some embodiments, the substitution(s) decrease off-target binding of the variant Cas12i4 polypeptide by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, as compared to a parent polypeptide. In some embodiments, the substitution(s) decrease off-target binding affinity of the variant Cas12i4 polypeptide by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, as compared to a parent polypeptide.

Non-limiting examples of alterations that can alter the ability of a variant Cas12i4 polypeptide to bind to off-target DNA are substitutions listed in Table 11. In some embodiments, a variant Cas12i4 polypeptide comprising one or more substitutions listed in Table 11 exhibits decreased off-target specificity relative to a parent polypeptide. In some embodiments, a variant Cas12i4 polypeptide comprising one or more substitutions listed in Table 11 exhibits decreased off-target binding relative to a parent polypeptide. In some embodiments, a variant Cas12i4 polypeptide comprising one or more substitutions listed in Table 11 exhibits decreased off-target binding affinity relative to a parent polypeptide.

In some embodiments, the substitution(s) that increase on-target specificity of the variant Cas12i4 polypeptide by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween further decrease off-target specificity of the variant Cas12i4 polypeptide by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, as compared to a parent polypeptide. In some embodiments, the substitution (s) that increase on-target binding of the variant Cas12i4 polypeptide by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween further decrease off-target binding of the variant Cas12i4 polypeptide by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, as compared to a parent polypeptide. In some embodiments, the substitution(s) that increase on-target binding affinity of the variant Cas12i4 polypeptide by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween, further decrease off-target binding affinity of the variant Cas12i4 polypeptide by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, as compared to a parent polypeptide.

In some embodiments, a variant Cas12i4 polypeptide of any one of SEQ ID NOs: 2-59 further comprises one or more substitutions listed in Table 11. In some embodiments, a variant Cas12i4 polypeptide comprises one or more substitutions listed in Table 2 and Table 11.

In some embodiments, the variant Cas12i4 polypeptide of any one of SEQ ID NOs: 2-59 comprising one or more substitutions listed in Table 4 and/or Table 5 and/or Table 6 and/or Table 7 and/or Table 8 and/or Table 9 and/or Table 10 and/or Table 11 exhibits increased on-target enzymatic activity. In some embodiments, the variant Cas12i4 polypeptide comprising one or more substitutions listed in Table 4 and/or Table 5 and/or Table 6 and/or Table 7 and/or Table 8 and/or Table 9 and/or Table 10 and/or Table 11 exhibits increased on-target enzymatic activity. In some embodiments, the variant Cas12i4 polypeptide exhibits increased on-target enzymatic activity (e.g., by about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween) as compared to a parent polypeptide.

In some embodiments, the variant Cas12i4 polypeptide of any one of SEQ ID NOs: 2-59 comprising one or more substitutions listed in Table 4 and/or Table 5 and/or Table 6 and/or Table 7 and/or Table 8 and/or Table 9 and/or Table 10 and/or Table 11 exhibits an increased ratio of on-target enzymatic activity to off-target enzymatic activity. In some embodiments, the variant Cas12i4 polypeptide comprising one or more substitutions listed in Table 4 and/or Table 5 and/or Table 6 and/or Table 7 and/or Table 8 and/or Table 9 and/or Table 10 and/or Table 11 exhibits an increased ratio of on-target enzymatic activity to off-target enzymatic activity. In some embodiments, on-target enzymatic activity of the variant Cas12i4 polypeptide (e.g., the variant Cas12i4 polypeptide of any one of SEQ ID NOs: 2-59 comprising one or more substitutions listed in Table 4 and/or Table 5 and/or Table 6 and/or Table 7 and/or Table 8 and/or Table 9 and/or Table 10 and/or Table 11) is at least 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween higher than off-target enzymatic activity of the variant Cas12i4 polypeptide, as compared to a parent polypeptide. In some embodiments, on-target enzymatic activity of the variant Cas12i4 polypeptide (e.g., the variant Cas12i4 polypeptide comprising one or more substitutions listed in Table 4 and/or Table 5 and/or Table 6 and/or Table 7 and/or Table 8 and/or Table 9 and/or Table 10 and/or Table 11) is at least 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, or more or any percentage therebetween higher than off-target enzymatic activity of the variant Cas12i4 polypeptide, as compared to a parent polypeptide.

In some embodiments, enzymatic activity of the variant Cas12i4 polypeptide (e.g., the variant Cas12i4 polypeptide of any one of SEQ ID NOs: 2-59 at an off-target locus is no more than 10% (e.g., 10%, 9%, 8%, 7%, 6%, 5%, 4%, 3%, 2%, 1%, or 0%) of the enzymatic activity at the on-target locus. In some embodiments, enzymatic activity of the variant Cas12i4 polypeptide (e.g., the variant Cas12i4 polypeptide of any one of SEQ ID NOs: 2-59 comprising one or more substitutions listed in Table 4 and/or Table 5 and/or Table 6 and/or Table 7 and/or Table 8 and/or Table 9 and/or Table 10 and/or Table 11) at an off-target locus is no more than 10% (e.g., 10%, 9%, 8%, 7%, 6%, 5%, 4%, 3%, 2%, 1%, or 0%) of the enzymatic activity at the on-target locus. In some embodiments, enzymatic activity of the variant Cas12i4 polypeptide (e.g., the variant Cas12i4 polypeptide of any one of SEQ ID NOs: 2-59 at an off-target locus is no more than 5% (e.g., 5%, 4%, 3%, 2%, 1%, or 0%) of the enzymatic activity at the on-target locus. In some embodiments, enzymatic activity of the variant Cas12i4 polypeptide (e.g., the variant Cas12i4 polypeptide of any one of SEQ ID NOs: 2-59 comprising one or more substitutions listed in Table 4 and/or Table 5 and/or Table 6 and/or Table 7 and/or Table 8 and/or Table 9 and/or Table 10 and/or Table 11) at an off-target locus is no more than 5% (e.g., 5%, 4%, 3%, 2%, 1%, or 0%) of the enzymatic activity at the on-target locus. By comparison, enzymatic activity of SpCas9 at an off-target locus is up to 95% (e.g., 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, or 0%) of the enzymatic activity at the on-target locus.

In some embodiments, editing efficiency of the variant Cas12i4 polypeptide (e.g., the variant Cas12i4 polypeptide of any one of SEQ ID NOs: 2-59 at an off-target locus is no more than 10% (e.g., 10%, 9%, 8%, 7%, 6%, 5%, 4%, 3%, 2%, 1%, or 0%) of the editing efficiency at the on-target locus. In some embodiments, editing efficiency of the variant Cas12i4 polypeptide (e.g., the variant Cas12i4 polypeptide of any one of SEQ ID NOs: 2-59 comprising one or more substitutions listed in Table 4 and/or Table 5 and/or Table 6 and/or Table 7 and/or Table 8 and/or Table 9 and/or Table 10 and/or Table 11) at an off-target locus is no more than 10% (e.g., 10%, 9%, 8%, 7%, 6%, 5%, 4%, 3%, 2%, 1%, or 0%) of the editing efficiency at the on-target locus. In some embodiments, editing efficiency of the variant Cas12i4 polypeptide (e.g., the variant Cas12i4 polypeptide of any one of SEQ ID NOs: 2-59 at an off-target locus is no more than 5% (e.g., 5%, 4%, 3%, 2%, 1%, or 0%) of the editing efficiency at the on-target locus. In some embodiments, editing efficiency of the variant Cas12i4 polypeptide (e.g., the variant Cas12i4 polypeptide of any one of SEQ ID NOs: 2-59 comprising one or more substitutions listed in Table 4 and/or Table 5 and/or Table 6 and/or Table 7 and/or Table 8 and/or Table 9 and/or Table 10 and/or Table 11) at an off-target locus is no more than 5% (e.g., 5%, 4%, 3%, 2%, 1%, or 0%) of the editing efficiency at the on-target locus. By comparison, editing efficiency of SpCas9 at an off-target locus is up to 95% (e.g., 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, or 0%) of the editing efficiency at the on-target locus.

In some embodiments, editing by the variant Cas12i4 polypeptide (e.g., the variant Cas12i4 polypeptide of any one of SEQ ID NOs: 2-59 at an off-target locus is no more than 10% (e.g., 10%, 9%, 8%, 7%, 6%, 5%, 4%, 3%, 2%, 1%, or 0%) of the editing at the on-target locus. In some embodiments, editing by the variant Cas12i4 polypeptide (e.g., the variant Cas12i4 polypeptide of any one of SEQ ID NOs: 2-59 comprising one or more substitutions listed in Table 4 and/or Table 5 and/or Table 6 and/or Table 7 and/or Table 8 and/or Table 9 and/or Table 10 and/or Table 11) at an off-target locus is no more than 10% (e.g., 10%, 9%, 8%, 7%, 6%, 5%, 4%, 3%, 2%, 1%, or 0%) of the editing at the on-target locus.

In some embodiments, editing by the variant Cas12i4 polypeptide (e.g., the variant Cas12i4 polypeptide of any one of SEQ ID NOs: 2-59 at an off-target locus is no more than 5% (e.g., 5%, 4%, 3%, 2%, 1%, or 0%) of the editing at the on-target locus. In some embodiments, editing by the variant Cas12i4 polypeptide (e.g., the variant Cas12i4 polypeptide of any one of SEQ ID NOs: 2-59 comprising one or more substitutions listed in Table 4 and/or Table 5 and/or Table 6 and/or Table 7 and/or Table 8 and/or Table 9 and/or Table 10 and/or Table 11) at an off-target locus is no more than 5% (e.g., 5%, 4%, 3%, 2%, 1%, or 0%) of the editing at the on-target locus. By comparison, editing of SpCas9 at an off-target locus is up to 95% (e.g., 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, or 0%) of the editing at the on-target locus.

RNA Guide

In some embodiments, a composition or complex as described herein comprises a targeting moiety (e.g., an RNA guide, antisense, oligonucleotides, peptide oligonucleotide conjugates) that binds the target nucleic acid and interacts with the Cas12i4 polypeptide (e.g., parent polypeptide or variant Cas12i4 polypeptide). The targeting moiety may bind a target nucleic acid (e.g., with specific binding affinity to the target nucleic acid).

In some embodiments, the targeting moiety comprises, or is, an RNA guide. In some embodiments, the RNA guide directs the Cas12i4 polypeptide (e.g., parent polypeptide or variant Cas12i4 polypeptide) to a particular nucleic acid sequence. Those skilled in the art reading the below examples of particular kinds of RNA guides will understand that, in some embodiments, an RNA guide is site-specific. That is, in some embodiments, an RNA guide associates specifically with one or more target nucleic acid sequences (e.g., specific DNA or genomic DNA sequences) and not to non-targeted nucleic acid sequences (e.g., non-specific DNA or random sequences).

In some embodiments, the composition as described herein comprises an RNA guide that associates with the Cas12i4 polypeptide (e.g., parent polypeptide or variant Cas12i4 polypeptide) and directs the Cas12i4 polypeptide to a target nucleic acid sequence (e.g., DNA).

The RNA guide may target (e.g., associate with, be directed to, contact, or bind) one or more nucleotides of a target sequence, e.g., a site-specific sequence or a site-specific target. In some embodiments, the nucleoprotein (e.g., the parent polypeptide or variant Cas12i4 polypeptide plus an RNA guide) is activated upon binding to a target nucleic acid that is complementary to a DNA-targeting sequence in the RNA guide (e.g., a sequence-specific substrate or target nucleic acid).

In some embodiments, an RNA guide comprises a spacer having a length of from about 11 nucleotides to about 100 nucleotides. For example, the DNA-targeting segment can have a length of from about 11 nucleotides to about 80 nucleotides, from about 11 nucleotides to about 50 nucleotides, from about 11 nucleotides to about 40 nucleotides, from about 11 nucleotides to about 30 nucleotides, from about 11 nucleotides to about 25 nucleotides, from about 11 nucleotides to about 20 nucleotides, or from about 11 nucleotides to about 19 nucleotides. For example, the spacer can have a length of from about 19 nucleotides to about 20 nucleotides, from about 19 nucleotides to about 25 nucleotides, from about 19 nucleotides to about 30 nucleotides, from about 19 nucleotides to about 35 nucleotides, from about 19 nucleotides to about 40 nucleotides, from about 19 nucleotides to about 45 nucleotides, from about 19 nucleotides to about 50 nucleotides, from about 19 nucleotides to about 60 nucleotides, from about 19 nucleotides to about 70 nucleotides, from about 19 nucleotides to about 80 nucleotides, from about 19 nucleotides to about 90 nucleotides, from about 19 nucleotides to about 100 nucleotides, from about 20 nucleotides to about 25 nucleotides, from about 20 nucleotides to about 30 nucleotides, from about 20 nucleotides to about 35 nucleotides, from about 20 nucleotides to about 40 nucleotides, from about 20 nucleotides to about 45 nucleotides, from about 20 nucleotides to about 50 nucleotides, from about 20 nucleotides to about 60 nucleotides, from about 20 nucleotides to about 70 nucleotides, from about 20 nucleotides to about 80 nucleotides, from about 20 nucleotides to about 90 nucleotides, or from about 20 nucleotides to about 100 nucleotides.

In some embodiments, the spacer of the RNA guide may be generally designed to have a length of between 11 and 50 nucleotides (e.g., 11, 12, 13, 14, 15, 16, 17, 18, 19, 20, 21, 22, 23, 24, 25, 26, 27, 28, 29, 30, 31, 32, 33, 34, or 35 nucleotides) and be complementary to a specific target nucleic acid sequence. In some particular embodiments, the RNA guide may be designed to be complementary to a specific DNA strand, e.g., of a genomic locus. In some embodiments, the DNA targeting sequence is designed to be complementary to a specific DNA strand, e.g., of a genomic locus.

The RNA guide may be substantially identical to a complementary strand of a reference nucleic acid sequence. In some embodiments, the RNA guide comprises a sequence having least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to a complementary strand of a reference nucleic acid sequence, e.g., target nucleic acid. The percent identity between two such nucleic acids can be determined manually by inspection of the two optimally aligned nucleic acid sequences or by using software programs or algorithms (e.g., BLAST, ALIGN, CLUSTAL) using standard parameters.

In some embodiments, the RNA guide has at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to a complementary strand of a target nucleic acid.

In some embodiments, the RNA guide comprises a spacer that is a length of between 11 and 50 nucleotides (e.g., 11, 12, 13, 14, 15, 16, 17, 18, 19, 20, 21, 22, 23, 24, 25, 26, 27, 28, 29, 30, 31, 32, 33, 34, or 35 nucleotides) and at least 80%, at least 90%, at least 95%, at least 96%, at least 97%, at least 98%, at least 99% complementary to a target nucleic acid. In some embodiments, the RNA guide comprises a sequence at least 80%, at least 90%, at least 95%, at least 96%, at least 97%, at least 98%, at least 99% complementary to a target DNA sequence. In some embodiments, the RNA guide comprises a sequence at least 80%, at least 90%, at least 95%, at least 96%, at least 97%, at least 98%, at least 99% complementary to a target genomic sequence. In some embodiments, the RNA guide comprises a sequence, e.g., RNA sequence, that is a length of up to 50 and at least 80%, at least 90%, at least 95%, at least 96%, at least 97%, at least 98%, at least 99% complementary to a target nucleic acid. In some embodiments, the RNA guide comprises a sequence at least 80%, at least 90%, at least 95%, at least 96%, at least 97%, at least 98%, at least 99% complementary to a target DNA sequence. In some embodiments, the RNA guide comprises a sequence at least 80%, at least 90%, at least 95%, at least 96%, at least 97%, at least 98%, at least 99% complementary to a target genomic sequence.

In certain embodiments, the RNA guide includes, consists essentially of, or comprises a direct repeat sequence linked to a DNA targeting sequence. In some embodiments, the RNA guide includes a direct repeat sequence and a DNA targeting sequence or a direct repeat-DNA targeting sequence-direct repeat sequence. In some embodiments, the RNA guide includes a truncated direct repeat sequence and a DNA targeting sequence, which is typical of processed or mature crRNA. In some embodiments, the Cas12i4 polypeptide (e.g., parent polypeptide or variant Cas12i4 polypeptide) forms a complex with the RNA guide, and the RNA guide directs the complex to associate with site-specific target nucleic acid that is complementary to at least a portion of the RNA guide.

In some embodiments, the direct repeat sequence of the RNA guide has a length of between 12-100, 13-75, 14-50, or 15-40 nucleotides (e.g., 15, 16, 17, 18, 19, 20, 21, 22, 23, 24, 25, 26, 27, 28, 29, 30, 31, 32, 33, 34, 35, 36, 37, 38, 39, or 40 nucleotides).

In some embodiments, the direct repeat sequence is a sequence of Table 12 or a portion of a sequence of Table 12. The direct repeat sequence can comprise nucleotide 1 through nucleotide 36 of any one of SEQ ID NOs: 60, 108, 109, 110, 111, 112, 113, 114, 115, 116, 117, 118, 119, 120, 121, 122, 123, or 124. The direct repeat sequence can comprise nucleotide 2 through nucleotide 36 of any one of SEQ ID NOs: 60, 108, 109, 110, 111, 112, 113, 114, 115, 116, 117, 118, 119, 120, 121, 122, 123, or 124. The direct repeat sequence can comprise nucleotide 3 through nucleotide 36 of any one of SEQ ID NOs: 60, 108, 109, 110, 111, 112, 113, 114, 115, 116, 117, 118, 119, 120, 121, 122, 123, or 124. The direct repeat sequence can comprise nucleotide 4 through nucleotide 36 of any one of SEQ ID NOs: 60, 108, 109, 110, 111, 112, 113, 114, 115, 116, 117, 118, 119, 120, 121, 122, 123, or 124. The direct repeat sequence can comprise nucleotide 5 through nucleotide 36 of any one of SEQ ID NOs: 60, 108, 109, 110, 111, 112, 113, 114, 115, 116, 117, 118, 119, 120, 121, 122, 123, or 124. The direct repeat sequence can comprise nucleotide 6 through nucleotide 36 of any one of SEQ ID NOs: 60, 108, 109, 110, 111, 112, 113, 114, 115, 116, 117, 118, 119, 120, 121, 122, 123, or 124. The direct repeat sequence can comprise nucleotide 7 through nucleotide 36 of any one of SEQ ID NOs: 60, 108, 109, 110, 111, 112, 113, 114, 115, 116, 117, 118, 119, 120, 121, 122, 123, or 124. The direct repeat sequence can comprise nucleotide 8 through nucleotide 36 of any one of SEQ ID NOs: 60, 108, 109, 110, 111, 112, 113, 114, 115, 116, 117, 118, 119, 120, 121, 122, 123, or 124. The direct repeat sequence can comprise nucleotide 9 through nucleotide 36 of any one of SEQ ID NOs: 60, 108, 109, 110, 111, 112, 113, 114, 115, 116, 117, 118, 119, 120, 121, 122, 123, or 124. The direct repeat sequence can comprise nucleotide 10 through nucleotide 36 of any one of SEQ ID NOs: 60, 108, 109, 110, 111, 112, 113, 114, 115, 116, 117, 118, 119, 120, 121, 122, 123, or 124. The direct repeat sequence can comprise nucleotide 11 through nucleotide 36 of any one of SEQ ID NOs: 60, 108, 109, 110, 111, 112, 113, 114, 115, 116, 117, 118, 119, 120, 121, 122, 123, or 124. The direct repeat sequence can comprise nucleotide 12 through nucleotide 36 of any one of SEQ ID NOs: 60, 108, 109, 110, 111, 112, 113, 114, 115, 116, 117, 118, 119, 120, 121, 122, 123, or 124. The direct repeat sequence can comprise nucleotide 13 through nucleotide 36 of any one of SEQ ID NOs: 60, 108, 109, 110, 111, 112, 113, 114, 115, 116, 117, 118, 119, 120, 121, 122, 123, or 124. The direct repeat sequence can comprise nucleotide 14 through nucleotide 36 of any one of SEQ ID NOs: 60, 108, 109, 110, 111, 112, 113, 114, 115, 116, 117, 118, 119, 120, 121, 122, 123, or 124.

In some embodiments, the direct repeat sequence has at least 95% identity (e.g., at least 95%, 96%, 97%, 98% or 99% identity) to a sequence of Table 12 or a portion of a sequence of Table 12. The direct repeat sequence can have at least 95% identity to a sequence comprising nucleotide 1 through nucleotide 36 of any one of SEQ ID NOs: 60, 108, 109, 110, 111, 112, 113, 114, 115, 116, 117, 118, 119, 120, 121, 122, 123, or 124. The direct repeat sequence can have at least 95% identity to a sequence comprising 2 through nucleotide 36 of any one of SEQ ID NOs: 60, 108, 109, 110, 111, 112, 113, 114, 115, 116, 117, 118, 119, 120, 121, 122, 123, or 124. The direct repeat sequence can have at least 95% identity to a sequence comprising 3 through nucleotide 36 of any one of SEQ ID NOs: 60, 108, 109, 110, 111, 112, 113, 114, 115, 116, 117, 118, 119, 120, 121, 122, 123, or 124. The direct repeat sequence can have at least 95% identity to a sequence comprising 4 through nucleotide 36 of any one of SEQ ID NOs: 60, 108, 109, 110, 111, 112, 113, 114, 115, 116, 117, 118, 119, 120, 121, 122, 123, or 124. The direct repeat sequence can have at least 95% identity to a sequence comprising 5 through nucleotide 36 of any one of SEQ ID NOs: 60, 108, 109, 110, 111, 112, 113, 114, 115, 116, 117, 118, 119, 120, 121, 122, 123, or 124. The direct repeat sequence can have at least 95% identity to a sequence comprising 6 through nucleotide 36 of any one of SEQ ID NOs: 60, 108, 109, 110, 111, 112, 113, 114, 115, 116, 117, 118, 119, 120, 121, 122, 123, or 124. The direct repeat sequence can have at least 95% identity to a sequence comprising 7 through nucleotide 36 of any one of SEQ ID NOs: 60, 108, 109, 110, 111, 112, 113, 114, 115, 116, 117, 118, 119, 120, 121, 122, 123, or 124. The direct repeat sequence can have at least 95% identity to a sequence comprising 8 through nucleotide 36 of any one of SEQ ID NOs: 60, 108, 109, 110, 111, 112, 113, 114, 115, 116, 117, 118, 119, 120, 121, 122, 123, or 124. The direct repeat sequence can have at least 95% identity to a sequence comprising 9 through nucleotide 36 of any one of SEQ ID NOs: 60, 108, 109, 110, 111, 112, 113, 114, 115, 116, 117, 118, 119, 120, 121, 122, 123, or 124. The direct repeat sequence can have at least 95% identity to a sequence comprising 10 through nucleotide 36 of any one of SEQ ID NOs: 60, 108, 109, 110, 111, 112, 113, 114, 115, 116, 117, 118, 119, 120, 121, 122, 123, or 124. The direct repeat sequence can have at least 95% identity to a sequence comprising 11 through nucleotide 36 of any one of SEQ ID NOs: 60, 108, 109, 110, 111, 112, 113, 114, 115, 116, 117, 118, 119, 120, 121, 122, 123, or 124. The direct repeat sequence can have at least 95% identity to a sequence comprising 12 through nucleotide 36 of any one of SEQ ID NOs: 60, 108, 109, 110, 111, 112, 113, 114, 115, 116, 117, 118, 119, 120, 121, 122, 123, or 124. The direct repeat sequence can have at least 95% identity to a sequence comprising 13 through nucleotide 36 of any one of SEQ ID NOs: 60, 108, 109, 110, 111, 112, 113, 114, 115, 116, 117, 118, 119, 120, 121, 122, 123, or 124.

In some embodiments, the direct repeat sequence has at least 90% identity (e.g., at least 90%, 91%, 92%, 93%, 94%, 95%, 96%, 97%, 98% or 99% identity) to a sequence of Table 12 or a portion of a sequence of Table 12. The direct repeat sequence can have at least 90% identity to a sequence comprising nucleotide 1 through nucleotide 36 of any one of SEQ ID NOs: 60, 108, 109, 110, 111, 112, 113, 114, 115, 116, 117, 118, 119, 120, 121, 122, 123, or 124. The direct repeat sequence can have at least 90% identity to a sequence comprising 2 through nucleotide 36 of any one of SEQ ID NOs: 60, 108, 109, 110, 111, 112, 113, 114, 115, 116, 117, 118, 119, 120, 121, 122, 123, or 124. The direct repeat sequence can have at least 90% identity to a sequence comprising 3 through nucleotide 36 of any one of SEQ ID NOs: 60, 108, 109, 110, 111, 112, 113, 114, 115, 116, 117, 118, 119, 120, 121, 122, 123, or 124. The direct repeat sequence can have at least 90% identity to a sequence comprising 4 through nucleotide 36 of any one of SEQ ID NOs: 60, 108, 109, 110, 111, 112, 113, 114, 115, 116, 117, 118, 119, 120, 121, 122, 123, or 124. The direct repeat sequence can have at least 90% identity to a sequence comprising 5 through nucleotide 36 of any one of SEQ ID NOs: 60, 108, 109, 110, 111, 112, 113, 114, 115, 116, 117, 118, 119, 120, 121, 122, 123, or 124. The direct repeat sequence can have at least 90% identity to a sequence comprising 6 through nucleotide 36 of any one of SEQ ID NOs: 60, 108, 109, 110, 111, 112, 113, 114, 115, 116, 117, 118, 119, 120, 121, 122, 123, or 124. The direct repeat sequence can have at least 90% identity to a sequence comprising 7 through nucleotide 36 of any one of SEQ ID NOs: 60, 108, 109, 110, 111, 112, 113, 114, 115, 116, 117, 118, 119, 120, 121, 122, 123, or 124. The direct repeat sequence can have at least 90% identity to a sequence comprising 8 through nucleotide 36 of any one of SEQ ID NOs: 60, 108, 109, 110, 111, 112, 113, 114, 115, 116, 117, 118, 119, 120, 121, 122, 123, or 124. The direct repeat sequence can have at least 90% identity to a sequence comprising 9 through nucleotide 36 of any one of SEQ ID NOs: 60, 108, 109, 110, 111, 112, 113, 114, 115, 116, 117, 118, 119, 120, 121, 122, 123, or 124. The direct repeat sequence can have at least 90% identity to a sequence comprising 10 through nucleotide 36 of any one of SEQ ID NOs: 60, 108, 109, 110, 111, 112, 113, 114, 115, 116, 117, 118, 119, 120, 121, 122, 123, or 124. The direct repeat sequence can have at least 90% identity to a sequence comprising 11 through nucleotide 36 of any one of SEQ ID NOs: 60, 108, 109, 110, 111, 112, 113, 114, 115, 116, 117, 118, 119, 120, 121, 122, 123, or 124. The direct repeat sequence can have at least 90% identity to a sequence comprising 12 through nucleotide 36 of any one of SEQ ID NOs: 60, 108, 109, 110, 111, 112, 113, 114, 115, 116, 117, 118, 119, 120, 121, 122, 123, or 124. The direct repeat sequence can have at least 90% identity to a sequence comprising 13 through nucleotide 36 of any one of SEQ ID NOs: 60, 108, 109, 110, 111, 112, 113, 114, 115, 116, 117, 118, 119, 120, 121, 122, 123, or 124.

In some embodiments, the direct repeat sequence is at least 90% identical to the reverse complement of any one of SEQ ID NOs: 60, 108, 109, 110, 111, 112, 113, 114, 115, 116, 117, 118, 119, 120, 121, 122, 123, or 124. In some embodiments, the direct repeat sequence is at least 95% identical to the reverse complement of any one of SEQ ID NOs: 60, 108, 109, 110, 111, 112, 113, 114, 115, 116, 117, 118, 119, 120, 121, 122, 123, or 124. In some embodiments, the direct repeat sequence is the reverse complement of any one of SEQ ID NOs: 60, 108, 109, 110, 111, 112, 113, 114, 115, 116, 117, 118, 119, 120, 121, 122, 123, or 124.

TABLE 12

Direct repeat sequences.

| Sequence identifier | Direct Repeat Sequence |
|---|---|
| SEQ ID NO: 60 | UCUCAACGAUAGUCAGACAUGUGUCCUCAGUGACAC |
| SEQ ID NO: 108 | UUUUAACAACACUCAGGCAUGUGUCCACAGUGACAC |
| SEQ ID NO: 109 | UUGAACGGAUACUCAGACAUGUGUUUCCAGUGACAC |
| SEQ ID NO: 110 | UGCCCUCAAUAGUCAGAUGUGUGUCCACAGUGACAC |
| SEQ ID NO: 111 | UCUCAAUGAUACUUAGAUACGUGUCCUCAGUGACAC |
| SEQ ID NO: 112 | UCUCAAUGAUACUCAGACAUGUGUCCCCAGUGACAC |
| SEQ ID NO: 113 | UCUCAAUGAUACUAAGACAUGUGUCCUCAGUGACAC |
| SEQ ID NO: 114 | UCUCAACUAUACUCAGACAUGUGUCCUCAGUGACAC |
| SEQ ID NO: 115 | UCUCAACGAUACUCAGACAUGUGUCCUCAGUGACAC |
| SEQ ID NO: 116 | UCUCAACGAUACUAAGAUAUGUGUCCUCAGCGACAC |
| SEQ ID NO: 117 | UCUCAACGAUACUAAGAUAUGUGUCCCCAGUGACAC |
| SEQ ID NO: 118 | UCUCAACGAUACUAAGAUAUGUGUCCACAGUGACAC |
| SEQ ID NO: 119 | UCUCAACAAUACUCAGACAUGUGUCCCCAGUGACAC |
| SEQ ID NO: 120 | UCUCAACAAUACUAAGGCAUGUGUCCCCAGUGACCC |
| SEQ ID NO: 121 | UCUCAAAGAUACUCAGACACGUGUCCCCAGUGACAC |
| SEQ ID NO: 122 | UCUCAAAAAUACUCAGACAUGUGUCCUCAGUGACAC |
| SEQ ID NO: 123 | GCGAAACAACAGUCAGACAUGUGUCCCCAGUGACAC |
| SEQ ID NO: 124 | CCUCAACGAUAUUAAGACAUGUGUCCGCAGUGACAC |
| SEQ ID NO: 61 | AGACAUGUGUCCUCAGUGACAC |

In some embodiments, the direct repeat sequence is $AGN_1N_2N_3N_4GUGUN_5N_6N_7CAGN_8GACN_9C$ (SEQ ID NO: 125), wherein $N_1$ is A or G, $N_2$ is C or U, $N_3$ is A or G, $N_4$ is U or C, $N_5$ is C or U, $N_6$ is C or U, $N_7$ is U, A, C, or G, $N_8$ is U or C, and $N_9$ is A or C. In some embodiments, the direct repeat sequence of SEQ ID NO: 125 is referred to as the Cas12i4 mature DR.

In some embodiments, the direct repeat sequence is at least 90% identical to SEQ ID NO: 61 or a portion of SEQ ID NO: 61. In some embodiments, the direct repeat sequence is at least 95% identical to SEQ ID NO: 61 or a portion of SEQ ID NO: 61. In some embodiments, the direct repeat sequence is 100% identical to SEQ ID NO: 61 or a portion of SEQ ID NO: 61. In some embodiments, the direct repeat sequence of SEQ ID NO: 61 is referred to as the Cas12i4 mature DR.

In some embodiments, the composition or complex described herein includes one or more (e.g., two, three, four, five, six, seven, eight, or more) RNA guides, e.g., a plurality of RNA guides.

In some embodiments, the RNA guide has an architecture similar to, for example International Publication Nos. WO 2014/093622 and WO 2015/070083, the entire contents of each of which are incorporated herein by reference.

Unless otherwise noted, all compositions and complexes and polypeptides provided herein are made in reference to the active level of that composition or complex or polypeptide, and are exclusive of impurities, for example, residual solvents or by-products, which may be present in commercially available sources. Enzymatic component weights are based on total active protein. All percentages and ratios are calculated by weight unless otherwise indicated. All percentages and ratios are calculated based on the total composition unless otherwise indicated. In the exemplified composition, the enzymatic levels are expressed by pure enzyme by weight of the total composition and unless otherwise specified, the ingredients are expressed by weight of the total compositions.

Modifications

The RNA guide or any of the nucleic acid sequences encoding the Cas12i4 polypeptides may include one or more covalent modifications with respect to a reference sequence, in particular the parent polyribonucleotide, which are included within the scope of this invention.

Exemplary modifications can include any modification to the sugar, the nucleobase, the internucleoside linkage (e.g. to a linking phosphate/to a phosphodiester linkage/to the phosphodiester backbone), and any combination thereof. Some of the exemplary modifications provided herein are described in detail below.

The RNA guide or any of the nucleic acid sequences encoding components of the Cas12i4 polypeptides described herein may include any useful modification, such as to the sugar, the nucleobase, or the internucleoside linkage (e.g. to a linking phosphate/to a phosphodiester linkage/to the phosphodiester backbone). One or more atoms of a pyrimidine nucleobase may be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleoside linkage. Modifications may be modifications of ribonucleic acids (RNAs) to deoxyribonucleic acids (DNAs), threose nucleic acids (TNAs), glycol nucleic acids (GNAs), peptide nucleic acids (PNAs), locked nucleic acids (LNAs) or hybrids thereof). Additional modifications are described herein.

In some embodiments, the modification may include a chemical or cellular induced modification. For example, some nonlimiting examples of intracellular RNA modifications are described by Lewis and Pan in "RNA modifications and structures cooperate to guide RNA-protein interactions" from Nat Reviews *Mol Cell Biol*, 2017, 18:202-210.

Different sugar modifications, nucleotide modifications, and/or internucleoside linkages (e.g., backbone structures) may exist at various positions in the sequence. One of ordinary skill in the art will appreciate that the nucleotide analogs or other modification(s) may be located at any position(s) of the sequence, such that the function of the sequence is not substantially decreased. The sequence may include from about 1% to about 100% modified nucleotides (either in relation to overall nucleotide content, or in relation to one or more types of nucleotide, i.e. any one or more of A, G, U or C) or any intervening percentage (e.g., from 1% to 20%>, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%).

In some embodiments, sugar modifications (e.g., at the 2' position or 4' position) or replacement of the sugar at one or more ribonucleotides of the sequence may, as well as backbone modifications, include modification or replacement of the phosphodiester linkages. Specific examples of a sequence include, but are not limited to, sequences including modified backbones or no natural internucleoside linkages such as internucleoside modifications, including modification or replacement of the phosphodiester linkages. Sequences having modified backbones include, among others, those that do not have a phosphorus atom in the backbone. For the purposes of this application, and as sometimes referenced in the art, modified RNAs that do not have a phosphorus atom in their internucleoside backbone can also be considered to be oligonucleosides. In particular embodiments, a sequence will include ribonucleotides with a phosphorus atom in its internucleoside backbone.

Modified sequence backbones may include, for example, phosphorothioates, chiral phosphorothioates, phosphorodithioates, phosphotriesters, aminoalkylphosphotriesters, methyl and other alkyl phosphonates such as 3'-alkylene phosphonates and chiral phosphonates, phosphinates, phosphoramidates such as 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included. In some embodiments, the sequence may be negatively or positively charged.

The modified nucleotides, which may be incorporated into the sequence, can be modified on the internucleoside linkage (e.g., phosphate backbone). Herein, in the context of the polynucleotide backbone, the phrases "phosphate" and "phosphodiester" are used interchangeably. Backbone phosphate groups can be modified by replacing one or more of the oxygen atoms with a different substituent. Further, the modified nucleosides and nucleotides can include the wholesale replacement of an unmodified phosphate moiety with another internucleoside linkage as described herein. Examples of modified phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be modified by the replacement of a linking oxygen with nitrogen (bridged phosphoramidates), sulfur (bridged phosphorothioates), and carbon (bridged methylene-phosphonates).

The α-thio substituted phosphate moiety is provided to confer stability to RNA and DNA polymers through the unnatural phosphorothioate backbone linkages. Phosphorothioate DNA and RNA have increased nuclease resistance and subsequently a longer half-life in a cellular environment.

In specific embodiments, a modified nucleoside includes an alpha-thio-nucleoside (e.g., 5'-O-(1-thiophosphate)-adenosine, 5'-O-(1-thiophosphate)-cytidine (a-thio-cytidine), 5'-O-(1-thiophosphate)-guanosine, 5'-O-(1-thiophosphate)-uridine, or 5'-O-(1-thiophosphate)-pseudouridine).

Other internucleoside linkages that may be employed according to the present invention, including internucleoside linkages which do not contain a phosphorous atom, are described herein.

In some embodiments, the sequence may include one or more cytotoxic nucleosides. For example, cytotoxic nucleosides may be incorporated into sequence, such as bifunctional modification. Cytotoxic nucleoside may include, but are not limited to, adenosine arabinoside, 5-azacytidine, 4'-thio-aracytidine, cyclopentenylcytosine, cladribine, clofarabine, cytarabine, cytosine arabinoside, 1-(2-C-cyano-2-deoxy-beta-D-arabino-pentofuranosyl)-cytosine, decitabine, 5-fluorouracil, fludarabine, floxuridine, gemcitabine, a combination of tegafur and uracil, tegafur ((RS)-5-fluoro-1-(tetrahydrofuran-2-yl)pyrimidine-2,4(1H,3H)-dione), troxacitabine, tezacitabine, 2'-deoxy-2'-methylidenecytidine (DMDC), and 6-mercaptopurine. Additional examples include fludarabine phosphate, N4-behenoyl-1-beta-D-arabinofuranosylcytosine, N4-octadecyl-1-beta-D-arabinofuranosylcytosine, N4-palmitoyl-1-(2-C-cyano-2-deoxy-beta-D-arabino-pentofuranosyl) cytosine, and P-4055 (cytarabine 5'-elaidic acid ester).

In some embodiments, the sequence includes one or more post-transcriptional modifications (e.g., capping, cleavage, polyadenylation, splicing, poly-A sequence, methylation, acylation, phosphorylation, methylation of lysine and arginine residues, acetylation, and nitrosylation of thiol groups and tyrosine residues, etc.). The one or more post-transcriptional modifications can be any post-transcriptional modification, such as any of the more than one hundred different nucleoside modifications that have been identified in RNA (Rozenski, J, Crain, P, and McCloskey, J. (1999). The RNA Modification Database: 1999 update. *Nucl Acids Res* 27: 196-197) In some embodiments, the first isolated nucleic acid comprises messenger RNA (mRNA). In some embodiments, the mRNA comprises at least one nucleoside selected from the group consisting of pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine. In some embodiments, the mRNA comprises at least one nucleoside selected from the group consisting of 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine. In some embodiments, the mRNA comprises at least one nucleoside selected from the group consisting of 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine. In some embodiments, mRNA comprises at least one nucleoside selected from the group consisting of inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

The sequence may or may not be uniformly modified along the entire length of the molecule. For example, one or more or all types of nucleotide (e.g., naturally-occurring nucleotides, purine or pyrimidine, or any one or more or all of A, G, U, C, I, pU) may or may not be uniformly modified in the sequence, or in a given predetermined sequence region thereof. In some embodiments, the sequence includes a pseudouridine. In some embodiments, the sequence includes an inosine, which may aid in the immune system characterizing the sequence as endogenous versus viral RNAs. The incorporation of inosine may also mediate improved RNA stability/reduced degradation. See for example, Yu, Z. et al. (2015) RNA editing by ADAR1 marks dsRNA as "self". Cell Res. 25, 1283-1284, which is incorporated by reference in its entirety.

Target Nucleic Acid

The methods disclosed herein are applicable for a variety of target nucleic acids. In some embodiments, the target nucleic acid is a DNA, such as a DNA locus. In some embodiments, the target nucleic acid is an RNA, such as an RNA locus or mRNA. In some embodiments, the target nucleic acid is single-stranded (e.g., single-stranded DNA). In some embodiments, the target nucleic acid is double-stranded (e.g., double-stranded DNA). In some embodiments, the target nucleic acid comprises both single-stranded and double-stranded regions. In some embodiments, the target nucleic acid is linear. In some embodiments, the target nucleic acid is circular. In some embodiments, the target nucleic acid comprises one or more modified nucleotides, such as methylated nucleotides, damaged nucleotides, or nucleotides analogs. In some embodiments, the target nucleic acid is not modified.

The target nucleic acid may be of any length, such as about at least any one of 100 bp, 200 bp, 500 bp, 1000 bp, 2000 bp, 5000 bp, 10 kb, 20 kb, 50 kb, 100 kb, 200 kb, 500 kb, 1 Mb, or longer. The target nucleic acid may also comprise any sequence. In some embodiments, the target nucleic acid is GC-rich, such as having at least about any one of 40%, 45%, 50%, 55%, 60%, 65%, or higher GC content. In some embodiments, the target nucleic acid has a GC content of at least about 70%, 80%, or more. In some embodiments, the target nucleic acid is a GC-rich fragment in a non-GC-rich target nucleic acid. In some embodiments, the target nucleic acid is not GC-rich. In some embodiments, the target nucleic acid has one or more secondary structures or higher-order structures. In some embodiments, the target nucleic acid is not in a condensed state, such as in a chromatin, to render the target nucleic acid inaccessible by the Cas12i4 polypeptide/RNA guide complex.

In some embodiments, the target nucleic acid is present in a cell. In some embodiments, the target nucleic acid is present in the nucleus of the cell. In some embodiments, the target nucleic acid is endogenous to the cell. In some embodiments, the target nucleic acid is a genomic DNA. In some embodiments, the target nucleic acid is a chromosomal DNA. In some embodiments, the target nucleic acid is a protein-coding gene or a functional region thereof, such as a coding region, or a regulatory element, such as a promoter, enhancer, a 5' or 3' untranslated region, etc. In some embodiments, the target nucleic acid is a non-coding gene, such as transposon, miRNA, tRNA, ribosomal RNA, ribozyme, or lincRNA. In some embodiments, the target nucleic acid is a plasmid.

In some embodiments, the target nucleic acid is exogenous to a cell. In some embodiments, the target nucleic acid is a viral nucleic acid, such as viral DNA or viral RNA. In some embodiments, the target nucleic acid is a horizontally transferred plasmid. In some embodiments, the target nucleic acid is integrated in the genome of the cell. In some embodiments, the target nucleic acid is not integrated in the genome of the cell. In some embodiments, the target nucleic acid is a plasmid in the cell. In some embodiments, the target nucleic acid is present in an extrachromosomal array.

In some embodiments, the target nucleic acid is an isolated nucleic acid, such as an isolated DNA or an isolated RNA. In some embodiments, the target nucleic acid is present in a cell-free environment. In some embodiments, the target nucleic acid is an isolated vector, such as a plasmid. In some embodiments, the target nucleic acid is an ultrapure plasmid.

The target nucleic acid is a segment of the target nucleic acid that hybridizes to the RNA guide. In some embodiments, the target nucleic acid has only one copy of the target nucleic acid. In some embodiments, the target nucleic acid has more than one copy, such as at least about any one of 2, 3, 4, 5, 10, 100, or more copies of the target nucleic acid. For example, a target nucleic acid comprising a repeated sequence in a genome of a viral nucleic acid or a bacterium may be targeted by the nucleoprotein.

The target sequence is adjacent to a protospacer adjacent motif or PAM of the disclosure as described herein. The PAM may be immediately adjacent to the target sequence or, for example, within a small number (e.g., 1, 2, 3, 4, or 5) of nucleotides of the target sequence. In the case of a double-stranded target, the targeting moiety (e.g., an RNA guide) binds to a first strand of the target and a PAM sequence as described herein is present in the second, complementary strand. In such a case, the PAM sequence is immediately adjacent to (or within a small number, e.g., 1, 2, 3, 4, or 5 nucleotides of) a sequence in the second strand that is complementary to the sequence in the first strand to which the binding moiety binds.

In some embodiments, the sequence-specificity requires a complete match of the spacer sequence in the RNA guide to the non-PAM strand of a target nucleic acid. In other embodiments, the sequence specificity requires a partial (contiguous or non-contiguous) match of the spacer sequence in the RNA guide to the non-PAM strand of a target nucleic acid.

In some embodiments, the RNA guide or a complex comprising the RNA guide and a Cas12i4 polypeptide described herein binds to a target nucleic acid at a sequence defined by the region of complementarity between the RNA guide and the target nucleic acid. In some embodiments, the PAM sequence described herein is located directly upstream of the target sequence of the target nucleic acid (e.g., directly 5' of the target sequence). In some embodiments, the PAM sequence described herein is located directly 5' of the target sequence on the non-spacer-complementary strand (e.g., non-target strand) of the target nucleic acid.

In some embodiments, PAM sequences corresponding to Cas12i4 (e.g., the parent Cas12i4 polypeptide or variant Cas12i4 polypeptides) include 5'-TTN-3' and 5'-NTTN-3', wherein N is any nucleotide (e.g., A, G, T, or C). In some embodiments, the PAM sequence comprises 5'-TTH-3', 5'-TTY-3', 5'-TTC-3', 5'-NTTH-3', 5'-NTTY-3', or 5'-NTTC-3', wherein N is any nucleotide, H is A, C, or T, and Y is C or T. In some embodiments, the PAM sequence comprises 5'-TTA-3', 5'-TTC-3', 5'-TTG-3', 5'-TTT-3', 5'-NTTA-3', 5'-NTTC-3', 5'-NTTG-3', or 5'-NTTT-3'. For example, in some embodiments, the PAM comprises 5'-ATTA-3', 5'-CTTA-3', 5'-TTTC-3', 5'-TTA-3', 5'-GTTA-3', 5'-CTTC-3', 5'-CTTG-3', 5'-TTC-3', 5'-TTTA-3', 5'-GTTC-3', 5'-GTTG-3', 5'-TTG-3', 5'-ATTC-3', 5'-TTTT-3', 5'-GTTT-3', 5'-ATTT-3', 5'-TTT-3', 5'-CTTT-3', 5'-TTTG-3', or 5'-CTT-3'.

In some embodiments, PAM sequences corresponding to Cas12i4 (e.g., the parent Cas12i4 polypeptide or variant Cas12i4 polypeptides) include 5'-NTN-3', 5'-NNTN-3', 5'-VTN-3', and 5'-NVTN-3', wherein N is any nucleotide (e.g., A, G, T, or C) and V is A, G, or C. In some embodiments, the PAM sequence comprises 5'-NTC-3', 5'-NTA-3', 5'-NTG-3', 5'-NTT-3', 5'-NNTC-3', 5'-NNTA-3', 5'-NNTG-3', or 5'-NNTT-3'. For example, in some embodiments, the PAM sequence comprises 5'-AATC-3', 5'-CCTG-3', 5'-CTA-3', 5'-TCTC-3', 5'-CTG-3', 5'-GCTG-3', 5'-CTC-3', 5'-GCTC-3', 5'-TCTG-3', 5'-ACTG-3', 5'-GATA-3', 5'-TATC-3', 5'-ATC-3', 5'-ATA-3', 5'-GATC-3', 5'-ACTA-3', 5'-GATG-3', 5'-TGTG-3', 5'-TCTT-3', 5'-CCTT-3', GCTT-3', or 5'-ACTT-3'.

In some embodiments, a Cas12i4 polypeptide (e.g., the parent Cas12i4 polypeptide or a variant Cas12i4 polypeptide) recognizes a PAM sequence set forth as 5'-ATAA-3', 5'-CAAT-3', 5'-CGAT-3', 5'-GAGA-3', 5'-CAAG-3', 5'-ACGT-3', 5'-GGCC-3', 5'-GGAC-3', 5'-GGCA-3', 5'-GTAC-3', 5'-GACC-3', or 5'-TTAC-3'.

In some embodiments, the target nucleic acid is present in a readily accessible region of the target nucleic acid. In some embodiments, the target nucleic acid is in an exon of a target gene. In some embodiments, the target nucleic acid is across an exon-intron junction of a target gene. In some embodiments, the target nucleic acid is present in a non-coding region, such as a regulatory region of a gene. In some embodiments, wherein the target nucleic acid is exogenous to a cell, the target nucleic acid comprises a sequence that is not found in the genome of the cell.

Suitable DNA/RNA binding conditions include physiological conditions normally present in a cell. Other suitable DNA/RNA binding conditions (e.g., conditions in a cell-free system) are known in the art; see, e.g., Sambrook, supra. The strand of the target nucleic acid that is complementary to and hybridizes with the RNA guide is referred to as the "complementary strand" and the strand of the target nucleic acid that is complementary to the "complementary strand" (and is therefore not complementary to the RNA guide) is referred to as the "noncomplementary strand" or "non-complementary strand".

Preparation

In some embodiments, the variant Cas12i4 polypeptide of the present invention can be prepared by (a) culturing bacteria which produce the variant Cas12i4 polypeptide of the present invention, isolating the variant Cas12i4 polypeptide, optionally, purifying the variant Cas12i4 polypeptide, and complexing the variant Cas12i4 polypeptide with RNA guide. The variant Cas12i4 polypeptide can be also prepared by (b) a known genetic engineering technique, specifically, by isolating a gene encoding the variant Cas12i4 polypeptide of the present invention from bacteria, constructing a recombinant expression vector, and then transferring the vector into an appropriate host cell that expresses the RNA guide for expression of a recombinant protein that complexes with the RNA guide in the host cell. Alternatively, the variant Cas12i4 polypeptide can be prepared by (c) an in vitro coupled transcription-translation system and then complexes with RNA guide. Bacteria that can be used for preparation of the variant Cas12i4 polypeptide of the present invention are not particularly limited as long as they can produce the variant Cas12i4 polypeptide of the present invention. Some nonlimiting examples of the bacteria include *E. coli* cells described herein.

Vectors

The present invention provides a vector for expressing the variant Cas12i4 polypeptide described herein or nucleic acids encoding the variant described herein may be incorporated into a vector. In some embodiments, a vector of the invention includes a nucleotide sequence encoding variant Cas12i4 polypeptide. In some embodiments, a vector of the invention includes a nucleotide sequence encoding the variant Cas12i4 polypeptide.

The present invention also provides a vector that may be used for preparation of the variant Cas12i4 polypeptide or compositions comprising the variant Cas12i4 polypeptide as described herein. In some embodiments, the invention includes the composition or vector described herein in a cell. In some embodiments, the invention includes a method of expressing the composition comprising the variant Cas12i4 polypeptide, or vector or nucleic acid encoding the variant Cas12i4 polypeptide, in a cell. The method may comprise the steps of providing the composition, e.g., vector or nucleic acid, and delivering the composition to the cell.

Expression of natural or synthetic polynucleotides is typically achieved by operably linking a polynucleotide encoding the gene of interest, e.g., nucleotide sequence encoding the variant Cas12i4 polypeptide, to a promoter and incorporating the construct into an expression vector. The expression vector is not particularly limited as long as it includes a polynucleotide encoding the variant Cas12i4 polypeptide of the present invention and can be suitable for replication and integration in eukaryotic cells.

Typical expression vectors include transcription and translation terminators, initiation sequences, and promoters useful for expression of the desired polynucleotide. For example, plasmid vectors carrying a recognition sequence for RNA polymerase (pSP64, pBluescript, etc.). may be used. Vectors including those derived from retroviruses such as lentivirus are suitable tools to achieve long-term gene transfer since they allow long-term, stable integration of a transgene and its propagation in daughter cells. Examples of vectors include expression vectors, replication vectors, probe generation vectors, and sequencing vectors. The expression vector may be provided to a cell in the form of a viral vector.

Viral vector technology is well known in the art and described in a variety of virology and molecular biology manuals. Viruses which are useful as vectors include, but are not limited to phage viruses, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers.

The kind of the vector is not particularly limited, and a vector that can be expressed in host cells can be appropriately selected. To be more specific, depending on the kind of the host cell, a promoter sequence to ensure the expression of the variant Cas12i4 polypeptide from the polynucleotide is appropriately selected, and this promoter sequence and the polynucleotide are inserted into any of various plasmids etc. for preparation of the expression vector.

Additional promoter elements, e.g., enhancing sequences, regulate the frequency of transcriptional initiation. Typically, these are located in the region 30-110 bp upstream of the start site, although a number of promoters have recently been shown to contain functional elements downstream of the start site as well. Depending on the promoter, it appears that individual elements can function either cooperatively or independently to activate transcription.

Further, the disclosure should not be limited to the use of constitutive promoters. Inducible promoters are also contemplated as part of the disclosure. The use of an inducible promoter provides a molecular switch capable of turning on expression of the polynucleotide sequence which it is operatively linked when such expression is desired or turning off the expression when expression is not desired. Examples of inducible promoters include, but are not limited to a metallothionine promoter, a glucocorticoid promoter, a progesterone promoter, and a tetracycline promoter.

The expression vector to be introduced can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate transcriptional control sequences to enable expression in the host cells. Examples of such a marker include a dihydrofolate reductase gene and a neomycin resistance gene for eukaryotic cell culture; and a tetracycline resistance gene and an ampicillin resistance gene for culture of *E. coli* and other bacteria. By use of such a selection marker, it can be confirmed whether the polynucleotide encoding the variant Cas12i4 polypeptide of the present invention has been transferred into the host cells and then expressed without fail.

The preparation method for recombinant expression vectors is not particularly limited, and examples thereof include methods using a plasmid, a phage or a cosmid.

Methods of Expression

The present invention includes a method for protein expression, comprising translating the variant Cas12i4 polypeptide described herein.

In some embodiments, a host cell described herein is used to express the variant Cas12i4 polypeptide. The host cell is not particularly limited, and various known cells can be preferably used. Specific examples of the host cell include bacteria such as *E. coli*, yeasts (budding yeast, *Saccharomyces cerevisiae*, and fission yeast, *Schizosaccharomyces pombe*), nematodes (*Caenorhabditis elegans*), *Xenopus laevis* oocytes, and animal cells (for example, CHO cells, COS cells and HEK293 cells). The method for transferring the expression vector described above into host cells, i.e., the transformation method, is not particularly limited, and known methods such as electroporation, the calcium phosphate method, the liposome method and the DEAE dextran method can be used.

After a host is transformed with the expression vector, the host cells may be cultured, cultivated or bred, for production of the variant Cas12i4 polypeptide. After expression of the variant Cas12i4 polypeptide, the host cells can be collected and variant Cas12i4 polypeptide purified from the cultures etc. according to conventional methods (for example, filtration, centrifugation, cell disruption, gel filtration chromatography, ion exchange chromatography, etc.).

In some embodiments, the methods for variant Cas12i4 polypeptide expression comprises translation of at least 5 amino acids, at least 10 amino acids, at least 15 amino acids, at least 20 amino acids, at least 50 amino acids, at least 100 amino acids, at least 150 amino acids, at least 200 amino acids, at least 250 amino acids, at least 300 amino acids, at least 400 amino acids, at least 500 amino acids, at least 600 amino acids, at least 700 amino acids, at least 800 amino acids, at least 900 amino acids, or at least 1000 amino acids of the variant Cas12i4 polypeptide. In some embodiments, the methods for protein expression comprises translation of about 5 amino acids, about 10 amino acids, about 15 amino acids, about 20 amino acids, about 50 amino acids, about 100 amino acids, about 150 amino acids, about 200 amino acids, about 250 amino acids, about 300 amino acids, about 400 amino acids, about 500 amino acids, about 600 amino acids, about 700 amino acids, about 800 amino acids, about 900 amino acids, about 1000 amino acids or more of the variant Cas12i4 polypeptide.

A variety of methods can be used to determine the level of production of a mature variant Cas12i4 polypeptide in a host cell. Such methods include, but are not limited to, for example, methods that utilize either polyclonal or monoclonal antibodies specific for the variant Cas12i4 polypeptide or a labeling tag as described elsewhere herein. Exemplary methods include, but are not limited to, enzyme-linked immunosorbent assays (ELISA), radioimmunoassays (RIAs), fluorescent immunoassays (FIA), and fluorescent activated cell sorting (FACS). These and other assays are well known in the art (See, e.g., Maddox et al., *J. Exp. Med.* 158:1211 [1983]).

The present disclosure provides methods of in vivo expression of the variant Cas12i4 polypeptide in a cell, comprising providing a polyribonucleotide encoding the variant Cas12i4 polypeptide to a host cell wherein the polyribonucleotide encodes the variant Cas12i4 polypeptide, expressing the variant Cas12i4 polypeptide in the cell, and obtaining the variant Cas12i4 polypeptide from the cell.

Introduction of Alteration or Mutation

Nucleic acid sequences encoding variant polypeptides or variant polypeptides may be generated by synthetic methods known in the art. Using the nucleic acid sequence encoding the parent polypeptide itself as a framework, alternations or mutations can be inserted one or more at a time to alter the nucleic acid sequence encoding the parent polypeptide. Along the same lines, the parent polypeptide may be altered or mutated by introducing the changes into the polypeptide sequence as it is synthetically synthesized. This may be accomplished by methods well known in the art.

The production and introduction of alteration or mutation into a parent polypeptide sequence can be accomplished using any methods known by those of skill in the art. In particular, in some embodiments, oligonucleotide primers for PCR may be used for the rapid synthesis of a DNA template including the one or more alterations or mutations in the nucleic acid sequence encoding for the variant polypeptide. Site-specific mutagenesis may also be used as a technique useful in the preparation of individual peptides, or biologically functional equivalent proteins or peptides, through specific mutagenesis of the underlying DNA. The technique further provides a ready ability to prepare and test variants, incorporating one or more of the foregoing considerations, by introducing one or more nucleotide sequence changes into the DNA. Site-specific mutagenesis allows the production of variants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

Introduction of structural variations, such as fusion of polypeptides as amino- and/or carboxyl-terminal extensions can be accomplished in a similar fashion as introduction of alterations or mutations into the parent polypeptide. The additional peptides may be added to the parent polypeptide or variant polypeptide by including the appropriate nucleic acid sequence encoding the additional peptides to the nucleic acid sequence encoding the parent polypeptide or variant polypeptide. Optionally, the additional peptides may be appended directly to the variant polypeptide through synthetic polypeptide production. In an aspect, the invention also provides methods for introducing an alteration or mutation into the parent polypeptide sequence to produce a variant Cas12i4 polypeptide that has increased on-target binding with two or more loci (e.g., 2, 3, 4, 5, 6, 7, 8, 9, or more) of a target nucleic acid, as compared to a parent polypeptide.

In an aspect, the invention also provides methods for introducing an alteration or mutation into the parent polypeptide sequence to produce a plurality of variant Cas12i4 polypeptides (e.g., separate variant Cas12i4 polypeptides having the same amino acid sequence), that when individually complexed with a plurality of distinct RNA guides, have increased on-target binding with two or more loci of a target nucleic acid, as compared to a plurality of parent polypeptides and RNA guides.

In an aspect, the invention also provides methods for introducing an alteration or mutation into the parent polypeptide sequence to produce a variant Cas12i4 polypeptide that has increased on-target ternary complex formation with two or more target loci of a target nucleic acid, as compared to a parent polypeptide.

In an aspect, the invention also provides methods for introducing an alteration or mutation into the parent polypeptide sequence to produce a plurality of variant Cas12i4 polypeptides (e.g., separate variant Cas12i4 polypeptides having the same amino acid sequence), that when individually complexed with a plurality of distinct RNA guides, have increased ternary complex formation with two or more loci of a target nucleic acid, as compared to a plurality of parent polypeptides and RNA guides.

In an aspect, the invention also provides methods for introducing an alteration or mutation into the parent polypeptide sequence to produce a Cas12i4 polypeptides exhibit targeting of an increased number of target nucleic acids or target loci, as compared to a parent polypeptide.

In an aspect, the invention also provides methods for introducing an alteration or mutation into the parent polypeptide sequence to produce a plurality of variant Cas12i4 polypeptides (e.g., separate variant Cas12i4 polypeptides having the same amino acid sequence), that when individually complexed with a plurality of distinct RNA guides, exhibit targeting of an increased number of target nucleic acids or target loci, as compared to a plurality of parent polypeptides and RNA guides.

In an aspect, the invention also provides methods for introducing an alteration or mutation into the parent polypeptide sequence to enhance stability of the Cas12i4 polypeptide. Stability of the Cas12i4 polypeptide can be determined by or may include a technique not limited to thermal denaturation assays, thermal shift assays, differential scanning calorimetry (DSC), differential scanning fluorimetry (DSF), isothermal titration calorimetry (ITC), pulse-chase methods, bleach-chase methods, cycloheximide-chase methods, circular dichroism (CD) spectroscopy, crystallization, and fluorescence-based activity assays.

Variant Binary Complexing

Generally, the variant Cas12i4 polypeptide and the RNA guide bind to each other in a molar ratio of about 1:1 to form the variant binary complex. The variant Cas12i4 polypeptide and the RNA guide, either alone or together, do not naturally occur.

In some embodiments, the variant Cas12i4 polypeptide can be overexpressed in a host cell and purified as described herein, then complexed with the RNA guide (e.g., in a test tube) to form a variant ribonucleoprotein (RNP) (e.g., variant binary complex).

In some embodiments, the variant binary complex exhibits increased binding affinity to a target nucleic acid, increased on-target binding activity, increased on-target binding specificity, increased ternary complex formation with a target nucleic acid, and/or increased stability over a range of incubation times.

In some embodiments, the variant binary complex exhibits decreased off-target binding to a non-target nucleic acid and/or decreased dissociation from a target nucleic acid over a range of incubation times.

In some embodiments, the variant binary complex exhibits increased target nucleic acid complex formation, target nucleic acid activity, and/or target nucleic acid specificity over a range of incubation times.

In some embodiments, complexation of a binary complex occurs at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., or 55° C. In some embodiments, the variant Cas12i4 polypeptide does not dissociate from the RNA guide or bind to a free RNA at about 37° C. over an incubation period of at least about any one of 10 mins, 15 mins, 20 mins, 25 mins, 30 mins, 35 mins, 40 mins, 45 mins, 50 mins, 55 mins, 1 hr, 2 hr, 3 hr, 4 hr, or more hours. In some embodiments, after binary complex formation, the variant ribonucleoprotein complex does not exchange the RNA guide with a different RNA.

In some embodiments, the variant Cas12i4 polypeptide and RNA guide are complexed in a binary complexation buffer. In some embodiments, the variant Cas12i4 polypeptide is stored in a buffer that is replaced with a binary complexation buffer to form a complex with the RNA guide. In some embodiments, the variant Cas12i4 polypeptide is stored in a binary complexation buffer.

In some embodiments, the binary complexation buffer has a pH in a range of about 7.3 to 8.6. In one embodiment, the pH of the binary complexation buffer is about 7.3. In one embodiment, the pH of the binary complexation buffer is about 7.4. In one embodiment, the pH of the binary complexation buffer is about 7.5. In one embodiment, the pH of the binary complexation buffer is about 7.6. In one embodiment, the pH of the binary complexation buffer is about 7.7. In one embodiment, the pH of the binary complexation buffer is about 7.8. In one embodiment, the pH of the binary complexation buffer is about 7.9. In one embodiment, the pH of the binary complexation buffer is about 8.0. In one embodiment, the pH of the binary complexation buffer is about 8.1. In one embodiment, the pH of the binary complexation buffer is about 8.2. In one embodiment, the pH of the binary complexation buffer is about 8.3. In one embodiment, the pH of the binary complexation buffer is about 8.4. In one embodiment, the pH of the binary complexation buffer is about 8.5. In one embodiment, the pH of the binary complexation buffer is about 8.6.

The thermostability of the variant Cas12i4 polypeptide can increase under favorable conditions such as the addition of an RNA guide, e.g., binding an RNA guide.

In some embodiments, the variant Cas12i4 polypeptide can be overexpressed and complexed with the RNA guide in a host cell prior to purification as described herein. In some embodiments, mRNA or DNA encoding the variant Cas12i4 polypeptide is introduced into a cell so that the variant Cas12i4 polypeptide is expressed in the cell. The RNA guide, which guides the variant Cas12i4 polypeptide to the desired target nucleic acid is also introduced into the cell, whether simultaneously, separately or sequentially from a single mRNA or DNA construct, such that the necessary ribonucleoprotein complex is formed in the cell.

Assessing Variant Binary Complex Stability and Functionality

Provided herein in certain embodiments are methods for identifying an optimal variant Cas12i4 polypeptide/RNA guide complex (referred to herein as the variant binary complex) including (a) combining a variant Cas12i4 polypeptide and an RNA guide in a sample to form the variant binary complex; (b) measuring a value of the variant binary complex; and (c) determining the variant binary complex is optimal over the reference molecule, if the value of the variant binary complex is greater than a value of a reference molecule. In some embodiments, the value may include, but is not limited to, a stability measurement (e.g., $T_m$ value, thermostability), a rate of binary complex formation, RNA guide binding specificity, and/or complex activity.

In some embodiments, an optimal variant Cas12i4 polypeptide/RNA guide complex (i.e., a variant binary complex) is identified by the steps of: (a) combining a variant Cas12i4 polypeptide and an RNA guide in a sample to form the variant binary complex; (b) detecting a $T_m$ value of the variant binary complex; and (c) determining the variant binary complex is stable if the $T_m$ value of the variant binary complex is greater than a $T_m$ value of a reference molecule or a $T_m$ reference value by at least 8° C.

The methods involving a step of measuring the thermostability of a variant Cas12i4 polypeptide/RNA guide complex (i.e., a variant binary complex) may include, without limitation, methods of determining the stability of a variant binary complex, methods of determining a condition that promotes a stable variant binary complex, methods of screening for a stable variant binary complex, and methods for identifying an optimal gRNA to form a stable variant binary complex. In certain embodiments, a thermostability value of a variant binary complex may be measured.

Additionally, in certain embodiments, a thermostability value of a reference molecule may also be measured. In certain embodiments, a variant binary complex may be determined to be stable if the measured thermostability value of the variant binary complex is greater than the measured thermostability value of the reference molecule or a thermostability reference value, measured under the same experimental conditions, as described herein. In certain embodiments, the reference molecule may be the variant Cas12i4 polypeptide absent an RNA guide.

In certain embodiments, the thermostability value that is measured may be a denaturation temperature value. In these embodiments, the thermostability reference value is a denaturation temperature reference value. In certain embodiments, the thermostability value that is measured may be a $T_m$ value. In these embodiments, the thermostability reference value may be a $T_m$ reference value. In certain embodiments, the thermostability value may be measured using a thermal shift assay. In certain embodiments, an assay used to measure thermostability may involve a technique described herein including, but not limited to, thermal denaturation assays, thermal shift assays, differential scanning calorimetry (DSC), differential scanning fluorimetry (DSF), isothermal titration calorimetry (ITC), pulse-chase methods, bleach-chase methods, cycloheximide-chase methods, circular dichroism (CD) spectroscopy, crystallization, and fluorescence-based activity assays.

In certain embodiments, a variant binary complex may be identified if the rate of variant Cas12i4 polypeptide/RNA guide complex formation, RNA guide binding specificity, and/or complex activity of the variant binary complex is greater than a value of the reference molecule or the reference value (e.g., a value of a parent polypeptide/RNA guide complex, referred to herein as a parent binary complex). For example, in certain embodiments, the variant binary complex may be identified if the value of a rate of variant Cas12i4 polypeptide/RNA guide complex formation, RNA guide binding specificity, and/or complex activity of the variant binary complex is at least X % greater than a value of the reference molecule or the reference value (e.g., a value of a parent binary complex). In certain embodiments, the methods described herein may further comprise steps that include measuring the activity of the variant binary complex as described herein.

Variant Ternary Complexing

In some embodiments, the variant Cas12i4 polypeptide, RNA guide, and target nucleic acid, as described herein, form a variant ternary complex (e.g., in a test tube or cell). Generally, the variant Cas12i4 polypeptide, the RNA guide, and the target nucleic acid associate with each other in a molar ratio of about 1:1:1 to form the variant ternary complex. The variant Cas12i4 polypeptide, the RNA guide, and the target nucleic acid, either alone or together, do not naturally occur.

In some embodiments, the variant binary complex (e.g., complex of variant Cas12i4 polypeptide and RNA guide) as described herein, is further complexed with the target nucleic acid (e.g., in a test tube or cell) to form a variant ternary complex.

In some embodiments, complexation of the ternary complex occurs at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., or 55° C. In some embodiments, the variant binary complex does not dissociate from the target nucleic acid or bind to a free nucleic acid (e.g., free DNA) at about 37° C. over an incubation period of at least about any one of 10 mins, 15 mins, 20 mins, 25 mins, 30 mins, 35 mins, 40 mins, 45 mins, 50 mins, 55 mins, 1 hr, 2 hr, 3 hr, 4 hr, or more hours. In some embodiments, after ternary complex formation, a variant binary complex does not exchange the target nucleic acid with a different nucleic acid.

In some embodiments, the variant Cas12i4 polypeptide, RNA guide, and target nucleic acid are complexed in a ternary complexation buffer. In some embodiments, the variant Cas12i4 polypeptide is stored in a buffer that is replaced with a ternary complexation buffer to form a complex with the RNA guide and target nucleic acid. In some embodiments, the variant Cas12i4 polypeptide is stored in a ternary complexation buffer.

In some embodiments, the variant binary complex and target nucleic acid are complexed in a ternary complexation buffer. In some embodiments, the variant binary complex is stored in a buffer that is replaced with a ternary complexation buffer to form a complex with the target nucleic acid. In some embodiments, the variant binary complex is stored in a ternary complexation buffer.

In some embodiments, the ternary complexation buffer has a pH in a range of about 7.3 to 8.6. In one embodiment, the pH of the ternary complexation buffer is about 7.3. In one embodiment, the pH of the ternary complexation buffer is about 7.4. In one embodiment, the pH of the ternary complexation buffer is about 7.5. In one embodiment, the pH of the ternary complexation buffer is about 7.6. In one embodiment, the pH of the ternary complexation buffer is about 7.7. In one embodiment, the pH of the ternary complexation buffer is about 7.8. In one embodiment, the pH of the ternary complexation buffer is about 7.9. In one embodiment, the pH of the ternary complexation buffer is about 8.0. In one embodiment, the pH of the ternary complexation buffer is about 8.1. In one embodiment, the pH of the ternary complexation buffer is about 8.2. In one embodiment, the pH of the ternary complexation buffer is about 8.3. In one embodiment, the pH of the ternary complexation buffer is about 8.4. In one embodiment, the pH of the ternary complexation buffer is about 8.5. In one embodiment, the pH of the ternary complexation buffer is about 8.6.

The thermostability of a variant Cas12i4 polypeptide can increase under favorable conditions such as the addition of an RNA guide and target nucleic acid.

Assessing Variant Ternary Complex Stability and Functionality

Provided herein in certain embodiments are methods for identifying an optimal variant ternary complex including (a) combining a variant Cas12i4 polypeptide, an RNA guide, and a target nucleic acid in a sample to form the variant ternary complex; (b) measuring a value of the variant ternary complex; and (c) determining the variant ternary complex is optimal over the reference molecule, if the value of the variant ternary complex is greater than a value of a reference molecule. In some embodiments, the value may include, but is not limited to, a stability measurement (e.g., $T_m$ value, thermostability), a rate of ternary complex formation, a DNA binding affinity measurement, a DNA binding specificity measurement, and/or a complex activity measurement (e.g., nuclease activity measurement).

In some embodiments, an optimal variant ternary complex is identified by the steps of: (a) combining a variant Cas12i4 polypeptide, an RNA guide, and a target nucleic acid in a sample to form the variant ternary complex; (b) detecting a $T_m$ value of the variant ternary complex; and (c) determining the variant ternary complex is stable if the $T_m$ value of the variant ternary complex is greater than a $T_m$ value of a reference molecule or a $T_m$ reference value by at least 8° C.

The methods involving a step of measuring the thermostability of a variant ternary complex may include, without limitation, methods of determining the stability of a variant ternary complex, methods of determining a condition that promotes a stable variant ternary complex, methods of screening for a stable variant ternary complex, and methods for identifying an optimal binary complex to form a stable variant ternary complex. In certain embodiments, a thermostability value of a variant ternary complex may be measured.

Additionally, in certain embodiments, a thermostability value of a reference molecule may also be measured. In certain embodiments, a variant ternary complex may be determined to be stable if the measured thermostability value of the variant ternary complex is greater than the measured thermostability value of the reference molecule or a thermostability reference value, measured under the same experimental conditions, as described herein. In certain embodiments, the reference molecule may be the variant Cas12i4 polypeptide absent an RNA guide and/or target nucleic acid.

In certain embodiments, the thermostability value that is measured may be a denaturation temperature value. In these embodiments, the thermostability reference value is a denaturation temperature reference value. In certain embodiments, the thermostability value that is measured may be a $T_m$ value. In these embodiments, the thermostability reference value may be a $T_m$ reference value. In certain embodiments, the thermostability value may be measured using a thermal shift assay. In certain embodiments, an assay used to measure thermostability may involve a technique described herein including, but not limited to, differential scanning fluorimetry (DSF), differential scanning calorimetry (DSC), or isothermal titration calorimetry (ITC).

In certain embodiments, a variant ternary complex may be identified if the rate of ternary complex formation, DNA binding affinity, DNA binding specificity, and/or complex activity (e.g., nuclease activity) of the variant ternary complex is greater than a value of the reference molecule or the reference value (e.g., a value of a parent ternary complex). For example, in certain embodiments, the variant ternary complex may be identified if the value of a rate of ternary complex formation, DNA binding affinity, DNA binding specificity, and/or complex activity of the variant ternary complex is at least X % greater than a value of the reference molecule or the reference value (e.g., a value of a parent ternary complex). In certain embodiments, the methods described herein may further comprise steps that include measuring the activity of the variant ternary complex as described herein.

Delivery

Compositions or complexes described herein may be formulated, for example, including a carrier, such as a carrier and/or a polymeric carrier, e.g., a liposome, and delivered by known methods to a cell (e.g., a prokaryotic, eukaryotic, plant, mammalian, etc.). Such methods include, but not limited to, transfection (e.g., lipid-mediated, cationic polymers, calcium phosphate, dendrimers); electroporation or other methods of membrane disruption (e.g., nucleofection), viral delivery (e.g., lentivirus, retrovirus, adenovirus, AAV), microinjection, microprojectile bombardment ("gene gun"), fugene, direct sonic loading, cell squeezing, optical transfection, protoplast fusion, impalefection, magnetofection, exosome-mediated transfer, lipid nanoparticle-mediated transfer, and any combination thereof.

In some embodiments, the method comprises delivering one or more nucleic acids (e.g., nucleic acids encoding the variant Cas12i4 polypeptide, RNA guide, donor DNA, etc.), one or more transcripts thereof, and/or a pre-formed variant Cas12i4 polypeptide/RNA guide complex (i.e., variant binary complex) to a cell. Exemplary intracellular delivery methods, include, but not limited to: viruses or virus-like agents; chemical-based transfection methods, such as those using calcium phosphate, dendrimers, liposomes, or cationic polymers (e.g., DEAE-dextran or polyethylenimine); non-chemical methods, such as microinjection, electroporation, cell squeezing, sonoporation, optical transfection, impalefection, protoplast fusion, bacterial conjugation, delivery of plasmids or transposons; particle-based methods, such as using a gene gun, magnetofection or magnet assisted transfection, particle bombardment; and hybrid methods, such as nucleofection. In some embodiments, the present application further provides cells produced by such methods, and organisms (such as animals, plants, or fungi) comprising or produced from such cells.

Cells

Compositions or complexes described herein may be delivered to a variety of cells. In some embodiments, the cell is an isolated cell. In some embodiments the cell is in cell culture. In some embodiments, the cell is ex vivo. In some embodiments, the cell is obtained from a living organism, and maintained in a cell culture. In some embodiments, the cell is a single-cellular organism.

In some embodiments, the cell is a prokaryotic cell. In some embodiments, the cell is a bacterial cell or derived from a bacterial cell. In some embodiments, the bacterial cell is not related to the bacterial species from which the parent polypeptide is derived. In some embodiments, the cell is an archaeal cell or derived from an archaeal cell. In some embodiments, the cell is a eukaryotic cell. In some embodiments, the cell is a plant cell or derived from a plant cell. In some embodiments, the cell is a fungal cell or derived from a fungal cell. In some embodiments, the cell is an animal cell or derived from an animal cell. In some embodiments, the cell is an invertebrate cell or derived from an invertebrate cell. In some embodiments, the cell is a vertebrate cell or derived from a vertebrate cell. In some embodiments, the cell is a mammalian cell or derived from a mammalian cell. In some embodiments, the cell is a human cell. In some embodiments, the cell is a zebra fish cell. In some embodiments, the cell is a rodent cell. In some embodiments, the cell is synthetically made, sometimes termed an artificial cell.

In some embodiments, the cell is derived from a cell line. A wide variety of cell lines for tissue culture are known in the art. Examples of cell lines include, but are not limited to, 293T, MF7, K562, HeLa, and transgenic varieties thereof. Cell lines are available from a variety of sources known to those with skill in the art (see, e.g., the American Type Culture Collection (ATCC) (Manassas, Va.)). In some embodiments, a cell transfected with one or more nucleic acids (such as Ago-coding vector and gDNA) or Ago-gDNA complex described herein is used to establish a new cell line comprising one or more vector-derived sequences to establish a new cell line comprising modification to the target nucleic acid. In some embodiments, cells transiently or non-transiently transfected with one or more nucleic acids (such as variant Cas12i4 polypeptide-encoding vector and RNA guide) or variant Cas12i4 polypeptide/RNA guide complex (i.e., variant binary complex) described herein, or cell lines derived from such cells are used in assessing one or more test compounds.

In some embodiments, the cell is a primary cell. For example, cultures of primary cells can be passaged 0 times, 1 time, 2 times, 4 times, 5 times, 10 times, 15 times or more. In some embodiments, the primary cells are harvest from an individual by any known method. For example, leukocytes may be harvested by apheresis, leukocytapheresis, density gradient separation, etc. Cells from tissues such as skin, muscle, bone marrow, spleen, liver, pancreas, lung, intestine, stomach, etc. can be harvested by biopsy. An appropriate solution may be used for dispersion or suspension of the harvested cells. Such solution can generally be a balanced salt solution, (e.g. normal saline, phosphate-buffered saline (PBS), Hank's balanced salt solution, etc.), conveniently supplemented with fetal calf serum or other naturally occurring factors, in conjunction with an acceptable buffer at low concentration. Buffers can include HEPES, phosphate buffers, lactate buffers, etc. Cells may be used immediately, or they may be stored (e.g., by freezing). Frozen cells can be thawed and can be capable of being reused. Cells can be frozen in a DMSO, serum, medium buffer (e.g., 10% DMSO, 50% serum, 40% buffered medium), and/or some other such common solution used to preserve cells at freezing temperatures.

In some embodiments, the variant Cas12i4 polypeptide has nuclease activity that induces double-stranded breaks or single-stranded breaks in a target nucleic acid, (e.g. genomic DNA). The double-stranded break can stimulate cellular endogenous DNA-repair pathways, including Homology Directed Recombination (HDR), Non-Homologous End Joining (NHEJ), or Alternative Non-Homologues End-Joining (A-NHEJ). NHEJ can repair cleaved target nucleic acid without the need for a homologous template. This can result in deletion or insertion of one or more nucleotides into the target nucleic acid. HDR can occur with a homologous template, such as the donor DNA. The homologous template can comprise sequences that are homologous to sequences flanking the target nucleic acid cleavage site. In some cases, HDR can insert an exogenous polynucleotide sequence into the cleaved target nucleic acid. The modifications of the target DNA due to NHEJ and/or HDR can lead to, for example, mutations, deletions, alterations, integrations, gene correction, gene replacement, gene tagging, transgene knock-in, gene disruption, and/or gene knock-outs.

In some embodiments, the cell culture is synchronized to enhance the efficiency of the methods. In some embodiments, cells in S and G2 phases are used for HDR-mediated gene editing. In some embodiments, the cell can be subjected to the method at any cell cycle. In some embodiments, cell over-plating significantly reduces the efficacy of the method. In some embodiments, the method is applied to a cell culture at no more than about any one of 40%, 45%, 50%, 55%, 60%, 65%, or 70% confluency.

In some embodiments, binding of the variant Cas12i4 polypeptide/RNA guide complex (i.e., variant binary complex) to the target nucleic acid in the cell recruits one or more endogenous cellular molecules or pathways other than DNA repair pathways to modify the target nucleic acid. In some embodiments, binding of the variant binary complex blocks access of one or more endogenous cellular molecules or pathways to the target nucleic acid, thereby modifying the target nucleic acid. For example, binding of the variant binary complex may block endogenous transcription or translation machinery to decrease the expression of the target nucleic acid.

Kits

The invention also provides kits that can be used, for example, to carry out a method described herein. In some embodiments, the kits include a variant Cas12i4 polypeptide of the invention, e.g., a variant comprising a substitution of Table 2 or a variant polypeptide of Table 3. In some embodiments, the kits include a polynucleotide that encodes such a variant Cas12i4 polypeptide, and optionally the polynucleotide is comprised within a vector, e.g., as described herein. The kits also can optionally include an RNA guide, e.g., as described herein. The RNA guide of the kits of the invention can be designed to target a sequence of interest, as is known in the art. The nuclease variant and the RNA guide can be packaged within the same vial or other vessel within a kit or can be packaged in separate vials or other vessels, the contents of which can be mixed prior to use. The kits can additionally include, optionally, a buffer and/or instructions for use of the nuclease variant and/or RNA guide.

All references and publications cited herein are hereby incorporated by reference.

| Sequence identifier | Sequence |
|---|---|
| 222 | ATGGCCAGCATCTCACGCCCCTACGGGACCAAGCTGCGGCCTGATG<br>CCCGGAAAAAGGAAATGCTGGACAAATTTTTCAACACTCTCACCAA<br>GGGCCAAAGGGTATTTGCCGATCTGGCGCTGTGTATATACGGGAGC<br>CTGACACTCGAGATGGCCAAGAGCCTAGAGCCGGAATCTGACAGCG<br>AGCTCGTTTGTGCCATCGGGTGGTTTAGACTCGTAGACAAAACCATT<br>TGGAGTAAGGATGGGATAAAGCAGGAGAATCTCGTGAAGCAATAT<br>GAGGCCTATTCCGGAAAAGAGGCGTCAGAGGTGGTGAAGACTTACC<br>TGAATAGCCCCTCATCCGACAAATACGTATGGATTGATTGCCGACA<br>AAAGTTTTTACGGTTCCAGCGGGAACTTGGAACGAGGAACCTGAGC<br>GAAGATTTTGAATGTATGCTGTTTGAGCAGTATATCCGGCTTACCAA<br>AGGCGAGATTGAAGGATACGCCGCCATTTCTAATATGTTTGGTAAT<br>GGCGAGAAGGAGGACAGATCAAAGAAGAGGATGTACGCTACTCGT<br>ATGAAGGACTGGTTGGAGGCAAATGAAAATATTACCTGGGAGCAGT<br>ACCGAGAAGCGCTCAAAAACCAGTTGAACGCAAAGAATCTGGAGC<br>AAGTGGTGGCCAACTATAAGGGCAATGCCGGCGGCGCCGATCCATT<br>TTTCAAGTATAGTTTCTCGAAGGAAGGTATGGTGTCCAAGAAAGAG<br>CACGCGCAGCAGCTGGACAAGTTCAAAACAGTCCTGAAGAATAAA<br>GCCCGCGATTTAAATTTCCCCAACAAGGAGAAGCTCAAGCAGTACT<br>TAGAAGCTGAGATTGGTATCCCAGTTGATGCAAACGTATACTCACA<br>GATGTTCTCTAACGGGGTGTCGGAGGTCCAACCAAAAACAACACGA<br>AACATGTCCTTTAGCAATGAGAAGCTAGATCTGTTGACTGAACTGA<br>AGGACTTAAACAAGGGCGATGGATTCGAATACGCCAGAGAAGTGC<br>TTAATGGCTTCTTCGATAGTGAACTCCACACTACAGAAGATAAATTC<br>AACATTACTAGTCGGTACCTTGGTGGGGACAAATCCAACAGGCTCA<br>GCAAGTTGTATAAGATTTGGAAGAAGGAGGGGGGTTGATTGTGAAGA<br>AGGAATTCAGCAGTTCTGCGAGGCTGTGAAGGATAAAATGGGCCAG<br>ATCCCCATCCGGAATGTCCTCAAATATTTATGGCAGTTTAGGGAGA<br>CCGTCAGTGCCGAGGACTTCGAAGCTGCAGCAAAGGCAAACCACCT<br>AGAGGAGAAAATAAGCCGAGTGAAAGCTCACCCGATTGTGATTTCC<br>AACAGGTATTGGGCTTTCGGCACAAGCGCTCTGGTTGGCAACATCA |

| Sequence identifier | Sequence |
|---|---|
| | TGCCAGCTGACAAGCGTCACCAGGGGGAGTATGCCGGACAGAACTT
CAAAATGTGGCTGCGCGCAGAGCTGCATTATGATGGCAAGAAAGCC
AAACATCACCTCCCGTTCTATAATGCCAGGTTTTTCGAAGAAGTCTA
TTGTTACCATCCATCTGTCGCTGAAATCACTCCTTTTAAAACCAAAC
AATTCGGCTGCGAGATCGGGAAGGATATTCCGGATTATGTCTCTGT
GGCTCTGAAGGACAATCCCTACAAGAAGGCGACTAAAAGGATTCTA
CGGGCCATCTACAACCCCGTTGCTAACACTACACGAGTGGATAAAA
CAACCAATTGCTCCTTCATGATCAAAAGAGAGAACGACGAGTATAA
ACTGGTCATAAATAGGAAGATCTCGCGAGACCGCCCTAAGAGGATA
GAAGTCGGACGCACCATCATGGGCTATGACCGAAACCAGACCGCGT
CTGACACCTACTGGATCGGTCGGCTTGTGCCTCCTGGGACCAGAGG
AGCTTACAGAATTGGGGAGTGGAGTGTGCAGTATATCAAATCCGGA
CCAGTGCTGTCTTCCACACAGGGTGTTAATAACTCCACAACCGATC
AGCTCGTCTACAACGGTATGCCTTCAAGTAGCGAGCGCTTTAAGGC
GTGGAAGAAGGCCAGAATGGCATTTATCCGCAAACTCATCAGACAA
CTGAATGATGAGGGGTTAGAATCAAAAGGGCAGGACTATATTCCTG
AAAATCCAAGTTCCTTCGACGTGAGGGGGGAAACGTTGTATGTGTT
CAACTCCAATTACCTTAAGGCCCTGGTATCAAAACACAGGAAGGCT
AAGAAGCCTGTGGAAGGCATCCTTGACGAGATCGAAGCCTGGACCT
CCAAAGACAAAGATTCCTGTTCACTGATGCGGCTCTCTAGCCTGAG
TGATGCCTCCATGCAAGGTATAGCCTCACTAAAGAGCCTGATTAAC
TCTTACTTTAATAAAAATGGTTGCAAGACAATAGAGGATAAAGAAA
AATTTAACCCAGTCTTGTATGCAAAACTGGTGGAGGTCGAACAGGA
ACGTACAAACAAACGGAGCGAGAAAGTGGGAAGAATCGCTGGATC
TCTAGAGCAGCTGGCGCTGCTTAACGGCGTCGAAGTGGTTATTGGA
GAGGCAGATCTGGGAGAAGTTGAGAAAGGGAAGTCTAAGAAACAG
AATAGCCGTAACATGGACTGGTGCGCCAAGCAGGTGGCACAGAGA
TTGGAGTACAAGCTGGCTTTTCACGGCATCGGTTACTTTGGCGTTAA
TCCCATGTACACGAGTCACCAGGACCCCTTCGAGCATCGCCGTGTA
GCCGACCATATCGTGATGCGTGCAAGATTTGAGGAAGTTAACGTAG
AGAACATCGCTGAATGGCATGTGAGAAACTTTAGCAATTACCTCCG
CGCCGACAGCGGCACCGGCCTTTACTACAAGCAGGCCACGATGGAC
TTTTTGAAGCATTATGGACTGGAGGAGCACGCCGAGGGCTTGGAAA
ACAAAAAAATTAAGTTCTATGACTTCAGGAAGATTCTTGAAGACAA
AAACCTGACGTCTGTGATCATACCTAAACGCGGAGGGCGCATTTAC
ATGGCTACAAACCCTGTTACTTCCGACAGCACACCCATCACTTACGC
CGGAAAAACCTATAATCGGTGCAATGCAGACGAGGTGGCAGCTGCC
AATATAGTGATCTCCGTCCTGGCACCAAGAAGTAAAAAGAATAGGG
AACAAGACGATATCCCCCTCATAACTAAAAAGGCAGAGTCGAAGTC
TCCCCCAAAGGATCGCAAACGGTCTAAGACCTCACAGTTGCCCCAA
AAG |
| 223 | ATGGCTAGCATCAGCAGACCCTACGGCACCAAGCTGAGACCCGACG
CTAGAAAGAAGGAGATGCTGGACAAGTTTTTCAATACCCTGACCAA
GGGGCAGCGTGTGTTCGCCGACCTGGCCCTGTGCATCTACGGCAGC
CTGACCCTGGAGATGGCCAAGAGCCTGGAGCCCGAGAGCGACAGC
GAACTGGTGTGTGCCATCGGCTGGTTCAGACTGGTGGATAAAACCA
TCTGGAGCAAGGACGGCATCAAGCAAGAGAACCTGGTGAAGCAGT
ACGAGGCCTACAGCGGCAAGGAGGCTAGCGAGGTGGTGAAGACCT
ACCTGAACAGCCCTAGCAGCGACAAGTACGTGTGGATCGACTGCAG
ACAGAAGTTCCTGAGATTTCAGAGAGAGCTGGGCACAAGAAACCTG
AGCGAGGATTTCGAGTGCATGCTGTTCGAGCAGTACATCAGACTGA
CCAAGGGAGAGATCGAGGGCTACGCCGCCATCAGCAACATGTTCGG
CAACGGCGAGAAGGAGGACCGGAGCAAGAAGAGAATGTACGCCAC
AAGAATGAAGGACTGGCTGGAGGCCAACGAGAACATCACCTGGGA
GCAGTACAGAGAGGCCCTGAAGAATCAGCTGAACGCCAAGAACCT
GGGAGCAAGTGGTGGCCAACTACAAGGGCAACGCCGGCGGCGCCGA
CCCCTTCTTCAAGTACAGCTTCAGCAAGGAGGGCATGGTGAGCAAG
AAGGAGCACGCTCAGCAGCTCGATAAGTTCAAAACCGTGCTGAAGA
ACAAGGCTAGAGACCTGAACTTCCCCAACAAGGAGAAGCTGAAGC
AGTACCTGGAGGCCGAGATCGGCATCCCCGTGGACGCCAACGTGTA
CTCTCAGATGTTCAGCAACGGCGTGAGCGAGGTGCAGCCCAAGACC
ACAAGAAACATGAGCTTCAGCAACGAGAAGCTGGACCTGCTGACC
GAGCTGAAGGACCTGAACAAGGGCGACGGCTTCGAGTACGCTAGA
GAGGTGCTGAACGGCTTCTTCGATAGCGAACTGCATACAACCGAGG
ACAAGTTCAACATTACAAGCAGATACCTGGGCGGCGACAAGAGCA
ACAGACTGAGCAAGCTGTACAAGATCTGGAAGAAGGAGGGCGTGG
ACTGCGAGGAGGGCATTCAGCAGTTCTGCGAGGCCGTGAAGGACA
AGATGGGGCAGATCCCCATCAGAAACGTGCTGAAGTACCTGTGGCA
GTTCAGAGAGACCGTGAGCGCCGAAGACTTCGAGGCAGCCGCCAA
AGCCAACCACCTGGAGGAGAAAATTAGCAGAGTGAAAGCCCACCC
CATCGTGATTAGCAATAGATACTGGGCCTTCGGCACAAGCGCCCTG
GTGGGCAACATCATGCCCGCCGACAAGAGACACCAAGGCGAGTAC
GCCGGGCAGAACTTCAAGATGTGGCTGAGAGCCGAGCTGCACTACG
ACGGCAAGAAGGCCAAGCACCACCTGCCCTTCTACAACGCTAGATT
CTTCGAAGAGGTGTACTGCTACCACCCTAGCGTGGCCGAGATCACC |

| Sequence identifier | Sequence |
|---|---|
| | CCCTTCAAGACCAAGCAGTTCGGCTGCGAGATCGGCAAGGACATCC<br>CCGACTACGTGAGCGTGGCCCTGAAGGACAACCCCTACAAGAAGGC<br>CACCAAGAGAATCCTGAGAGCCATCTACAACCCCGTGGCCAACACC<br>ACAAGAGTCGATAAGACCACCAACTGCAGCTTCATGATCAAGAGAG<br>AGAACGACGAGTATAAGCTGGTAATCAACAGAAAAATTTCCCGAG<br>ACAGACCCAAGAGAATCGAGGTCGGCAGAACCATAATGGGCTACG<br>ACAGAAATCAGACCGCTAGCGACACCTACTGGATCGGCAGACTGGT<br>GCCCCCCGGCACAAGAGGCGCCTACAGAATCGGCGAGTGGAGCGT<br>GCAGTACATCAAGAGCGGCCCCGTGCTGAGCAGCACCCAAGGCGTG<br>AACAACAGCACCACCGATCAGCTGGTGTACAACGGCATGCCTAGCA<br>GCAGCGAGAGATTCAAGGCCTGGAAGAAGGCTAGAATGGCCTTCAT<br>CAGAAAGCTGATCAGACAGCTGAACGACGAGGGTCTGGAGAGCAA<br>GGGCCAAGACTACATCCCCGAGAACCCTAGCAGCTTCGACGTGAGA<br>GGCGAGACCCTGTACGTGTTCAACTCCAACTATCTGAAAGCTCTGG<br>TGAGCAAGCACAGAAAGGCCAAGAAGCCCGTGGAGGGCATCCTGG<br>ACGAGATCGAGGCCTGGACAAGCAAGGACAAGGACAGCTGCAGCC<br>TGATGAGACTGAGCAGCCTGAGCGACGCTAGCATGCAAGGCATCGC<br>TAGCCTGAAGAGCCTGATCAACAGCTACTTCAACAAGAACGGCTGC<br>AAGACCATCGAGGACAAGGAGAAGTTCAACCCCGTGCTGTACGCCA<br>AGCTGGTGGAGGTGGAGCAGAGAAGAACCAACAAGAGAAGCGAGA<br>AGGTAGGAAGAATCGCCGGCAGCCTGGAGCAGCTGGCCCTGCTGA<br>ACGGCGTGGAGGTGGTGATCGGCGAGGCCGACCTGGGCGAGGTGG<br>AGAAGGGCAAGAGCAAGAAGCAGAACAGCAGAAACATGGACTGGT<br>GCGCCAAGCAAGTGGCTCAGAGACTGGAGTACAAGCTGGCCTTCCA<br>CGGCATCGGCTACTTCGGCGTGAACCCCATGTACACAAGCCACCAA<br>GACCCCTTCGAGCACAGAAGAGTGGCCGACCACATCGTGATGAGAG<br>CTAGATTCGAGGAAGTAAACGTGGAGAACATCGCCGAGTGGCACGT<br>GAGAAACTTCAGCAACTACCTGCGCGCGGACAGCGGCACCGGCCTG<br>TACTACAAGCAAGCCACCATGGACTTCCTGAAGCACTACGGCCTGG<br>AGGAGCACGCCGAGGGCCTGGAGAACAAGAAGATCAAGTTCTACG<br>ACTTCAGAAAGATCCTGGAGGACAAGAACCTGACAAGCGTGATCAT<br>CCCCAAGAGAGGCGGCAGAATCTACATGGCCACCAACCCCGTGACA<br>AGCGACAGCACCCCCATCACCTACGCCGGCAAGACCTACAACAGAT<br>GCAACGCCGACGAGGTGGCAGCCGCGAATATAGTGATCAGCGTGCT<br>AGCCCCCCGAAGCAAGAAGAACAGAGAGCAAGACGACATCCCCCT<br>GATCACCAAGAAGGCCGAGAGCAAGAGCCCCCCCAAGGACAGAAA<br>GAGAAGCAAGACATCTCAGCTGCCTCAGAAG |
| 224 | ATGGCCAGCATCAGCCGGCCCTACGGCACCAAGCTGCGGCCCGACG<br>CCCGGAAGAAGGAGATGCTGGACAAGTTCTTCAACACCCTGACCAA<br>GGGCCAGCGGGTGTTCGCCGACCTGGCCCTGTGCATCTACGGCAGC<br>CTGACCCTGGAGATGGCCAAGAGCCTGGAGCCCGAGAGCGACAGC<br>GAGCTGGTGTGCGCCATCGGCTGGTTCCGGCTGGTGGACAAGACCA<br>TCTGGAGCAAGGACACGGCATCAAGCAGGAGAACCTGGTGAAGCAGT<br>ACGAGGCCTACAGCGGCAAGGAGGCCAGCGAGGTGGTGAAGACCT<br>ACCTGAACAGCCCCAGCAGCGACAAGTACGTGTGGATCGACTGCCG<br>GCAGAAGTTCCTGCGGTTCCAGCGGGAGCTGGGCACCCGGAACCTG<br>AGCGAGGACTTCGAGTGCATGCTGTTCGAGCAGTACATCCGGCTGA<br>CCAAGGGCGAGATCGAGGGCTACGCCGCCATCAGCAACATGTTCGG<br>CAACGGCGAGAAGGAGGACCGGAGCAAGAAGCGGATGTACGCCAC<br>CCGGATGAAGGACTGGCTGGAGGCCAACGAGAACATCACCTGGGA<br>GCAGTACCGGGAGGCCCTGAAGAACCAGCTGAACGCCAAGAACCTT<br>GGGAGCAGGTGGTGGCCAACTACAAGGGCAACGCCGGCGGCGCCGA<br>CCCCTTCTTCAAGTACAGCTTCAGCAAGGAGGGCATGGTGAGCAAG<br>AAGGAGCACGCCCAGCAGCTGGACAAGTTCAAGACCGTGCTGAAG<br>AACAAGGCCCGGGACCTGAACTTCCCCAACAAGGAGAAGCTGAAG<br>CAGTACCTGGAGGCCGAGATCGGCATCCCCGTGGACGCCAACGTGT<br>ACAGCCAGATGTTCAGCAACGGCGTGAGCGAGGTGCAGCCCAAGA<br>CCACCCGGAACATGAGCTTCAGCAACGAGAAGCTGGACCTGCTGAC<br>CGAGCTGAAGGACCTGAACAAGGGCGACGGCTTCGAGTACGCCCG<br>GGAGGTGCTGAACGGCTTCTTCGACAGCGAGCTGCACACCACCGAG<br>GACAAGTTCAACATCACCAGCCGGTACCTGGGCGGCGACAAGAGC<br>AACCGGCTGAGCAAGCTGTACAAGATCTGGAAGAAGGAGGGCGTG<br>GACTGCGAGGAGGGCATCCAGCAGTTCTGCGAGGCCGTGAAGGAC<br>AAGATGGGCCAGATCCCCATCCGGAACGTGCTGAAGTACCTGTGGC<br>AGTTCCGGGAGACCGTGAGCGCCGAGGACTTCGAGGCCGCCGCCAA<br>GGCCAACCACCTGGAGGAGAAGATCAGCCGGGTGAAGGCCCACCC<br>CATCGTGATCAGCAACCGGTACTGGGCCTTCGGCACCAGCGCCCTG<br>GTGGGCAACATCATGCCCGCCGACAAGCGGCACCAGGGCGAGTAC<br>GCCGGCCAGAACTTCAAGATGTGGCTGCGGGCCGAGCTGCACTACG<br>ACGGCAAGAAGGCCAAGCACCACCTGCCCTTCTACAACGCCCGGTT<br>CTTCGAGGAGGTGTACTGCTACCACCCCAGCGTGGCCGAGATCACC<br>CCCTTCAAGACCAAGCAGTTCGGCTGCGAGATCGGCAAGGACATCC<br>CCGACTACGTGAGCGTGGCCCTGAAGGACAACCCCTACAAGAAGGC<br>CACCAAGCGGATCCTGCGGGCCATCTACAACCCCGTGGCCAACACC<br>ACCCGGGTGGACAAGACCACCAACTGCAGCTTCATGATCAAGCGGG |

| Sequence identifier | Sequence |
|---|---|
| | AGAACGACGAGTACAAGCTGGTGATCAACCGGAAGATCAGCCGGG<br>ACCGGCCCAAGCGGATCGAGGTGGGCCGGACCATCATGGGCTACG<br>ACCGGAACCAGACCGCCAGCGACACCTACTGGATCGGCCGGCTGGT<br>GCCCCCCGGCACCCGGGGCGCCTACCGGATCGGCGAGTGGAGCGTG<br>CAGTACATCAAGAGCGGCCCCGTGCTGAGCAGCACCCAGGGCGTGA<br>ACAACAGCACCACCGACCAGCTGGTGTACAACGGCATGCCCAGCAG<br>CAGCGAGCGGTTCAAGGCCTGGAAGAAGGCCCGGATGGCCTTCATC<br>CGGAAGCTGATCCGGCAGCTGAACGACGAGGGCCTGGAGAGCAAG<br>GGCCAGGACTACATCCCCGAGAACCCCAGCAGCTTCGACGTGCGGG<br>GCGAGACCCTGTACGTGTTCAACAGCAACTACCTGAAGGCCCTGGT<br>GAGCAAGCACCGGAAGGCCAAGAAGCCCGTGGAGGGCATCCTGGA<br>CGAGATCGAGGCCTGGACCAGCAAGGACAAGGACAGCTGCAGCCT<br>GATGCGGCTGAGCAGCCTGAGCGACGCCAGCATGCAGGGCATCGCC<br>AGCCTGAAGAGCCTGATCAACAGCTACTTCAACAAGAACGGCTGCA<br>AGACCATCGAGGACAAGGAGAAGTTCAACCCCGTGCTGTACGCCAA<br>GCTGGTGGAGGTGGAGCAGCGGCGGACCAACAAGCGGAGCGAGAA<br>GGTGGGCCGGATCGCCGGCAGCCTGGAGCAGCTGGCCCTGCTGAAC<br>GGCGTGGAGGTGGTGATCGGCGAGGCCGACCTGGGCGAGGTGGAG<br>AAGGGCAAGAGCAAGAAGCAGAACAGCCGGAACATGGACTGGTGC<br>GCCAAGCAGGTGGCCCAGCGGCTGGAGTACAAGCTGGCCTTCCACG<br>GCATCGGCTACTTCGGCGTGAACCCCATGTACACCAGCCACCAGGA<br>CCCCTTCGAGCACCGGCGGGTGGCCGACCACATCGTGATGCGGGCC<br>CGGTTCGAGGAGGTGAACGTGGAGAACATCGCCGAGTGGCACGTG<br>CGGAACTTCAGCAACTACCTGCGGGCCGACAGCGGCACCGGCCTGT<br>ACTACAAGCAGGCCACCATGGACTTCCTGAAGCACTACGGCCTGGA<br>GGAGCACGCCGAGGGCCTGGAGAACAAGAAGATCAAGTTCTACGA<br>CTTCCGGAAGATCCTGGAGGACAAGAACCTGACCAGCGTGATCATC<br>CCCAAGCGGGGCGGCCGGATCTACATGGCCACCAACCCCGTGACCA<br>GCGACAGCACCCCCATCACCTACGCCGGCAAGACCTACAACCGGTG<br>CAACGCCGACGAGGTGGCCGCCGCCAACATCGTGATCAGCGTGCTG<br>GCCCCCCCGGAGCAAGAAGAACCGGGAGCAGGACGACATCCCCCTG<br>ATCACCAAGAAGGCCGAGAGCAAGAGCCCCCCCAAGGACCGGAAG<br>CGGAGCAAGACCAGCCAGCTGCCCCAGAAG |
| 225 | ATGGCCTCAATAAGTCGGCCGTACGGAACAAAACTCAGACCAGATG<br>CCAGGAAAAAGGAAATGCTCGATAAATTCTTCAATACCCTGACAAA<br>AGGACAGCGAGTCTTTGCGGATCTTGCGCTCTGTATTTATGGTTCAC<br>TGACACTGGAGATGGCGAAGTCACTCGAGCCAGAATCAGATAGTGA<br>ACTTGTATGTGCCATCGGCTGGTTTAGATTGGTGGACAAGACTATAT<br>GGAGCAAGGATGGCATCAAGCAAGAAAACTTGGTCAAGCAGTACG<br>AGGCGTATAGTGGTAAAGAGGCGTCAGAGGTCGTGAAAACGTATCT<br>TAACAGTCCTAGTTCAGACAAGTATGTCTGGATAGACTGTCGCCAA<br>AAGTTTCTTCGCTTCCAGCGGGAACTCGGGACCCGAAATCTTAGTG<br>AGGACTTTGAGTGCATGTTGTTCGAACAATATATCCGGCTGACTAA<br>AGGTGAGATCGAGGGATACGCCGCAATTAGTAACATGTTCGGAAAC<br>GGAGAAAAAGAGGATAGGTCTAAGAAGCGGATGTACGCGACACGA<br>ATGAAGGATTGGCTGGAAGCAAATGAGAACATCACCTGGGAGCAG<br>TATAGGGAGGCTTTGAAAAATCAACTGAATGCTAAAAACTTGGAGC<br>AAGTCGTCGCAAATTATAAGGGAAACGCAGGTGGCGCCGACCCATT<br>CTTTAAGTATAGCTTCAGTAAGGAAGGAATGGTTTCAAAGAAAGAG<br>CACGCCCAGCAGCTTGATAAGTTCAAGACCGTACTGAAAAATAAAG<br>CGCGGGACCTCAATTTCCCTAATAAGGAAAAATTGAAGCAATACTT<br>GGAGGCTGAGATTGGTATACCGGTAGATGCAAATGTCTATAGCCAA<br>ATGTTTAGTAACGGTGTGAGTGAGGTACAACCAAAGACAACGCGAA<br>ATATGAGTTTTTCAAATGAGAAGTTGGATCTTTTGACGGAATTGAA<br>GGATCTTAACAAGGGTGACGGCTTCGAGTACGCTCGGGAAGTCTTG<br>AACGGTTTTTTTGATTCCGAGTTGCACACCACTGAGGACAAGTTTAA<br>CATCACCAGTCGATACCTGGGGGGCGATAAATCTAACAGGCTCAGT<br>AAACTCTACAAGATATGGAAGAAAGAAGGAGTCGATTGCGAGGAA<br>GGTATCCAACAGTTCTGCGAAGCTGTGAAGGACAAAATGGGACAA<br>ATCCCCATAAGGAATGTGCTTAAATATCTTTGGCAGTTCCGCGAAA<br>CAGTCCAGTGCAGAAGACTTCGAAGCTGCAGCCAAAGCCAACCACCT<br>CGAAGAGAAAATCAGCAGAGTAAAAGCGCATCCTATCGTCATAAGT<br>AATCGCTACTGGGCGTTTGGTACTTCTGCGCTCGTTGGGAATATCAT<br>GCCGGCAGACAAAAGACACCAAGGGGAGTACGCTGGGCAAAATTT<br>CAAAATGTGGCTCAGGGCGGAGCTCCATTATGATGGAAAGAAAGC<br>AAAGCATCATCTGCCTTTTTATAACGCGCGGTTCTTTGAAGAAGTCT<br>ACTGTTATCATCCAAGCGTAGCTGAAATAACGCCCTTTAAAACTAA<br>ACAGTTTGGGTGCGAAATAGGGAAAGATATTCCCGATTATGTGTCC<br>GTGGCGCTGAAAGATAATCCATACAAAAAGGCTACGAAGCGGATC<br>CTGCGCGCCATTTATAATCCCGTCGCGAACACCACCCGCGTGGATA<br>AGACAACTAATTGTTCCTTTATGATAAAGCGCGAAAACGATGAGTA<br>TAAACTGGTCATTAACCGCAAGATCTCTCGAGACAGGCCAAAACGC<br>ATAGAGGTAGGCCGAACCATTATGGGTTATGACAGGAATCAGACCG<br>CCTCTGATACATATTGGATTGGGAGGCTCGTGCCTCCTGGTACGAG<br>GGGCGCTTACCGCATTGGAGAATGGTCAGTGCAGTACATCAAGTCC |

| Sequence identifier | Sequence |
|---|---|
| | GGGCCCGTGCTTAGTTCTACCCAAGGGGTTAATAACTCAACTACGG<br>ACCAACTGGTGTATAACGGAATGCCAAGTAGTTCCGAACGGTTTAA<br>AGCATGGAAGAAGGCTAGAATGGCGTTTATACGGAAACTCATACGA<br>CAATTGAATGATGAGGGACTTGAGAGCAAGGGTCAAGATTACATCC<br>CAGAGAATCCAAGCTCTTTTGACGTCAGGGGTGAGACACTGTATGT<br>TTTCAATAGCAACTATTTGAAAGCACTCGTTTCTAAACACCGGAAG<br>GCCAAAAAACCTGTGGAAGGGATACTCGACGAGATTGAAGCCTGG<br>ACTTCTAAAGATAAAGATAGTTGTTCCCTTATGCGGCTCTCTAGCTT<br>GAGCGATGCGTCAATGCAAGGGATTGCCTCTTTGAAAAGTCTCATC<br>AACAGCTACTTCAATAAGAACGGTTGCAAGACGATCGAGGATAAG<br>GAGAAGTTCAATCCTGTTTTGTATGCCAAATTGGTAGAAGTGGAGC<br>AGAGAAGAACTAACAAGAGATCTGAGAAGGTAGGCAGGATTGCCG<br>GATCCCTTGAACAGCTGGCACTCCTTAATGGGGTCGAAGTGGTCAT<br>TGGTGAAGCCGACCTTGGCGAAGTCGAAAAGGGCAAGTCCAAGAA<br>GCAGAACAGTCGCAACATGGATTGGTGCGCAAAACAGGTAGCACA<br>AAGGCTCGAATATAAGCTCGCCTTCCACGGCATTGGGTACTTCGGC<br>GTTAACCCAATGTACACCAGTCACCAAGACCCCTTTGAGCATAGAA<br>GAGTAGCAGATCATATAGTGATGAGGGCCAGATTCGAAGAAGTGA<br>ACGTCGAGAATATCGCAGAATGGCACGTAAGGAATTTCTCCAATTA<br>TCTGCGCGCTGATTCTGGTACAGGCCTCTACTACAAGCAGGCCACC<br>ATGGATTTTCTGAAACATTACGGGCTCGAGGAGCACGCCGAAGGTC<br>TGGAGAATAAGAAGATTAAGTTTTATGACTTCCGAAAGATTCTGGA<br>GGACAAGAATCTTACCTCCGTGATCATCCCAAAGCGAGGGGGACGC<br>ATCTATATGGCTACCAATCCCGTGACTAGCGACAGCACTCCAATAA<br>CGTATGCCGGCAAAACCTACAATCGCTGTAACGCTGACGAGGTGGC<br>TGCCGCCAATATAGTCATATCCGTGCTTGCTCCCCGAAGTAAAAAG<br>AATCGGGAGCAAGACGATATTCCTTTGATAACGAAAAAAAGCCGAG<br>AGTAAATCTCCACCCAAAGATCGGAAGAGATCAAAGACCTCACAAC<br>TCCCGCAAAAG |
| 226 | ATGGCATCTATCAGCAGACCATACGGAACCAAACTGAGACCAGATG<br>CTCGGAAAAAGGAGATGCTGGACAAGTTCTTCAACACCCTGACCAA<br>GGGACAGAGGGTGTTCGCCGATCTGGCCCTGTGCATCTACGGCTCT<br>CTGACCCTGGAAATGGCTAAGTCGCTCGAACCTGAGAGCGACTCCG<br>AGCTGGTTTGTGCCATTGGATGGTTCAGACTGGTCGATAAGACCAT<br>CTGGAGCAAGGACGGCATCAAGCAGGAGAACCTGGTGAAACAGTA<br>CGAGGCCTACAGCGGCAAGGAGGCGTCTGAAGTCGTGAAGACCTA<br>CCTGAACAGCCCTTCTAGTGATAAGTACGTGTGGATCGACTGTAGA<br>CAGAAGTTCCTGAGATTTCAGCGGGAACTGGGCACCAGAAACCTGA<br>GCGAGGACTTTGAATGCATGCTGTTCGAGCAGTACATCGACTGAC<br>CAAGGGCGAAATCGAGGGATATGCCGCCATTAGCAACATGTTCGGC<br>AACGGCGAGAAGAGGATAGAAGCAAGAAGAGAATGTACGCTACA<br>CGGATGAAGGACTGGCTGGAGGCCAACGAGAACATCACCTGGGAG<br>CAGTATAGAGAAGCCCTGAAGAACCAGCTGAACGCCAAGAACCTC<br>GAGCAGGTGGTGGCTAACTACAAGGGCAACGCCGGCGGCGCCGAT<br>CCTTTCTTCAAGTACTCCTTCAGCAAGGAGGGCATGGTGTCCAAGA<br>AGGAGCATGCCCAGCAACTGGACAAATTCAAGACAGTGCTGAAGA<br>ACAAGGCCCGGGATCTGAACTTCCCCAACAAGGAGAAGCTCAAAC<br>AGTACCTGGAAGCCGAGATCGGCATCCCCGTCGACGCCAATGTGTA<br>CTCTCAGATGTTCTCCAACGGCGTGTCTGAAGTGCAACCTAAGACA<br>ACAAGAAATATGAGCTTTAGCAATGAGAAGCTGGACCTGCTGACAG<br>AACTGAAAGATCTGAACAAAGGCGATGGGTTCGAATACGCCCGCG<br>AAGTGCTGAACGGGTTCTTTGATTCTGAGCTGCACACGACAGAAGA<br>TAAGTTCAATATCACCTCGCGGTACCTGGGAGGCGACAAGAGCAAT<br>AGACTGAGCAAGCTGTATAAGATCTGGAAGAAGGAGGGCGTGGAC<br>TGCGAGGAGGGCATCCAACAGTTCTGCGAGGCTGTGAAGGATAAG<br>ATGGGCCAAATCCCTATCAGGAACGTTCTCAAGTACCTGTGGCAGT<br>TCAGAGAAACCGTGAGCGCCGAGGATTTCGAGGCCGCCGCTAAGGC<br>CAACCACCTGGAGGAGAAGATCAGCAGAGTGAAGGCCCACCCTAT<br>CGTGATCAGCAACAGATACTGGGCCTTCGGCACCTCTGCTCTGGTC<br>GGAAATATCATGCCCGCCGATAAGCGGCACCAGGGCGAGTACGCC<br>GGCCAGAACTTCAAGATGTGGCTGCGGGCCGAACTTCATTACGACG<br>GCAAAAAGGCTAAACACCACCTGCCTTTCTACAACGCCAGATTCTT<br>CGAGGAGGTGTACTGCTACCACCCCAGCGTGGCCGAAATCACACCT<br>TTCAAGACTAAGCAGTTTGGATGTGAAATCGGTAAGGATATCCCCG<br>ACTACGTCAGCGTGGCACTGAAAGACAACCCTTACAAAAAAGCTAC<br>CAAACGGATTCTGAGAGCCATCTACAACCCCGTTGCCAATACCACA<br>AGAGTGGACAAAACAACCAACTGCTCTTTCATGATCAAAAGAGAGA<br>ATGACGAATACAAGCTGGTAATAAACAGAAAGATCAGCAGAGACC<br>GGCCTAAGCGCATCGAGGTGGGAAGAACCATTATGGGCTACGATAG<br>AAACCAGACCGCCAGCGATACCTACTGGATCGGCAGACTGGTGCCC<br>CCTGGCACAAGAGGCGCCTACAGAATCGGCGAATGGTCCGTGCAGT<br>ACATCAAGAGCGGCCCTGTGCTGAGCTCTACCCAGGGAGTGAACAA<br>CAGCACCACCGATCAGCTGGTGTACAACGGTATGCCTAGCAGCAGC<br>GAGCGGTTCAAGGCATGGAAGAAGGCCCGGATGGCCTTCATCCGGA<br>AGCTGATCAGACAGCTGAATGACGAGGGCCTGGAAAGCAAGGGAC |

| Sequence identifier | Sequence |
|---|---|
|  | AGGACTACATCCCAGAGAACCCTAGCAGCTTCGACGTGCGGGGCGA<br>GACGCTGTACGTGTTCAACAGCAACTATCTGAAAGCCCTGGTCAGC<br>AAGCACAGAAAGGCCAAGAAGCCCGTGGAAGGTATCCTGGATGAG<br>ATCGAGGCCTGGACCAGCAAGGACAAGGACAGCTGCAGCCTGATG<br>CGGCTGTCTTCTCTGAGCGACGCCTCCATGCAGGGCATCGCCAGCCT<br>GAAAAGCCTAATCAACAGCTACTTTAACAAGAACGGCTGCAAGACA<br>ATCGAGGACAAGGAAAAGTTTAACCCTGTGCTGTATGCCAAACTGG<br>TGGAGGTGGAACAGCGGCGGACCAACAAGCGGAGCGAAAAAGTGG<br>GCAGAATCGCCGGAAGCCTGGAGCAGCTTGCCCTGCTGAATGGCGT<br>GGAAGTGGTGATAGGCGAGGCCGACCTGGGCGAAGTGGAGAAGGG<br>CAAGAGCAAGAAGCAGAACTCCAGAAACATGGACTGGTGCGCCAA<br>ACAGGTGGCCCAGAGACTGGAATATAAGCTGGCTTTTCACGGCATC<br>GGCTACTTCGGCGTTAATCCTATGTACACCAGCCACCAGGACCCCTT<br>CGAGCACCGGAGAGTGGCCGACCACATAGTGATGAGAGCCCGGTTC<br>GAGGAAGTGAACGTGGAGAACATCGCCGAGTGGCACGTGCGGAAT<br>TTTTCTAATTACCTGAGAGCCGACAGCGGAACAGGCCTGTACTACA<br>AGCAGGCCACAATGGACTTCCTGAAGCACTACGGCCTGGAAGAGCA<br>CGCCGAGGGCCTGGAAAACAAGAAGATCAAGTTCTACGACTTCCGG<br>AAAATCCTGGAGGATAAGAACCTCACCTCTGTCATCATCCCTAAGC<br>GAGGCGGAAGAATCTACATGGCCACAAACCCAGTGACCAGCGACT<br>CCACCCCTATCACCTACGCCGGCAAGACATACAACAGGTGTAACGC<br>CGACGAAGTGGCCGCTGCCAACATCGTGATCTCTGTGCTGGCTCCT<br>AGATCAAAGAAGAATAGAGAACAAGACGACATTCCCTGATCACA<br>AAGAAAGCAGAGAGCAAGTCCCCACCTAAGGACAGAAAGAGAAGC<br>AAAACCTCCCAGTTGCCTCAAAAA |
| 227 | ATGGCCTCAATCTCTAGGCCATATGGGACCAAATTGAGACCTGATG<br>CTCGAAAAAAGGAGATGCTGGATAAGTTTTTCAACACACTTACCAA<br>AGGCCAGAGAGTATTCGCTGACCTGGCTCTGTGTATCTATGGCTCTC<br>TGACCCTGGAGATGGCCAAATCTCTGGAGCCTGAGAGCGATTCCGA<br>ACTTGTGTGCGCTATTGGTTGGTTCAGGCTGGTTGACAAACAATCT<br>GGTCTAAAGATGGAATTAAGCAGGAAAACCTGGTGAAGCAATATG<br>AGGCATATTCAGGAAAAGAGGCTTCCGAGGTGGTTAAGACTTACCT<br>TAACTCACCATCAAGTGATAAGTACGTCTGGATCGACTGTAGGCAG<br>AAATTTCTGCGCTTTCAGAGGGAACTCGGCACTCGCAATCTGTCCG<br>AAGATTTTGAGTGCATGCTGTTTGAACAGTATATCCGCCTCACAAA<br>GGGCGAAATTGAGGGTTACGCTGCAATCTCCAACATGTTCGGTAAT<br>GGCGAGAAGGAAGATAGGTCCAAGAAGCGCATGTACGCAACACGA<br>ATGAAAGACTGGCTCGAAGCCAACGAGAATATTACATGGGAGCAG<br>TACCGGGAAGCTCTGAAGAATCAACTCAATGCGAAAAACCTGGAAC<br>AGGTGGTTGCGAATTACAAAGGGAATGCTGGTGGTGCTGACCCCTT<br>CTTTAAATACTCCTTCTCAAAGGAGGGTATGGTTTCAAAGAAAGAG<br>CATGCTCAGCAGCTCGACAAGTTCAAGACAGTGTTGAAGAATAAGG<br>CCAGGGATTTGAACTTCCCAAACAAAGAAAAGCTGAAGCAATACCT<br>GGAAGCTGAGATTGGCATTCCCGTTGATGCTAACGTGTACAGCCAA<br>ATGTTCTCCAATGGCGTCAGTGAGGTCCAACCGAAAACAACAAGAA<br>ACATGTCCTTCTCTAACGAGAAGCTCGATTTGTTGACTGAATTGAAG<br>GATCTGAACAAAGGAGACGGCTTCGAATATGCTCGGGAAGTGTTGA<br>ACGGCTTTTTCGACAGCGAGTTGCACACTACTGAAGATAAATTCAA<br>CATCACCTCTAGGTATCTCGGCGGGATAAGAGCAATAGACTCTCT<br>AAGTTGTACAAGATATGGAAAAAGGAGGGCGTGGATTGTGAGGAG<br>GGAATCCAGCAGTTCTGTGAGGCCGTGAAGGACAAGATGGGTCAA<br>ATCCCTATCCGGAACGTGCTGAAGTACCTGTGGCAATTCCGAGAGA<br>CGGTGTCCGCTGAAGATTTTGAGGCCGCTGCCAAAGCAAATCACCT<br>GGAGGAGAAGATAAGTAGGGTGAAGGCACACCCCATCGTGATTAG<br>TAACAGATATTGGGCATTTGGAACCTCAGCGTTGGTTGGAAACATT<br>ATGCCCGCTGATAAAAGACATCAAGGAGAGTATGCCGGGCAGAATT<br>TCAAAATGTGGCTCCGCGCAGAACTCCACTATGACGGGAAAAAGGC<br>CAAGCATCACTTGCCATTTTACAACGCCCGCTTCTTCGAGGAGGTCT<br>ATTGCTACCACCCCTCCGTCGCAGAGATCACACCATTTAAAACCAA<br>ACAGTTTGGTTGCGAGATCGGGAAGGACATTCCAGATTACGTAAGC<br>GTCGCACTTAAAGACAATCCTTACAAGAAGGCGACAAAAAGGATCC<br>TCAGAGCCATTTATAACCCCGTGGCCAACACCACAAGGGTGGACAA<br>GACTACCAACTGTTCCTTCATGATTAAGCGGGAGAACGACGAGTAC<br>AAATTGGTGATTAACCGCAAGATTAGCAGAGACAGACCAAAAAGG<br>ATTGAAGTAGGACGGACCATCATGGGGTATGATCGGAATCAGACTG<br>CCAGCGATACATACTGGATCGGAAGATTGGTGCCACCTGGTACCAG<br>GGGAGCATACCGGATCGGAGAGTGGTCTGTACAGTACATTAAATCT<br>GGCCCCGTGCTTTCCTCTACCCAGGGCGTTAACAACTCTACTACAGA<br>CCAGCTCGTTTACAACGGAATGCCAAGTTCTTCCGAAAGATTTAAG<br>GCCTGGAAAAAGGCCCGGATGGCCTTCATCCGAAAGCTGATCCGCC<br>AGCTGAATGACGAAGGGTTGGAATCTAAGGGCCAGGACTACATTCC<br>TGAGAATCCTAGCAGTTTTGATGTTCGCGGAGAGACGCTGTACGTG<br>TTTAATTCTAACTATCTTAAAGCCCTCGTGAGTAAGCATAGGAAGG<br>CTAAAAAACCAGTCGAAGGTATATTGGACGAAATCGAAGCATGGA<br>CCAGCAAGGACAAAGACTCTTGTTCTCTGATGCGACTGTCCAGCTT |

| Sequence identifier | Sequence |
|---|---|
| | GAGCGATGCTTCCATGCAGGGCATTGCAAGCCTGAAAAGTCTTATT<br>AACAGCTACTTCAACAAAAATGGGTGCAAAACTATCGAGGACAAA<br>GAGAAGTTCAACCCCGTGCTCTATGCAAAGTTGGTTGAAGTGGAGC<br>AGCGACGGACAAATAAACGGAGTGAGAAGGTCGGACGGATTGCTG<br>GGAGCCTCGAACAATTGGCCCTGTTGAATGGGGTGGAGGTGGTGAT<br>CGGGGAAGCAGACCTTGGAGAAGTAGAGAAGGGCAAAAGTAAAAA<br>GCAGAATTCCCGAAATATGGATTGGTGTGCCAAACAGGTGGCTCAG<br>AGGCTGGAGTATAAACTCGCCTTTCATGGTATCGGGTATTTCGGCGT<br>GAATCCTATGTACACCAGTCATCAGGACCCGTTTGAACACAGGAGG<br>GTCGCTGACCATATTGTGATGAGAGCCAGGTTTGAAGAAGTCAATG<br>TAGAGAACATCGCCGAATGGCACGTGCGAAATTTCTCAAACTATCT<br>CCGGGCCGACTCCGGAACGGGTCTTTATTACAAACAAGCTACCATG<br>GATTTCCTGAAGCATTACGGCCTGGAAGAGCATGCCGAGGGTCTGG<br>AAAACAAGAAGATAAAATTCTACGATTTCCGGAAGATCCTCGAGGA<br>CAAGAACCTGACCTCCGTCATCATTCCCAAACGGGGTGGACGAATC<br>TACATGGCCACAAATCCCGTTACGTCCGACAGCACCCCTATTACAT<br>ACGCCGGCAAGACCTATAACCGGTGCAACGCAGATGAAGTCGCCGC<br>TGCAAATATAGTTATCTCCGTTCTGGCCCCGAGGTCCAAGAAAAAC<br>AGAGAACAGGACGACATCCCCCTGATTACCAAAAAAGCTGAGTCA<br>AAATCTCCGCCCAAAGACAGGAAGCGGAGCAAGACCTCCCAGCTG<br>CCCCAGAAG |
| 228 | ATGGCTTCAATTTCCCGCCCCTATGGCACTAAGCTGCGCCCTGACGC<br>CCGGAAAAAGGAGATGCTGGACAAGTTTTTTAATACACTGACCAAG<br>GGACAGCGCGTGTTCGCCGACCTGGCCCTGTGTATCTACGGCTCTCT<br>GACGCTGGAGATGGCTAAGTCCCTGGAGCCCGAGTCTGACTCTGAG<br>CTGGTGTGCGCTATCGGGTGGTTCAGACTGGTGGATAAGACCATCT<br>GGTCTAAAGATGGCATTAAGCAGGAGAACCTGGTGAAGCAATACG<br>AGGCCTACTCAGGGAAGGAGGCCAGCGAAGTGGTGAAAACCTACC<br>TCAATAGCCCAAGCAGCGACAAGTACGTGTGGATTGATTGCCGCCA<br>GAAGTTTCTCCGCTTCCAGCGGGAGCTGGGGACTAGGAATCTGAGC<br>GAAGATTTTGAGTGCATGCTGTTTGAACAGTACATCCGGCTGACTA<br>AAGGGGAGATCGAGGGCTATGCCGCCATCAGCAACATGTTTGGCAA<br>CGGGGAGAAAGAGGACAGAAGTAAAAAACGGATGTATGCAACCCG<br>CATGAAGGACTGGCTGGAAGCCAATGAGAACATCACCTGGGAACA<br>GTATCGCGAAGCTCTGAAGAACCAGCTGAATGCCAAGAATCTGGAA<br>CAGGTGGTGGCCAATTACAAAGGGAACGCCGGGGGGCCGATCCCT<br>TCTTCAAATACTCTTTCAGTAAGGAAGGCATGGTGAGTAAGAAGGA<br>GCACGCCCAGCAGCTGGATAAGTTTAAAACGGTGCTCAAGAACAAG<br>GCCAGGGACCTGAACTTTCCCAATAAGGAGAAGCTGAAGCAGTACC<br>TGGAGGCCGAGATCGGCATCCCCGTGGACGCGAACGTGTACTCCCA<br>GATGTTCAGCAATGGAGTGAGCGAGGTGCAGCCCAAGACCACCCG<br>GAACATGAGCTTTTCTAACGAAAAACTGGACCTGCTGACCGAGCTG<br>AAGGACCTGAATAAGGGCGACGGATTTGAGTACGCACGGGAAGTG<br>CTGAATGGCTTCTTTGATAGCGAGCTGCACACCACAGAGGATAAGT<br>TCAATATCACCTCCAGGTACCTGGGAGGCGATAAGAGCAACAGACT<br>CTCTAAGCTGTATAAGATTTGGAAGAAGGAAGGGGTGGACTGCGAG<br>GAGGGCATCCAGCAGTTCTGCGAGGCCGTGAAGGACAAGATGGGC<br>CAGATCCCTATCAGAAACGTGCTGAAGTATCTGTGGCAGTTCCGCG<br>AGACCGTGAGCGCCGAGGACTTTGAGGCCGCCGCTAAGGCTAACCA<br>CCTGGAAGAAAAGATCTCCCGGGTGAAAGCCCACCCTATTGTGATC<br>TCCAATAGATACTGGGCCTTCGGAACTTCTGCCCTGGTGGGAAATA<br>TCATGCCCGCCGACAAAAGACACCAGGGGGAGTATGCTGGCCAGA<br>ACTTCAAGATGTGGCTTAGGGCCGAGCTGCACTATGATGGCAAGAA<br>GGCCAAGCATCACCTGCCTTTCTACAATGCTAGATTCTTTGAAGAGG<br>TGTACTGTTACCACCCTAGCGTGGCCGAGATCACCCCCTTTAAGACT<br>AAACAGTTTGGCTGTGAGATTGGCAAGGACATCCCCGATTACGTGA<br>GCGTGGCTCTGAAGGACAACCCATATAAGAAAGCCACCAAACGCAT<br>CCTCCGGGCTATCTATAACCCCGTGGCCAATACTACCCGGGTGGAC<br>AAGACAACCAACTGTAGCTTCATGATCAAAAGAGAGAACGACGAG<br>TATAAGCTGGTGATCAACAGAAAAATCTCCCGGGACCGCCCCAAAA<br>GGATTGAGGTGGGACGCACCATTATGGGATACGATAGGAACCAGA<br>CCGCCTCAGACACCTACTGGATCGGCCGGCTGGTGCCTCCTGGCAC<br>TAGGGGGGCCTACCGCATCGGCGAATGGTCCGTGCAGTACATTAAA<br>TCCGGCCCCGTGCTGAGCTCCACACAGGGAGTGAATAATTCCACCA<br>CCGACCAGCTGGTGTACAACGGCATGCCCAGCAGCAGCGAGCGGTT<br>CAAGGCCTGGAAGAAGGCCCGGATGGCTTTTATACGGAAGCTGATC<br>CGCCAGCTGAACGATGAGGGCCTGGAATCCAAGGGCCAGGACTAC<br>ATTCCCGAAACCCTTCATCCTTCGACGTGAGAGGCGAAACTCTGT<br>ACGTGTTCAATTCCAACTACCTCAAGGCCCTGGTGTCTAAGCACAG<br>GAAGGCCAAGAAGCCCGTGGAAGGCATCCTGGACGAGATTGAGGC<br>ATGGACCAGCAAGGACAAGGATAGCTGTTCTCTCATGAGACTGAGC<br>AGCCTGTCCGATGCAAGCATGCAGGGGATCGCCTCCCTGAAGAGCC<br>TGATTAACTCTTACTTTAACAAAAATGGCTGCAAGACCATCGAGGA<br>TAAAGAGAAGTTTAATCCCGTGCTGTACGCAAAACTCGTGGAGGTG<br>GAGCAGAGGCGCACCAACAAGAGGAGCGAGAAAGTGGGGCGGATC |

| Sequence identifier | Sequence |
|---|---|
| | GCTGGAAGTCTGGAACAGCTGGCCCTGCTGAACGGCGTGGAGGTCG<br>TGATTGGCGAAGCGGACCTGGGCGAGGTGGAGAAGGGGAAGTCTA<br>AGAAGCAGAACTCTAGGAATATGGACTGGTGCGCCAAGCAGGTGG<br>CCCAGAGACTGGAATACAAACTGGCCTTTCATGGCATTGGATACTT<br>CGGCGTGAATCCTATGTACACATCACACCAGGATCCATTCGAGCAC<br>AGGAGAGTGGCCGACCACATCGTGATGAGAGCCAGATTCGAGGAG<br>GTGAACGTGGAGAACATCGCAGAGTGGCACGTGAGGAACTTTTCCA<br>ACTATCTGCGGGCCGACTCTGGGACTGGACTGTATTACAAGCAGGC<br>CACCATGGACTTCCTGAAGCACTATGGCCTGGAGGAGCACGCTGAA<br>GGGCTGGAAAACAAGAAAATAAAGTTTTACGACTTCCGGAAGATTC<br>TGGAGGATAAGAACCTGACCTCTGTTATCATCCCAAAGCGGGGCGG<br>CAGAATCTACATGGCCACCAACCCCGTGACCTCCGACAGCACCCCC<br>ATTACCTACGCCGGAAAGACATACAACGATGCAATGCTGACGAGG<br>TGGCCGCCGCCAACATAGTGATTTCCGTGCTGGCCCCAAGGAGTAA<br>GAAGAACCGAGAGCAGGACGACATTCCACTGATTACCAAGAAGGC<br>TGAATCCAAATCCCCACCAAAGGACAGGAAGAGGAGCAAGACCTC<br>TCAGCTGCCTCAGAAG |

EXAMPLES

The following examples are provided to further illustrate some embodiments of the present invention but are not intended to limit the scope of the invention; it will be understood by their exemplary nature that other procedures, methodologies, or techniques known to those skilled in the art may alternatively be used.

Example 1—Preparation of Variant Constructs

In this Example, variant constructs were generated.

DNA templates comprising single mutations were constructed via two PCR steps using mutagenic forward and mutagenic reverse primers ordered from IDT™ (Integrated DNA Technologies, Inc.). In the first step, two sets of PCR reactions were conducted in 384 plates to generate two fragments. The overlapping regions of two PCR fragments contained the desired single mutations and allowed the assembly of the entire DNA template via a second PCR. In the second step, the purified fragments from the first step were used as the template for the overlapping PCR (OL PCR) and the Fw and Rv oligos annealing to the vector backbone as the OL PCR primers. The resulting linear DNA templates contained a T7 promoter, a T7 terminator, and the open-reading frame for the polypeptide.

These linear DNA templates were used directly in a cell-free transcription and translation system to express the polypeptide variants containing the single mutations. The variant constructs were further individually transferred into transient transfection vectors. Additionally, DNA templates comprising combinatorial mutations were prepared by PCR and subsequently transferred into transient transfection vectors.

Example 2—Florescence Polarization Assay for Variant Binary Complex Detection In this Example, the ability of a wild-type or variant nuclease polypeptide and an RNA guide to form a binary complex is assessed through a fluorescence polarization assay.

Linear ssDNA fragments comprising the reverse complement of the T7 RNA polymerase promoter sequence upstream of the direct repeat sequence and desired 20 bp RNA guide target are synthesized by IDT™. Linear dsDNA in vitro transcription (IVT) templates are then generated by annealing a universal T7 forward oligo (95-4° C. at 5° C./minute) to the reverse complement ssDNA and filled in with Klenow fragment (New England Biolabs®) for 15 minutes at 25° C. The resulting IVT template is then transcribed into an RNA guide using the HiScribe T7 High Yield RNA Synthesis Kit (New England Biolabs) at 37° C. for 4 hours. Following transcription, each RNA guide is purified using an RNA Clean and Concentrator Kit (Zymo) and stored at −20° C. until use.

The RNA guide is then labeled with 6-carboxyfluorescein (6-FAM) (IDT™). 25 nM nuclease polypeptide (wild-type or variant Cas12i4 polypeptide) in 1× assay buffer (20 mM Tris-HCl (pH 7.5), 150 mM KCl, 5 mM $MgCl_2$, 1 mM DTT) is titrated with increasing concentrations of labeled RNA guide (7.5-250 nM). Complexes are incubated at 37° C. for 30 minutes before taking fluorescence polarization measurements using a microplate reader (Infinite® 200 Pro, Tecan).

Binary complex formation at different temperatures is also investigated. Further binding experiments as described above are performed isothermally at 25, 50, 60, and 70° C.

Formation of a binary complex upon titration of a nuclease polypeptide (wild-type or variant Cas12i4 polypeptide) with increasing concentrations of RNA guide (or formation of a binary complex upon titration of RNA guide with increasing concentrations of a nuclease polypeptide) results in changes in fluorescence polarization signal, in millipolarization (mP) units. A binding curve is generated by plotting changes in fluorescence polarization signal over a range of RNA guide concentrations.

This Example indicates how binding affinities of nuclease polypeptides (wild-type or variant Cas12i4 polypeptide) to RNA guides can be determined and compared.

Example 3—RNA Electrophoretic Mobility Shift Assay for Variant Binary Complex Detection This Example describes use of an RNA EMSA to determine the ability of a nuclease polypeptide (wild-type or variant) to bind to an RNA guide.

Synthetic RNA guides from IDT™ are labeled with a 5' IRDye® 800CW (also referred to as IR800 dye or IR800) using 5' EndTag Labeling Kit (Vector® Laboratories) and IRDye® 800CW Maleimide (LICOR® Biosciences), as previously detailed in Yan et al., 2018. After labeling, the RNA guides are cleaned and concentrated via phenol chloroform extraction. Concentrations are quantified by Nanodrop™.

For RNA binding assays, nuclease polypeptides (wild-type or variant Cas12i4 polypeptides) are diluted to 2.5 µM in 1× binding buffer (50 mM NaCl, 10 mM Tris-HCl, 10 mM $MgCl_2$, 1 mM DTT, pH 7.9. Polypeptides are then serially diluted from 2.5 µM to 37.5 µM in 1× binding buffer. The polypeptides are again diluted 1:10 in 1× binding buffer plus 50 nM IR800 labeled RNA guide and mixed thoroughly. These reactions can further include 0.5-5 µg tRNA, which serves as a competitive inhibitor to decrease nonspecific binding of polypeptide to RNA and thereby facilitate accurate specific binding determinations. Reactions are incubated at 37° C. for 1 hour. 1 µL 100λ bromophenol blue is added to the reactions for dye front visualization, then the entire reaction is loaded onto a 6% DNA Retardation Gel (ThermoFisher Scientific™), which runs for 90 minutes at 80V. The gel is imaged on the Licor® Odyssey® CLx.

This assay relies on the principle that the rate at which RNA migrates through the gel is determined by its size. An RNA only sample is able to migrate a particular distance. However, if the RNA binds to a polypeptide, a band that represents a larger, less mobile RNA complex appears, which is "upshifted" on the gel.

Therefore, the intensities of two bands are measured: 1) an RNA only band and 2) a polypeptide-bound "upshifted" RNA band. If all RNA is bound to a polypeptide, only an upshifted band is observed. As the concentration of polypeptide decreases, the intensity of the upshifted band decreases, while the intensity of the RNA only band increases. In comparing RNA binding affinities for nuclease polypeptides (wild-type or variant Cas12i4 polypeptides), a higher polypeptide/RNA affinity is characterized by more specific binding at lower concentrations of polypeptide.

This Example indicates how binding affinities of wild-type nuclease polypeptides to RNA guides and binding affinities of variant Cas12i4 polypeptides to RNA guides can be determined and compared.

Example 4—DNA Electrophoretic Mobility Shift Assay for Variant Cas12i4 Ternary Complex Detection This Example describes use of a DNA Electrophoretic Mobility Shift Assay (EMSA) to determine the ability of an RNA guide, a Cas12i4 polypeptide (wild-type or variant Cas12i4), and a target DNA substrate to form a ternary complex.

Cas12i4 wild-type of SEQ ID NO: 2 and Cas12i4 variant of SEQ ID NO: 4 were transformed into E. coli BL21 (DE3) (New England BioLabs®) and BL21(DE3)pLySS (Novagen®), respectively, and expressed under a T7 promoter. Transformed cells were initially grown overnight in 5 mL Luria Broth (TEKNOVA™)+50 µg/mL kanamycin, followed by inoculation into 1 L Terrific Broth media (TEKNOVA™)+50 µg/mL kanamycin. Cas12i4 wild type and variants cells were grown at 37° C. until an $OD_{600}$ of 0.6-0.8 and 3, respectively, then protein expression was induced with 0.5 mM IPTG. Cultures were then grown at 18° C. for an additional 14-18 hours. Cultures were harvested and pelleted via centrifugation, then resuspended in 1 mL extraction buffer per 5 g cell pellet (50 mM HEPES, pH 7.5, 500 mM NaCl, 5% glycerol, 0.5 mM TCEP). Cells were lysed via cell disruptor (Constant System Limited), then centrifuged at 20,000×g for 20 minutes at 4° C. in order to clarify the lysate. 0.2% polyethylenimine (PEI) was added to the clarified lysate and incubated at 4° C. with constant end-over-end rotation for 20 minutes. The lysate was then centrifuged again at 20,000×g for 10 minutes. Wild type Cas12i4 was purified via ion exchange and hydrophobic chromatography, and variant Cas12i4 was purified via immobilized metal affinity and ion exchange chromatography. After purification, fractions were run on SDS-PAGE gels, and fractions containing protein of the appropriate size were pooled and concentrated using 30kD Amicon® Ultra15 Centrifugal Units. Proteins were buffer exchanged into 12.5 mM HEPES pH 7.0, 120 mM NaCl, 0.5 mM TCEP, and 50% glycerol. Concentrations were then measured using the Nanodrop™ (ThermoFisher Scientific™) and proteins were stored at −20° C.

RNPs were prepared using a 2:1 ratio of synthetic RNA guide (Integrated DNA Technologies, IDT™) to polypeptide. The RNA guide sequences are shown in Table 13. crRNA 1 (SEQ ID NO: 62) corresponded to Target 1 (SEQ ID NO: 65), crRNA 2 (SEQ ID NO: 63) corresponded to Target 2 (SEQ ID NO: 66), and crRNA 3 (SEQ ID NO: 64) corresponded to Target 3 (SEQ ID NO: 67). The RNPs were complexed for 30 minutes at 37° C. in 1× NEBuffer™ 2 (NEB2; New England Biolabs®; 50 mM NaCl, 10 µM Tris-HCl, 10 mM $MgCl_2$, 1 mM DTT, pH 7.9). After complexing, a 5 point 1:2 serial dilution from 5 M to 37.5 µM was performed, using 1× NEB2 as a dilution buffer. Apo reactions (polypeptide without RNA guide) were prepared in the same manner, making up the volume of RNA guide with $H_2O$.

TABLE 13

| DNA EMSA RNA guide sequences. | |
|---|---|
| RNA Guide | Sequence |
| crRNA 1 (AAVS1_T6) | AGACAUGUGUCCUCAGUGACACGUAGCCUCUCCCGCUCUG (SEQ ID NO: 62) |
| crRNA 2 (AAVS1_T7) | AGACAUGUGUCCUCAGUGACACGGGAAGUGGUUGGUCAGC (SEQ ID NO: 63) |
| crRNA 3 (EMX1_T4) | AGACAUGUGUCCUCAGUGACACGGGGAGGCCUGGAGUCAU (SEQ ID NO: 64) | dsDNA target substrates of the sequences in Table 14 were generated by PCR from an oligo (Integrated DNA Technologies, Inc.) using the primers in Table 15. Before PCR, the 5' end of the forward primer was labeled an IR800 dye, as described in Yan et al., 2018. Using Amnplitaq Gold® (ThermoFisher Scientific™), the dsDNA substrate was then amplified with the IR800 labeled forward primer and unlabeled reverse primer. The resulting dsDNA was purified with a DNA Clean and Concentrator Kit (Zymo) and quantified by Nanodrop™ (ThermoFisher Scientific™).

RNP samples and Apo (control) samples were diluted 1:10 into 1× binding buffer (50 mM NaCl, 10 mM Tris-HCl, 1 mM TCEP, 10% glycerol, 2 mM EDTA, pH 8.0) plus 20 nM IR800 labeled target DNA substrate and mixed thoroughly. Reactions were incubated at 37° C. for 1 hour. Bromophenol blue was added to the reactions for dye front visualization, then the entire reaction was loaded onto a 6% DNA Retardation Gel (ThermoFisher Scientific™), which ran for 90 minutes at 80V. The gel was imaged on the Licor® Odyssey® CLx.

TABLE 14

DNA EMSA Target Substrates.

| Target Identifier | Sequence |
| --- | --- |
| Target 1 (AAVS1_T6) | CGCAAAGTGTTGGGATTACAGGCGTGAGCCCGGCCATTCTGAGACTGTGTTGC AGGCATTGTACATCTTCGCCTGATGCACAGCAGGTATCTCCTGCCACAAGGAA AACCTCCTGCAGAACCACAGTAGGGATGCAACACGCTACCCCCTGTGTTGACC TTGATGCTACACTCTCACCCACCGCACCAACCTTGATGCTACACTCTCACCCA CCGCACCAACCTTGATGCTACACTCTCACCCACCGCACCAACCTTGATGCTAC ACTCTCACCCACCGCACCAACCTTGATGCTACACTCTCACCCACCGCACCAAC CTTGATGCTACACTCTCACCCACTGCACCAACCTTGATGCTACACTGTTGCCT GCGTTTCTCCTTGACATTCTTTGTAGCCTCTCCCGCTCTGGTTCAGGGCCCAG CTAGGGATCCAGATCTGGGTGATTTAGGCTCCCTCTGTCTGGATCAGTCCTCC TTTTCCCTTGGACCCCAGGGAGGCCGGGAATGCCTCCAGGGGGTCTGTGAAC TTTCTGACGTTGTATTTTCCTGCAGAAATTGCTCATAACTTGCATCAGCTTCT CAGAGGGGG (SEQ ID NO: 65) |
| Target 2 (AAVS1_T7) | CCTGAGCCCATCACTGTTGCAAAGGTGACAGGAAGGCCTGGTGATGTGCGCAC CCTGGGAGCCAGGCTATGGGCCCGGTCACATTGAAACCATATGGGGCAAAGTGT GGGTGAGGAAAGTCAAGATGAGGTCACAGGGGAAGGGAGAATTGGATTTTCGTA GGCCCAAGCAGCAGCTGTGCTGCAGGGACACGCAGCAGCACCATGTCCTGTGC AGAAGGGACCCTCCCTGGCCACTTTGCACAGGGGCATGGAACTGGCAGGAAGA AGACATGATGTGTTTTTGAAACATTTGAAGCCAGCTCACTTGGAATTCCAGCA TCCAAGTCAGCTGGAAGAGGGGGAGTTACCCTTGGAGGCAGGCGGAATCGACC ATTGGATAGCTCCAAGTGCTGACAAGGGCGGACACGGGAGCTGATTTCTGCCT GGTGGGAAAGGTGATGATTCCAGCTACTTTGGGAAGTGGTTGGTCAGCATGGA TTATAGCCGAAGGCCCCAGCTTTGCCTTGTTCTAGCAGTTCCACTCCTGGGCA GCCCGAGAGAGGCCTTCCCAACCATGGGCAGATGTTCATCATAGTATTGTTTG CAGTAGTAAGAGGTCGGAGCCCACACCAAAG (SEQ ID NO: 66) |
| Target 3 (EMX1_T4) | AGGACAAAGTACAAACGGCAGAAGCTGGAGGAGGAAGGGCCTGAGTCCGAGCA GAAGAAGAAGGGCTCCCATCACATCAACCGGTGGCGCATTGCCACGAAGCAGG CCAATGGGGAGGACATCGATGTCACCTCCAATGACTAGGGTGGGCAACCACAA ACCCACGAGGGCAGAGTGCTGCTTGCTGCTGGCCAGGCCCCTGCGTGGGCCCA AGCTGGACTCTGGCCACTCCCTGGCCAGGCTTTGGGGAGGCCTGGAGTCATGG CCCCACAGGGCTTGAAGCCCGGGGCCGCCATTGACAGAGGGACAAGCAATGGG CTGGCTGAGGCCTGGGACCACTTGGCCTTCTCCTCGGAGAGCCTGCCTGCCTG GGCGGGCCCGCCCGCCACCGCAGCCTCCCAGCTGCTCTCCGTGTCTCCAATCT CCCTTTTGTTTTGATGCATTTCTGTTTTAATTTATTTTCCAGGCACCACTGTA GTTTAGTGATCCC (SEQ ID NO: 67) |

TABLE 15

Primers for DNA EMSA Target Substrate Generation.

| Target Identifier | Forward Primer Sequence | Reverse Primer Sequence |
| --- | --- | --- |
| Target 1 (AAVS1_T6) | CGCAAAGTGTTGGGATTACAGGCGT (SEQ ID NO: 68) | CCCCCTCTGAGAAGCTGATGCAAG T (SEQ ID NO: 69) |
| Target 2 (AAVS1_T7) | CCCCCTCTGAGAAGCTGATGCAAGT (SEQ ID NO: 70) | CTTTGGTGTGGGCTCCGACCTCTT A (SEQ ID NO: 71) |
| Target 3 (EMX1_T4) | AGGACAAAGTACAAACGGCAGAAGC TGG (SEQ ID NO: 72) | GGGATCACTAAACTACAGTGGTGC CTGG (SEQ ID NO: 73) |

Figure 1B:
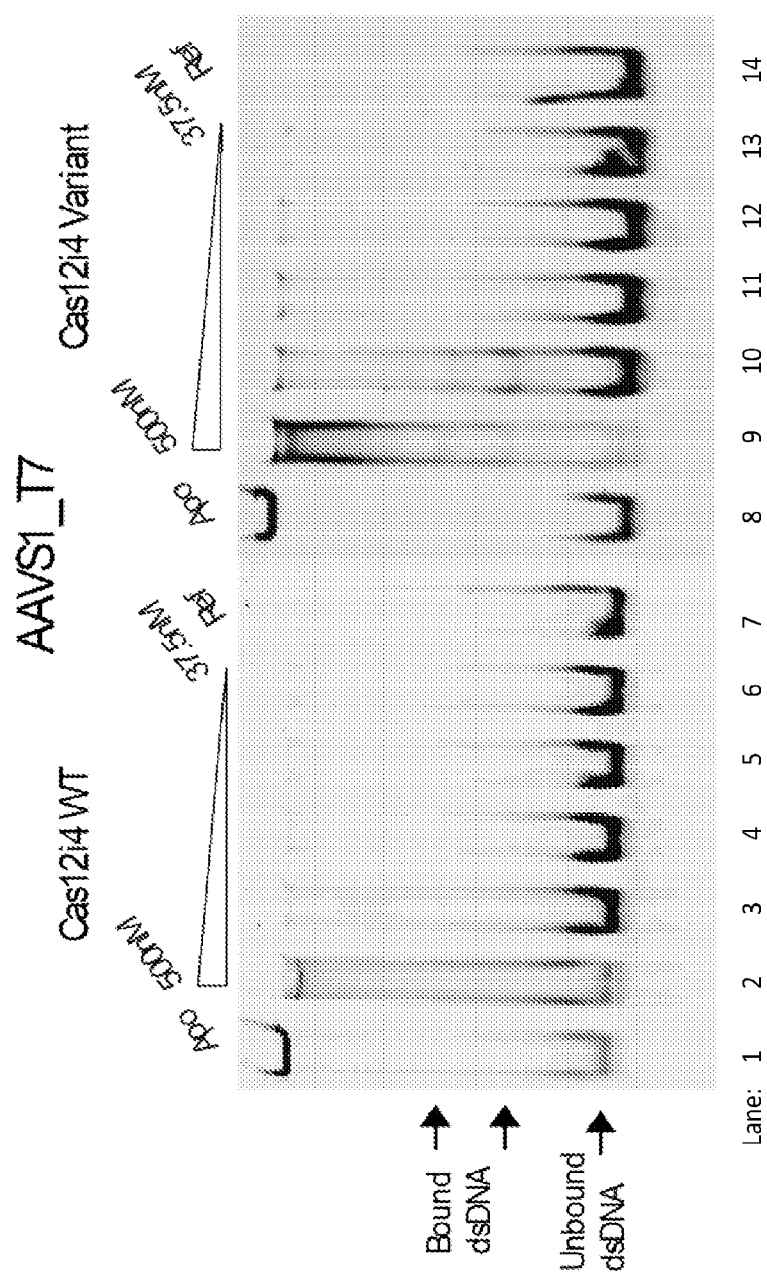
FIG. 1B is a DNA EMSA gel showing the ability of RNPs prepared with a) wild-type Cas12i4 (SEQ ID NO: 2) or variant Cas12i4 of SEQ ID NO: 4 and b) an RNA guide of SEQ ID NO: 63 to bind an AAVS1 dsDNA target (SEQ ID NO: 66). Bound dsDNA and unbound dsDNA bands are indicated.
Figure 1C:
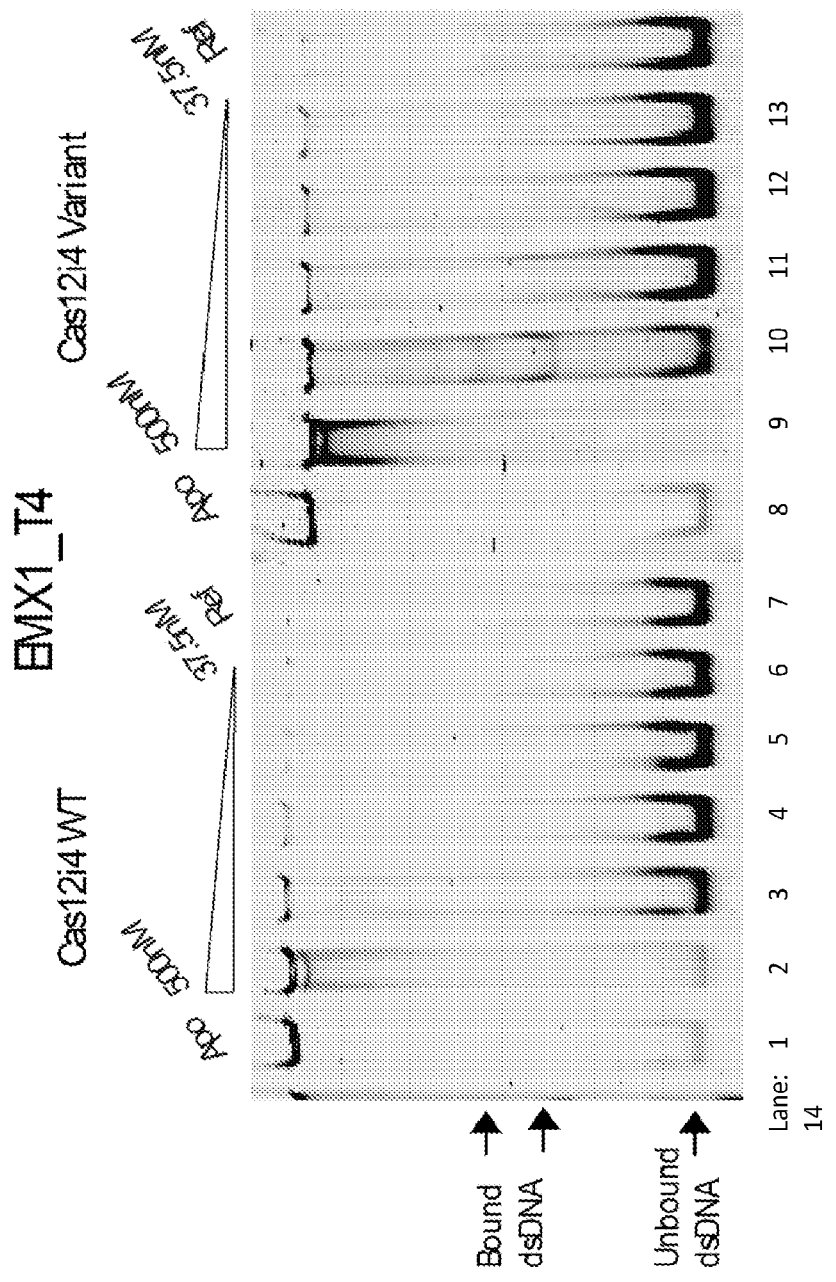
FIG. 1C is a DNA EMSA gel showing the ability of RNPs prepared with a) wild-type Cas12i4 (SEQ ID NO: 2) or variant Cas12i4 of SEQ ID NO: 4 and b) an RNA guide of SEQ ID NO: 64 to bind an EMX1 dsDNA target (SEQ ID NO: 67). Bound dsDNA and unbound dsDNA bands are indicated.

FIG. 1A, FIG. 1B, and FIG. 1C show EMSA gels for Target 1 (AAVS1_T6), Target 2 (AAVS1_T7), and Target 3 (EMX1_T4), respectively. In each gel, the "Apo" lanes (lanes 1 and 8) included target DNA plus wild-type Cas12i4 (lane 1) or Cas12i4 variant of SEQ ID NO: 4 (lane 8). The "Ref" lanes included target DNA alone. Lanes 2-6 in FIG. 1A, FIG. 1B, and FIG. 1C corresponded to decreasing concentrations of RNPs comprising wild-type Cas12i4 (SEQ ID NO: 2), from 500 nM to 37 nM. Lanes 9-13 in FIG. 1A, FIG. 1B, and FIG. 1C corresponded to decreasing concentrations of RNPs comprising the Cas12i4 variant of SEQ ID NO: 4, from 500 nM to 37 nM.

The gels of FIG. 1A, FIG. 1B, and FIG. 1C show bands of DNA that migrated different distances. In this assay, the rate at which DNA migrates through the gel is determined by its size. A DNA only sample is able to migrate a particular distance. However, if an RNP binds to the DNA, a band that represents a larger, less mobile DNA complex appears, which is "upshifted" on the gel. Therefore, the arrows in FIG. 1A, FIG. 1B, and FIG. 1C point to "unbound dsDNA" and the "bound dsDNA," wherein the "bound dsDNA" migrated less than the "unbound dsDNA."

FIG. 1A shows that for the highest concentration of wild-type Cas12i4 RNP (lane 2) and for the highest concentration of variant Cas12i4 RNP (lane 9) only unbound dsDNA bands were present, indicating that wild-type and variant Cas12i4 RNPs did not form a ternary complex with AAVS1_T6 target DNA.

FIG. 1B shows that even at the highest concentrations of wild-type Cas12i4 RNP (lane 2), only unbound dsDNA bands were present, indicating that wild-type Cas12i4 RNPs did not form a ternary complex with AAVS1_T7 target DNA. However, bound dsDNA bands were observed with RNPs prepared with variant Cas12i4 (lanes 9-10). Therefore, RNPs prepared with variant Cas12i4 had a higher affinity for AAVS1_T7 target DNA than wild-type Cas12i4.

Likewise, FIG. 1C shows that at even the highest concentrations of wild-type Cas12i4 RNP (lane 2), only unbound dsDNA bands were present, indicating that wild-type Cas12i4 RNPs did not form a ternary complex with EMX1 target DNA. However, bound dsDNA bands were observed with RNPs prepared with variant Cas12i4 (lane 10). Therefore, RNPs prepared with variant had a higher affinity for EMX1 target DNA than wild-type Cas12i4.

Based upon the data in FIG. 1A, FIG. 1B, and FIG. 1C, RNPs prepared with variant Cas12i4 had a higher affinity for multiple dsDNA targets, compared to the affinity of wild-type Cas12i4 RNPs for dsDNA targets.

In order to show that upshifting of substrate DNA was sequence dependent, RNPs were incubated with mis-matching target substrates. These reactions were carried out in the same manner, making up any volumes of polypeptide with 1× NEB2 buffer. Reactions comprising Cas12i4 polypeptide (wild-type or variant), crRNA 1 (SEQ ID NO: 62), and DNA Target 3 (SEQ ID NO: 67) are shown in FIG. 1D.

Figure 1D:
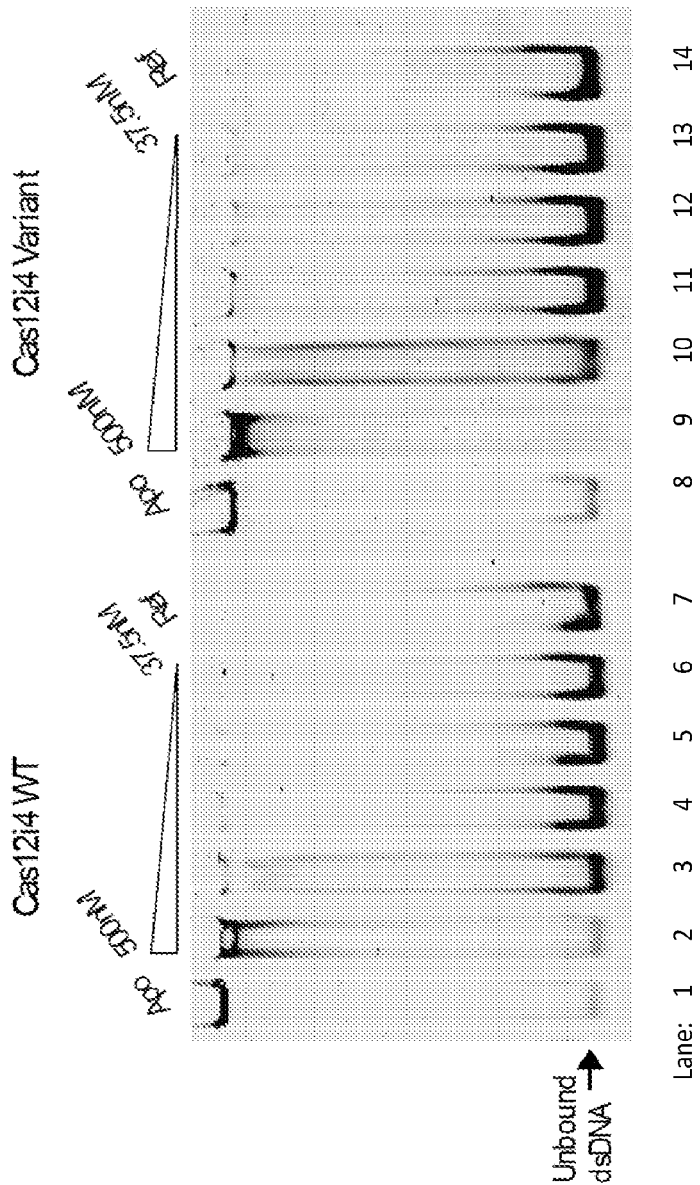
FIG. 1D is a control DNA EMSA gel showing the ability of RNPs prepared with a) wild-type Cas12i4 (SEQ ID NO: 2) or variant Cas12i4 of SEQ ID NO: 4 and b) an RNA guide of SEQ ID NO: 62 to bind an EMX1 dsDNA target (SEQ ID NO: 67). Unbound dsDNA bands are indicated.

In the gel in FIG. 1D, the "Apo" lanes (lanes 1 and 8) included Target 3 DNA (SEQ ID NO: 67) plus wild-type Cas12i4 (lane 1) and variant Cas12i4 (lane 8). The "Ref" lanes included Target 3 DNA alone. Lanes 2-6 in FIG. 1D corresponded to decreasing concentrations of wild-type Cas12i4 RNPs prepared with crRNA 1 (SEQ ID NO: 62), from 500 n to 37 nM. Lanes 9-13 in FIG. 1D corresponded to decreasing concentrations of RNPs prepared with variant Cas12i4 of SEQ ID NO: 4 and crRNA 1 (SEQ ID NO: 62), from 500 nM to 37 nM.

As shown in FIG. 1D, dsDNAs remained unbound by RNP across all concentrations, indicating that RNPs for both wild-type and variant Cas12i4 were unable to form a ternary complex. Therefore, the ability of an RNP to bind to a target DNA substrate, as shown in FIG. 1B and FIG. 1C, was dependent upon the sequences of the RNA guide and the target DNA substrate.

Overall, this Example shows that RNPs (binary complexes) prepared with variant Cas12i4 polypeptide had higher affinity to multiple DNA targets (to produce a ternary complex) than the affinity of wild-type Cas12i4 RNPs to the DNA targets.

Example 5—In Vitro Cleavage Assay for Determination of Variant Cas12i4 Ternary Complex Formation This Example describes methods for assessing in vitro biochemical activity of Cas12i4 (wild-type or variant Cas12i4) RNPs on a target DNA substrate as a means for determining ternary complex formation.

The RNA guides and dsDNA substrates in this Example are identical to those in Table 13 and Table 14, respectively. dsDNA substrates in this assay remained unlabeled. RNP and apo samples were generated and incubated in the same manner as described in Example 4, then serially diluted from 1 µM to 15.7 nM in 1× NEB2. RNP and apo samples were then further diluted 1:10 into 1× NEB2, and a target dsDNA substrate was added at 20 nM. Reactions were mixed thoroughly then incubated at 37° C. for 1 hour, then quenched with 1 µL 20 mg/mL Proteinase K (ThermoFisher Scientific™). Reactions were incubated for another 15 minutes at 50° C., then the entire reaction was run on a 2% agarose E-gel (ThermoFisher Scientific™). Gels were visualized by ethidium bromide on a Gel Doc™ EZ Gel Imager (BioRad®).

Figure 2A:
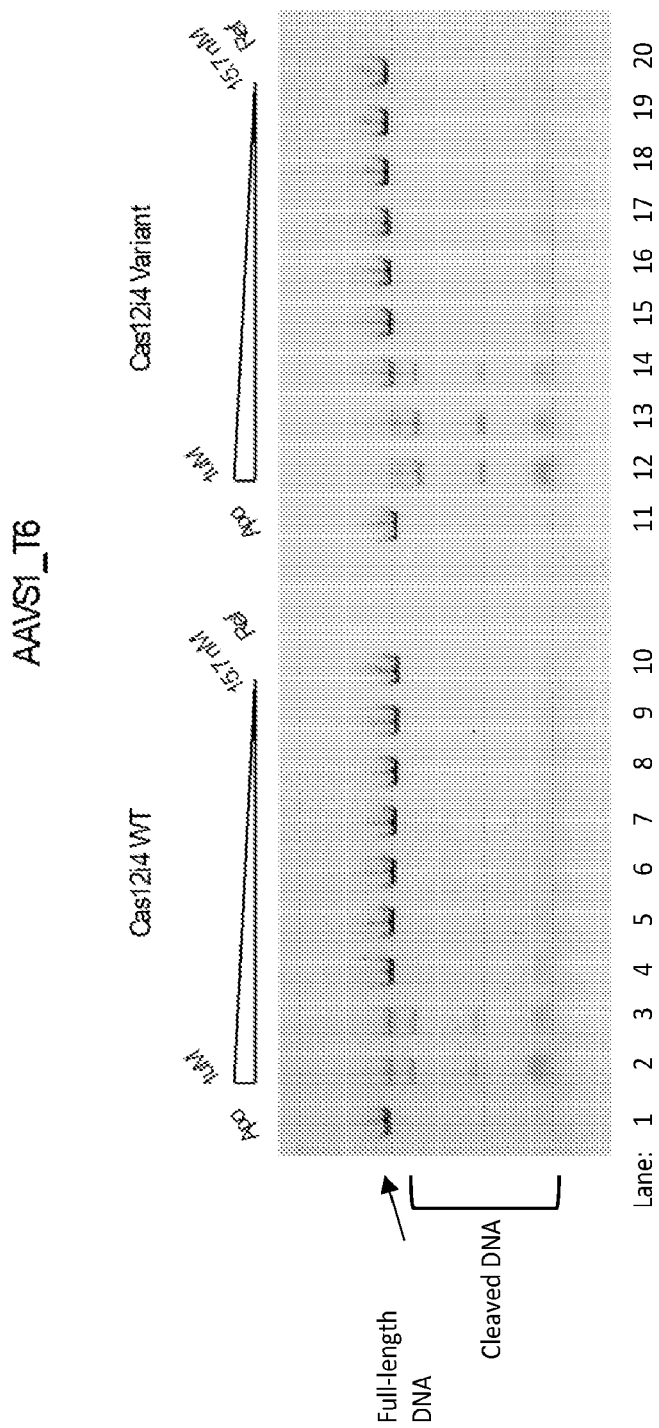
FIG. 2A is a gel showing cleavage of an AAVS1 dsDNA target (SEQ ID NO: 65) by RNPs prepared with a) wild-type Cas12i4 (SEQ ID NO: 2) or variant Cas12i4 of SEQ ID NO: 4 and b) an RNA guide of SEQ ID NO: 62. Full-length and cleaved DNA bands are indicated.
Figure 2B:
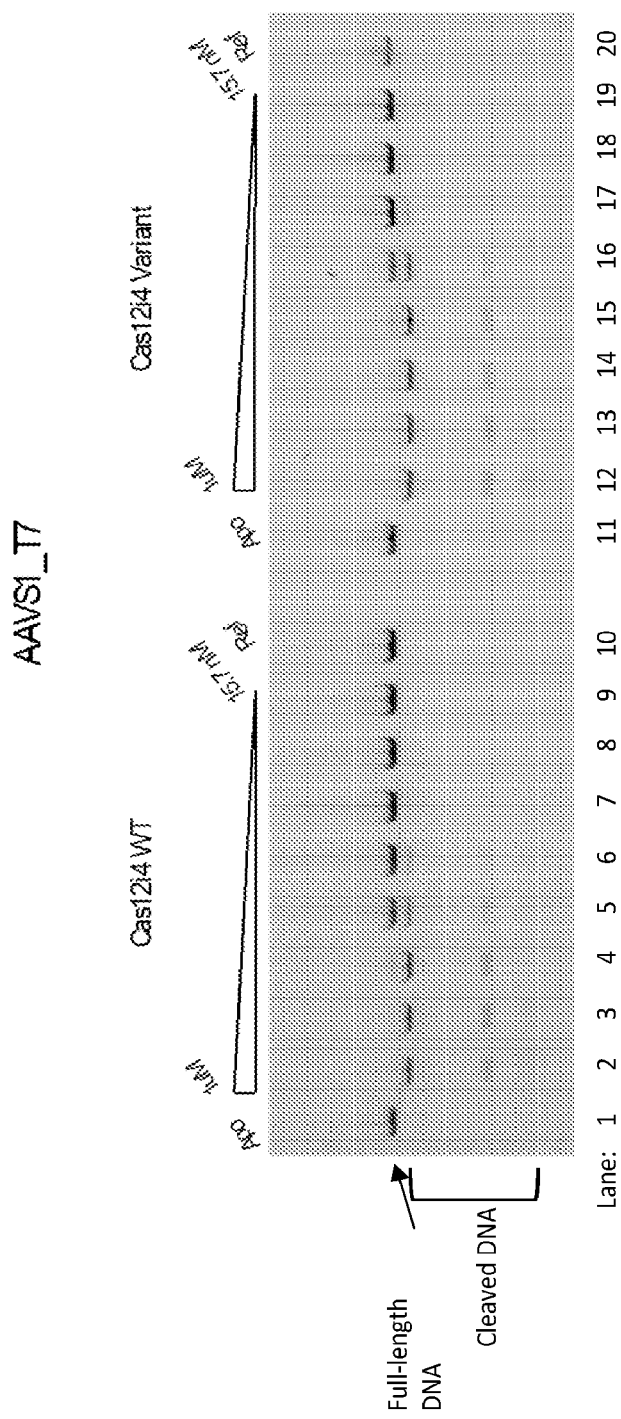
FIG. 2B is a gel showing cleavage of an AAVS1 dsDNA target (SEQ ID NO: 66) by RNPs prepared with a) wild-type Cas12i4 (SEQ ID NO: 2) or variant Cas12i4 of SEQ ID NO: 4 and b) an RNA guide of SEQ ID NO: 63. Full-length and cleaved DNA bands are indicated.
Figure 2C:
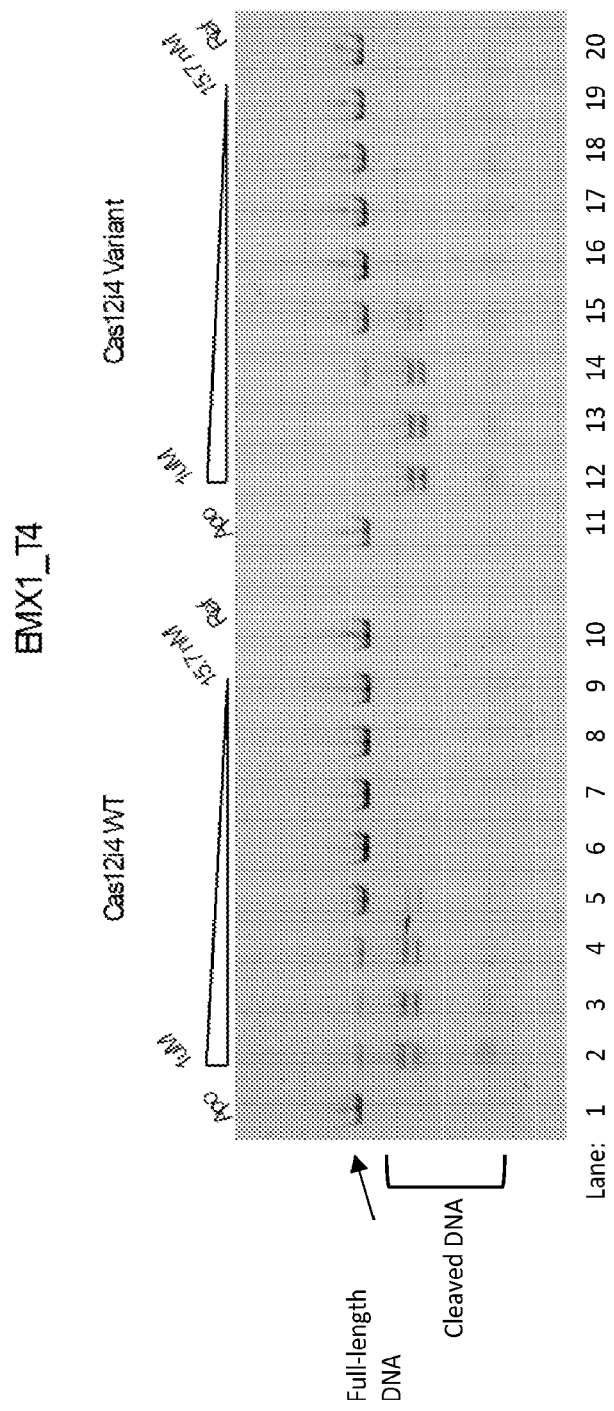
FIG. 2C is a gel showing cleavage of an EMX1 dsDNA target (SEQ ID NO: 67) by RNPs prepared with a) wild-type Cas12i4 (SEQ ID NO: 2) or variant Cas12i4 of SEQ ID NO: 4 and b) an RNA guide of SEQ ID NO: 64. Full-length and cleaved DNA bands are indicated.

FIG. 2A, FIG. 2B, and FIG. 2C show cleavage gels for Target 1 (AAVS1_T6), Target 2 (AAVS1_T7), and Target 3 (EMX1_T4), respectively. In each gel, the "Apo" lanes (lanes 1 and 11) included target DNA plus wild-type Cas12i4 (lane 1) or Cas12i4 variant of SEQ ID NO: 4 (lane 11). The "Ref" lanes included target DNA alone. Lanes 2-9 in FIG. 2A, FIG. 2B, and FIG. 2C correspond to decreasing concentrations of RNPs comprising wild-type Cas12i4 (SEQ ID NO: 2), from 1 µM to 15.7 nM. Lanes 12-19 in FIG. 2A, FIG. 2B, and FIG. 2C correspond to decreasing concentrations of RNPs comprising the Cas12i4 variant of SEQ ID NO: 4, from 1 µM to 15.7 nM.

In FIG. 2A, FIG. 2B, and FIG. 2C, the intensities of two types of bands were measured: 1) a full-length (uncleaved) DNA band and 2) one or more downshifted cleaved DNA bands. An inactive RNP was characterized by a full-length DNA band (e.g., the RNP was unable to form a ternary complex with the DNA substrate). An active RNP yielded one or more downshifted cleaved DNA bands (e.g., the RNP was able to form a ternary complex with the DNA substrate). As the concentration of an active RNP decreased, the intensity of the full-length band increased, and the intensity of the cleaved band(s) decreased. In comparing activity of multiple RNPs, an RNP having higher activity than another was characterized by more intense cleaved bands at lower RNP concentrations.

FIG. 2A, FIG. 2B, and FIG. 2C show that wild-type Cas12i4 and variant Cas12i4 cleaved each of the targets in vitro. However, variant Cas12i4 was able to cleave each of the targets at lower RNP concentrations. Therefore, the variant Cas12i4 of SEQ ID NO: 4 exhibited higher cleavage activity than wild-type Cas12i4.

Example 6—In Vitro Stability Assays of Variant Cas12i4 Polypeptides and Variant Binary Complexes In this Example, the stability of a variant RNP is assessed.

For the accelerated stability study, RNPs (5 μM) are generated in the same manner as described in Example 4, and the samples are subsequently stored at 25° C. for 48 hours.

In vitro cleavage assays (as described in Example 5) are performed on the RNP samples. These results are compared with those of Example 5 to determine the extent to which variant RNPs stored at 25° C. for 48 hours retain biochemical activity.

Apo polypeptide (without RNA guide) is also incubated at 25° C. for 48 hours. RNA EMSA assays are performed on the apo samples using the method described in Example 3. These results are compared with those of Example 3 to determine the extent to which a variant nuclease is able to form a binary complex with an RNA guide.

Apo samples incubated at 25° C. for 48 hours are also complexed with RNA guides to form RNPs, using the method described in Example 4. In vitro cleavage assays are then performed according to the methods of Example 5. The assay results are compared with those of Example 5 to assess activity levels of variant RNPs formed with protein incubated at 25° C.

The methods of this Example allow for comparison of the stability of wild-type and variant Cas12i4 polypeptides and wild-type and variant RNPs (binary complexes). A nuclease polypeptide demonstrating greater specific binding to an RNA guide than another nuclease polypeptide to the RNA guide is indicative of a more stable polypeptide. An RNP demonstrating more robust in vitro cleavage of a target DNA than cleavage by another RNP with a different nuclease polypeptide is indicative of a more stable binary complex.

Example 7—Targeting of Mammalian Genes by Variant Nucleases

This Example describes indel assessment on multiple targets using wild-type Cas12i4 and Cas12i4 variants introduced into mammalian cells by transient transfection.

The nucleases of SEQ ID NO: 2, SEQ ID NO: 3, and SEQ ID NO: 4 were cloned into a pcda3.1 backbone (Invitrogen®). RNA guides were cloned into a pUC19 backbone (New England Biolabs). The plasmids were then maxiprepped and diluted to 1 μg/μL. The RNA guide and target sequences are shown in Table 16.

TABLE 16

Mammalian targets and corresponding crRNAs.

| Target identifier | crRNA sequence | Target sequence |
| --- | --- | --- |
| AAVS1_T1 | AGACAUGUGUCCUCAGUGACACUGUCCC CCCAAGUUUUGGACCCCU (SEQ ID NO: 74) | TGTCCCCCCAAGTTTTGGA CCCCT (SEQ ID NO: 75) |
| AAVS1_T3 | AGACAUGUGUCCUCAGUGACACUGAGA AUGGUGCGUCCUAGGUGU (SEQ ID NO: 76) | GTGAGAATGGTGCGTCCTA GGTGT (SEQ ID NO: 77) |
| AAVS1_T5 | AGACAUGUGUCCUCAGUGACACAACUGG CCCUGGCUUUGGCAGCCU (SEQ ID NO: 78) | AACTGGCCCTGGCTTTGGC AGCCT (SEQ ID NO: 79) |
| AAVS1_T6 | AGACAUGUGUCCUCAGUGACACGUAGCC UCUCCCGCUCUGGUUCAG (SEQ ID NO: 80) | GTAGCCTCTCCCGCTCTGG TTCAG (SEQ ID NO: 81) |
| AAVS1_T7 | AGACAUGUGUCCUCAGUGACACGGGAAG UGGUUGGUCAGCAUGGAU (SEQ ID NO: 82) | GGGAAGTGGTTGGTCAGCA TGGAT (SEQ ID NO: 83) |
| EMX1_T1 | AGACAUGUGUCCUCAGUGACACGGGAAG UGGUUGGUCAGCAUGGAU (SEQ ID NO: 84) | GGGCGCAGGGCCACCTGG ACCCTG (SEQ ID NO: 85) |
| EMX1_T2 | AGACAUGUGUCCUCAGUGACACGGAUGG CGACUUCAGGCACAGGAU (SEQ ID NO: 86) | GGATGGCGACTTCAGGCAC AGGAT (SEQ ID NO: 87) |
| EMX1_T4 | AGACAUGUGUCCUCAGUGACACGGGGAG GCCUGGAGUCAUGGCCCC (SEQ ID NO: 88) | GGGGAGGCCTGGAGTCAT GGCCCC (SEQ ID NO: 89) |
| EMX1_T6 | AGACAUGUGUCCUCAGUGACACGAGCCA GUGUUGCUAGUCAAGGGC (SEQ ID NO: 90) | GAGCCAGTGTTGCTAGTCA AGGGC (SEQ ID NO: 91) |
| EMX1_T7 | AGACAUGUGUCCUCAGUGACACAGCAAG GGACUAUUCAGGGAUGAA (SEQ ID NO: 92) | AGCAAGGGACTATTCAGG GATGAA (SEQ ID NO: 93) |
| EMX1_T8 | AGACAUGUGUCCUCAGUGACACAAAAUU GAGCAAUCUACCCUGGUC (SEQ ID NO: 94) | AAAATTGAGCAATCTACCC TGGTC (SEQ ID NO: 95) |
| VEGFA_T1 | AGACAUGUGUCCUCAGUGACACUGGGGG UGACCGCCGGAGCGCGGC (SEQ ID NO: 96) | TGGGGGTGACCGCCGGAG CGCGGC (SEQ ID NO: 97) |
| VEGFA_T2 | AGACAUGUGUCCUCAGUGACACAAUCCU CCACCAGUCAUGGUGACA (SEQ ID NO: 98) | AATCCTCCACCAGTCATGG TGACA (SEQ ID NO: 99) |
| VEGFA_T3 | AGACAUGUGUCCUCAGUGACACGUUGAC AUUGUCCACACCUGGAAU (SEQ ID NO: 100) | GTTGACATTGTCCACACCT GGAAT (SEQ ID NO: 101) |

TABLE 16-continued

Mammalian targets and corresponding crRNAs.

| Target identifier | crRNA sequence | Target sequence |
|---|---|---|
| VEGFA_T5 | AGACAUGUGUCCUCAGUGACACUUAAAC UCUCCAUGGACCAGGCUC (SEQ ID NO: 102) | TTAAACTCTCCATGGACCA GGCTC (SEQ ID NO: 103) |
| VEGFA_T6 | AGACAUGUGUCCUCAGUGACACGCCCAU ACUGGGGACCAAGGAAGU (SEQ ID NO: 104) | GCCCATACTGGGGACCAAG GAAGT (SEQ ID NO: 105) |
| VEGFA_T7 | AGACAUGUGUCCUCAGUGACACGCCGUA ACCCUUCGUGGGUAGAGA (SEQ ID NO: 106) | GCCGTAACCCTTCGTGGGT AGAGA (SEQ ID NO: 107) |

Approximately 16 hours prior to transfection, 100 µl of 25,000 HEK293T cells in DMEM/10% FBS+Pen/Strep were plated into each well of a 96-well plate. On the day of transfection, the cells were 70-90% confluent. For each well to be transfected, a mixture of 0.5 µl of Lipofectamine™ 2000 and 9.5 µl of Opti-MEM was prepared and then incubated at room temperature for 5-20 minutes (Solution 1). After incubation, the Lipofectamine™:OptiMEM™ mixture was added to a separate mixture containing 126 ng of nuclease plasmid and 174 ng of guide plasmid and water up to 10 µL (Solution 2). In the case of negative controls, the crRNA was not included in Solution 2. The solution 1 and solution 2 mixtures were mixed by pipetting up and down and then incubated at room temperature for 25 minutes. Following incubation, 20 µL of the Solution 1 and Solution 2 mixture were added dropwise to each well of a 96 well plate containing the cells. 72 hours post transfection, cells are trypsinized by adding 10 µL of TrypLE™ to the center of each well and incubated for approximately 5 minutes. 100 µL of D10 media was then added to each well and mixed to resuspend cells. The cells were then spun down at 500 g for 10 minutes, and the supernatant was discarded. QuickExtract™ buffer (Lucigen®) was added to ⅕ the amount of the original cell suspension volume. Cells were incubated at 65° C. for 15 minutes, 68° C. for 15 minutes, and 98° C. for 10 minutes.

Samples for Next Generation Sequencing were prepared by two rounds of PCR. The first round (PCR1) was used to amplify specific genomic regions depending on the target. PCR1 products were purified by column purification. Round 2 PCR (PCR2) was done to add Illumina® adapters and indexes. Reactions were then pooled and purified by column purification. Sequencing runs were done with a 150 cycle NextSeq™ v2.5 mid or high output kit.

Figure 3:
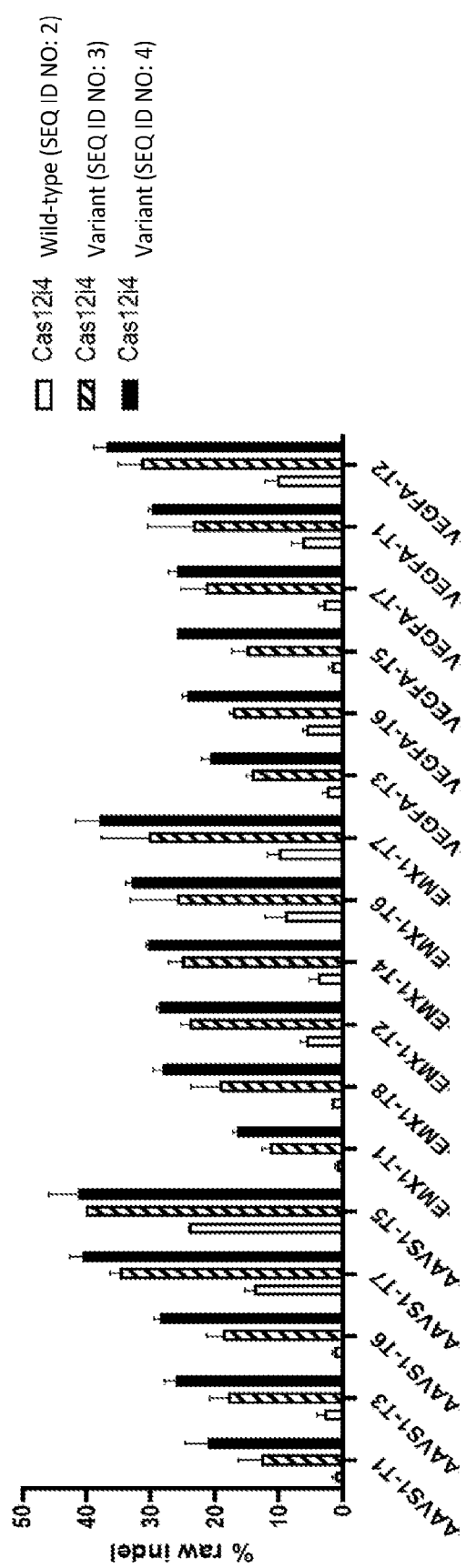
FIG. 3 is a graph showing indels induced in AAVS1, EMX1, and VEGFA targets (SEQ ID NOs: 75, 77, 79, 81, 83, 85, 87, 89, 91, 93, 95, 97, 99, 101, 103, 105, and 107) by wild-type Cas12i4 (SEQ ID NO: 2) and the Cas12i4 variants of SEQ ID NO: 3 and SEQ ID NO: 4 in mammalian cells.

FIG. 3 shows indel activity for wild-type Cas12i4 of SEQ ID NO: 2, variant Cas12i4 of SEQ ID NO: 3, and variant Cas12i4 of SEQ ID NO: 4. Variant Cas12i4 of SEQ ID NO: 3 and variant Cas12i4 of SEQ ID NO: 4 demonstrated higher indel activity at each of the targets compared to wild-type Cas12i4 of SEQ ID NO: 2. Therefore, engineered Cas12i4 variants demonstrated increased nuclease activity in mammalian cells.

Example 8—Targeting of Mammalian Genes by Variant Nuclease Using 5'-NTTN-3' and 5'-NVTN-3' PAM Sequences This Example describes indel assessment on multiple targets adjacent to a 5'-NTTN-3' or 5'-NVTN-3' PAM using wild-type Cas12i4 and Cas12i4 variants introduced into mammalian cells by transient transfection.

The nuclease and RNA guide constructs were prepared and transfected into HEK293T cells as described in Example 7. The RNA guide and target sequences are shown in Table 17.

TABLE 17

Mammalian targets, PAMs, and corresponding crRNAs.

| Target gene | Target sequence | crRNA sequence | PAM |
|---|---|---|---|
| AAVS1 | CTCATTCTTCCCTTAGGGG T (SEQ ID NO: 126) | AGACAUGUGUCCUCAGUGACAC CUCAUUCUUCCCUUAGGGGU (SEQ ID NO: 127) | NTTN |
| AAVS1 | CCCCCCAAGTCCCTCACCT C (SEQ ID NO: 128) | AGACAUGUGUCCUCAGUGACAC CCCCCCAAGUCCCUCACCUC (SEQ ID NO: 129) | NTTN |
| AAVS1 | ACCAGGTCGTGGCCGCCTC T (SEQ ID NO: 130) | AGACAUGUGUCCUCAGUGACAC ACCAGGUCGUGGCCGCCUCU (SEQ ID NO: 131) | NTTN |
| AAVS1 | TAGGCCTGCATCATCACCG T (SEQ ID NO: 132) | AGACAUGUGUCCUCAGUGACAC UAGGCCUGCAUCAUCACCGU (SEQ ID NO: 133) | NTTN |
| AAVS1 | ACTGGCCCTGGCTTTGGCA G (SEQ ID NO: 134) | AGACAUGUGUCCUCAGUGACAC ACUGGCCCUGGCUUUGGCAG (SEQ ID NO: 135) | NTTN |

TABLE 17-continued

Mammalian targets, PAMs, and corresponding crRNAs.

| Target gene | Target sequence | crRNA sequence | PAM |
|---|---|---|---|
| AAVS1 | TAGCCTCTCCCGCTCTGGT T (SEQ ID NO: 136) | AGACAUGUGUCCUCAGUGACAC UAGCCUCUCCCGCUCUGGUU (SEQ ID NO: 137) | NTTN |
| AAVS1 | TAGCCGAAGGCCCCAGCT TT (SEQ ID NO: 138) | AGACAUGUGUCCUCAGUGACAC UAGCCGAAGGCCCCAGCUUU (SEQ ID NO: 139) | NTTN |
| AAVS1 | GCGGGTATGGGAAGGGCT TT (SEQ ID NO: 140) | AGACAUGUGUCCUCAGUGACAC GCGGGUAUGGGAAGGGCUUU (SEQ ID NO: 141) | NTTN |
| AAVS1 | ACACGGGCCACCGTTTCTC A (SEQ ID NO: 142) | AGACAUGUGUCCUCAGUGACAC ACACGGGCCACCGUUUCUCA (SEQ ID NO: 143) | NVTN |
| AAVS1 | ACCCCCAAGTCCCTCACC T (SEQ ID NO: 144) | AGACAUGUGUCCUCAGUGACAC ACCCCCAAGUCCCUCACCU (SEQ ID NO: 145) | NVTN |
| AAVS1 | GGTGTTCACCAGGTCGTGG C (SEQ ID NO: 146) | AGACAUGUGUCCUCAGUGACAC GGUGUUCACCAGGUCGUGGC (SEQ ID NO: 147) | NVTN |
| AAVS1 | GGCCTGCATCATCACCGTT T (SEQ ID NO: 148) | AGACAUGUGUCCUCAGUGACAC GGCCUGCAUCAUCACCGUUU (SEQ ID NO: 149) | NVTN |
| AAVS1 | GCCCTGGCTTTGGCAGCCT G (SEQ ID NO: 150) | AGACAUGUGUCCUCAGUGACAC GCCCUGGCUUUGGCAGCCUG (SEQ ID NO: 151) | NVTN |
| AAVS1 | GCCTCTCCCGCTCTGGTTC A (SEQ ID NO: 152) | AGACAUGUGUCCUCAGUGACAC GCCUCUCCCGCUCUGGUUCA (SEQ ID NO: 153) | NVTN |
| AAVS1 | ATTATAGCCGAAGGCCCCA G (SEQ ID NO: 154) | AGACAUGUGUCCUCAGUGACAC AUUAUAGCCGAAGGCCCCAG (SEQ ID NO: 155) | NVTN |
| AAVS1 | GTGCAGAGGGTGGGCCGGG G (SEQ ID NO: 156) | AGACAUGUGUCCUCAGUGACAC GUGCAGAGGGUGGGCCGGGG (SEQ ID NO: 157) | NVTN |
| EMX1 | TGCTGAGAACCACCCAGGG T (SEQ ID NO: 158) | AGACAUGUGUCCUCAGUGACAC UGCUGAGAACCACCCAGGGU (SEQ ID NO: 159) | NTTN |
| EMX1 | GGTGCCCTAGGAAGCTGCC T (SEQ ID NO: 160) | AGACAUGUGUCCUCAGUGACAC GGUGCCCUAGGAAGCUGCCU (SEQ ID NO: 161) | NTTN |
| EMX1 | ATGCCCAAAGGTCAGATGA T (SEQ ID NO: 162) | AGACAUGUGUCCUCAGUGACAC AUGCCCAAAGGUCAGAUGAU (SEQ ID NO: 163) | NTTN |
| EMX1 | GGGGAGGCCTGGAGTCATG G (SEQ ID NO: 164) | AGACAUGUGUCCUCAGUGACAC GGGGAGGCCUGGAGUCAUGG (SEQ ID NO: 165) | NTTN |
| EMX1 | GCACCACTGTAGTTTAGTG A (SEQ ID NO: 166) | AGACAUGUGUCCUCAGUGACAC GCACCACUGUAGUUUAGUGA (SEQ ID NO: 167) | NTTN |
| EMX1 | TTTGAGCCAGTGTTGCTAG T (SEQ ID NO: 168) | AGACAUGUGUCCUCAGUGACAC UUUGAGCCAGUGUUGCUAGU (SEQ ID NO: 169) | NTTN |
| EMX1 | CTTTAGCAAGGGACTATTC A (SEQ ID NO: 170) | AGACAUGUGUCCUCAGUGACAC CUUUAGCAAGGGACUAUUCA (SEQ ID NO: 171) | NTTN |

TABLE 17-continued

Mammalian targets, PAMs, and corresponding crRNAs.

| Target gene | Target sequence | crRNA sequence | PAM |
|---|---|---|---|
| EMX1 | AGCAATCTACCCTGGTCCTC (SEQ ID NO: 172) | AGACAUGUGUCCUCAGUGACAC AGCAAUCUACCCUGGUCCUC (SEQ ID NO: 173) | NTTN |
| EMX1 | AGAACCACCCAGGGTCCAGG (SEQ ID NO: 174) | AGACAUGUGUCCUCAGUGACAC AGAACCACCCAGGGUCCAGG (SEQ ID NO: 175) | NVTN |
| EMX1 | GGGTGCCCTAGGAAGCTGCC (SEQ ID NO: 176) | AGACAUGUGUCCUCAGUGACAC GGGUGCCCUAGGAAGCUGCC (SEQ ID NO: 177) | NVTN |
| EMX1 | AGATGATAGCATAGGTACAC (SEQ ID NO: 178) | AGACAUGUGUCCUCAGUGACAC AGAUGAUAGCAUAGGUACAC (SEQ ID NO: 179) | NVTN |
| EMX1 | ACTCCAGGCCTCCCCAAAGC (SEQ ID NO: 180) | AGACAUGUGUCCUCAGUGACAC ACUCCAGGCCUCCCCAAAGC (SEQ ID NO: 181) | NVTN |
| EMX1 | ACTAAACTACAGTGGTGCCT (SEQ ID NO: 182) | AGACAUGUGUCCUCAGUGACAC ACUAAACUACAGUGGUGCCU (SEQ ID NO: 183) | NVTN |
| EMX1 | CTTTGAGCCAGTGTTGCTAG (SEQ ID NO: 184) | AGACAUGUGUCCUCAGUGACAC CUUUGAGCCAGUGUUGCUAG (SEQ ID NO: 185) | NVTN |
| EMX1 | CCTTGCTAAAGAAACATGTG (SEQ ID NO: 186) | AGACAUGUGUCCUCAGUGACAC CCUUGCUAAAGAAACAUGUG (SEQ ID NO: 187) | NVTN |
| EMX1 | GAGCAATCTACCCTGGTCCT (SEQ ID NO: 188) | AGACAUGUGUCCUCAGUGACAC GAGCAAUCUACCCUGGUCCU (SEQ ID NO: 189) | NVTN |
| VEGFA | TGGGGGTGACCGCCGGAGCG (SEQ ID NO: 190) | AGACAUGUGUCCUCAGUGACAC UGGGGGUGACCGCCGGAGCG (SEQ ID NO: 191) | NTTN |
| VEGFA | TGGGCTGCTTGGGGTTGTCA (SEQ ID NO: 192) | AGACAUGUGUCCUCAGUGACAC UGGGCUGCUUGGGGUUGUCA (SEQ ID NO: 193) | NTTN |
| VEGFA | TCCACACCTGGAATCGGCTT (SEQ ID NO: 194) | AGACAUGUGUCCUCAGUGACAC UCCACACCUGGAAUCGGCUU (SEQ ID NO: 195) | NTTN |
| VEGFA | GTGTAGAGAGGAAAATGTGG (SEQ ID NO: 196) | AGACAUGUGUCCUCAGUGACAC GUGUAGAGAGGAAAAUGUGG (SEQ ID NO: 197) | NTTN |
| VEGFA | GGGGCTTTGTTTGGGAAGCT (SEQ ID NO: 198) | AGACAUGUGUCCUCAGUGACAC GGGGCUUUGUUUGGGAAGCU (SEQ ID NO: 199) | NTTN |
| VEGFA | ACACTTCCTTGGTCCCCAGT (SEQ ID NO: 200) | AGACAUGUGUCCUCAGUGACAC ACACUUCCUUGGUCCCCAGU (SEQ ID NO: 201) | NTTN |
| VEGFA | GTGGGTAGAGAAGGATTCTG (SEQ ID NO: 202) | AGACAUGUGUCCUCAGUGACAC GUGGGUAGAGAAGGAUUCUG (SEQ ID NO: 203) | NTTN |
| VEGFA | AAATCCTCCCTTGACCCACC (SEQ ID NO: 204) | AGACAUGUGUCCUCAGUGACAC AAAUCCUCCCUUGACCCACC (SEQ ID NO: 205) | NTTN |
| VEGFA | CCAAGGGGAGGGCTCACGC (SEQ ID NO: 206) | AGACAUGUGUCCUCAGUGACAC CCAAGGGGAGGGCUCACGC (SEQ ID NO: 207) | NVTN |

TABLE 17-continued

Mammalian targets, PAMs, and corresponding crRNAs.

| Target gene | Target sequence | crRNA sequence | PAM |
|---|---|---|---|
| VEGFA | ACAACCCCAAGCAGCCCACA (SEQ ID NO: 208) | AGACAUGUGUCCUCAGUGACAC ACAACCCCAAGCAGCCCACA (SEQ ID NO: 209) | NVTN |
| VEGFA | AAAGCCGATTCCAGGTGTGG (SEQ ID NO: 210) | AGACAUGUGUCCUCAGUGACAC AAAGCCGAUUCCAGGUGUGG (SEQ ID NO: 211) | NVTN |
| VEGFA | TGTGTAGAGAGGAAAATGTG (SEQ ID NO: 212) | AGACAUGUGUCCUCAGUGACAC UGUGUAGAGAGGAAAAUGUG (SEQ ID NO: 213) | NVTN |
| VEGFA | ATCCAGCTTCCCAAACAAAG (SEQ ID NO: 214) | AGACAUGUGUCCUCAGUGACAC AUCCAGCUUCCCAAACAAAG (SEQ ID NO: 215) | NVTN |
| VEGFA | CTGGGGACCAAGGAAGTGTC (SEQ ID NO: 216) | AGACAUGUGUCCUCAGUGACAC CUGGGGACCAAGGAAGUGUC (SEQ ID NO: 217) | NVTN |
| VEGFA | GGTAGAGAAGGATTCTGTGC (SEQ ID NO: 218) | AGACAUGUGUCCUCAGUGACAC GGUAGAGAAGGAUUCUGUGC (SEQ ID NO: 219) | NVTN |
| VEGFA | TTCAAATCCTCCCTTGACCC (SEQ ID NO: 220) | AGACAUGUGUCCUCAGUGACAC UUCAAAUCCUCCCUUGACCC (SEQ ID NO: 221) | NVTN |

Figure 4:
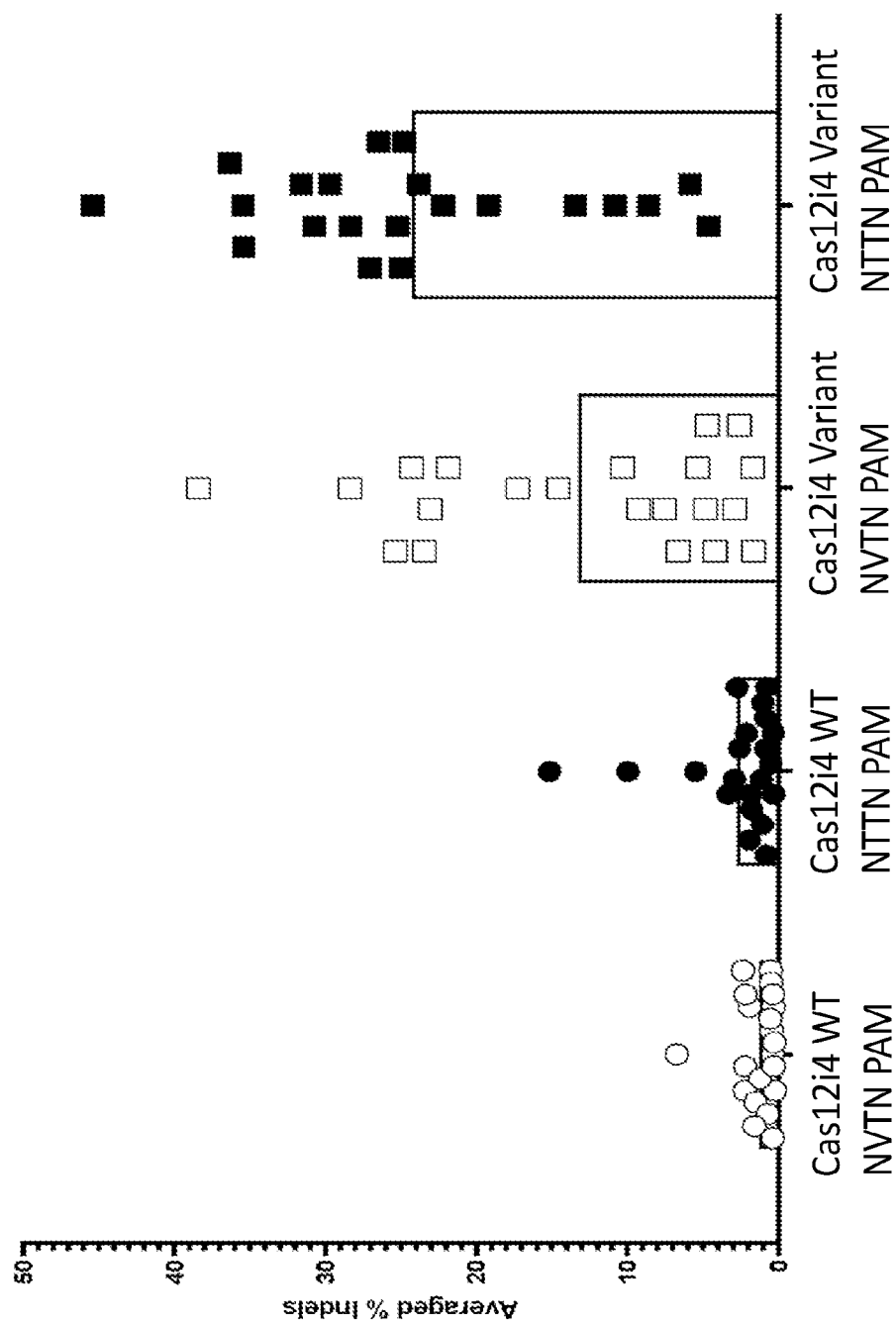
FIG. 4 is a graph showing indels induced in AAVS1, EMX1, and VEGFA targets adjacent to 5'-NTTN-3' or 5'-NVTN-3' PAM sequences by wild-type Cas12i4 (SEQ ID NO: 2) and the Cas12i4 variant of SEQ ID NO: 4 in mammalian cells.

Indels were analyzed as described in Example 7, and results are shown in FIG. 4. Open shapes represent targets with 5'-NVTN-3' PAMs, and closed shapes represent targets with 5'-NTTN-3' PAMs. Circles represent wild-type Cas12i4 (SEQ ID NO: 2), and squares represent Cas12i4 variant of SEQ ID NO: 4. Bars represent mean indels across all targets. Variant Cas12i4 of SEQ ID NO: 4 showed higher indel activity than wild-type Cas12i4 of SEQ ID NO: 2, and use of a 5'-NTTN-3' PAM resulted in higher indel levels than use of a 5'-NVTN-3' PAM.

This example shows that indels can be induced by Cas12i4 (wild-type or variant Cas12i4) using a 5'-NTTN-3' PAM or 5'-NVTN-3' PAM.

What is claimed is:

1. A variant Cas12i4 polypeptide comprising the sequence set forth in SEQ ID NO: 4.
2. The variant Cas12i4 polypeptide of claim 1, which further comprises a nuclear localization signal (NLS).
3. The variant Cas12i4 polypeptide of claim 1, which further comprises a peptide tag, a fluorescent protein, a base-editing domain, a DNA methylation domain, a histone residue modification domain, a localization factor, a transcription modification factor, a light-gated control factor, a chemically inducible factor, or a chromatin visualization factor.
4. A composition comprising a variant Cas12i4 polypeptide of claim 1, wherein the composition further comprises an RNA guide or a nucleic acid encoding the RNA guide, wherein the RNA guide comprises a direct repeat sequence and a spacer sequence.
5. The composition of claim 4, wherein the direct repeat sequence comprises:
   a nucleotide 1 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
   b nucleotide 2 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
   c nucleotide 3 through nucleotide 36 of a sequence that is at least 90% identical to a sequence of any one of SEQ ID NOs: 60, 108, 109, 110, 111, 112, 113, 114, 115, 116, 117, 118, 119,120, 121, 122, 123, or 124;
   d nucleotide 4 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
   e nucleotide 5 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
   f nucleotide 6 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
   g nucleotide 7 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
   h nucleotide 8 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
   i nucleotide 9 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
   j nucleotide 10 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
   k nucleotide 11 through nucleotide 36 of a sequence that is at least 90% identical to a sequence of any one of SEQ TD NOs: 60, 108, 109, 110, 111, 112, 113, 114, 115, 116, 117, 118, 119, 120, 121, 122, 123, or 124;
   l nucleotide 12 through nucleotide 36 of a sequence that is at least 90% identical to a sequence of any one of SEQ ID NOs: 60, 108, 109, 110, 111, 112, 113, 114, 115, 116, 117, 118, 119, 120, 121, 122, 123, or 124;
   m nucleotide 13 through nucleotide 36 of a sequence that is at least 90% identical to a sequence of any one of SEQ ID NOs: 60, 108, 109, 110, 111, 112, 113, 114, 115, 116, 117, 118,119, 120, 121, 122, 123, or 124;
   n nucleotide 14 through nucleotide 36 of a sequence that is at least 90% identical to a sequence of any one of SEQ ID NOs: 60, 108, 109, 110, 111, 112, 113, 114, 115, 116, 117, 118,119, 120, 121, 122, 123, or 124; or
   o sequence that is at least 90% identical to a sequence of SEQ ID NO: 61 or a portion thereof.
6. The composition of claim 4, wherein the spacer sequence is about 15 nucleotides to about 35 nucleotides in length.
7. The composition of claim 4, wherein the spacer sequence binds to a target strand sequence of a target nucleic acid, and wherein a non-target strand sequence of the target nucleic acid sequence is adjacent to a protospacer adjacent motif (PAM) sequence.
8. The composition of claim 7, wherein the PAM sequence is 5'-TTN-3', 5'-NTTN-3', 5'-NTN-3', 5'-NNTN-3', 5'-VTN-3', or 5'-NVTN-3', wherein N is any nucleotide and V is A, G, or C.
9. The composition of claim 4, wherein the composition is present in a delivery system comprising a nanoparticle, a liposome, an exosome, a microvesicle, or a gene-gun.
10. The composition of claim 9, wherein the nanoparticle comprises a lipid nanoparticle.
11. A nucleic acid molecule encoding a variant Cas12i4 polypeptide of claim 1.
12. The nucleic acid molecule of claim 11, which comprises mRNA.
13. The nucleic acid molecule of claim 11, wherein the nucleic acid is codon-optimized for expression in a cell.
14. The nucleic acid molecule of claim 11, wherein the nucleic acid is operably linked to a promoter.
15. A cell comprising the variant Cas12i4 polypeptide of claim 1.
16. The cell of claim 15, which is a mammalian cell.
17. The cell of claim 16, which is a human cell.
18. A method of making a variant binary complex, the method comprising contacting a variant Cas12i4 polypeptide of claim 1 with an RNA guide, wherein the RNA guide comprises a direct repeat sequence and a spacer sequence.
19. A method of binding a variant binary complex to a target nucleic acid, wherein the variant binary complex comprises a variant Cas12i4 polypeptide of claim 1 and an RNA guide, wherein the RNA guide comprises a direct repeat sequence and a spacer sequence, comprising contacting said variant binary complex with the target nucleic acid.
20. A method for editing a gene in a cell, the method comprising contacting the cell with a composition of claim 4.

* * * * *